US010131953B2

(12) United States Patent
Jarrard et al.

(10) Patent No.: US 10,131,953 B2
(45) Date of Patent: Nov. 20, 2018

(54) UNBIASED DNA METHYLATION MARKERS DEFINE AN EXTENSIVE FIELD DEFECT IN HISTOLOGICALLY NORMAL PROSTATE TISSUES ASSOCIATED WITH PROSTATE CANCER: NEW BIOMARKERS FOR MEN WITH PROSTATE CANCER

(71) Applicant: Wisconsin Alumni Research Foundation, Madison, WI (US)

(72) Inventors: David Frazier Jarrard, Madison, WI (US); Bing Yang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/226,291

(22) Filed: Mar. 26, 2014

(65) Prior Publication Data

US 2014/0296355 A1 Oct. 2, 2014

Related U.S. Application Data

(63) Continuation-in-part of application No. 13/288,607, filed on Nov. 3, 2011.

(60) Provisional application No. 61/806,218, filed on Mar. 28, 2013, provisional application No. 61/806,566, filed on Mar. 29, 2013.

(51) Int. Cl.
*C40B 30/04* (2006.01)
*C12Q 1/68* (2018.01)
*C12Q 1/6886* (2018.01)

(52) U.S. Cl.
CPC ..... *C12Q 1/6886* (2013.01); *C12Q 2600/154* (2013.01)

(58) Field of Classification Search
CPC ........................ C12Q 1/6886; C12Q 2600/154
See application file for complete search history.

(56) References Cited

U.S. PATENT DOCUMENTS

2012/0135877 A1 5/2012 Jarrard

OTHER PUBLICATIONS

Walker et al., Methods in Molecular Biology, Epigenetic Protocols, Second Edition, Department of Biology University of Alabama at Birmingham, Published by Human Press, 2011.*
Cui et al., Hypermethylation of theCaveolin-1Gene Promoter in Prostate Cancer, The Prostate 46:249-256 (2001).*
"The Polymerase Chain Reaction," published by Integrated DNA Technologies, 2005 and 2011 (no known author).*
Matthew Truong, et al.; "Using the Epigenetic Field Defect to Detect Prostate Cancer in Biopsy Negative Patients", The Journal of Urology, vol. 189, No. 6, Nov. 15, 2012, XP055141138, ISSN: 0022-5347, DOI:10.1016/j.juro.2012.11.074.
International Search Authority, Notification of Transmittal of the International Search Report and the Written Opinion of the International Searching Authority, or the Declaration; International App. No. PCT/US2014/031957, dated Oct. 6, 2014.

* cited by examiner

*Primary Examiner* — Reza Ghafoorian
(74) *Attorney, Agent, or Firm* — Quarles & Brady LLP

(57) ABSTRACT

A method of detecting the presence of a prostate cancer field defect in a human subject comprising the step of (a) obtaining genomic DNA from the human subject and (b) quantitating methylation in at least one target region selected from the group consisting of CAV1, EVX1, MCF2L, FGF1, NCR2 and WNT2 and EXT1 and SPAG4 target, wherein significant methylation changes indicate the presence of prostate cancer or a prostate cancer field defect, wherein the change is relative to tissue from a second human subject who does not have prostate cancer.

12 Claims, 39 Drawing Sheets

Specification includes a Sequence Listing.

CAV1

Methylation (%)

0 20 40 60 80

NTA T TAA TAO

* * *

CAV1 (caveolin 1, caveolae protein), Chr7

SEQ ID NO:1

```
agaagc ctgcggctgc cccctcgccg ccgaggtcct gcgggtcctg cgggtcctgc
gtgctgagcc ggggcgtgcg cgggcggggg ccttcggacc gcgcggcggg gcctgccctg
acccctggcg gcgggcgggg gaggcaggcg cgccctgcag agtacagagg ggtgtggtgt
cctctgcgag atcctcttaa aaagctggct acgcgcaggc ggtttctgtg cacggagccg
tagctgtcgg agcggttagt tcgatttcga gctcgaggtt tcccccgccg ccaggctgac
ttctcatcgc ttgtttttct ttttgcattt ttcctcccac cgccgttgcc gccctccccg
tcctggccgt ccgccctccg ccctctgcag ggacatctct acaccgttcc catccgggaa
cagggcaaca tctacaagcc caacaacaag gccatggcag acgagctgag cgagaagcaa
gtgtacgacg cgcacaccaa ggagatcgac ctggtcaacc gcgaccctaa acacctcaac
gatgacgtgg tcaaggtaag ccaaggcgac caacagggaa gggctgggac agctctcctc
tggcagttag cccgtgcatc cttctttagc attgccgtgt acgcacaccc caccccgccc
cctacacgcg cacacacaca cacacacaga gttttgtggg tttgatgtgt gggagctccc
gcagtcggca gaaacgttac atctcccttc ccccatctcc ccccaatagt tagttcagct
gaaattcagc taaagtgagt tttgtagaag ttcctataac tacactttta tcctagcaaa
tgagcctatt gacctcagca acagacggcc catactcctt gggacggtga gatggttcct
atccattccc aggttgaaag tctagtgaca ggtccccact gcacgtggca ttaagacagt
cagataattg tgtcaggtct tgtgctgagg atgagtcaga atacaagatg ggcatgttcc
cccaactaaa acgatgggaa gtgattttct taaa
```

Fig. 1

EVX1 (even-skipped homeobox 1), Chr7

SEQ ID NO:2

```
accgtgcccc tccgctcccc gggcctccca ctgcgcccac ccttcacttc ggcgcaggcc
aggaggaaga cactcccttc ccctagggca ggatggctgg ggggacccac ctgagcaact
ctctctgcta tctgcgttct ggcgggggtc tcctactgtg ttctggcatt ggcgggactg
agggtgacag cagtgccttg agtgcggggt gctgaggggg cggatgcaag tcctggactt
gggggattcg aagctcaccc caagcaccca gtgtttcaac tgctcgggga atgcttcaat
tgctcgggga agacactttc cccaggcgag ggcaagatca aacgccgatc cgggcagttt
gtggctggca gggtgtaaga ggcatggagg cgcggaagcc aggagtccat aaaggaccgt
aaaattgcgg cccacttggg cagcccgggt gctgcagccc tccgaccagt ttgcacgtcg
gtcagaggtc caaattacct tgtcacttcc cgggcttcgc ggcgccaggt cggaaatggt
cccaatggtc taattgcctt tggtctccgg ttgcatttga aaaggcagag atcgggtcct
ccccccttcc cctttccttc ctagtcccac ttctccaccc aaaggaaaag gagctgcagg
gggctggagc cccacccttc tcagaggtag gcccaaaggg gggctggttt aactggagaa
cccctcccca ccaaaggcta atgggaaagg ggtggatagc ccggaaggga gtttccctct
gtgccaacaa tcacctcccc agaaggggt agaaaactgg gcgcgggttg gtggggggga
ggagagggga gcccaccagc agacactcct ccacagaact gtaggagtgg gtggaaagag
cctgggggcg gggggagaa agaccacccc ctggtcttgg cagccaacgc cttgttgaat
acctgcacct accccttact atcttatcac cgatttcacc cagcctcctt cccataaccc
tcagaacaac ctggactcca ctcacatata
```

Fig. 2

MCF2L (cell line derived transforming sequence-like), Chr13

SEQ ID NO:3 cc tgaggggtct gttccagggg agccagggct ctccgtgtcc cgacgcggtt
gcctcacccc atgcccctca ggaaatgctg aaatacagca ggaactgcga gggggctgag
gacctgcagg aggcgctgag ctccatcctg ggcatcctga aggccgtgaa cgactccatg
cacctcatcg ctatcaccgg ctatgacgta aggcgcccag atgcccggtc ttccccgccg
cctccgtgga atacaccagc ccagcaactt ggcggcctcc ctgcacacgc ccctcgcttt
ggtgtgaatg tgcaggttct gggcaggagg tctggggtgg tccctagata agcccactcc
caggccccac agccgggtcc acagacccca cagccgggtc cacagacccc actgggctct
ctgggacgtg gagaaaatca ggaagcgtcc cttgcttgga gggcacgcat ctccagcagg
aacgcagctc agacctcctc actccttgtc ttctcctggg gaggaggcgt ggctcggagc
agacgtgact tctgttttct gggctgcgat ttgcaggctg gtgacttaga gcaagtggcc
ccagaaggca gatgtcactt tccccgtaga gccccacatc aggtcacagc ttattcatct
tttgtccgtc tttatgtcca cccagcactc attctcaggt gttttttttt taactaatag
agttgattta ttgcagcaat ttttggtttg tgagataatt gagtataaat cagaggccct
gaggcttccc ctagtgttga catttagcat gggtgccaca cctgccacac atggtgaact
agcgctgatg ctgattagtg actgagggcc gttccccttg gagctcactc tgggtgctgt
gcattctgcg gtttggacag gcgtgtaaca tcctacaccc agcgctagag catcacacag
agcagcttca ctgtcctaga agcccatgtg ccccgccagt ccatccctcc tcccccagcc
cctggcacct gctgacctgt cagtctccac gagcttgc

Fig. 3

FGF1 (fibroblast growth factor 1), Chr5

SEQ ID NO:4

ATAATCGTGAGAAGGAAGCTCATGCTTCTGTCCTCGACTGGCTTGTAGTCTAGTCAAGAAGACTTGAGGGC
TGATGAGCTTTTCAGAGATGGAAATAGAGGATACTGTGCCCCGTGGCCTCTGCTCTGCCCAGCCCCCTACC
AGTAACCAACAATTTTCCAGAAGAATTTCCAAATTCCCTTCTCCAAAGTCTCCACTGGCTCCACTTTCATT
TGCTTGCAGAAAAAAGTCTAAATGCTTTGGAACAGCATCATTCAAGGTCCTCTATGATCTGACTCCAAGCT
AGCTTGCACTAACCCTGTGTGTCCCTGAAAACCCCCCGCTCAGCGGCATCAGCCATGCATGCTGGGCGAAG
ATGCCCTCTACTTGCCCACCCCTGGGCCTCTGTTCAAGTGATTCCTTTATTCCATGCCCACATATGTAAAA
CCTGTTTGTCCTTCCTGCTGAGATGCCACATCTTCCAGAAAGTCCTCCTGACCCCTTCCTCTTCAGCCCTC
CATCCATCCCCCCAGCCCTTGGCACAACCTTCACAGCACTTATCATAGCTTGTCATGGTATTTATGACTTA
GCTTCTCACCTTCTTTCAAGGACAGGAAGCTTATCTCATTCATCCTGAATAATCACAACAAAAATAATAGC
TAAAATTATGAGATGTTAGAATGCATATTTTATTTATATGAGGCAATGTGCTAGGTGCTTCCCTTGCACTA
TCTTGTTGCAACCTTTTGACAAACACGTGAGGTAGGTATATCACTGGCCTCCTTTTATAAAGGAAGCTCAG
AGAGATGAATTGACTTTCTGGACTTAAGTTCAGGAAGCTTCACTTCAAAACCCATGCCCTTGACCATGACT
TCACCTTTATTACCTAACTGTGTCTGGGTGAGTTCCTTGTATATAAGTCCTTACTGGGGCCGGGGCAGGGA
GGGGTGTCAAGAGGATGGGACAGTGAAGACAAGAGCAGCCTCCCCAAGGTCATGTGACAAGTCACGGTCAC
ATAAACATCACGAATGCGGGAGCTTTAGCGACCACATTTTCTCCTACACCTTTTACCTAGGAAATGGAAGT
CACAGTTTTCAAAGGGAAACTAAACGTTTTTGACTGTGCAAAGGATTAGATGACAGTATGTTGAATGCAAA
TTGATTGAGTCTGATTTAATTTGGATGGTGATGTGCCAAGTCACACAGCCCTGTTGGACCAGGTGCCTGAA
GCAAAGAACTTTCCTTGCACCCAGCTACCATGGCCTCTGCCTGAGCCTGGGAGGAGACATTTAACAAGGGA
AATTCCTTCTCCCTCCCTCACTGGACTGAACCTGTCCCTTTTCTTAAAGAAAGGGAGTGGCGTGGAGCCCA
GGCCCTCCCCCAGGGGCCTGCCTGCTCAGCTCCAGAC

Fig. 4

NCR2 (natural cytotoxicity triggering receptor 2), Chr6

SEQ ID NO:5

```
tt tagagggagt gaggtgtaga agaaagcaga ctcaactgtg acacagcaga
gaccatctgc ctttccagag cttactgcag ctgaaaagac agataatagt gtgtgggcag
agggtgaacc tggagacttg aaggaaacag gcccctcttc ttggtggaca gtagaggaaa
ataaaggaaa aaatcagggt gaggaaactg accaaactgg gctcaaaatc catgcatgct
cactgacact tttctggcag cagtggccag gagcagactt catccttgtg aggtgggtat
ggcaaccaac cctgcgagta gtgggatggg gaaggggttg cctctgcacc tatgtgcaat
tatgtggcag tctctgacca ccttcctggt ttcctgctct gattgcaggg gggacatatg
gtggaaaacc atgatggagc tcaggagcct ggatacccaa aaagccacct gccaccttca
acaggtcacg gaccttccct ggacctcagt ttcctcacct gtagagagag aaatattata
tcacactgtt gcaaggacta agataagcga tgatgatgat gaacacactt tgtgaataat
aaaattatct gaatgtttta ttcctgttgt ttcctaagtt tccttcaaac tctgtctgca
tccgcacatt tgatctctag ggaccagct tctctagttt gccctctttc ctccatcata
accctttctt atcttcagtt cacctgatgt cccctgtacg tctgggagct gccttagatg
ctgttataat cagggaaggg cactgtacac aagcccagtg agtagaaagg ctgtgggcga
gcaaggcttg gaaacaagac ctgggtttgt tttctcagct cagccctgta tgaactcgga
cagataggtc actgcccctc tctgaacgtc cgtttctttc tctagaaaat gaaggggtg
gagatgagtt ctgaaacccc ttccccatga ggataagtca ataagcatga actcaacacc
tgcctgtgcc cagctcaggg accaagcacc acaggacaca aacaaaagga gccagcctgg
gaacacagtt gtgagtccat aggtggcggg gcccctgtgc aagattccag cacaggctga
gggaagggga cagtggaggg ggagcaaagc tgaaaatatg tggctggaga gggatagaaa
agcaggacac tagtgggtac cagacagtgg gggaaggagc ccaacaagga tgaggaactt
tgctgtgaag tcatgttagt caggatgcca tgaccttcca tgagcccgaa agagggcaca
cagtcccagg aag
```

Fig. 5

WNT2 (wingless-type MMTV integration site family member 2), Chr7

SEQ ID NO:6 aaacacccaa cttcacttta agaacatcct tcattgatac
aaaggtttgt gatcttggat cagagataat gaactgcaat cctggcacag ttcttggctg
tgcagttaat aatattatgt agatgtttat tgtttttaaa ttttagaatc aaaatttact
tatagttaca gaacagaggt cctcgacttt agtcactcat tcttttatca tccaaataaa
atgtctccag tccctccatc agcggctgtg catgggaaac caccctccca ccccaaccaa
gctccttgcc cagtgcctct gaagacccca gggggagtat cctgccgcta tagcctgttg
ctctggtgtg gcccacttat ccattgatcc attggtattt ggcttggaca ctggccacca
cccatctttc attccctcca aagcagcact agcagagatt gtcactggtg acacattttc
cttgagattc tgatgtcttg gaggcatagg gtaggaaaca atctctaatt gaataacgat
ttccccgttc ttagaaatgt aatgccagct tctgccgcag gaattcttca ccgctgtaac
cctccatagg ccccagactc ccgccacggt gcaggggttt ctcaccttct cctctgcatc
cctgggtctg gatgattctg aaccctgact gcatattaga atcaatcaac tgaggaacca
caagtacctt caaggcccag gcctcacgtc caccctaggt tctaatttgc ccagtctggg
gagaggctgg aaatgatccc caggtgattt taatatgtag ccaggagtga cacctactga
cctgccctct ccagttgcca ggaagaaagc ctcaaattcc tgttatttta ctatgtggag
taatttcacc ctttttgttt cccctctctt tcaagaccat gaaatccctc aaactgtagc
cagattgtaa aagaacattt ttcccttttt ccgccagcta tacacacata tgcaggcctt
taaaaactgg atcataccac atatattgtt ctacattttg cttttatcgc ttgactt

Fig. 6

Probe sequences for methylation array

CAV1:
CHR07FS115953929 115953929 115953978
ATCGACCTGGTCAACCGCGACCCTAAACACCTCAACGATGACGTGGTCAA
(SEQ ID NO:78)

EVX1:
CHR07FS027250107 27250107 27250156
TTGTCACTTCCCGGGCTTCGCGGCGCCAGGTCGGAAATGGTCCCAATGGT
(SEQ ID NO:79)

MCF2L:
CHR13FS112788866 112788866 112788915
TCTTCTCCTGGGGAGGAGGCGTGGCTCGGAGCAGACGTGACTTCTGTTTT
(SEQ ID NO:80)

FGF1
CHR05FS142028596 142028596 142028645
ACAAGCTATGATAAGTGCTGTGAAGGTTGTGCCAAGGGCTGGGGGGATGG
(SEQ ID NO:81)

NCR2:
CHR06FS041426494 41426494 41426555
GTTTCCTCACCTGTAGAGAGAGAAATATTATATCACACTGTTGCAAGGACTA
AGATAAGCGA (SEQ ID NO:82)

CHR06FS041426614 41426614 41426665
GTTTCCTAAGTTTCCTTCAAACTCTGTCTGCATCCGCACATTTGATCTCTAG
(SEQ ID NO:83)

CHR06FS041426769 41426769 41426818
TTATAATCAGGGAAGGGCACTGTACACAAGCCCAGTGAGTAGAAAGGCTG
(SEQ ID NO:84)

WNT2 :
CHR07FS116730563 116730563 116730619
CGGCAGAAGCTGGCATTACATTTCTAAGAACGGGGAAATCGTTATTCAATTA
GAGAT (SEQ ID NO:85)

Fig. 7

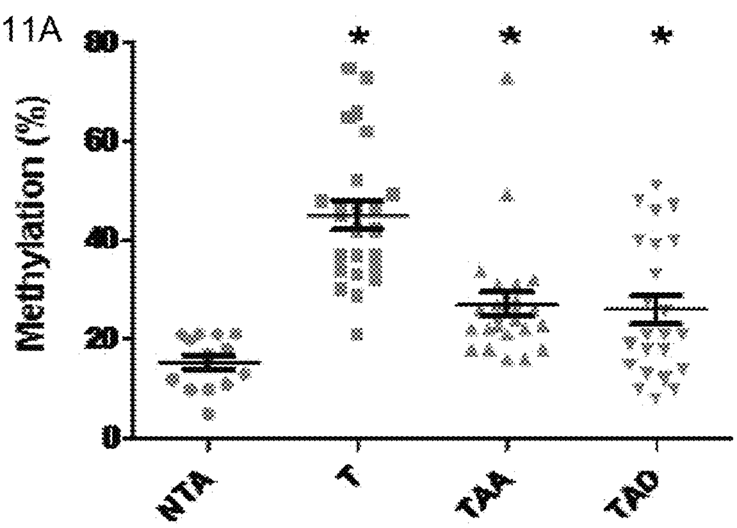
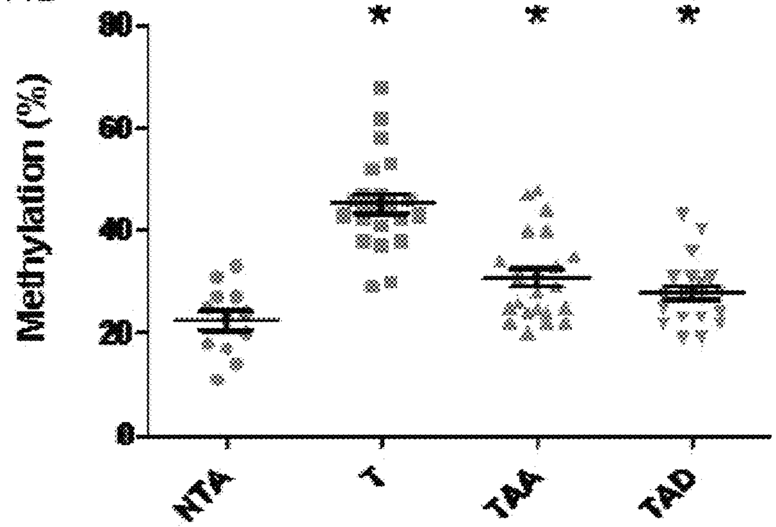
Fig. 11 A & B

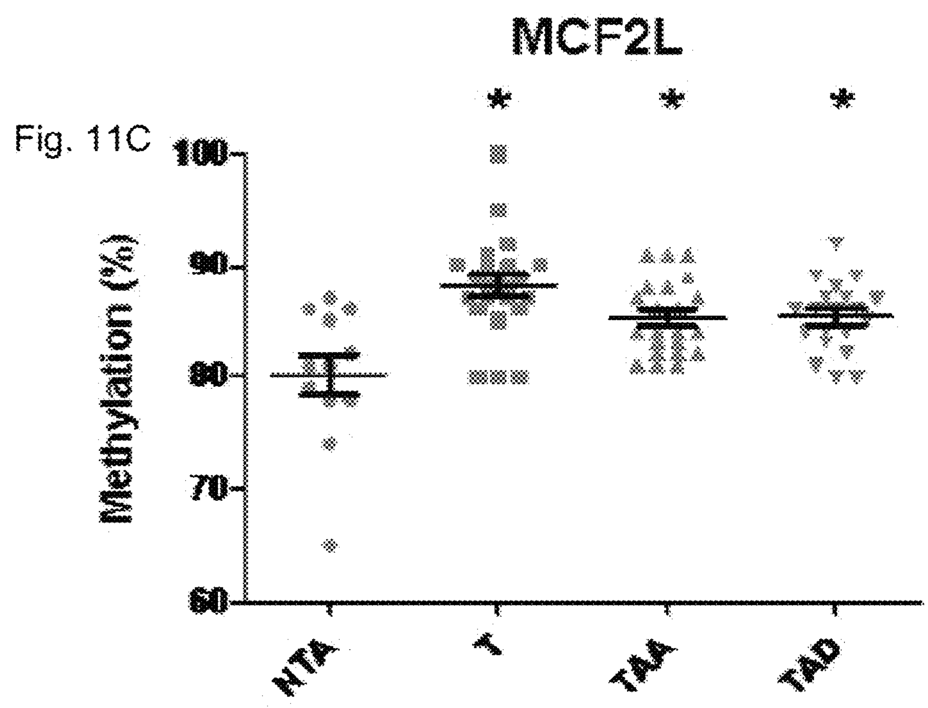
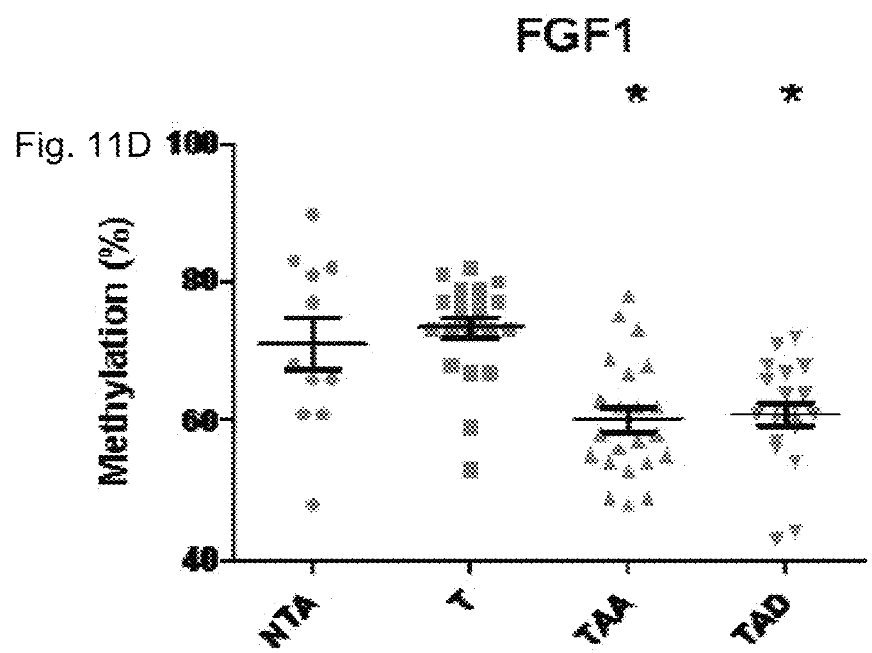
Fig. 11 C & D

NCR2

WNT2

Fig. 11 E & F

| | |
|---|---|
| CAV1 | F-GGGTAATATTTATAAGTTTAATAATAAGGT (SEQ ID NO:43)<br>R-biotin-TAAAAACTATCCCAACCCTTC (SEQ ID NO:44)<br>Seq-AAGTTTAATAATAAGGTTATGGTAG (SEQ ID NO:45) |
| EVX1 | F-GGAGGAGAGGAAGTTAGGAGTTTATAAAGGA (SEQ ID NO:46)<br>R-biotin-CAAATACAACCCAAAACCAAAAACAAT (SEQ ID NO:47)<br>Seq-GAAGTTACGAGTTTATAAAGGAT (SEQ ID NO:48) |
| FGF1 | F-GGATGGGATAGTGAAGATAAGAGT (SEQ ID NO:49)<br>R-biotin-TTCAACATACTATCATCTAATCCTTTACAC (SEQ ID NO:50)<br>Seq-TTTTTTTAAGGTTATGTGATAA (SEQ ID NO:51) |
| MCF2L | F-biotin-GAGTTGAGTTTTATTTTGGGTATTTTGAAG (SEQ ID NO:52)<br>R-ACCCCCAAATTACTAAACTAATATATTCC (SEQ ID NO:53)<br>Seq-CAAATTACTAAACTAATATATTCCA (SEQ ID NO:54) |
| NCR2 | F-biotin-GTTGTGGGAGAGTAAGGTTTGGAAATAA (SEQ ID NO:55)<br>R-CTCATCTCCACCCCCTTCATTTT (SEQ ID NO:56)<br>Seq-CCCCCTTCATTTTCT (SEQ ID NO:57) |
| WNT2 | F-TTTTGGAGGTATAGGGTAGGAAATAA (SEQ ID NO:58)<br>R-biotin-AATTCAAAATCATCCAAACCCAAA (SEQ ID NO:59)<br>Seq-AGGAAATAATTTTTAATTGAATA (SEQ ID NO:60) |

Fig. 12

CAV1 promoter (SEQ ID NO:61)

catgtgtttt aaggcagaga tggaacttgg gcgatgggcg gggggtgggg
gaggtgggaa gggacggctt aggacagggc aggattgtgg attgtttctg
ccgccttggt tgcccatact gggcatctct gcaggcgcgt cggctccctc
cacccctgct gagatgatgc actgcgaaaa cattcgctct ccccgggacg

Fig. 14

EVX1 promoter

Island 1 (SEQ ID NO:62)

agctgccaag gcagaagggg gaagcgggtc ccagaaccac ccacctccgg ctgtccccac cgcgaggacc cagcagtctg gcgcccccac cacggcctgg aagatgacgg agggcccaag actaatattc acgacagcca gaccacgctt attgtttaga aggaagctcc ctttgttctt actttttaac caaagagaag cgaaaacatt tttttcctga tcacattttc accgacacct gagccgacaa gccagctcct ggcccccggc tcaggactcc tcgctctctc ccttctcggg gccctgtcgc cgttgaaagg cccgctgcag gctggggagg gtgatcgggg ccgcgggcca tctcccccga gccgggcggg cagactgcgg aggcaggccc cacacgcgcc gcttttccga gcccggtttt cttcaggagc gaagctgttc cagctgaccc gcgcgtctgg gggcctatgc ccggcttccg attccattta aaacgacccg cgcatcttat ctccgtcgcc tccccggggt tcccacccac ccccctccgg cccgggccag gccagcccag ccccggcgga agccaagctg ggagcttttg aagtccggag aatttcaatc cgagaggagc cggctggacc ggagcccgtc gccccagcgg gggaagggac ggggggcctg ccgtgtggca ggtgggggat gggtgtcccc cgccgcgaga aatgagaagc cgccgggcct ggagcggcct ccacctcagc tgctatcacc ccctctccgc tgtcatggga tt

Island 2 (SEQ ID NO:63)

ttttttgt cttctttcct ttaaaaaccc aaccgctctt aatgtgaggt tgatgaaagg atgcttttgg aagaagtgac atttggttaa aacgttttcc ccctaatgcg ccggtggaaa ggggcggggg tgggtgtggt tccctaggct cctaagactg gccagtcagc tttgaaagag cggggcagaa gtcgggagag gg

Fig. 15

EVX1 promoter

Island 3 (SEQ ID NO:64)

cttatgagtc aaacctctat gaaccccaac ctttttgtac tcggggaggc tgaacccctg cccaaaatag cgcggtgaaa gctactgcct tctcccaagt aggggcctcc agtactgcca cagcaggggc cgcattcctg gcgcctcttc attcgaaaaa cctctttcca ggagacttcg ctgattctga acgaatactt Fig. 15 (Continued)

MCF2L promoter

Island 1 (SEQ ID NO:65)

actataagg gggagtactg cgtcaccttc atctttttat ccctttggcc ttgctccgtg
cctgaaagct caccacactg gaacgtccag gtgcacatgt gccactggac accgggatgt
tgccggatgc tcttttggac gctggaatgc tggtgcattg ttgccggatg ctggaatggt
gcacgcacgc tctgttggac gctggaatgc tggtgcattg ttgccggatg ctggaatggt
gcacgcatgc cctgttggac tctggaatgc tggtgcattg ttgccaaatg ccggaatggt
acacggatgc tctgttggac gctggaatgc tggtgcattg ttgccggatg ctggaatggt
gcacgcatgc tctgttggac gctggaatgc tggcgcatgt g

Island 2(SEQ ID NO:66)

a accacaaaag gatagctgcg gttttgggcg aggagagctc agagagtttc ttgcatatgg
ccctgtgatg gcggccatgg ccctgcatag acacgagctg gaatctgcag gtggcagcca
ggacgctgcg tgtgtcgagt gcacagtgtg gcttggtgcc aaccatggcg agggtggaga
gccccgtgcc tgcagcgcgc gcttccctca ctgggtcctg cgtccttggg caggcgatgc
ccctgcgggg aggggctggt ccatccccgg ccagccacgg acccacgcat ggacccagcg
acccacggac ctgcttacct gggcgcggcg cgggtggcat gcggccacac ggaaggggcg
cgctgggctg ctgcggcctc tgcagcttct acacctgcca cggggcggcc ggaggtaaag
ggaggcggcg gccaggcgcg gccccgcgga ggcagctgca ctcgctcggt ccactcgcgg
cttcgcggct gcccgcaaac caggagggcg tggagacccg gaaccggggg gaagggcggg
ggcacttgtg cggcacccgc ggggctccca ggggacctcg gcggtgacac gaatttctag
gtgaccttgg cggtgacacg aatttctagg tgacctgtgt gatacactag gtgacctagt
gacacaggtg acacttccag gtgaccgcgg cggtgacccg cggggctccc aggtgacctc
gttggtgagc cccggggctc cccgacgacc gcggcggtga cacgcggggc tcccaggtga
ccccggcggt gcactcacag gactcccagg tgacccgcgg tggtgacaca ccggggcggg
cgcgcgccgc ttccgcttcc gccgagccgc cccccgcccc ccgcggcgca gcgcgcgccc
ccctcccggt ggcgcggaac caatcctggg cagggaggcg gcggctggag gctgaaagcg
ctgccgtggc cccctccccg cctccgccgc gccccctcc

Fig. 16

FGF1

Island 1 (SEQ ID NO:67)

gcttc tcctgtgcct gcctcatatt ctgggttctc tccagagctc gcgtccactg
cctgccagtc agcagatgga tgactctgtt cacctcagcc gcgacacgcc ccacagcgag
tgcagcagtc gtcctgccag atgggctgct cctggctgcg tccattctct cagtaaatag
cctctccatt catccttccg gtccctctat gcccg

Island 2 (SEQ ID NO:68)

a gccgctcctg tcatcttccc tttctctctc cccatcagcc tgcgagggac taaaagccgg
cgatttttcc ttgctgtatt tctttctttt tttttttttt tttttgagac ggagtctcgc
tctgtccccc aggctggagt gcagtggccc gatctcagct cactgcaagc tccgcctccc
aggttcacac ctttctcctg cctcagcctc ccaagtagct gggactacag gcgcccgcca
ccgcgcccag ctaatttttt gtatttttag tagagacggg gtttcaccga gttagccagg
atggtctcga tctcctgacc tcatgacccg cccacctcgg cctcccaaag tgctgggatt
acaggcgtga gccaccgcgc ccggcctgtt tctttctctt ttttcttgag accgagtctc
gctctgttgc ccaggctgga gtacagtggc atgatctcag ctcactgcaa cctctgtctc
ccaggttcaa gcaattctcc tgcctcagcc ttccgagtag ctgggactaa aggctcccgt
caccaccgtt gcccagctaa ttttt

Island 3 (SEQ ID NO:69)

gattattt tggaatagca cagggttttg tttttttttc gtttttttggt ttttcttgag
acggagtttc gctgttgttg ctcaggctgg agtgcaatgc cacaatctca
gctcatcaca acctccgcct cccgggttca agcgattctc ctgcctcagc
ctcctgagta gctgggatta caggcatgcg ccaccatgcc cg

Fig. 17

Island 4 (SEQ ID NO:70)

```
cct ccttcatggg tattccacat tgcttacaca gtgacaggga ttaaaaacaa aactaaaggc
    tgggcgtggt ggctcacgcc tgtaatccca gcactttggg aggctgaggc gggtggatca
    cgaggtcagg agatcgagac catcttggct aacacggtga aaccccgtct ctactaaaaa
    tacaaaaaat tagccgggcg cggtggcagg cgcctgtagt cccagctact caggaggctg
    aggcaggaga atggcgtgaa cctgggaggc ggagcttgca gtgagccgag attgtgccac
    tgcaatccgg cctgggctaa agagcgggac tccgtct
```

Island 5 (SEQ ID NO:71)

```
a tgtattgatg atcacattca ctactcacac ttacaaagta cagctcccag gccgggcgcg
  gtggcttacg cctgtaatcc cagcactttg ggaggccgag gcaggcggat cacgaggtca
  tgagttcaag accagcctgg ccaacatggt gaaaccccat ctctactaaa aatataaaaa
  ttagcctggt gtggtggcg
```

Fig. 17 (Continued)

NCR2

Island 1 (SEQ ID NO:72, located between exons two and three)

gtt gtgaacttgt gtttttccgt tttatatgta tatgccactt gtttttttgt tttgttttat
ttcgttttga ggcggagtct cgctctgtct ggagtgcagt ggtgcaatct cggctcactg
caacctccac ctccagggtt caagcgattc tcctgcctca gcctccggtg tagctgggac
tacaggcgcc tgccacc

Island 2 (SEQ ID NO:73, located between exons two and three)

aag tagctgggat tacaggcgcc tgctaccacg cctggctaat tttttgtatt ttagtagaga
cgtggtctca ccatgttggc caggctggtc tcaaactcct gacctcaagt gatccacctg
cctcggcctc caaaactgcc gggattacag gcgtgagcca ccacgcctgg ccgctaacaa
gtaattttaa agtatca

Island 3 (SEQ ID NO:74, located between exons four and five)

tttaacttt tgaacttttc cgaagctttc catattttct atgtcctcca agtgcccatc
atatctttta ttttctcctt tcattgacct ctgtctttct tcagagcttt ctggaaacct
ttgccgcttc tcggccaccc acttgcttag aagccccatg cgggccgcgg ggtgctgtgg
gctccaggcg gattgggcgg g

Island 4 (SEQ ID NO:75, located between exons four and five)

ccagaatcc caactcagta agaccttgta aatccatgac attagcccca attcccactc
gtcccaaatc ccataacctt tccaccctgc acctgaagtg cgcagtcatc agcacaagct
cctgtatgct cagcttctct gaacgtcacc gcggtactct ccctgacatc tgcctgttct
ccgaggacaa tgctttctcc g

Fig. 18

WNT2 promoter

Island 1 (SEQ ID NO:76)

gc caaccacctt ttctttccta agtgtctgga tttacttcaa gaaaatgcgg gacaaagaag
ggtggaggta agctttcgtt tattcccctg cttcacgggg gaaggaggtt tgtgagcata
agcatgtaag tacatgagag gcgtgttgct ctttggtgcc tatcataccc tccccatggc
cggcgtgcac acacggcgag cagaaacgct cccccgcccc gctgcctgcc gccccacgcg
ccctccctgc acctcccgcc cgaccgacgc agaccaagca gaacttccct gggtcgcggc
ccagcgatac ggagcggccc tggcgaggag ccctgctctt cccgagtcgt gggtggcgcg
gtgcttgttt ccctcccctc cctttccgga cccaaacggg gatgtatctg ggtcagcctg
ggaggggccg gacctgccag ggaccagcgt gggggaaggg ggtggcgatg acagcatctt
tcaggttttt ggcgtctctg agcttcgcct cgtccagcct ctcaccgcgc tcgctgccgg
cgagggctga cgctctggcc agtccaggcc cgagggtggg ctggagagag ggagagcccg
tccttccgat ctgggcggca ccccctcccc cacgccctgc gaacaattcg cctcccacac
atacacacag gcgcatactc tattccccag agcacgctcc tcgggcgggc agtgagtccc
tccgccccag gaaaagagca atggaacagt tcacggccgc cacgagttcc tggtcttcct
tcctttccgg tgataaacgg cgcggctaca agccagctac tgctcaaaat gctccacccg
cgggcccaag cccctctctc ttggctgggc gggggcccag gtccaggacc gagggtccct
taacctccac aaggcgcaca ggctgagcgc ccaggcggca ggaggtgcaa gggcgcacac
ccccggcgaa cgcctggctg cctcggttcc tctctatgtg

Fig. 19

Island 2 (SEQ ID NO:77)

```
ataga cgcggcagct ccaaatttac aagtgctagc tcttcatccc agcttcaggg agagaagcga
      agcaatgagt tgagaatcat ctctggattc ttgtatccca tgcatagtaa tctccttatc
      ccctggcccc cttcctcgtt tcctcacatt gcacgctcag ggacttgttt gccagcggat
      ggcctcggca atccggaacg cacgctccga gagcccacgg atgctctttg gcctggagct
      tccctaaagg ttcctgtatt cgcgtgtgct cgtaaccatg cagcgatgtt ccccccttccc
      cgcctcacct catccccaga catctcttgc catcatttca tgcacccgtg tctaaaaccc
      cgcgtttctc cccaccccccg ccaggcgcag caccc
```

Fig. 19 (Continued)

EXT1 (exostosin glycosyltransferase), Chr8

SEQ ID NO:18 catcttttg agtattgttt attgtaatgt aagaaccagt catgcctggg
gtacactcaa gctggatcct tgccataagg gcaggctggg gtgaatggtg
gtacactctt ggtaaatgtg acatgataag aaatatatat ttgggccagg
cacattgtcc tgcacctgta atcacagaac ttggggaggc taaggcaggc
aaattgcttc aggccaggag ttagagacca gcctggccaa catggtgaaa
acctcctctc aactaaaaat acgaagatta gctgggcgtg gtggctcctg
cccgtagtcc cagctactcg ggaggttgag gcatgagaat cgcttgaacc
cgggaggtgg aggttgcagt gagctgagat cacaccactg ctttccagcc
tgggcaacag agtgagactc tgtctcaaaa atttggtctc tgccccttga
cacccaactg ctaaaaccct tgtaatttcc tgagtgatag aggtgataag
aatgtcttcc acagaattcc caaatccctt ggaatttcct gggtgataaa
ccttttgttc taatgaggtg attcttagtg ggttcctgga tagcttcaaa
gtggtgatgt catcagaaag actaaactgt cattagaagc ttggaacttc
taacccaccc taccccctatt ctccagggag gagagagggg ctggaaattg
tttaattatc tatcatgcct atgtgatgaa accccctcaa aatttctaaa
ctatgaggtt tggagagcct ccaggttgat aaccatatcc acatgccggg
aggatggtgc accccgactc catggggata gaagcctctg tgtttgggac
ttttctggac atcacacagt gtacctcttc atctggctgt tcatgtgtat
ccattatgtc ctttttaata aatcagtaat agtaagctgt tttcttgagt
tctgtgaccc cttctagcaa acgattgaac ttgaggaggg agtcatgaga
tcccctgact tgtaggcagt tggtgagaag tataggagac ccagacttgt
gattggcatt tgaagtgagg gataatcttg tggctctgag cccctaacct
gtggtgtctg cattaactct gggtaattac tgtcagaatt gaattcaatc
attagatatc aagtaggttt ccaggaagtt ggagaacttg ttgttggtgt
gaggggaaga aacccataag tttggtgtca gagcattgcc agtagagaaa
caggtccccc ccacatatga gttggatggt gttatgctct tggtagggca
tttgttttga

Fig. 20

SPAG4 (sperm associated antigen 4), Chr20 T

SEQ ID NO:39

```
 tctcccga ccctggatct gaggcaggag atgcctcccc cgcgggtgtt
caagagcttt ctgagtacgg gccaggccag ctgcgatccc ctctgaccct
cgggttcccc tctccgaact ccagttctct ctgagccccc ggccccc gtt
tgagtatcga gcccctctcc gagcctcaac tcattcctag cccccatcca
attatcctag ccgaccctct cttcctgagc cccaggccca cccccggccc
ctcccaagcc ccttctgaac ccggacacca cgcaggctga gccccgcctc
tccctgccgt gggcccctct ctgaccctct gtcctggcct caggcctgct
cttccagggg ctgagcgtgt tgttatccct ggcaggagac gtgctggtca
gcatgtacag gtcagaggaa gggacgctgg cgccccagga acagctcttt
ggagggggtg gggagcaggg ccggaacctt gctggcgctt gagccgattc
agatctgatt gagtcatgtt ggcaagagct gggtctagga ccctggggtg
gggactggag ggttgagcag gtcggggcct cagcctccct ccggttcccc
agggaggtct gttccatccg cttcctgttc acggctgtgt cgctgctgag
cctctttctg tcaggtgagg ggcagtgaat tccctggagc ccctgccctg
ggtgctttgg aggcaaaccc agcacatttt ctcctacatc ctcggtcctg
cagctcctgg cattcccctg cagaaccccc taattccccc tcagactccc
acggtcctcc ccaggcttaa ccccctcaag cctctttcca ctgtcccccct
atgccgggga aacccattct cttccttttc cttctgagac ccctccctct
ctttctccag cattctggct ggggcttctg tacctggtct ctcctttgga
gaatgtgagt tggggagact gtcttggggt agggggttgg caggttgtga
acccggagat tgtgggggtc ccctggactg tcggtctgct ggggtggggg
ta
```

Fig. 21

Probe sequences for methylation array

EXT1:
CHR08FS119036611 119036611 119036660
CACCATCCTCCCGGCATGTGGATATGGTTATCAACCTGGAGGCTCTCCAA
(SEQ ID NO:86)

SPAG4:
CHR20FS033669015 33669015 33669064
ATCTGATTGAGTCATGTTGGCAAGAGCTGGGTCTAGGACCCTGGGGTGGG
(SEQ ID NO:87)

Fig. 22

| | |
|---|---|
| EXT1 | F-TAGGAGTTAGAGATTAGTTTGGTTAATATG (SEQ ID NO:88)<br>R-biotin-CCAAATTTTTAAAACAAAATCTCACTCTAT (SEQ ID NO:89)<br>Seq-CAACTCACTACAACCTCCA (SEQ ID NO:90) |
| SPAG4 | F-GGTAGGAGAAGTGTTGGTTAGTATGT (SEQ ID NO:91)<br>R-biotin-CCTAAACCCAACTCTTACCA (SEQ ID NO:92)<br>Seq- TTAGTATGTATAGGTTAGAGGAAG (SEQ ID NO:93) |

Fig. 25

EXT1

Island 1 (SEQ ID NO:94), 458bps

CGTCCTCCCCGCGGGCAGTGCCGGCCCCGAGCAGCGCTTCGCAGGCCCCC
GCGCGAACGCTGCCGACCGCCGCGTTCGGTCGCCGAATGTTACCCGGTTC
TGAATGTTACACTTACACATTCCATTCCCGACACGACAGCGCTGACCTCA
TCCATCCACGCAGCCCGCGCTGCCATTGGCCGAGCGTCACGTCCGGGGGG
GGCGGTGCTTCCGCTGCGCCCATTCATAACCCCCGGCCGCGGGCCGAGGC
GCCGGCGCGGCGTTGGGGGCGTAGGGGGCGCAGGGAGCCGGGGCTCCCGG
GTTGCAAGCTGCCGGCGGGCTGCCGGGCAGGTGGAGCGCGGGACGGCCCG
GTGCGAGCCCCGCGGCCCCTCGGCGCGCCCAGGCCCGGATCTCGGCCTGC
GCCGTGCCGGGGACCAGAGGCGCCTGCGGAAACGCGGCGGCCGGGGAAGG
AGGCACCG

Fig. 26

SPAG4

Island 1 (SEQ ID NO:95), 2190 bps

GAGGTCAGGAGTTCACGACCAGCCTGGCCAACATGGTAAAACCCCGTCTC
TACAAAAATACAAAAATTAGCCAGGCATGATGGCGGGTGTCTGTAATCCC
AACTACTCGGGAGGCTGAGGCAGGAGAATCGCTTGAACCCGGGAGGCGGA
GGTTGCACTGAGCCGAGATTGCACTACTGCCCTCCAGCCTGGGCGACACA
GCAGGACTCTGTCTCAAAAAATAAAAATAAAATAAAAATAAAAATGCTGG
GCGCAGTGGCTCATGCCTGTAATCCCAGCACTTTAGGAGGCCGGGGCGGG
TGGATCACCTGAGATCGGGAGTTCAAGACCAGCCTGACTAACATGGAGAA
ACCCCGTCTCTACTAAAAATACAAAATTAGCCAGGCATGGTGGTGCATGT
CTGTAATCCCAGCCACTCAGGAGGCTGAGGCGGGAGAATCGCTTGAACCC
GGGAGGCGGAGGTTGCAGTGGACCAAGATCGCGCCATTGCACTCCAGCCT
GGGCAACAGAATGAGACTCCATCTCAAAAAAAAAAAAAAAAAGAAAGAAAG
AAAGAAAGAAAGAAAGAAAGAAAGAAAGAAAGAAAGAAAGAAAGAAAGAA
AGAAAAAAAACTGTTATAGACTGAGTGCCATTTTAGATGGGGTTTTCTGGG
AAGTGCTGTGACATCATCGCTTGCTGTAAAAGAGGCCGGGCGCGGTGGCT
GACGCCTGTACTCCCAGCGCTTTGGGAGGCCGAGGCGGGAGGATCGCTTG
AGCCTAGGAGTTCGAAGTTACAATGAGCTATGATCAGGCCACTGCACTCC
AGCCTGGGCAATGAGAAAGACCCTGTCTCTTAAACAACAACAAAGTCAGA
AGGAGAGGCTGCCATGGCTACGGCTCCAGGTGACGTCACGGCCAGCTCCG
TGACGCGCGGCCAGGGCAGCCCGCGGAGACCGAGGCTCCTCTGTGACGTC
AGCAGCCGGCCGGGACACAGCGGGAGGGCAGGTGCGGCCGCGGGGCCTGC
CGACTTCACGCAGGGTCCGTGGGGTCCCCGCGGCGCGCAGCGGCTGAAGG
AGGCCCCAGGGCCTTGGCGACCGCAGCGGCGGCTTTAGCGTCAGTGACTA
GGCAGCAGGGGGTCAGGATGCGGCGAAGCTCCCGCCCGGGCTCGGCCTCG
TCCTCGCGCAAGCACACGCCCAACTTTTTCAGCGAGAACAGCTCAATGAG
CATCACCTCGGAGGACAGCAAAGGGCTCCGGTCAGCGGAGCCCGGGCCTG
GGGAGCCCGAGGGCAGAAGAGCCCGGGGCCCGAGCTGCGGTGAGCCCGCC
TTGAGCGCGGGAGTGCCCGGAGGAACCACATGGGCAGGAAGCTCTCAGCA
GAAGCCAGCGCCTCGGAGCCACAACTGGCAGACAGCCTGTGGCGCGGCAA
CCGTGAGGGGCGGGGCCTCGGGTGCGGGCGGGGTCGACCCCGGGTGAGCC
AGTGGAGGGGGCGGGGCCTAAAGGGCGGTGCTGGGCGGGGACGGGGCTAA
GATGATATCTGGGCACCTCCTACAAGGTGGGTCCTGTAGGGTAAAGGGAT
GGTGCTAAATGAGATCCCTTAAGGGGCGGAGCCTCGGTGTCCTGGACGGT
TATGGGAAGGGGCGGGGAAAATCTTGTGGTTGGGTGCCACTGAGGGGGCG
CGGCCTCAATGTTAGCGTGAGTGGCTCCCAGGACAATTGGGTTCCACCAA
GATCTAAGGCTGGGGGCGGGTCATCCGTTTGGGGGAGGGACCAACTCTTT
TTTTTTTTTTTTTGCAACGGAGTTTCGCTCCTGTTGCCCATGCCATGCAA
TGGCATGATCTCGGCTCACCGCAACCTCCGCCTCCCGGGTTCAAACGATT
CTCCCGCCTCAGCCTCCCGAGTAGCTGGGATTACAGGCGTGCGCCACCAT
GCCCGGCCAATTTTTGTGTTTTTAGTAGAGACGGGGTTTCTCCGTGTTAA
TCAGGCTGGCCTCGAACTCCCGACCTCAGGTGATCCGCCCGCCTCGGCCT
CCCAAATCGCTGGGATTACAGGCGTGAGCCACCGCGCCCGGCCAGGAGAC
CAACTCTTGACGGAGCCTCCCTGAGGGGCGGGGCTTCAGAGGGCGGAGCT
GGAGCCGGGATAGGGCTGCGGTGGACCAAAGCCTGTGAGAGACTTCCCA
GCTGTCTGGCTTGTGGACTGAGCAATCTGCGGCCCGGTCT

Fig. 27

SPAG4

Island 2 (SEQ ID NO:96), 282 bps
CGGCCCGGTCTCGAGGGGAAAATAGGTCTGTGGTCCGCAAGGCCCCAGTG
GAGCCCTTGGGTTCCCGCAGAACCGACTGGGTCTCCAGTAGTCTCTGAGG
AGCCGCTCGACCTTCTCCCGACCCTGGATCTGAGGCAGGAGATGCCTCCC
CCGCGGGTGTTCAAGAGCTTTCTGAGTACGGGCCAGGCCAGCTGCGATCC
CCTCTGACCCTCGGGTTCCCCTCTCCGAACTCCAGTTCTCTCTGAGCCCC
CGGCCCCCGTTTGAGTATCGAGCCCCTCTCCG Island 3 (SEQ ID NO:97), 234bps
CGGCAGCAGTCGCTCTGTCCGACGGTTCCGATGGTCCCTCCGCCCGCCTG
CAGCCCCACGTGTTCCCTGGGAATTGCTGGGCTTTTGAAGGCGACCAAGG
CCAGGTGGTGATCCAACTGCCGGGCCGAGTGCAGCTGAGCGACATCACTC
TGCAGCATCCACCGCCCAGCGTGGAGCACACCGGAGGAGCCAACAGCGCC
CCCCGCGATTTCGCGGTCTTTGTGAGTGCGGACG Fig. 27 (continued)

SEQUENCE LISTING

<160> NUMBER OF SEQ ID NOS: 97

<210> SEQ ID NO 1
<211> LENGTH: 1050
<212> TYPE: DNA
<213> ORGANISM: Homo sapiens

<400> SEQUENCE: 1
agaagcctgc ggctgccccc tcgccgccga ggtcctgcgg gtcctgcggg tcctgcgtgc 60
tgagccgggg cgtgcgcggg cgggggcctt cggaccgcgc ggcggggcct gccctgaccc 120
ctggcggcgg gcgggggagg caggcgcgcc ctgcagagta cagaggggtg tggtgtcctc 180
tgcgagatcc tcttaaaaag ctggctacgc gcaggcggtt tctgtgcacg gagccgtagc 240
tgtcggagcg gttagttcga tttcgagctc gaggtttccc ccgccgccag gctgacttct 300
catcgcttgt ttttcttttt gcatttttcc tcccaccgcc gttgccgccc tccccgtcct 360
ggccgtccgc cctccgccct ctgcagggac atctctacac cgttcccatc cgggaacagg 420
gcaacatcta caagcccaac aacaaggcca tggcagacga gctgagcgag aagcaagtgt 480
acgacgcgca caccaaggag atcgacctgg tcaaccgcga ccctaaacac ctcaacgatg 540
acgtggtcaa ggtaagccaa ggcgaccaac agggaagggc tgggacagct ctcctctggc 600
agttagcccg tgcatccttc tttagcattg ccgtgtacgc acaccccacc ccgcccccta 660
cacgcgcaca cacacacaca cacagagttt tgtgggtttg atgtgtggga gctcccgcag 720
tcggcagaaa cgttacatct cccttccccc atctcccccc aatagttagt tcagctgaaa 780
ttcagctaaa gtgagttttg tagaagttcc tataactaca cttttatcct agcaaatgag 840
cctattgacc tcagcaacag acggcccata ctccttggga cggtgagatg gttcctatcc 900
attcccaggt tgaaagtcta gtgacaggtc cccactgcac gtggcattaa gacagtcaga 960
taattgtgtc aggtcttgtg ctgaggatga gtcagaatac aagatgggca tgttccccca 1020
actaaaacga tgggaagtga ttttcttaaa 1050

<210> SEQ ID NO 2
<211> LENGTH: 1050
<212> TYPE: DNA
<213> ORGANISM: Homo sapiens

<400> SEQUENCE: 2
accgtgcccc tccgctcccc gggcctccca ctgcgcccac ccttcacttc ggcgcaggcc 60
aggaggaaga cactcccttc ccctaggca ggatggctgg ggggacccac ctgagcaact 120
ctctctgcta tctgcgttct ggcgggggtc tcctactgtg ttctggcatt ggcgggactg 180
agggtgacag cagtgccttg agtgcggggt gctgaggggg cggatgcaag tcctggactt 240
gggggattcg aagctcaccc caagcaccca gtgtttcaac tgctcgggga atgcttcaat 300
tgctcgggga agacactttc cccaggcgag ggcaagatca aacgccgatc cgggcagttt 360
gtggctggca gggtgtaaga ggcatggagg cgcggaagcc aggagtccat aaaggaccgt 420

```
aaaattgcgg cccacttggg cagcccgggt gctgcagccc tccgaccagt ttgcacgtcg    480

gtcagaggtc caaattacct tgtcacttcc cgggcttcgc ggcgccaggt cggaaatggt    540

cccaatggtc taattgcctt tggtctccgg ttgcatttga aaaggcagag atcgggtcct    600

ccccccttcc cctttccttc ctagtcccac ttctccaccc aaaggaaaag gagctgcagg    660

gggctggagc cccacccttc tcagaggtag gcccaaaggg gggctggttt aactggagaa    720

cccctcccca ccaaaggcta atgggaaagg ggtggatagc ccggaaggga gtttccctct    780

gtgccaacaa tcacctcccc agaagggggt agaaaactgg gcgcgggttg gtggggggga    840

ggagagggga gcccaccagc agacactcct ccacagaact gtaggagtgg gtggaaagag    900

cctgggggcg ggggggagaa agaccacccc ctggtcttgg cagccaacgc cttgttgaat    960

acctgcacct accccttact atcttatcac cgatttcacc cagcctcctt cccataaccc   1020

tcagaacaac ctggactcca ctcacatata                                    1050
```

<210> SEQ ID NO 3
<211> LENGTH: 1050
<212> TYPE: DNA
<213> ORGANISM: Homo sapiens

<400> SEQUENCE: 3

```
cctgaggggt ctgttccagg ggagccaggg ctctccgtgt cccgacgcgg ttgcctcacc     60

ccatgcccct caggaaatgc tgaaatacag caggaactgc gagggggctg aggacctgca    120

ggaggcgctg agctccatcc tgggcatcct gaaggccgtg aacgactcca tgcacctcat    180

cgctatcacc ggctatgacg taaggcgccc agatgcccgg tcttccccgc cgcctccgtg    240

gaatacacca gcccagcaac ttggcggcct ccctgcacac gcccctcgct ttggtgtgaa    300

tgtgcaggtt ctgggcagga ggtctggggt ggtccctaga taagcccact cccaggcccc    360

acagccgggt ccacagaccc cacagccggg tccacagacc ccactgggct ctctgggacg    420

tggagaaaat caggaagcgt cccttgcttg gagggcacgc atctccagca ggaacgcagc    480

tcagacctcc tcactccttg tcttctcctg gggaggaggc gtggctcgga gcagacgtga    540

cttctgtttt ctgggctgcg atttgcaggc tggtgactta gagcaagtgg ccccagaagg    600

cagatgtcac tttccccgta gagccccaca tcaggtcaca gcttattcat cttttgtccg    660

tctttatgtc cacccagcac tcattctcag gtgttttttt tttaactaat agagttgatt    720

tattgcagca atttttggtt tgtgagataa ttgagtataa atcagaggcc ctgaggcttc    780

ccctagtgtt gacatttagc atgggtgcca cacctgccac acatggtgaa ctagcgctga    840

tgctgattag tgactgaggg ccgttcccct tggagctcac tctgggtgct gtgcattctg    900

cggtttggac aggcgtgtaa catcctacac ccagcgctag agcatcacac agagcagctt    960

cactgtccta gaagcccatg tgccccgcca gtccatccct cctcccccag cccctggcac   1020

ctgctgacct gtcagtctcc acgagcttgc                                    1050
```

<210> SEQ ID NO 4
<211> LENGTH: 1386
<212> TYPE: DNA
<213> ORGANISM: Homo sapiens

<400> SEQUENCE: 4

```
ataatcgtga gaaggaagct catgcttctg tcctcgactg gcttgtagtc tagtcaagaa     60

gacttgaggg ctgatgagct tttcagagat ggaaatagag gatactgtgc cccgtggcct    120

ctgctctgcc cagcccccta ccagtaacca acaattttcc agaagaattt ccaaattccc    180
```

```
ttctccaaag tctccactgg ctccactttc atttgcttgc agaaaaaagt ctaaatgctt    240
tggaacagca tcattcaagg tcctctatga tctgactcca agctagcttg cactaaccct    300
gtgtgtccct gaaaaccccc cgctcagcgg catcagccat gcatgctggg cgaagatgcc    360
ctctacttgc ccacccctgg gcctctgttc aagtgattcc tttattccat gcccacatat    420
gtaaaacctg tttgtccttc ctgctgagat gccacatctt ccagaaagtc ctcctgaccc    480
cttcctcttc agccctccat ccatcccccc agcccttggc acaaccttca cagcacttat    540
catagcttgt catggtattt atgacttagc ttctcacctt ctttcaagga caggaagctt    600
atctcattca tcctgaataa tcacaacaaa aataatagct aaaattatga gatgttagaa    660
tgcatatttt atttatatga ggcaatgtgc taggtgcttc ccttgcacta tcttgttgca    720
accttttgac aaacacgtga ggtaggtata tcactggcct ccttttataa aggaagctca    780
gagagatgaa ttgactttct ggacttaagt tcaggaagct tcacttcaaa acccatgccc    840
ttgaccatga cttcaccttt attacctaac tgtgtctggg tgagttcctt gtatataagt    900
ccttactggg gccggggcag ggaggggtgt caagaggatg ggacagtgaa gacaagagca    960
gcctccccaa ggtcatgtga caagtcacgg tcacataaac atcacgaatg cgggagcttt   1020
agcgaccaca ttttctccta caccttttac ctaggaaatg gaagtcacag ttttcaaagg   1080
gaaactaaac gtttttgact gtgcaaagga ttagatgaca gtatgttgaa tgcaaattga   1140
ttgagtctga tttaatttgg atggtgatgt gccaagtcac acagccctgt tggaccaggt   1200
gcctgaagca aagaactttc cttgcaccca gctaccatgg cctctgcctg agcctgggag   1260
gagacattta acaagggaaa ttccttctcc ctccctcact ggactgaacc tgtccctttt   1320
cttaaagaaa gggagtggcg tggagcccag gccctccccc aggggcctgc ctgctcagct   1380
ccagac                                                               1386
```

```
<210> SEQ ID NO 5
<211> LENGTH: 1325
<212> TYPE: DNA
<213> ORGANISM: Homo sapiens

<400> SEQUENCE: 5

tttagaggga gtgaggtgta gaagaaagca gactcaactg tgacacagca gagaccatct     60
gcctttccag agcttactgc agctgaaaag acagataata gtgtgtgggc agagggtgaa    120
cctggagact tgaaggaaac aggcccctct tcttggtgga cagtagagga aaataaagga    180
aaaaatcagg gtgaggaaac tgaccaaact gggctcaaaa tccatgcatg ctcactgaca    240
cttttctggc agcagtggcc aggagcagac ttcatccttg tgaggtgggt atggcaacca    300
accctgcgag tagtgggatg gggaaggggt tgcctctgca cctatgtgca attatgtggc    360
agtctctgac caccttcctg gtttcctgct ctgattgcag gggggacata tggtggaaaa    420
ccatgatgga gctcaggagc ctggataccc aaaaagccac ctgccacctt caacaggtca    480
cggaccttcc ctggacctca gtttcctcac ctgtagagag agaaatatta tatcacactg    540
ttgcaaggac taagataagc gatgatgatg atgaacacac tttgtgaata ataaaattat    600
ctgaatgttt tattcctgtt gtttcctaag tttccttcaa actctgtctg catccgcaca    660
tttgatctct aggggaccag cttctctagt ttgccctctt tcctccatca taaccctttc    720
ttatcttcag ttcacctgat gtcccctgta cgtctgggag ctgccttaga tgctgttata    780
atcagggaag ggcactgtac acaagcccag tgagtagaaa ggctgtgggc gagcaaggct    840
```

tggaaacaag acctgggttt gttttctcag ctcagccctg tatgaactcg gacagatagg 900
tcactgcccc tctctgaacg tccgtttctt tctctagaaa atgaaggggg tggagatgag 960
ttctgaaacc ccttccccat gaggataagt caataagcat gaactcaaca cctgcctgtg 1020
cccagctcag ggaccaagca ccacaggaca caaacaaaag gagccagcct gggaacacag 1080
ttgtgagtcc ataggtggcg gggcccctgt gcaagattcc agcacaggct gagggaaggg 1140
gacagtggag ggggagcaaa gctgaaaata tgtggctgga gagggataga aaagcaggac 1200
actagtgggt accagacagt gggggaagga gcccaacaag gatgaggaac tttgctgtga 1260
agtcatgtta gtcaggatgc catgaccttc catgagcccg aaagagggca cacagtccca 1320
ggaag 1325

<210> SEQ ID NO 6
<211> LENGTH: 1057
<212> TYPE: DNA
<213> ORGANISM: Homo sapiens

<400> SEQUENCE: 6
aaacacccaa cttcacttta agaacatcct tcattgatac aaaggtttgt gatcttggat 60
cagagataat gaactgcaat cctggcacag ttcttggctg tgcagttaat aatattatgt 120
agatgtttat tgtttttaaa ttttagaatc aaaatttact tatagttaca gaacagaggt 180
cctcgacttt agtcactcat tcttttatca tccaaataaa atgtctccag tccctccatc 240
agcggctgtg catgggaaac caccctccca ccccaaccaa gctccttgcc cagtgcctct 300
gaagacccca gggggagtat cctgccgcta tagcctgttg ctctggtgtg gcccacttat 360
ccattgatcc attggtattt ggcttggaca ctggccacca cccatctttc attccctcca 420
aagcagcact agcagagatt gtcactggtg acacattttc cttgagattc tgatgtcttg 480
gaggcatagg gtaggaaaca atctctaatt gaataacgat ttccccgttc ttagaaatgt 540
aatgccagct tctgccgcag gaattcttca ccgctgtaac cctccatagg ccccagactc 600
ccgccacggt gcaggggttt ctcaccttct cctctgcatc cctgggtctg gatgattctg 660
aaccctgact gcatattaga atcaatcaac tgaggaacca caagtacctt caaggcccag 720
gcctcacgtc caccctaggt tctaatttgc ccagtctggg gagaggctgg aaatgatccc 780
caggtgattt taatatgtag ccaggagtga cacctactga cctgccctct ccagttgcca 840
ggaagaaagc ctcaaattcc tgttatttta ctatgtggag taatttcacc ctttttgttt 900
cccctctctt tcaagaccat gaaatccctc aaactgtagc cagattgtaa aagaacattt 960 ttccctttttt ccgccagcta tacacacata tgcaggcctt taaaaactgg atcataccac 1020
atatattgtt ctacattttg cttttatcgc ttgactt 1057

<210> SEQ ID NO 7
<211> LENGTH: 4123
<212> TYPE: DNA
<213> ORGANISM: Homo sapiens

<400> SEQUENCE: 7
agattactat ggaatcggta gggtcctgac cgctggggaa gcaggaaagc gtatcctggg 60
aagaaaggct tggcttggac tccggagaag aatactacat cgagacctgc tggggaattt 120
tattttattt tattattttt ttggtcttgg ttgtactgag ggaggaagaa gaggttgtgt 180
ggcccggtcg aacttgtggc agcctgaagg ccccctcagg cggcgccgcg ggcagccccg 240
cagccggggc ctggtgcagc ctccgcggcc gctgtcaggg aagcgcaggc ggccaatgga 300

```
acccgggagc ggtcgctgct gctgaggcgg cagtgtcggc agtccaaccg cgactgcccg    360
cacccccctcc gcgggggtcc cccagaggat caactaaacc ttgaactaag aagaaaaatg    420
tgttgtgagc agggggagcc tcagctgcct caggccgttc aggacagaag ggtgtttctg    480
aaggccggag caagttttga agaagtccct atcagattac acttggttga ctactccgga    540
gcagccacta agagggatga acaggcctgc gtggaaattg aatgagattc ttggaagctc    600
gaagtctggc tgtggccatg ggagatacag tagtggagcc tgccccccttg aagccaactt    660
ctgagcccac ttctggccca ccagggaata atggggggtc cctgctaagt gtcatcacgg    720
agggggtcgg ggaactatca gtgattgacc ctgaggtggc ccagaaggcc tgccaggagg    780
tgttggagaa agtcaagctt ttgcatggag gcgtggcagt ctctagcaga ggcaccccac    840
tggagttggt caatggggat ggtgtggaca gtgagatccg ttgcctagat gatccacctg    900
cccagatcag ggaggaggaa gatgagatgg gggccgctgt ggcctcaggc acagccaaag    960
gagcaagaag acggcggcag aacaactcag ctaaacagtc ttggctgctg aggctgtttg   1020
agtcaaaact gtttgacatc tccatggcca tttcatacct gtataactcc aaggagcctg   1080
gagtacaagc ctacattggc aaccggctct tctgctttcg caacgaggac gtggacttct   1140
atctgcccca gttgcttaac atgtacatcc acatggatga ggacgtgggt gatgccatta   1200
agccctacat agtccaccgt tgccgccaga gcattaactt ttccctccag tgtgccctgt   1260
tgcttggggc ctattcttca gacatgcaca tttccactca acgacactcc cgtgggacca   1320
agctacggaa gctgatcctc tcagatgagc taaagccagc tcacaggaag agggagctgc   1380
cctccttgag cccggcccct gacacagggc tgtctccctc caaaaggact caccagcgct   1440
ctaagtcaga tgccactgcc agcataagtc tcagcagcaa cctgaaacga acagccagca   1500
accctaaagt ggagaatgag gatgaggagc tctcctccag caccgagagt attgataatt   1560
cattcagttc ccctgttcga ctggctcctg agagagaatt catcaagtcc ctgatggcga   1620
tcggcaagcg gctggccacg ctccccacca aagagcagaa aacacagagg ctgatctcag   1680
agctctccct gctcaaccat aagctccctg cccgagtctg gctgcccact gctggctttg   1740
accaccacgt ggtccgtgta ccccacacac aggctgttgt cctcaactcc aaggacaagg   1800
ctccctacct gatttatgtg gaagtccttg aatgtgaaaa ctttgacacc accagtgtcc   1860
ctgcccggat ccccgagaac cgaattcgga gtacgaggtc cgtagaaaac ttgcccgaat   1920
gtggtattac ccatgagcag cgagctggca gcttcagcac tgtgcccaac tatgacaacg   1980
atgatgaggc ctggtcggtg gatgacatag gcgagctgca agtggagctc cccgaagtgc   2040
ataccaacag ctgtgacaac atctcccagt tctctgtgga cagcatcacc agccaggaga   2100
gcaaggagcc tgtgttcatt gcagcagggg acatccgccg gcgccttttcg gaacagctgg   2160
ctcatacccc gacagccttc aaacgagacc cagaagatcc ttctgcagtt gctctcaaag   2220
agccctggca ggagaaagta cggcggatca gagagggctc cccctacggc catctcccca   2280
attggcggct cctgtcagtc attgtcaagt gtggggatga ccttcggcaa gagcttctgg   2340
cctttcaggt gttgaagcaa ctgcagtcca tttgggaaca ggagcgagtg cccctttgga   2400
tcaagccata caagattctt gtgatttcgg ctgatagtgg catgattgaa ccagtggtca   2460
atgctgtgtc catccatcag gtgaagaaac agtcacagct ctccttgctc gattacttcc   2520
tacaggagca cggcagttac accactgagg cattcctcag tgcacagcgc aattttgtgc   2580
aaagttgtgc tgggtactgc ttggtctgct acctgctgca agtcaaggac agacacaatg   2640
```

```
ggaatatcct tttggacgca gaaggccaca tcatccacat cgactttggc ttcatcctct   2700

ccagctcacc ccgaaatctg ggctttgaga cgtcagcctt taagctgacc acagagtttg   2760

tggatgtgat gggcggcctg gatggcgaca tgttcaacta ctataagatg ctgatgctgc   2820

aagggctgat tgccgctcgg aaacacatgg acaaggtggt gcagatcgtg gagatcatgc   2880

agcaaggttc tcagcttcct tgcttccatg gctccagcac cattcgaaac ctcaaagaga   2940

ggttccacat gagcatgact gaggagcagc tgcagctgct ggtggagcag atggtggatg   3000

gcagtatgcg gtctatcacc accaaactct atgacggctt ccagtacctc accaacggca   3060

tcatgtgaca cgctcctcag cccaggagtg gtggggggtc cagggcaccc tccctagagg   3120

gcccttgtct gagaaacccc aaaccaggaa accccaccta cccaaccatc cacccaaggg   3180

aaatggaagg caagaaacac gaaggatcat gtggtaactg cgagagcttg ctgaggggtg   3240

ggagagccag ctgtggggtc cagacttgtt ggggcttccc tgcccctcct ggtctgtgtc   3300

agtattacca ccagactgac tccaggactc actgccctcc agaaaacaga ggtgacaaat   3360

gtgagggaca ctggggcctt tcttctcctt gtaggggtct ctcagaggtt ctttccacag   3420

gccatcctct tattccgttc tggggcccag gaagtgggga agagtaggtt ctcggtactt   3480

aggacttgat cctgtggttg gccactggcc atgctgctgc ccagctctac cctcccagg   3540

gacctacccc tcccagggac cgacccctgg cccaagctcc ccttgctggc gggcgctgcg   3600

tgggccctgc acttgctgag gttccccatc atgggcaagg aagggaattc ccacagccct   3660

ccagtgtact gagggtactg gcctagccat gtggaattcc ctaccctgac tccttcccca   3720

aacccaggga aaagagctct caatttttta tttttaattt ttgtttgaaa taaagtcctt   3780

agttagccac ttgtgtcatt tccaggtttt ctgggggagt gcaggggggag atgggtgatg   3840

aggtatgaac ggatgcctca gtgtccaaga tacaaaaggc actacataga agtttgcttt   3900

ttccctgcct gtcttggtca ctaccacctc ttccctgaga agggcgggcc ttccatgttc   3960

tctcacccgc ttcaactcca cattgtccaa gtcacagaaa aagagaggcc tgaatggaga   4020

ttcgaccaca aacagtttta atggtctggt tttctcccta gttccccaac tgtttgttag   4080

tattattatt actacaagaa taaaggattc ctgagagcct gtc                     4123
```

```
<210> SEQ ID NO 8
<211> LENGTH: 2857
<212> TYPE: DNA
<213> ORGANISM: Homo sapiens

<400> SEQUENCE: 8

acccagtgag cggctagggt gcagcaggag tttgggggat agccccagtc ttgggatctc     60

tgtcctgggc tggggactgc cccctcccct ggcctggctc ctgacgcccg tgctgccggt    120

gaaacgctgt tgacatgtcc tgaattatta agcgtgggga gggctccgga gcacatgctg    180

agcggagcgg ctggggctgc gcggcgtggc ggagcagcgc tcgctccctc gctcactcgc    240

tcgctcgcag ggacacacgc aggggctgac agctgtgctg gtgctgataa gggaagccac    300

aaggagacga tcgaggagag agacaagcgg cagcagaggc agcagcggca gaggcagcac    360

cagggctgcg gagctgctgg gagtgggagt gactccccca cctcgggccc ccaccctgtc    420

cctgtcctct tcccgcttgc cctgagttta gaagagcagc cgctgccacc actgccactc    480

gggagggcac cagggctgct ggctagggag ggacagggca gggaggctct ggccagtccc    540

agcagccggg gacagatgcc gatcgagatt gtgtgcaaaa tcaaatttgc tgaggaggat    600

gcgaaaccca aggagaagga ggcaggggat gagcagagcc tcctcggggc tgttgcccct    660
```

```
ggagcagccc cccgagacct ggccaccttt gccagcacca gcaccctgca tggactgggc    720
cgggcctgtg gcccaggccc ccacggactg cgcagaaccc tgtgggcact ggccctactc    780
acctcgctgg ctgccttcct gtaccaggcg gctggcctgg cccggggcta cctgacccgg    840
cctcacctgg tggcaatgga ccccgctgcc ccagccccag tggcgggctt cccggctgtc    900
accctctgca atatcaaccg cttccggcat tcggcactca gcgatgccga catcttccac    960
ctggccaatc tgacagggct gccccccaaa gaccgggatg ggcaccgtgc ggctggcctg   1020
cgctacccag agcctgacat ggtagacatc ctcaaccgca ctggccacca gctcgccgac   1080
atgcttaaga gctgcaactt cagtgggcat cactgctccg ccagcaactt ctctgtggtc   1140
tatactcgct atgggaagtg ttacaccttc aacgcggacc cgcggagctc gctgcccagc   1200
cgggcagggg gcatgggcag tggcctggag atcatgctgg acatccagca ggaggagtac   1260
ctgcccatct ggagggagac aaatgagacg tcgtttgagg caggtattcg ggtgcagatc   1320
cacagccagg aggagccgcc ctacatccac cagctggggt tcggggtgtc cccaggcttc   1380
cagacctttg tgtcctgcca ggaacagcgg ctgacctacc tgccccagcc ctggggcaac   1440
tgccgcgcag agagtgagct cagggagcct gagcttcagg gctactcggc ctacagtgtg   1500
tctgcctgcc ggctgcgctg tgaaaaggag gccgtgcttc agcgctgcca ctgccggatg   1560
gtgcacatgc cagactccct gggtgggggc cctgagggcc cgtgcttctg ccccaccccc   1620
tgcaacctga cacgctatgg gaaagagatc tccatggtca ggatccccaa caggggctca   1680
gcccggtacc tggcgaggaa gtacaaccgc aacgagacct acatacggga gaacttcctg   1740
gtcctagatg tcttctttga ggccctgacc tctgaagcca tggagcagcg agcagcctat   1800
ggcctgtcag ccctgctggg agacctcggg ggacagatgg gcctgttcat tggggccagc   1860
atcctcacgt tgctggagat cctcgactac atctatgagg tgtcctggga tcgactgaag   1920
cgggtatgga ggcgtcccaa gaccccccctg cggacctcca ctgggggcat ctccactttg   1980
gggcttcagg agctgaagga acagagtccc tgcccgagcc ggggccgagt ggagggtggg   2040
ggggtcagca gtctgctccc caatcaccac cacccccacg gtcccccagg aggtctcttt   2100
gaagattttg cttgctagga cggtgctgtg actgaaagga cccaggagtc tgggacccct   2160
cctgggatcc ccagcacatt ctcctgctcc tgggagaggc ctgggggcgg tgctcactgg   2220
gagggccagg actcagttcc tgctctcatc ctcccctgcc ctgatgtcag ctgctttgca   2280
caaaggtcct tcttgtccac accccttatc cccaggctgg tgccccggga gggctggaga   2340
ccaggccatg ggccctcacg gagaggaagg gaaggaagga gagggagggg gaggatagag   2400
cccatcccag ccggggaggg ggagccctct gtacatttgt aaatatttag ggaaagccgg   2460
gtggggggag gggatacaga tgtagaaggt gggtagggct acaggggtgg gtgatttagg   2520
gacagccagg gtcccagccc caatgtcagc aggataggga gagccccagg actcaggagt   2580
gctgggctgg tcctacttcc tgcccctctc caggcccagc tcccctcttg gcagggggag   2640
aggatggccc agcaggcctg gcccagctcc cagttccccc tgcaccagcc ccacccctag   2700
agtcccttct atagggaggg ggcaggagac cttccagact tcggctgagc ttggagggtg   2760
ggaagggagc cttctcagtc ctctctccct ccagtctgat tttataaagt gctgacgaga   2820
ttgggaataa agaggcataa agaaaaaaaa aaaaaaa                            2857
```

<210> SEQ ID NO 9
<211> LENGTH: 5621
<212> TYPE: DNA

<213> ORGANISM: Homo sapiens

<400> SEQUENCE: 9

```
aagaaaatcc tgcttgacaa aaaccgtcac ttaggaaaag atgtcctttc gggcagccag     60
gctcagcatg aggaacagaa ggaatgacac tctggacagc acccggaccc tgtactccag    120
cgcgtctcgg agcacagact tgtcttacag tgaaagcgac ttggtgaatt ttattcaagc    180
aaattttaag aaacgagaat gtgtcttctt taccaaagat tccaaggcca cggagaatgt    240
gtgcaagtgt ggctatgccc agagccagca catggaaggc acccagatca accaaagtga    300
gaaatggaac tacaagaaac acaccaagga atttcctacc gacgcctttg ggatattca    360
gtttgagaca ctggggaaga aagggaagta tatacgtctg tcctgcgaca cggacgcgga    420
aatcctttac gagctgctga cccagcactg gcacctgaaa acacccaacc tggtcatttc    480
tgtgaccggg ggcgccaaga acttcgccct gaagccgcgc atgcgcaaga tcttcagccg    540
gctcatctac atcgcgcagt ccaaaggtgc ttggattctc acgggaggca cccattatgg    600
cctgatgaag tacatcgggg aggtggtgag agataacacc atcagcagga gttcagagga    660
gaatattgtg gccattggca tagcagcttg gggcatggtc tccaaccggg acaccctcat    720
caggaattgc gatgctgagg gctatttttt agcccagtac cttatggatg acttcacaag    780
agatccactg tatatcctgg acaacaacca cacacatttg ctgctcgtgg acaatggctg    840
tcatggacat cccactgtcg aagcaaagct ccggaatcag ctagagaagt atatctctga    900
gcgcactatt caagattcca actatggtgg caagatcccc attgtgtgtt ttgcccaagg    960
aggtggaaaa gagactttga aagccatcaa tacctccatc aaaaataaaa ttccttgtgt   1020
ggtggtggaa ggctcgggcc agatcgctga tgtgatcgct agcctggtgg aggtggagga   1080
tgccctgaca tcttctgccg tcaaggagaa gctggtgcgc tttttacccc gcacggtgtc   1140
ccggctgcct gaggaggaga ctgagagttg gatcaaatgg ctcaaagaaa ttctcgaatg   1200
ttctcaccta ttaacagtta ttaaaatgga agaagctggg gatgaaattg tgagcaatgc   1260
catctcctac gctctataca aagccttcag caccagtgag caagacaagg ataactggaa   1320
tgggcagctg aagcttctgc tggagtggaa ccagctggac ttagccaatg atgagatttt   1380
caccaatgac cgccgatggg agtctgctga ccttcaagaa gtcatgttta cggctctcat   1440
aaaggacaga cccaagtttg tccgcctctt tctggagaat ggcttgaacc tacggaagtt   1500
tctcacccat gatgtcctca ctgaactctt ctccaaccac ttcagcacgc ttgtgtaccg   1560
gaatctgcag atcgccaaga attcctataa tgatgccctc ctcacgtttg tctggaaact   1620
ggttgcgaac ttccgaagag gcttccggaa ggaagacaga aatggccggg acgagatgga   1680
catagaactc cacgacgtgt ctcctattac tcggcacccc ctgcaagctc tcttcatctg   1740
ggccattctt cagaataaga aggaactctc caaagtcatt tgggagcaga ccaggggctg   1800
cactctggca gccctgggag ccagcaagct tctgaagact ctggccaaag tgaagaacga   1860
catcaatgct gctggggagt ccgaggagct ggctaatgag tacgagaccc gggctgttga   1920
gctgttcact gagtgttaca gcagcgatga agacttggca gaacagctgc tggtctattc   1980
ctgtgaagct tggggtggaa gcaactgtct ggagctggcg gtggaggcca cagaccagca   2040
tttcatcgcc cagcctgggg tccagaattt tctttctaag caatggtatg gagagatttc   2100
ccgagacacc aagaactgga agattatcct gtgtctgttt attataccct tggtgggctg   2160
tggctttgta tcatttagga agaaacctgt cgacaagcac aagaagctgc tttggtacta   2220
tgtggcgttc ttcacctccc ccttcgtggt cttctcctgg aatgtggtct tctacatcgc   2280
```

```
cttcctcctg ctgtttgcct acgtgctgct catggatttc cattcggtgc cacaccccc   2340
cgagctggtc ctgtactcgc tggtctttgt cctcttctgt gatgaagtga gacagtggta   2400
cgtaaatggg gtgaattatt ttactgacct gtggaatgtg atggacacgc tggggctttt   2460
ttacttcata gcaggaattg tatttcggct ccactcttct aataaaagct ctttgtattc   2520
tggacgagtc attttctgtc tggactacat tattttcact ctaagattga tccacatttt   2580
tactgtaagc agaaacttag gacccaagat tataatgctg cagaggatgc tgatcgatgt   2640
gttcttcttc ctgttcctct ttgcggtgtg gatggtggcc tttggcgtgg ccaggcaagg   2700
gatccttagg cagaatgagc agcgctggag gtggatattc cgttcggtca tctacgagcc   2760
ctacctggcc atgttcggcc aggtgcccag tgacgtggat ggtaccacgt atgactttgc   2820
ccactgcacc ttcactggga atgagtccaa gccactgtgt gtggagctgg atgagcacaa   2880
cctgccccgg ttccccgagt ggatcaccat cccccctggtg tgcatctaca tgttatccac   2940
caacatcctg ctggtcaacc tgctggtcgc catgtttggc tacacggtgg gcaccgtcca   3000
ggagaacaat gaccaggtct ggaagttcca gaggtacttc ctggtgcagg agtactgcag   3060
ccgcctcaat atccccttcc ccttcatcgt cttcgcttac ttctacatgg tggtgaagaa   3120
gtgcttcaag tgttgctgca aggagaaaaa catggagtct tctgtctgct gtttcaaaaa   3180
tgaagacaat gagactctgg catgggaggg tgtcatgaag gaaaactacc ttgtcaagat   3240
caacacaaaa gccaacgaca cctcagagga aatgaggcat cgatttagac aactggatac   3300
aaagcttaat gatctcaagg gtcttctgaa agagattgct aataaaatca aataaaactg   3360
tatgaactct aatggagaaa aatctaatta tagcaagatc atattaagga atgctgatga   3420
acaattttgc tatcgactac taaatgagag attttcagac ccctgggtac atggtggatg   3480
attttaaatc accctagtgt gctgagacct tgagaataaa gtgtgtgatt ggtttcatac   3540
ttgaagacgg atataaagga agaatatttc ctttatgtgt ttctccagaa tggtgcctgt   3600
ttctctctgt gtctcaatgc ctgggactgg aggttgatag tttaagtgtg ttcttaccgc   3660
ctccttttc ctttaatctt atttttgatg aacacatata taggagaaca tctatcctat   3720
gaataagaac ctggtcatgc tttactcctg tattgttatt ttgttcattt ccaattgatt   3780
ctctactttt ccctttttg tattatgtga ctaattagtt ggcatattgt taaaagtctc   3840
tcaaattagg ccagattcta aaacatgctg cagcaagagg accccgctct cttcaggaaa   3900
agtgttttca tttctcagga tgcttcttac ctgtcagagg aggtgacaag gcagtctctt   3960
gctctcttgg actcaccagg ctcctattga aggaaccacc cccattccta aatatgtgaa   4020
aagtcgccca aaatgcaacc ttgaaaggca ctactgactt tgttcttatt ggatactcct   4080
cttattattt ttccattaaa aataatagct ggctattata gaaaatttag accatacaga   4140
gatgtagaaa gaacataaat tgtccccatt accttaaggt aatcactgct aacaatttct   4200
ggatggtttt tcaagtctat ttttttcta tgtatgtctc aattctcttt caaaatttta   4260
cagaatgtta tcatactaca tatatacttt ttatgtaagc tttttcactt agtattttat   4320
caaatatgtt tttattatat tcatagcctt cttaaacatt atatcaataa ttgcataata   4380
ggcaacctct agcgattacc ataattttgc tcattgaagg ctatctccag ttgatcattg   4440
ggatgagcat ctttgtgcat gaatcctatt gctgtatttg ggaaaatttt ccaaggttag   4500
attccaataa atatctattt attattaaat attaaaatat ctatttatta ttaaaaccat   4560
ttataaggct ttttcataaa tgtatagcaa ataggaatta ttaacttgag cataagatat   4620
```

```
gagatacatg aacctgaact attaaaataa aatattatat ttaaccctta gtttaagaag   4680
aagtcaatat gcttatttaa atattatgga tggtgggcag atcacttgag gtcaggagtt   4740
cgagaccagc ctggccaaca tggcaaaacc acatctctac taaaaataaa aaaattagct   4800
gggtgtggtg gtgcactcct gtaatcccag ctactcagaa ggctgaggta caagaattgc   4860
tggaacctgg gaggcggagg ttgcagtgaa ccaagattgc accactgcac tccagccggg   4920
gtgacagagt gagactccga ctgaaaataa ataaataaat aaataaataa ataaataaat   4980
attatggatg gtgaagggaa tggtatagaa ttggagagat tatcttactg aacacctgta   5040
gtcccagctt tctctggaag tggtcgtatt tgagcaggat gtgcacaagg caattgaaat   5100
gcccataatt agtttctcag ctttgaatac actataaact cactggctga aggaggaaat   5160
tttagaagga agctactaaa agatctaatt tgaaaaacta caaaagcatt aactaaaaaa   5220
gtttattttc cttttgtctg ggcagtagtg aaaataacta ctcacaacat tcactatgtt   5280
tgcaaggaat taacacaaat aaaagatgcc tttttactta aacaccaaga cagaaaactt   5340
gcccaatact gagaagcaac ttgcattaga gagggaactg ttaaatgttt tcaacccagt   5400
tcatctggtg gatgtttttg caggttactc tgagaatttt gcttatgaaa aatcattatt   5460
tttagtgtag ttcacaataa tgtattgaac atacttctaa tcaaaggtgc tatgtccttg   5520
tgtatggtac taaatgtgtc ctgtgtactt ttgcacaact gagaatcctg cagcttggtt   5580
taatgagtgt gttcatgaaa taaataatgg aggaattgtc a                       5621
```

<210> SEQ ID NO 10
<211> LENGTH: 2881
<212> TYPE: DNA
<213> ORGANISM: Homo sapiens

<400> SEQUENCE: 10

```
gcggcggggc tccggctgcg ctcgtggccg ggccgggcgg ggaggccggt cccgcgggcg     60
ggggcagggg cggctccgcg gcttctcccg ccgccgccgc caaggggagt ttccaggaag    120
tggccatatt ggatccattc agccgcagcc gcccgggcgg agcgcgtccc gcagccggct    180
ggtccctgtc gctgcccctg cgctcgtccc agcccacccg cccggtgcgg agctcgccat    240
ggcggccacc gacctggagc gcttctcgaa tgcagagcca gagccccgga gcctctccct    300
gggcggccat gtgggtttcg acagcctccc cgaccagctg gtcagcaagt cggtcactca    360
gggcttcagc ttcaacatcc tctgtgtggg ggagaccggc attggcaaat ccacactgat    420
gaacacactc ttcaacacga ccttcgagac tgaggaagcc agtcaccatg aggcatgcgt    480
gcgcctgcgg ccccagacct atgacctcca ggagagcaac gtgcagctca agctgaccat    540
tgtggatgcc gtgggctttg gggatcagat caataaggat gagagttaca ggcccatagt    600
tgactacatc gatgcgcagt ttgaaaatta tctgcaggag gagctgaaga tccgccgctc    660
gctcttcgac taccatgaca caaggatcca cgtttgcctc tacttcatca cgcccacagg    720
gcactccctg aagtctctag atctagtgac catgaagaaa ctagacagca aggtgaacat    780
tattcccatc atcgccaagg ctgacaccat ctccaagagc gagctccaca agttcaagat    840
caagatcatg ggcgagttgg tcagcaacgg ggtccagatc taccagttcc ccacggatga    900
tgaggctgtt gcagagatta acgcagtcat gaatgcacat ctgccctttg ccgtggtggg    960
cagcaccgag gaggtgaagg tggggaacaa gctggtccga gcacggcagt acccctgggg   1020
agtggtgcag gtggagaatg agaatcactg cgacttcgtg aagctgcggg agatgttgat   1080
ccgggtgaac atggaagacc tccgcgagca gacccacagc cggcactacg agctctaccg   1140
```

```
gcgctgcaag ttggaggaga tgggctttca ggacagcgat ggtgacagcc agcccttcag   1200
cctacaagag acatacgagg ccaagaggaa ggagttccta agtgagctgc agaggaagga   1260
ggaagagatg aggcagatgt ttgtcaacaa agtgaaggag acagagctgg agctgaagga   1320
gaaggaaagg gagctccatg agaagtttga gcacctgaag cgggtccacc aggaggagaa   1380
gcgcaaggtg gaggaaaagc gccgggaact ggaggaggag accaacgcct tcaatcgccg   1440
gaaggctgcg gtggaggccc tgcagtcgca ggccttgcac gccacctcgc agcagcccct   1500
gaggaaggac aaggacaaga agaacagatc agatatagga gcacaccagc cgggcatgag   1560
cctctccagc tctaaggtga tgatgaccaa ggccagtgtg gagcccttga actgcagcag   1620
ctggtggccc gccatacagt gctgcagctg cctggtcagg gatgcgacgt ggagggaagg   1680
attcctctga ggcagcagct ccaacacatg ggccagctc aggaccacca gggcatggaa   1740
ctggagacca tggtttttaa tgttagaaca gaaaacgcca tacttttcct atatcaatga   1800
tcaaaagtgc aaacaattta aatttccatc agggaacatc aaatgttgcc caaccctttt   1860
cattcctatc catggctccg taaggggctt gaggcttaat gcccatcctg tggccaagct   1920
gagcttccac tccgggacca aaaaaaaaaa aaagtctgct ttgtgacatc atcgttatga   1980
gcggaaagta cctagatgac aatgtttcca ttctgaaaaa tagaaacata ctattcaaga   2040
ccaaggtagc agaaaagtta cttgtatctg cttatcataa gacgaaactc tgcaacttgg   2100
caacggtggc cagttttcgt aatgaaacag tctttagtaa tttaatcttc atgcttcata   2160
acaaaccaaa accccatgag atttccacat tgcataattt tgccttacta acagaatcat   2220
atccttaagg atgaccatca ttcccccaac taaaacaaat acaaactaat gtatgatatt   2280
tttttaagtg ccagatcaat atggtctaaa gcttcaataa ggattgtgtg taggtgaata   2340
aagacagcta agtgaatgtg tgtaaagtgt agcaaaagca gacagatatt tatgtacagt   2400
attcatagaa tggaaagtta aatatttttg cagtgtgtat ttaaaagaga aactcaccat   2460
aatagtgccg tctaaaaatc tttgtaaagt taatttaatg tcctttagaa gtgggagtct   2520
ggtggaactg tgttggattt aagatacctt ttcactcttc cgtatgtcat gagccttgtg   2580
cgtcacctca ctgtggtgca tgtgcaaggg cgtgtgcacg cctgtgcttt gccatcccat   2640
gttgtaaaca gctgttccaa aggcacaaac gagtttaggg tagactctgt aaacacctcc   2700
ttactcacta tagtcaagaa gtccagcggc gtcccaatat agaggtccca gtgcagtctg   2760
tccagaatag ccagctccat cctcagcagc tcattcgggg aatagtcaga gccatagtgc   2820
tttgtgaagt cttttacttg tggaataaac tgtaaaaaga aaataaagag gccaaagccc   2880
t                                                                   2881
```

<210> SEQ ID NO 11
<211> LENGTH: 3755
<212> TYPE: DNA
<213> ORGANISM: Homo sapiens

<400> SEQUENCE: 11

```
agctgcagta gcctggaggt tcagagagcc gggctactct gagaagaaga caccaagtgg     60
attctgcttc ccctgggaca gcactgagcg agtgtggaga gaggtacagc cctcggccta    120
caagctcttt agtcttgaaa gcgccacaag cagcagctgc tgagccatgg ctgaagggga    180
aatcaccacc ttcacagccc tgaccgagaa gtttaatctg cctccaggga attacaagaa    240
gcccaaactc ctctactgta gcaacggggg ccacttcctg aggatccttc cggatggcac    300
```

```
agtggatggg acaagggaca ggagcgacca gcacattcag ctgcagctca gtgcggaaag    360
cgtgggggag gtgtatataa agagtaccga gactggccag tacttggcca tggacaccga    420
cgggctttta tacggctcac agacaccaaa tgaggaatgt ttgttcctgg aaaggctgga    480
ggagaaccat tacaacacct atatatccaa gaagcatgca gagaagaatt ggtttgttgg    540
cctcaagaag aatgggagct gcaaacgcgg tcctcggact cactatggcc agaaagcaat    600
cttgtttctc cccctgccag tctcttctga ttaaagagat ctgttctggg tgttgaccac    660
tccagagaag tttcgagggg tcctcacctg gttgacccaa aaatgttccc ttgaccattg    720
gctgcgctaa cccccagccc acagagcctg aatttgtaag caacttgctt ctaaatgccc    780
agttcacttc tttgcagagc cttttacccc tgcacagttt agaacagagg gaccaaattg    840
cttctaggag tcaactggct ggccagtctg ggtctgggtt tggatctcca attgcctctt    900
gcaggctgag tccctccatg caaaagtggg gctaaatgaa gtgtgttaag ggtcggcta     960
agtgggacat tagtaactgc acactatttc cctctactga gtaaacccta tctgtgattc   1020
ccccaaacat ctggcatggc tcccttttgt ccttcctgtg ccctgcaaat attagcaaag   1080
aagcttcatg ccaggttagg aaggcagcat tccatgacca gaaacaggga caaagaaatc   1140
ccccccttcag aacagaggca tttaaaatgg aaaagagaga ttggattttg gtgggtaact   1200
tagaaggatg gcatctccat gtagaataaa tgaagaaagg gaggcccagc cgcaggaagg   1260
cagaataaat ccttgggagt cattaccacg ccttgacctt cccaaggtta ctcagcagca   1320
gagagccctg ggtgacttca ggtggagagc actagaagtg gtttcctgat aacaagcaag   1380
gatatcagag ctgggaaatt catgtggatc tggggactga gtgtgggagt gcagagaaag   1440
aaagggaaac tggctgaggg gataccataa aaagaggatg atttcagaag gagaaggaaa   1500
aagaaagtaa tgccacacat tgtgcttggc ccctggtaag cagaggcttt ggggtcctag   1560
cccagtgctt ctccaacact gaagtgcttg cagatcatct ggggacctgg tttgaatgga   1620
gattctgatt cagtgggttg ggggcagagt ttctgcagtt ccatcaggtc ccccccaggt   1680
gcaggtgctg acaatactgc tgccttaccc gccatacatt aaggagcagg gtcctggtcc   1740
taaagagtta ttcaaatgaa ggtggttcga cgcccccgaac ctcacctgac ctcaactaac  1800
ccttaaaaat gcacacctca tgagtctacc tgagcattca ggcagcactg acaatagtta   1860
tgcctgtact aaggagcatg attttaagag gctttggccc aatgcctata aaatgcccat   1920
ttcgaagata tacaaaaaca tacttcaaaa atgttaaacc cttaccaaca gcttttccca   1980
ggagaccatt tgtattacca ttacttgtat aaatacactt cctgcttaaa cttgacccag   2040
gtggctagca aattagaaac accattcatc tctaacatat gatactgatg ccatgtaaag   2100
gcctttaata agtcattgaa atttactgtg agactgtatg ttttaattgc atttaaaaat   2160
atatagcttg aaagcagtta aactgattag tattcaggca ctgagaatga tagtaatagg   2220
atacaatgta taagctactc acttatctga tacttattta cctataaaat gagatttttg   2280
ttttccactg tgctattaca aattttcttt tgaaagtagg aactcttaag caatggtaat   2340
tgtgaataaa aattgatgag agtgttagct cctgtttcat atgaaattga agtaattgtt   2400
aactaaaaac aattccttag taactgaact gtcatattta gaatggaagg aaaatgacag   2460
tttgtgaaag ttcaaagcaa tagtgcaatt gaagaattga cctaagtaag ctgacattat   2520
ggttaataat agtattttag atttgtgcag caaaataatt tcataacttt tttgtttttg   2580
ttacttggat aagatcaatc tgttttattt tagtaaatct ttgcaggcaa gttagagaaa   2640
atgcagtgtg gcttaacgtc tctttagtat gaagatttgg ccagaaaaag atacccagag   2700
```

```
aggaaatcta agataattat aatggtccat actttttatt gtatgaatca aactcaagca   2760
taacattggc caaggaaaat taaataccat tgctaacttg tgaaatggaa gtctgtgatt   2820
tcggagatgc aaagcattgt agtaaaaaca ccaatgtgac ctcgaccatc tcagcccaga   2880
tatcattcat atatctgttc aatgactatt aaggtgccta ctgtgtgcta ggcactgtac   2940
tggatactgg ggaccttgtc tgtctggttt gctgctgtat cttctcccag ggcattatat   3000
ttatgatgaa agatgctgtg gattcaattc tttcagtcaa gaataaacac agactttgta   3060
ggttcctgct gaataaagca aatcccagaa acccagattt tggaagaatc agcaacccca   3120
gcataaaata aacccctatc aaaatgtcag aggacatggc aaggtaaact tagcattttc   3180
aactttagaa ccgggtcagc ttcaggggga ctgctttcaa atcagccaaa gagcctgtca   3240
gatcttctta gaaggaagag gttggtagtt ccctgctctg ttttgaacat gctctagttt   3300
attaacctgg ggacattccc attgctgtct taagtaagtc tcatagccag ctcctgtcac   3360
gtgactctca tatggattca ttttcgggcc agctctgaac aaagcatcat gaacatatgt   3420
gcttttggtc gtttgcaatg tgatggtggt ggaggtaggt attggtttcc ttggaaggca   3480
tgataagaaa gattcacaat ggccaacagt gtgtatgaac aaaaaactga ttggagcatc   3540
agctagtact gaaggtcctt gctttgtgtc agaggcaaag gaacccaagg cgccaagtcc   3600
tcagccttga gtgtactgct gacaactaaa ctcacaggct gcaaagcaga cctctgatga   3660
agatgcctgt tatttcacat cactgtcttt ttgtgtatca tagtctgcac cttacaaata   3720
ttaataaatg ttccaataat aggtgaaaaa aaaaa                              3755

<210> SEQ ID NO 12
<211> LENGTH: 1000
<212> TYPE: DNA
<213> ORGANISM: Homo sapiens

<400> SEQUENCE: 12

ccacgagcgc acaggaaaag gaccacatgg cctggcgagc cctacaccca ctgctactgc     60
tgctgctgct gttcccaggc tctcaggcac aatccaaggc tcaggtactt caaagtgtgg    120
cagggcagac gctaaccgtg agatgccagt acccgcccac gggcagtctc tacgagaaga    180
aaggctggtg taaggaggct tcagcacttg tgtgcatcag gttagtcacc agctccaagc    240
ccaggacgat ggcttggacc tctcgattca caatctggga cgaccctgat gctggcttct    300
tcactgtcac catgactgat ctgagagagg aagactcagg acattactgg tgtagaatct    360
accgcccttc tgacaactct gtctctaagt ccgtcagatt ctatctggtg gtatctccag    420
cctctgcctc cacacagacc ccctggactc cccgcgacct ggtctcttca cagacccaga    480
cccagagctg tgtgcctccc actgcaggag ccagacaagc ccctgagtct ccatctacca    540
tccctgtccc ttcacacccg tcctctcccc ttcctgtccc tctgccttcc aggccacaga    600
actccacgct ccgccctggc cctgcagccc ccattgccct ggtgcctgtg ttctgtggac    660
tcctcgtagc caagagcctg gtgctgtcag ccctgctcgt ctggtgggtt ttaaggaatc    720
ggcacatgca gcatcaaggg aggtctctgc tgcacccagc tcagcccagg ccccaggccc    780
atagacactt cccactgagc cacagggcac caggggggac atatggtgga aaaccgtgat    840
ggagctcagg agcctggata cccaaaaagc cacctgccac cttcaacagg tcacggacct    900
tccctggacc tcagtttcct cacctgtaga gagagaaata ttatatcaca ctgttgcaag    960
gactaagata agcgatgatg atgatgaaca cactttgtga                         1000
```

<210> SEQ ID NO 13
<211> LENGTH: 2364
<212> TYPE: DNA
<213> ORGANISM: Homo sapiens

<400> SEQUENCE: 13

```
ggccgggcgg gcatgggcct tcccggcccg gagctgggag tcgaaggggc gggaggcgtg     60
atggtgaact cgcaagaagt ttgagggacg cgcgggcccc gcgcccactc cccctccacc    120
ggacacggct ggggccggcg atgcctgaga gggggtcgga ggacgcagtg aacatatatg    180
catgtacagt gtggatcctc atctgagagg agggagatga aaacacaccc acctcacagg    240
ctgttgtgag gactaagggt gcggcagtgc ctggtacatg ggagccagcg ccggcagcca    300
ccatggcgtc acgcataggg ttgcgcatgc agctcatgcg ggagcaggcg cagcaggagg    360
agcagcggga gcgcatgcag caacaggctg tcatgcatta catgcagcag cagcagcagc    420
agcaacagca gcagctcgga gggccgccca ccccggccat caatacccc gtccacttcc     480
agtcgccacc acctgtgcct ggggaggtgt tgaaggtgca gtcctacctg gagaatccca    540
catcctacca tctgcagcag tcgcagcatc agaaggtgcg ggagtacctg tccgagacct    600
atgggaacaa gtttgctgcc cacatcagcc cagcccaggg ctctccgaaa cccccaccag    660
ccgcctcccc aggggtgcga gctggacacg tgctgtcctc ctccgctggc aacagtgctc    720
ccaatagccc catggccatg ctgcacattg gctccaaccc tgagagggag ttggatgatg    780
tcattgacaa cattatgcgt ctggacgatg tccttggcta catcaatcct gaaatgcaga    840
tgcccaacac gctaccccctg tccagcagcc acctgaatgt gtacagcagc gacccccagg    900
tcacagcctc cctggtgggc gtcaccagca gctcctgccc tgcggacctg acccagaagc    960
gagagctcac agatgctgag agcagggccc tggccaagga gcggcagaag aaagacaatc   1020
acaacttaat tgaaaggaga cgaaggttca acatcaatga ccgcatcaag gagttgggaa   1080
tgctgatccc caaggccaat gacctggacg tgcgctggaa caagggcacc atcctcaagg   1140
cctctgtgga ttacatccgg aggatgcaga aggacctgca aaagtccagg gagctggaga   1200
accactctcg ccgcctggag atgaccaaca agcagctctg gctccgtatc caggagctgg   1260
agatgcaggc tcgagtgcac ggcctcccta ccacctcccc gtccggcatg aacatggctg   1320
agctggccca gcaggtggtg aagcaggagc tgcctagcga agagggccca ggggaggccc   1380
tgatgctggg ggctgaggtc cctgaccctg agccactgcc agctctgccc ccgcaagccc   1440
cgctgcccct gcccacccag ccaccatccc cattccatca cctggacttc agccacagcc   1500
tgagctttgg gggcagggag gacgagggtc cccgggcta ccccgaaccc ctggcgccgg    1560
ggcatggctc ccccattcccc agcctgtcca agaaggatct ggacctcatg ctcctggacg  1620
actcactgct accgctggcc tctgatccac ttctgtccac catgtccccc gaggcctcca   1680
aggccagcag ccgccggagc agcttcagca tggaggaggg cgatgtgctg tgaccctggc   1740
tgcccctgtg ccagggaaca ggggccggcc tgggggctgg gagggccagg ggcacctccc   1800
tcccaccctt caggctgcac tgtgtgtgaa gtagccacct gccctgcctc cctcctcccc   1860
gttggcccct gtttggactt agtgcctgtc tggcagcctg tggggtcagg agaagcaccc   1920
ccagggcagc cctcttgact ggcgcagtgg gaagaggcct tcagcccctc tcccggagat   1980
ggaatcgcgg ggcagggagg ggcagggtgt tctagaggtg agaagagggc ctggtggaga   2040
ttccctgtct tctgagcccg agcccctcat taccagtgaa ggacatgctt gaggggttcg   2100
ggaagctcct catctgaggc aactggtcct gggggtgctc aggcctgcct tttgggact    2160
```

```
cagatggcag gaggtccacc ccgcagcctg gtcctcggct ctcccacagg tgggcacccc   2220

ccactttggt gctaatagct ctccaccagg tggtgtgagc gcgggggctg ccagaagcgg   2280

gaggggtcac tgccggaaga gcagctgccc tccgacccct cactttgtgc ctttagtaaa   2340

cactgtgctt tgtaaaaaaa aaaa                                          2364
```

<210> SEQ ID NO 14
<211> LENGTH: 1858
<212> TYPE: DNA
<213> ORGANISM: Homo sapiens

<400> SEQUENCE: 14

```
ctctgcctgg gtgtctccct ctctcagtgt gtgtgtctct ctgtctgttt tcacactctc     60

ctccccaatc gagcgaggcc cacacctggc gcatcactgc cgagccatta gctgcgggtt    120

tcctttcatc ttcgctgtgg cagacgtttc tatttatcca cttgcgctcg ccgagtggcg    180

tcaccagcgg tactgtaatg acgattgcag caggaggatg acagcttaga aagaagaggg    240

caatggggct tcctcccaga ggcggtgcgg cacagaggag cgctcgcttc acaaggtgac    300

cctagctccc accgccaccg ccgcggtcgc ggtccagacc gcgctccagc agctccgcgc    360

cctcccaggc acccggcctt tctttctccc tcttgcaacc aagatccgtc cggccgctgg    420

agacccaggg agccggggtt aggaactcac ttggggcttt cccctccccc accggagagc    480

cccgggatgg agagccgaaa ggacatggtt gtgtttctgg atgggggtca gcttggcact    540

ctggttggca agagagtctc aaatttgtcc gaagccgtgg gcagcccgct gccggagccg    600

cccgagaaaa tggtgccccg tggttgcctg agccctcggg ccgtccctcc ggccacccgg    660

gagcgcggcg ggggaggccc ggaggaggag ccggtagatg gactcgcagg cagcgcggcg    720

gggccgggcg ccgagcccca ggtagctggg gcggccatgc tcggcccagg acccccggcc    780

ccctcagtcg acagcctctc cggacagggg caacccagta gctcggacac cgagtcggat    840

ttctatgaag aaatcgaggt gagctgcacc ccggactgcg ccaccgggaa cgccgagtac    900

cagcacagca aagggtccgg ctccgaggcg ctggtcggca gtccgaacgg agggagcgag    960

acccccaaga gcaacggcgg cagtggtggg ggcggctcgc aaggcaccct ggcgtgcagc   1020

gccagtgacc agatgcgtcg ttaccgcacc gccttcaccc gagagcagat tgcgcggctg   1080

gagaaggaat tctaccggga gaactacgta tccaggccgc ggagatgtga gctggcggcc   1140

gccctaaacc tgccggaaac caccatcaag gtgtggttcc agaaccggcg catgaaggac   1200

aagcggcagc gcctggccat gacgtggccg cacccggcgg accccgcctt ctacacttac   1260

atgatgagcc atgcggcggc cgcgggcggc ctgccctacc ccttcccatc gcacctgccc   1320

ctgccctact actcgccggt gggcctgggc gccgcatccg ccgcctccgc cgccgcctcg   1380

cccttcagcg gctcgctgcg cccgctcgac acgttccgcg tgctgtcgca gccctacccg   1440

cggcccgaac tgctgtgcgc cttccgccac ccgccgctct accccgggcc cgcgcacgga   1500

ctgggcgcct ctgccggcgg cccctgctcc tgcctcgcct gtcacagcgg cccggccaac   1560

gggctggcgc cccgggctgc cgccgcctcg gacttcacct gtgcctccac ctcccgctcg   1620

gactccttcc tcaccttcgc gccctcggtg ctcagcaagg cctcctccgt cgcgctggac   1680

cagagggagg aggtgcccct cactagataa ggggccgccg gctggctgcc ggctccatga   1740

cgcccgtggg gtcacccccc ggccccggga ctcagccagc ctcgctcctc gctcctcgct   1800

cctcgcccct aggacgccaa gggggaaagg agagggcgga aaaggaccag cgggatcc     1858
```

<210> SEQ ID NO 15
<211> LENGTH: 43392
<212> TYPE: DNA
<213> ORGANISM: Homo sapiens

<400> SEQUENCE: 15

```
tcctggtcct gggggattca tggcatgaaa atattggtgg gcgatgtaag aacaaggctt     60

cctgctcaag ggagaagaaa ttgagaaaag atgcaaagta gtttttgaca ggggtgtttc    120

tagggtgggc cctgataaat taagaggatc ggaaagcaaa gatgtctgtg ccttctgttt    180

caagataggg cacatggagg cagtgacacc ctggagcttc tctgcaccat gacagagcac    240

aggactcatt ctgttctcta catcgcactc aacataggag gttccactat gctgtatcag    300

acctacccat ccagattcat cagatttgct tgcagagagc cccaagaaag gaacagaaat    360

agcaagaaag tgtctctggc ccaaagaggc acattcaatg agcttgaagg acagtgcagc    420

acttgttctc ctgaatggat caataaccaa ggacggacag agtgacatac tcatcagcag    480

atgccaagat gcacagctaa ggaagaaacc ctcctccaca gacacaccca agattcctgg    540

tcacatcata agcccctaga atttaggaca aaatggaaga aactagaaac tgactgaaat    600

taagtttctg ccacctgaag gaatggggct ttgtaaaaga aattaagacc agttacagaa    660

aaagagaaag ttacaattca catgggactt tgacagtttc cataatgttt tctgtttaaa    720

aagctctgga gtaaataagg caaaatgata cttaatcaag ctgggtggca ggtgtccatc    780

atacaatttg ccatatttca gataattgaa ctattttaca ataaaaatac tttgaaataa    840

aatatgttta tttgaatctt aaatttgtgg actaaaatgt gttccctcaa ccttagcaac    900

tattgtgctt taggcagtat tctcagagct tcaaatacat cacctcacta aagtttacaa    960

actcctattg ggtagatatc agtagtattt ttcattttgt aaataaagtg aagttaattt   1020

aaataaatag taggaaaaga aaactcttag ccatcttgat cagaaagatt tttaaaacac   1080

aaaatcgctg tttgcttgct tttttttga agaaaataag tgggaaaaaa ttatttaaaa    1140

tactcaaagt ggaaaagccc aatccacaga agcttcaagt tagaacaagg tgaggaaggg   1200

gtcaggtgat gtggcaagtc ttcatccaga aagccatttc cttccacata tgaaatgggc   1260

aactgtagga aggaggcctc aatgggattc agcagatgca atgaatagca gaaggcctat   1320

ggggtggtga tgctgataaa cagggtaaat actgagctga actcagagat cattaaaaga   1380

tgacatgttt atgcacttac acacagatgg ttaaaatgtt ggcatgttta tacacttgca   1440

tgtaaatagt caccgctctg aaatgtacgt tgcccttccc ctgaggaccc ttaacttcct   1500

aatgattcag caactaacca gcagtactct aatgcacagc tccagtgcca cggctgaagt   1560

ttgaaatgat tggttggtgg ctctgccata ctgattataa tatcatacct ggtgataact   1620

cctattataa cccaagctgg aattccttct ctgaacgcat tgccagaggc acatttggga   1680

agtctcggac tgctgagtgt tgggaaatgt tggaaagatg cctgcttctt aacactattg   1740

atatcattga gagtggtcaa acctttagat tccaaatctt atagtggtag ttaaaaaaaa   1800

gtagccaaga atgtgaaaag aacccatggt ggtagggatg ggaagaggaa gttgtaccag   1860

agcaaagcga catagagaag gagatgagag aacatgaaaa gcaacgaatt tcacaatttt   1920

gccataagct gaccctgact agcctactta agaacctcat gtctcagaag ttgctaacgg   1980

gttctctagt gatttatcaa ctgtaaaatg tttcattatc caacaatctc cttaggaaaa   2040

ggtattttta atgtatttaa gctctagtat cctcatcgct cagatggttg gtttggttcg   2100

cctgagtggc ttttagatct gtatttctag tgccctctaa tccatgggat gacctttaat   2160
```

```
gctgcttcca aaaaagaaaa atattagagg gcaaatgaat tgccaaatac tcatttttta   2220
agtaaatgat ttggagaaag ttattaactc gcctccaagc ccaaagttac ctgtgtgaga   2280
atcaaacaaa aacaattttg cttatatcat ctattcattt ccaattttgt acctatgcta   2340
acaatgttct tcttctcctt ttatttctca taaatcgaga gcagtttccc taagtcagct   2400
attataacca gactaagatg tgtttctctt tggtgccagc ttcttgttga ggcaggttaa   2460
tgaagagatt gtggtttttc ctctcattag gaatgcattt tggcattgac aacgcttcac   2520
tgatcattat gattccatgt gttgctgttg attagacttt tctacatgga ctttcccagc   2580
gagattgctt tccctcggtt gagtactagt taagcgttca cttaaaggcc tccctggaaa   2640
gtccttttct tgctggaatg caggacaagc tccctctgtg ttcctgttga ctttttttcac  2700
agttaacatt actcatcaca gctgaagact gaataacaat agatgggaag tggtttccac   2760
atttttccat agaacgtaac cccagttgac ttgtatgaag gaaaaattaa atgaatttat   2820
ggcagtcatt agaggtgggc taggtactat agaacatatt gaacctgaca gtccttttct   2880
agtgtattgt gtttgttaat atttgttaat ataatttgtt caaagaattt agaaatgcaa   2940
tctgacagaa atgaaattaa gaaaacgcaa ctttttggcc agttgtagtg gctcacgcct   3000
gtaatcccaa cacattagga gactagggca agaggattgc ttgaggccag gagtttgaga   3060
ccagacaggg taacagagtg agaccccgt ctctacaaac actttttaaa aatattagca    3120
gggtgtggtg gtgcacacct atagtttcag cattctatca ggaaactgaa gtggatcact   3180
tgggcccaag aggtccaggc tgcagtgacc tatgaatgca ccactgcatt ccagcttggg   3240
tgacagagga caccctgtca gaaagaaaag aaaaaaagaa aaggaaggaa ggaaggaaag   3300
aaggaaggaa ggaaggaagg aaggaaggaa ggaaggaagg aaggaaggaa ggaaggaagg   3360
aaggaaagaa agaaagaaag aaagaaagaa agaaagaaag aaagaaagaa agaaaagaaa   3420
ggaaggaagg aaggaaggaa ggaaggaagg aagaccctaa ttatttgttt actcataaat   3480
aagcttattt taaagcattc caaatttttt aacttttatt ttaggttcaa gagtacatgt   3540
gcaggtttgt taaattttgt gtcacaggga ttcgttgtac agattatttc atcacccagc   3600
tacaaagcct actccccaat agttattttt ctgctcctct ccctccccga cgctccaccc   3660
ctcaagtggg ccccagtgcc tgtttttttcc ctatttgttt ccatgagttc tcatcattta  3720
gctcccacta atgtggtatt tgggaaaatc caacttttga aagatcttta gtctgctaat   3780
catgaatggc caacataatt acaggcatgc caacatttgt aacattgtga cactttccct   3840
gccattctta gttaaaactg atcttttgtt ccaaaaattt ttgctaccaa caatagcctg   3900
tcctttatag ttcttttata cttttgtgtc ttctctctaa ctaaataatc aactctttca   3960
gcattccatc catttccctt tctcctccct cttactccca acccacattc ccctctccat   4020
tttaatttta acctgtgccc cttcaagtgt actccagctt ttttttaaa ataatttcaa    4080
gtgatacttt gacttttgac tgcatatgga agcataagta acatgtcctt tcatttttgg   4140
ataatgagtt tcctgattaa ttacagctca agagtaaaat gactgattac tatttaattc   4200
attttgtgct tctttacaat aaagtaaaga cagaagcccc agattcagga acagacaaaa   4260
tactttaatc gctatcacat ttttttaag tctagtcaat tagaaaagtc aaatctttcc    4320
tcacagccaa gcacattaaa aaaaaatctt ctctggtaat aaacttgaag ctttaaataa   4380
ttctacaatt ataaacattt tgtgtatttt gcaaatatgg cataacctgt tggcataaaa   4440
ttccattgtt ccagaaaata tcggtaataa aattatagaa aagttaaaga tcttcatttc   4500
```

```
ttatttcgaa gcgtttggga gacatttcag aaacggatgg gaaatgttaa attctgcatg   4560
cctgcttaag tttccatcca caccgactag atgtaaacga gtgtcaccaa aagtacacca   4620
caggcaccca cacagattcc ttccataagg gatccacaaa gtttagatgt gaaatgtacc   4680
taaaggttcc tagccgtctt tcatccctcc ctctgtgaaa cagggagaca catgtgtttt   4740
aaggcagaga tggaacttgg gcgatgggcg gggggtgggg gaggtgggaa gggacggctt   4800
aggacagggc aggattgtgg attgtttctg ccgccttggt tgcccatact gggcatctct   4860
gcaggcgcgt cggctccctc cacccctgct gagatgatgc actgcgaaaa cattcgctct   4920
ccccgggacg cctctcggtg gttcagagca gggaaaatgt tgcctcaggt ttaaaataat   4980
ctgcccaagc accccagcgc gggagaaacg ttctcactcg ctctctgctc gctgcgggcg   5040
ctccccgccc tctgctgcca gaaccttggg gatgtgccta gacccggcgc agcacacgtc   5100
cgggccaacc gcgagcagaa caaacctttg gcgggcggcc aggaggctcc ctcccagcca   5160
ccgccccccct ccagcgcctt tttttccccc catacaatac aagatcttcc ttcctcagtt   5220
cccttaaagc acagcccagg gaaacctcct cacagttttc atccagccac gggccagcat   5280
gtctgggggc aaatacgtag actcggaggt aggcatccgt gggggggcgc cggctcgggc   5340
gtgcggggag tgtccgcttc tgctatctgc ctctccaaat atcccgactg ctgccctggc   5400
cccagccctc tctccacttc ggagcactcc tctggcgttg gcaccgctga ggaatgggcc   5460
tgggcgggga ggtgaagaga agccaggaat gttttatgtt ttcctaatgg agagggggcc   5520
tagggagccc ctgagctagg aggacacgga aaaggggatt ggggtcctga gattgggtct   5580
gttgggccca ggacgcgttt tctggatggg tctaggatgc tcccttgtcg cgggaccccc   5640
gcggtccggc cctgcctgct gggggttcga agaggtggag tgcagggtgg aggtgttatt   5700
tacccgagtc ctggggacag tccccgggac tctccgccag gcgcccagac cggcaggtcc   5760
cgcaggcggc gcgcggtgtg tttgcacttt ccaaagttct tgaaccatct caagaactcc   5820
ttctgcatct tggcgtctgg caggggtgtt ccgagagagg tagacctccc ctccccaaac   5880
tgccaccatc acttccaacg ccctccacgc gctggagctc tgcccgggtg tggaaacctc   5940
gtcttccaac acgtagctgc ccttcagcca cccgcccgca gcctgggagt gccctgaggg   6000
tgggtcgggg gagctgcgca ggtgagactg agttctagga catttagggg gtctggtgcc   6060
tggctccgcc aaaaatgggg actttcggga ttgtgatcat cacggcggat tgagcaggga   6120
gagccgtgga gggacaagag agggccgagg cagggtgggg ggcgcgggca ggtgcgaggg   6180
ggatgcggcc aagaagcagc gataaaggga acattccacg ggtcgggcgg ctgctgttgg   6240
atcttagata aagctggaag ggattaccgg ggcaggggta atagggaccg gggacgggaa   6300
cgcgaaacag gtgaagcgct cagggcgaga gcgactcggc ttagggagtc cgggagaagc   6360
ctgcggctgc cccctcgccg ccgaggtcct gcgggtcctg cgggtcctgc gtgctgagcc   6420
ggggcgtgcg cgggcggggg ccttcggacc gcgcggcggg gcctgccctg acccctggcg   6480
gcgggcgggg gaggcaggcg cgccctgcag agtacagagg ggtgtggtgt cctctgcgag   6540
atcctcttaa aaagctggct acgcgcaggc ggtttctgtg cacggagccg tagctgtcgg   6600
agcggttagt tcgatttcga gctcgaggtt tcccccgccg ccaggctgac ttctcatcgc   6660
ttgtttttct ttttgcattt ttcctcccac cgccgttgcc gccctccccg tcctggccgt   6720
ccgccctccg ccctctgcag ggacatctct acaccgttcc catccgggaa cagggcaaca   6780
tctacaagcc caacaacaag gccatggcag acgagctgag cgagaagcaa gtgtacgacg   6840
cgcacaccaa ggagatcgac ctggtcaacc gcgaccctaa acacctcaac gatgacgtgg   6900
```

```
tcaaggtaag ccaaggcgac caacagggaa gggctgggac agctctcctc tggcagttag   6960
cccgtgcatc cttctttagc attgccgtgt acgcacaccc caccccgccc cctacacgcg   7020
cacacacaca cacacacaga gttttgtggg tttgatgtgt gggagctccc gcagtcggca   7080
gaaacgttac atctcccttc cccatctcc ccccaatagt tagttcagct gaaattcagc   7140
taaagtgagt tttgtagaag ttcctataac tacactttta tcctagcaaa tgagcctatt   7200
gacctcagca acagacggcc catactcctt gggacggtga gatggttcct atccattccc   7260
aggttgaaag tctagtgaca ggtccccact gcacgtggca ttaagacagt cagataattg   7320
tgtcaggtct tgtgctgagg atgagtcaga atacaagatg ggcatgttcc cccaactaaa   7380
acgatgggaa gtgattttct taaaaatact acagtggatg gaaatgccta ggactaaaga   7440
caaagaaaat acgtacttat tcatatacat atgaaagtta ctttaactag actaacaagt   7500
cacttgtgca caactaagca aatttacaaa accaaaaaca atgtatgcct cttggtttct   7560
tctatctatg gacacctgca cttagatgtg gaaagctgct tctttagtag ctacctgggt   7620
cagcctgccc tgagctaatg gcacattcag gttggagttc cttttcatac tttcaggatg   7680
tgcttggtga gattaaaaat aattggactg ggttattggc cagacttaga tctgactcag   7740
tggtcagttt taaattatca ttgttattag attttgaccc ttttagccaa tctagtggga   7800
ggaatttatt gcctaaacac atctggattg ggatatcatg ggctagagcc atccttggca   7860
aagggttttc tctgagaaat ggagggctaa ggaaaaatcc tggctcaggg actgcagtgt   7920
gaagatctac tcctatacaa cccccagcaa tcaatgaggc ggatgagcaa tttccaccca   7980
ccacgcctgc tatctatgga tgggaggagc tatagttcac aaaccgttta cattcatgaa   8040
taatatattt caaaagggga aacagtttaa tctgtaactg gaagggaaaa aaaaactgtc   8100
agaattgact cccttggctt cctggagtag gaaaaaggaa aattggagca tttgcagctt   8160
tttttgacta gctggattat ggaatattta aaagcaacag caacaaaagt accttataaa   8220
ctagaaaata gaattgctaa aaaactattt actaaaaaca ttaccttaaa gggagaggat   8280
atttgtgttt tcccccaccc ccacccttct catgtggctt tgaacaagaa ggagagttgc   8340
caggaaaaga ggcagatttc agagagggct ggcttcactg gatcctccct gttgttccac   8400
tgcactgtga gtgagattcc ctggagcaag cgaatctccc gggatgagtc agagaggcca   8460
acagtgtgga tgtgggtctc cacacatagc atgactaagt tgagaaagaa aggccccact   8520
gggaaaagag acttcaacac agatggaaaa aaaacataac aggcttggag gaaatagcag   8580
tttacaaaac agcatttcaa agagcaagtg tggggatcct caaattaaag aaattaaaag   8640
aaaaagctag agcaagctcc tgctagccta aagaaaccaa accctgacta cttgctcata   8700
gaactgtgag caaaacaaga cagtcaaacc aaaaaatcca cctagaaaag aatttggcag   8760
tctcactcag atgcctggcc tagaggggac ttcagagaat gccctacaga gagacaccaa   8820
gactacaaat gcaaattctg cccaaagagt gcctggccga tgaacagggt cctatctaca   8880
tcttatggag actcctattt tataaatatg tatcctcaag tccaagcaca aacaaaataa   8940
cagaaacagg gatgattctc tcccagtttc catgacagta aataataaat ttccctaaat   9000
tttactttca acaacataga ctttttttat ttttattttt atttatttat ttatttattt   9060
tttgagacgg agtctcactc tgtcacccag gctggagtgc agtggcatga tctgggatca   9120
ctgcaacctc cacctcccag gttcaagcaa ttcttctgtc tcagcctcct gagtagctgg   9180
gactacaagt gcacgccacc atgccgggtt aatatttgta tttttagtgg agacggggtt   9240
```

-continued

```
tcaccatgtt ggccaggctg gtcttgaact cctgacctca agtgatccac tggtcttggc   9300
ctcccaaagt gttgggatta cagatgtgag ccactacacc tggccaacaa cacagacttc   9360
ttaaaaaaat catgacaata attttgggtg cttcttaaaa gcacccaaag ctttactgct   9420
aatgcatggt agcttaaaac ttcacataat aagaaagaac cagtggccaa tggaatctac   9480
tgttaaaggt acccaatcaa gtaaggaaaa gttggtccta aaagcaagca gccctgtaaa   9540
agctgctctg tccaatatgg taatcactag ccatttgtgt ttccatttaa atttcaagta   9600
attaatatca agtaaaattt aaaattcagt tccttagtca cactagccac gttgtgagtg   9660
tgcaacaggt aaagctagtg gcacagacat agaacatttc catcagcaca gaaatctcta   9720
ttggacagtg ccagattagg gtgttctctg cattgtaaaa gcatcccctt gccaagttaa   9780
agaaaacaac aacaaaactc tagagaagaa atgaaacccc agtttcattt ctggagagga   9840
aagaaaactc atgtgtggca tgagtttata ttcaagaagg tgcagcatta ttacctattt   9900
tactagtaat aatgacacac attatagtat acaatccagt tccaataaaa ttaatttctc   9960
atcttactaa aagcttgctg ctccacatta tgagacaatt tacccaaata tagacattta  10020
cccaaaaata ttaagtagct tgtgaatact ttttaaaatt tcctttaatt aaagtggtca  10080
caaactcaaa cccttcattc tccctctgag atttctgtgt catcttttgt tcacattgtt  10140
attcacatgt ttattatgta cttattttga ttttctagat aaataaaatg gcttcaaatc  10200
tataattctg ataaaattag ccatcaatta atttatttat taaacccatg caatatgcta  10260
gattagatgc tttgctatgt aattcctaca ataaatccta gcaatcacaa agattacagt  10320
tagtgagacg acatgcacac aggtaaaaag tgtttttaaa aaatacatac atacaaccaa  10380
aacagtaagt cactgctaca tggaaactga ttggtccttt ttcctttttt tttttttgcc  10440
ttgactgcca ggaagcagtt tcaaatctat agctggattt taagtttcat taattcatgt  10500
tcccacatat ggttctgtat tttcacttcc ccctttttaac tgacatactg tcttatgtga  10560
tctctactgt aagccttctc atcattttgg aaacagacca aatataatat atatgataag  10620
gaatcaaaag taaatacagt agtgttgaat attgcataac aaaaaggttt ttaaataggg  10680
aatggtatca atatgaagtg ttagggagac ccagccatga aaaggatagc agggtcagag  10740
aaggaggatg tattgcagct ggtttaatgg agaatggtat gaaggaggtg cagtttgaat  10800
tgggtcatgg aggacagatg gattgcaaat agctggggca aaagcacagg aaggcattct  10860
aaacgagcca ggcatggaga caagaatgtc tcccacaagg gagttgtagt agctcaatca  10920
gactgggatt tgagatttca tgtggcagag tggtaggtga taaaggtgaa aagactgatc  10980
atagtaaaat gcggagtctg taaatccagc actcatgata agtttggaca tcatgtcaac  11040
agtggacagc cataaatgac tgcaagcatc ggtgtggtat aatgaaggtg acgtttttgt  11100
aaaatgactc tggtgaaggt acagaaggta atgaaaagta gccagtctag ttgagcagaa  11160
aagagttcag atgtaattgc atcatggtcc agatgtgaaa tgaagacaat gcgaagtggc  11220
attgtggatc gaaacataca tgcacaaaat gacagaattt tagaatttga agggatcatc  11280
atggttacca ggctggcctc caattcctct tttgtaatat taatagaaat taagggctaa  11340
caagtttaaa atgttatcca tctttttaca tagttactgc ccaaagtgaa tattttgaaa  11400
tgtatcatta aagaagaata gataagatta tgtgattcac catggactat tgtcatgaga  11460
ggaaaaatgt gtttagatga ttctgttagc actgagacaa atcaggatat ctgaaaggag  11520
gtctttgttg aaaaacagaa atatgcattc ataacttgct tttctaaaat tggaatgtaa  11580
tgattcttaa atatgcacag acacaaattt ttctttaaca gtcaagaaaa tgcacgcagg  11640
```

```
tgataatcag atcagttttg gttatagtac aaaggtttaa tgcctccgtg atccctttca  11700
acttgaaagc attctagagc aattggtgat taatatcagt ataacagtca tttataaaat  11760
tattatttat ttgatataca tctaatcaaa gcataagatt tatttttatt attattatta  11820
tactttaagt tttagggtac atgtgcacaa tgtgcaggtt agttacatat gtatacatgt  11880
gccatgctgg tgcgctgcac ccactaactc gttgtctagc attaggttta aaagatcaga  11940
ttgtctcggc accatgttaa tatctttttc tgttggcatt agtattagtt ttgcttgtgt  12000
atttgtttag gagatagctt cacaagttgg tgattgatat tctaccatgt atgaagtcat  12060
gcgtggaatt cagaatcccc agcttgtaaa attgcattat gatcatcttt agtgggaaat  12120
tgttctcaga atactgagca aaggatgata ccaaaatggc agctattatt cattcttaag  12180
catatgaaat gctttcaggt tcaacccaaa attacataca ttttaaatgc ttactaaaag  12240
agtcttttcc ctcctccatc tattaactgc aatcaaaaaa cttcggtttt aactgaacat  12300
gatttcatat tatttattaa aatttaaggc aaggtgcacc aagtaccctt gaattatgaa  12360
aagcttcatg atgtgggata ttctttcagt taacggcagg gttggctaca cttttaaggg  12420
gttcaaagta ggaacagctg caatagtgag ctgcatctgg aaagtccagt aatttgaaaa  12480
accacctgtt tatgtatcct gcccactcaa gtccataaaa taacagacac tttcatattc  12540
caaatgaaac tgctttttag tttgccctac ttttaaacat aactctttgt gatggaatga  12600
ccagaaacag ctggtctcta agaggacagg gctatgtgcg ctcacctgcg ggttggacc  12660
ttccataatc cccctggctg tggggaaagt tgagggctgc tgtctttata caaagatggt  12720
ttattccaag atacacacac tcttcttcca caccctggag accttgcata tttagtatct  12780
tctttaccat aatctgaggc cctagagaaa aagatttgca aactatactt gttttaaaac  12840
aactttctaa aaaagacact ctcagcccct agaaattatg cctaacacat agatgctcag  12900
aggcaacctg ttgtagtgca agaggattgt gccaagatta gaaaacaaat atttgcaact  12960
tttgtaactg tcttctctaa aacttgaatg tggtgattct aaagtaaaga ccgacacaaa  13020
attctttttc tttagcagtc aggaaaaggc atgcatgaag taatcagatc aggtgtggtt  13080
tcagcataat ggcctaatgc tttcatgatc tctttcaact ggaaagcgtt ctagtcccac  13140
tggacaccaa ggaggaagaa gggacggaaa atattaggcc cataggttta tcttcctcag  13200
tagtccacga gatttgagct tatatgtagg gagcaaaatt gtttgtctaa aagcagttaa  13260
taaatgcccc aaaaaggctg ggcgcagtga ctcactcctg taatcccagc actttgggag  13320
ctcaagattg gtggatcatg aggttaggag agcaagatca tcctggccaa cacggtgaaa  13380
ccccatctct atgaaaaata caaaaattag ctgggtgtgg tagcgcgtgt ttaatcccag  13440
ctactgggga agctgaggca ggagaatggc ttgaacccag gaggccaaga ttgcagtgag  13500
ccaagattgc gccactgcac tccagcctgg tgacacagcg agactccgtc tcaaaaaata  13560
aaataaataa aataaaataa aataaaataa aataaaataa aataaaataa aataaaataa  13620
aataaaaata aaatgaacgc cccaaaaata ttttgggcaa actattttgt gtttcttttc  13680
tttatttatt tatttctttt gagacaaaat cttgctctgt tgccccggct ggagtgcaat  13740
ggcacaatct tggctcactg tatcctcaac ctcctgggct caagcaactc ctgagtaact  13800
gggaccacag ggatgtgcca caattcccgg ctaattgttt tagccaggat ataaatgctg  13860
cctacataga gtttgtagct atctccttga ctttctttat gcagattcct tcacaaactt  13920
ttgatggatt cctttaccaa attctactgt ctgttaaaat cttctatctt tatatcttta  13980
```

```
gtccaaacaa cacgtcattt ataaacctta aaattgtttc tgggcaaata aacaaggcaa  14040

aataggaata tatattttta ggcaatttac ttctgttttg gtctcataaa aaattgtaat  14100

taaattgtag aaaatatttc aattcctctt taatatcctc tcctcacata ctggctctca  14160

acttctaatc ctcctattga aacattgatt gggaggccaa ggcaggcgga tcaactgagg  14220

tcaggagttt gagaccagcc tggccaacat ggtgaaaccc tgtctctact aaaaatacaa  14280

aagattagct gggcatggtg gcatgcacct gtagtcccag ctactttggt ggctgaggca  14340

cgagaatcgc tttaacccgg gaggcagaag ttacagtgtg ccaagatcaa gccactgaac  14400

tccagcctgg gcgacagagt gagactccat cacaaaaaaa taaaaataaa aattgaaatt  14460

tgcagccttt ttaaaacccc atagcctctt tataaaccca aaagcactat caaatttggc  14520

gaggtgtcaa aagaatcaga ggaatgttta caaatacaga tgcctgggcc cacctcagat  14580

atatatatat atatatatat atatatatat attttttttt tttttttttt tttgagacga  14640

tgtcttgctc tgtcacccag gctggagtgc agtggcatga tctcagctca ctgcaagctc  14700

cgtctcccgg gttcacgcca ttctcctgcc tcagcctccc aagtagctgg gactacaggc  14760

gcccgccacc acggctggct aatttttttct attttttagt agagacaggg tgtcaccgtg  14820

ttagccagga tggtctcaat ctcctgacct tgtgatccgc tcgcctcggc ctctcaaagt  14880

gctgggatta caggcgtgag ccactgcacc cggcccagat atattaaatt agaatatcta  14940

gaggtggagc ctgagtatct gtatttttca gagtttcaaa tgatcgttct tcaaatgatt  15000

acactgtgaa gtcagattta gaaatgactg tacccaaggt tggctaaaag atacacaccc  15060

tggttgattc tacctgaaga gagcaaataa gatacacagc aaagttgtag atgttttccc  15120

tgccagtaga atacttgcgg gttaggccat ttaaaaccct gccagagagt tttgaaacac  15180

tgtggagggc tcccaaatca acttgctcaa tggttctcca tcccttcagg ctacttgggc  15240

ttaaagccaa ctgcaagctt agagcctcag agtgacctag gaatggggtg accatatatt  15300

ctaggttgtc tcatacagac tagccagcac tactcagccg caagtaatag catccaggca  15360

tgctcagaag tgtcccattt ggaggaaaaa aacaatattg tcacaaatga attggcaatg  15420

gcctgtctct gattcttata cctggaatat actggaagtc cctactcatg ctattttcta  15480

gcagaatagg caaaatttct acattccagg catgtcaggc ctttccctga ttcctttctc  15540

taatgtcact cgtctgctgt cttttatcac agccattaaa ctgcacccta acttaaagag  15600

gatcccttat gttccaatct actcatccct cagatctttc tttctctgaa acacagggtt  15660

aatgagactg acatccttcc atcacatatt ttctcagcta ctcagtaaaa gatgtaaatg  15720

tttaaaatag tttaaactat ttttcagtta gtccaggaaa cataaaatgg catgcttgca  15780

cataaaccat tgtttagggt gggggaagtg tttttaattt tgccttaaag gaaatctgca  15840

tgatccacag gctatgcaac taccaaggga attagttggt agaacagaat tacacctgca  15900

cagaatacaa atttcctgcc tttcatggga actatgttga tgtttcagat atgaaataca  15960

tcttgttttc tttattgaac ctcgagaaga tgtctcttgt tggtcattat ttcatggcag  16020

gggaagtaca tattcctaaa gacacaaccg agtttccctt taaccatcat tagttgggct  16080

ggccattaag aaccagacgc ttttattttc aaagagactt aagttttgat gttgtacata  16140

tgtgcctaat attctatctc atagcaattt aaaggtgacg ttttaaaaag ctgcattcag  16200

tgtataaact tctcctgatc ccagcaagga tgttgtgatg attttattta aaaaggtaag  16260

ttgtgtctag atatggcagt gggtcatctc atgcatggtg cagatgtcaa acacaattac  16320

atttcttat ttgcaatgac taaaaaaaga agctgagccc aagcagtgag aaagtaggag  16380
```

```
attgggagga caagaagcaa aggaaaaaag taacatgagc accgttctcc ctgtcctgcc  16440
acttgctcca ttatggactg ggctgcgata tctcatatcc cagctccaca actcccaaca  16500
accatttatg tgcatggtgc ttccatgtgt gatgacccaa tcaggctcag gtgtggactg  16560
agtagttaaa ttataaccct tgtctctgaa gagtttaggg cttagtgggg aaacagacat  16620
gtaaacaaac ctgagtgagg tcatgtaatc aaaggacagg ccacagtcaa ccacaaagaa  16680
gagagttctc agcagtctcc aaagccgaac atatgtttac caggaacagg gtcccagcag  16740
agggagcaac aggagcaacc agagccttga ggggtcgtgg cctgttctgg gcaccagcag  16800
tggatcaatg tggccagagc cagggatact agcagaagcc agagcagcag ggccttcctt  16860
gtccagcaaa ggcatttgtc tctttgtagg ccacagcgac ccacagaggg ctttttaggc  16920
cagaaaaaag ccattaaggc cgggcgcggt ggctcacgcc tgtaatccca gcactttggg  16980
aggccgaggc gggtggatca cgaggtcagg agatcgagac catcctggct aacaaggtga  17040
aaccccgtct ctactaaaaa tacaaaaaat tagccgggcg cggtggcggg cgcctgtagt  17100
cccagctact cgggaggctg aggcaggaga atggcgtgaa cccaggaagc ggagcttgca  17160
gtgagccgag attgcgccat tgcagtccgc agtccggcct gggcaacaga gcgagactcc  17220
gtctcaaaaa aaaaaaaaaa aaaaaaaagc cattaaaaag ggagtcatgt ctcttgttgg  17280
tcattatttc atggcagggg aactacatat tcttaaagac acaaccattt cctcttaatc  17340
ctcattagct gtgctggcaa ttaaaaaacc aaaagttttt actttcaaga agatttaaat  17400
aacttctgag ggtgtacata tgtgcttaat attctgtctc acagtaattt aaaagtgaag  17460
ttttgaaaag ctgcatcctg cgcttgtcag aaccatgtct gatgagatat cccctttaaa  17520
gggctctcgg tgcaatgggg caaatcaagg gggtttgtgc aagtgggagt gagacaggag  17580
atggggtgct tcttccagca ctccctatag gctgactgag tgacaaagat cattttactg  17640
acacctccaa tggccctatg agatgggtac tattattatt atcaccatca tattcctttt  17700
gcagataagg aaactcaggc ttagcagatt gccagaacaa cacaggcagg aagtggtaga  17760
gtcagggttt gaacccaggt agtgaaactc caaagcccgg attcttaacc actgtcctcc  17820
agtgcctctc tgtaataagt catgatccca gaagccattg gtgtggccac aatatggaaa  17880
gagatgacag tgtcctcaca ctgggtgagc agcttatggt gattccagac atgatctctg  17940
ttgggagtga caggtctgag cttctaggat cagaccctag atcttggcaa gtggtttgag  18000
gaaagagaag gaccaatgta aaaccccagg cttcaaggaa tgtggatgct gggcagggag  18060
gattaagccc caaagaccag aaatggggta cacagggcag gtgtggccag agtagaacta  18120
gagtagaact tccagtgact agaaatagaa ccagacacgt tgcagtggtg gataaggtag  18180
aatcgcttaa gtctttaaag tgcccctgat cacccaagtt ggccagagac cctggggtgg  18240
ggctgattct gtctggatat acggggaggg gtaagcatga ggaaaggaag caggtcctga  18300
caggtacttt gcactaaaca gctccttata aggttctcaa tttgcctgct caatttctac  18360
agacatttgt gggaccacac cagtacattg taaaagcagg aaacaattga gaaaaacctg  18420
agttttatgt tggtaggaga aatgcctatg gaatatggca aatcgtttct ctgagacttc  18480
ctccctagta attacatatt tgttctcaaa aacaaatgcc agaaggaaga agcagattta  18540
atagtgcatt ttacaaggca ccattaatct ctaagaagaa caattaaaat gtctcagcaa  18600
tcatggttca ctgtatatct tttctatctt cttagaagta atatatggct ggaaatgggc  18660
ataccaaaat atgtcaagga agtggaattg cgttcattag atttcaccac taattatttt  18720
```

```
agttagcttc acagatctct cttccttgct tgttcttgag agcgaggctt tttagtagga  18780
agagaaattg tctaaaacga ttaataacca caaattcacc aaactatttt gggtaagtcc  18840
ctctatttct ctaggtctaa agctaggaat aagagtcatt ctcatataat gtactgtccc  18900
agaaagggca ttatattagt ctgttttcac gctgctgata aagacatatc cgggattggg  18960
tgatgtattt aaaaaaagag gtttaatgga ctcacagttc cacatgcctg gggaggcttc  19020
acaatcatgg aggaaggtga aaggcacatc ttacatggtg gcagacaaga cagaattgag  19080
agccaatcaa aaggggaaac cccttataaa agcatcagat ttcgtgggac ttatcactac  19140
cacaagaaca gtatgggga accgccacca tgattcaatt atctcccaca aaatgggaaa  19200
attatgggaa ctacaattca agatgagatt tgggtgggga cacagccaaa ccatatcagg  19260
cattcaacca atatttggga agcaccagcc ctgcaccagg cacggagcac gtcatgagtc  19320
ctgccgtacc acagcctgcc tgacagacct cagtcatcct ctggagcttg cctctgacat  19380
ctggacctcc tcagaatcag catctcttct ccttgccccc gccatccttt gtttttatct  19440
ctgctgtggc attcatcaaa gccttccaac tatcctgcgt cactgtcctt cagtgtcctc  19500
tctcctctcc cttccttctc accccacttt gtgcctgtat ccttcaagca gagcaatggc  19560
accctcactt ctgtggctgc ccagtgcccc atgcagagtc agacatcaga aaatagatgc  19620
tgaattcagt tgacactctg aaattctttt taaagtaagt taatgtgtgc tttgaatgaa  19680
aagacactgg gattacatta ttgagtgtct ttcttccttt gccacttttg tccctattgg  19740
ccatatttga aaatcttgtt ggaaaaaaaa attcaagaac ttaataaata aattcaaaaa  19800
catttagtct atttacttag gtgaagagaa aactcattct aatatgtgtg tatatttaaa  19860
atatttgtta tttagacttt ttttttaagt ctccaggttg aggaggacac aaatatatcc  19920
tcctaaacct tccagtaagc aagctgtggc atccagatga tctcctgggt catgggggat  19980
aaggctaatc tcctaggtgt ctggcagaca ggacaggcaa attcccagaa tgccaaaata  20040
taccatctgc tgctgtttgg cattgccctt aagtccagag tgtggaggct gggggtgggt  20100
ctctggctac aggagaagtc ccctggcaag ggaggggtga aaggagtgcc tgttgaaccc  20160
cccatctatc cccgcactat ggcaagattg agaggaatga ctagatcagg gaatggcccg  20220
aaagaaaaat ccaaaacctc ccaaccctgg acaaggccac agctttgaga aaccgaagcc  20280
tctgcttcct tctctttggc tttactgctt ctagatgcaa atacacagag ctctgagatt  20340
ttgtgtgctg ggaggtgata actgttaacc ctctattcca atagcacaga aatttctctt  20400
tgcctcagaa gtggtttctc atagatctca gatctctttt caggaaaaag aaaaacaaca  20460
acaataacaa cacattaatg actctgaaag agtcagacac cattaattcc attattggtg  20520
tctgtgccaa gtgaaatgaa cgtcagctct tttcccagat atgtttcctt cttttgcctc  20580
ctataataag agatgatttt actgtaataa tataagactc atcaatttga ctccaaatag  20640
ctttcctatc aacaggctaa gtgtaaaata ccaggatcat tattcagttg agaatagata  20700
gaactaggaa gtagccatca aaaaagaatg atgaggtgca ttgtggattt ggggtgtaac  20760
ttggtatcta acatacagcc agaatcacag tcatagcaca cttaatattt tatcagaaac  20820
ttgcgtgaac aagttaagag gactctcaac ttaaaaatga caccaattgc aatgatcttg  20880
ttaacatttg tgatgaaaat aatagcaaag tgacttagac aaattacaat agcccataaa  20940
aataagataa agtttaacac aaagtaagat gatgttaaaa gacttgaaat aaaacagata  21000
tgttaagtag gcaacacata ggtaagcata taaaaacaag aagataccag gatagagctg  21060
tcatttttgt gggagcctgt gatgtggaaa accaagatgc ctggtgagta taatggatat  21120
```

```
ggaaacccccc cttgtaataa ttccacagtt ccaaggggcc aaggtctcca ggttgagtca  21180
ctattgtaaa cacacccata gatgaatcca catgccatac ctccttgagt aagtggggac  21240
tcaaactagg tctgtcaatt gttccagaaa attaagcatc taaataattt aatgataatt  21300
taaaagaagc acaatgaaat atttcaagga atgtcacata caagattctg tacctcttct  21360
gctttggtta gactcattca gaataggttc ctgctttgat cttaagaggg aggtagagat  21420
tctggagaag ccctagggaa gagcaaaagg aaaggaataa ggagccaaga ggaaacccag  21480
ggtaaggctg aggagggact gtttcgtgta ggtgatttat tggaagggtt ggaaggaaac  21540
atggaatgac aattaccttt ggttattgtc aggttagtat gagacttaca agaaaagcac  21600
tgctcagacg caattaccat tcaagataag aaataatagg aaaggctagc acacttagct  21660
ttttatttaa aaaagtgtta ggtaggctga gcacggtggc tcactcctgt aatcccagca  21720
ctttgggagg ccaaggtgga tagatgactt gagcccagaa gcttgagacc agcctggaca  21780
acatggtgaa acctcatgtc tacaaaaaaa tacaaaaatt agccaggcat gatggcatgc  21840
acctgtagtc tcagctactt ggggggccaa gaggtgggaa gattgcttga gcccaggaag  21900
tcgaggctgc agtgagccat gattgtgcca ctgcatgaca gcctgggcaa ccgagtgaga  21960
gcctgcctca aaaaaaaaaa aaaaaaaagt gttaggtgac atgagagaag atcttccaag  22020
taataagagt ggctaatccc aggaatgtgt caccagaggt tattttgtaa tagtcgtgtg  22080
ttaaattcct tatttgtcta tataacttct caaatccttc tgcctctaca gttatagttt  22140
aactggcgca taacagcctt cacacacagc ctcataatta aacatagaca tacatatgaa  22200
cactttcccc tatgccagca ggatacttgg tttgtttagg ggcaaagagg aattgatgtg  22260
gcgttgtttc aatcagtggt tgaaaatgca agtggtaaac attgaaaaat agaacactgc  22320
aaaaggcatg cattgtatat accaaaaggt cagcatgaag cattatctgt atggcaagcc  22380
tgcccatcca ctccctccta cacgttgcat attcacacag ttttgcagct tgtataaacc  22440
cctattgtga tagaaactca tgaaagagtg tggtctctgc gaaagctggc tgttctgtga  22500
atttagacca gtggttcttc accctggctg caaatcatct ggggaacatt taaaaacact  22560
gttttaaaca ccccaaccct agaaattctg atttaattgg tctgtggtgg ggcccagaac  22620
tctgtattct ttttttaagg ctctcaggtg ctgctaatgt atagctaaaa ttgggtctgg  22680
tttagactct cagaatttct taataattaa acactttatc atgacaagac tttcaggacc  22740
ttaaaggcca cagtggggta gttatcattt cactaggtcc tcatctgggg aggtccttgg  22800
catttttact ggaatatatt tgtcactcaa atttctatta caaaaaattc tttcttgcac  22860
actgctttag caactacatg agatatactt tgtacatagc acaaatctca tatcacttat  22920
gtaatccagc tctgtggttc cttcctttcc tttgcctgtt tatttttaat tcttcccaag  22980
aggaagctta gccagttaga acaccagagt atcatccccc tccccctttt cccacctgag  23040
ttcatggctt agacatacta ggaatgaagc tgacaacatg cactagtttt tttcgaaatt  23100
atgcagcaaa attcccaaag tgcgagtggc cacagagatc ttcacagggc ccagggacag  23160
gcagacatca ttctttctcc agttcctggc acagaaaaga gaccttaggt tactgagaag  23220
ataccagtcc ctcctcagag cagacaagga aactgagcct cagaatgaaa gactgaattt  23280
cagtcctttc ttgaacatgg acctccaggg ttatattggg ccttggaaaa ggcacttaca  23340
ctctggactg tagtttcttc atctataaaa tcaagaggca gaaacagaca atctctaagt  23400
tgcctttatt tataaaattc cgagattcta gttgaccagt attcatacaa gagttgaagc  23460
```

```
ctgtaagagt gcagaaagcc cacacaaaga gacagtggaa gacctctcat cagtagtatt  23520
tttattaccc tcttcctagg ttttaccagt caacatcctc actgttaata tacagaccgt  23580
ggtatttaat taaatcatct ttgaaatact gagctatcaa cagatggcat gctgaatgca  23640
aaaggaccac aaataaatat ttggtactga agaagatcaa gagttggagt tcatttccca  23700
ttctgatctg ggctcagaac tctgtggtct tccctctaat catccttgcc accaaattgg  23760
ctgtatctgt tctaagatgg atcagaaaat cagttccaaa gttggctaca aactttcagg  23820
tttgggtttt gttttgtttt tttgttttgt tttgttttgt ttttgcaacc agccaattca  23880
tcttagttca catgacagag aagtgcataa ttacttgcaa ctttagttag agcagtggcc  23940
ttaagaaggt ctagctaaat aaaaagtgct cagactttct gagtgctgac agttgtcaaa  24000
ttcacctagt tcacatggcc ccatttctat cgtttgtttt gttttgtttt tgttttttaa  24060
cagcccatct gtgagcaata ggatcagatg actaagagct acagggcaga aacactgtta  24120
cttagagtca aattttccca ttacctagct gtaaagagtt tgtttctctc tgactcatat  24180
aaagtttacc atttaggccc ctgcatgatt ttaattccat cacttaacac cccagccata  24240
tgattctgaa ggtaaacatg aaggcgtttg aattccagac cacctaaaca ttcttaagga  24300
aatcatcatc tccacgggca gagctatgcc aaaatctgta ggttttaact caaatttcat  24360
gataagcaaa aattgaatta atttgtcttc cattttgttc accttttttgc caaaattatg  24420
cctggattag aataaataaa ttcaatcaat gaatgcaatc actaattctt acgccagata  24480
ataacacatt cagaattctc ctttccctgg gagattttat caggttagtg ttcttgtaaa  24540
caggagaaag agaaaaatat aacttagtaa atagcagtat tcactaattc attcatttat  24600
tcaacaaata ttaatttact acctactaca ttccagggag cttagagtct agtatcagaa  24660
ataataacca cacacacaca tacacacaca ctacattaaa taaggatgtg ataggctaga  24720
tgaaataaat aaataaataa aaggtccagg tgagaaaaga aggtgggggc tagaaagaag  24780
tcattgaaga aaaaacattt aggttaaaac attatgaata acttagagtg agccaagtgc  24840
agagtgctga aggagtgctc caggcaaaat caacagcaaa tggggagtcc ttgatgtaga  24900
aaagggtttg aggaattgtc ctgggagaaa tactcaagat tccagtctga attctagagg  24960
ttagtgattt agagaggcaa gtacgaaaat gacttcctct cttaccttaa aagtaagtgc  25020
accatagaag gaaatcaccc ttccttggta ataattcctg agtgagcctg agaagccaga  25080
ggccatctct attttatagg cactgtcccc ttttcagtta cccatggcta gctcattgac  25140
cttgtcctgg tcgtttcctc atttcactta ctccatcctc aaaacgtaga cgcttcataa  25200
atattgtata aatgaatgaa ctcacaaagt cacagtacag caaggcaaaa gtgcctgcaa  25260
taaacaagca ttctaggcta gaaatatttc tcaacttcaa attgtgtctt attacattgt  25320
attccgattt tctagagtgg tagttctcag tcaagggaaa gtttttcttc ccttccaggg  25380
gatatttggc attgtctgga gatagtttta gttgtcacga tttgggggat gcttctggct  25440
caacttgggt agagaagcgg ggatgcttat aatcatccta cagtgcacag gacagtaccc  25500
ccacccacac tccagtaatg aagaatcatt agacctaaaa tgttaatggt gtccaggtag  25560
aaaaaccctg ttgtagaggt tggggactgc gtcttgacag ccacattata cagtgtatca  25620
aacaattctg tataatgggc tgtaattatc cttgcctaga ttttgcaaga accctagtgt  25680
gtatcttttt cctcacttgc caagcaatgt tcaaacctgc agagatttat ttcattcatt  25740
ttctgtgtgt ttagtaaaca gactagaagc actggaggaa aaaatattcc agcaatgagg  25800
taagacgaaa gctattagta accctagttt aacttagctg aatagtagga aacaacctct  25860
```

```
accgtgagga agtgtattgt agaaactgaa aagacgctaa tgatgtttaa aaagctgtag  25920
ttcaaacaaa tgtgcatgca gaccaatggg tagactgaaa atgatgaaga catttccgtt  25980
tcttgtgtct ttgatagaaa agaaagagct tttattttct ttagtgtggc aatcattcag  26040
atttgtccca tgacatgccc agaaggttga agaataacaa actcccaagt gtaaacacag  26100
aatttagcga agaatccagg cctctggatg aatccctgta attgcatgtt tggataaaat  26160
aagattttca tacattaaac aaggtaggat ttttctatct gggacggaac tttcaacact  26220
tggaggggtt gtagttattt ctcctcaaag atggcaaaca tgagtgcccc gagttatccc  26280
tcctctctgt tcaagttcgc taactaatca cccagtatcc atgctatcgc tggcccttct  26340
gtggcctatt tttatactgt tcactgttca gtgtcacttg tttggtaaca ctcaacatca  26400
acatgtgcta ccaaattgac accagaggac aaaaaagaat caagatatgt acagcctgct  26460
ttgtactgag ccagctgcca ctagatgttt tttgtgataa tgaacacgtg aggccatgtg  26520
gacgcgagag atggctccgg gttccctcag acggctcaca gccagctggt ctgcagtgcg  26580
gttttagatt ccgatgtggg aaccccataa aaaagaatat gcaggccagg cgtggtggct  26640
catgcctgta atcccagcaa tttgggagcc tgaggcgggt ggatcacctg aggtcaggag  26700
ttcgagacca gcctcgccaa catggtgaaa tcctgcctct actaaaaata aaaaaaaaaa  26760
aaattagtca ggtgtggtgg cggatgcctg taatcccagc tacttgggag gctgaggcag  26820
gagaatcgct tgaacctggg aggcagaggt tgcagtgagc aaagatcgca ccattgcact  26880
tcagactggg caacaagaat gagactctgt cacaaaaaaa aaaaaaaaaa gtctgcaggc  26940
tgcataaaga ggtatgaaaa tgttccagaa atcccaaatc ctatccctga ggttcatttt  27000
ggtgagggaa tgtgtgtgca ttttctaggg cttccctaaa aaagtatcac aagctggatg  27060
gcctaaagct acagaaattt cttggggaca aatttcatga ttctggaagc tagaggtcca  27120
aaatcaaggt gtcagcaagg ctatgctttt tctgaagcct atagggaagg ccttccttgt  27180
ctctcctagt ttctggtggt ttgctggcaa tgtttggcat tctgtggatt gcagctacat  27240
aactccactc tgcctccatc attaatggcc ttctgcctga gtgttttcat atgaccatct  27300
tcatataagg acaccagtca tatttgatga gggttccacc ctactccagt atgacctcat  27360
cttcactaac tacatctgca atgaccctat atccaaataa agtcacattc tgagtgtctg  27420
gggattagaa cttcaacaga gcttgttgaa gggggcacaa ttcaatgcat aacaggatgg  27480
aaactagaaa cgggtatgtt tttatcagtg tagaaagatt tagcttaatt tttcaaagtg  27540
taataaaaac cccaggaaaa ctcatactcc ctcctaagaa gagcaaaaga tggagaaacc  27600
cgatggttac cttcaaacaa aaggaaagga ggaataagat gaaaaggaat taatccaaag  27660
caaagagagt ggcttatatg gaatgttggt gcaactttct ctgacacatc tgtgcactca  27720
tcagctgggg catcatctcc ctggggtaca tttggtcact gtgtgcctca tggtaataaa  27780
ctccagaagc ctcattgact tgctagagat gagctcatcc ttcttgcttg cttaatggca  27840
aaatacaaaa taagcagtca ctgacatgga acgatttcag gaatgccaaa aggttctcct  27900
tttccaaaat atctcttcca tcttcccaat actgttactg acatcactaa cacctctcca  27960
cttccggttg agacacctgg gccagagctc ctgatgtggc aggcagtgcc ctaaacgttt  28020
tgcataaatt aactgatgcc cagagcaaca accctaagat ataggtacta tcataccgca  28080
tcttacagat aagaaactta ggcacaaaga ggtttagtag tttagatgag ataaccctga  28140
tgagcagaga ttcgaaccca gcctccatgc tattaaccag gacatcatat tgcctttcat  28200
```

-continued

```
acatgctctt caaaggcaac acagtaatcg attatcacac tcactcacat ctgattgtca  28260
catttttcag atctgctctc ctagcagaga atgaagccta aggtatcctt gtttctcaaa  28320
gtgtcctccc cagaccagct gcatcaaaat gaggggatga ggtgcaaatg cctggaccct  28380
gcccttggag cactgattca taatctcaag tcccaagaat ctgcatttta acaagcatcc  28440
ccagaaattt cttaagtata ctaatgtatg ggaaccactg acactaaaga aatggaataa  28500
ggggaacgta caatgttaca gtaaaccagg aaaagccaga aagacatgac aacacagtga  28560
ggactctggt agccaatggt cagtcaaatg cccaggggcc ctggccagaa gagagttagg  28620
ttgctgagga gtaagagtga tgctgaatgt ggaggcttga gagcagaagg aagccagcca  28680
gctatatcct cttgcttgga tcacacaccc tttccttggt ggaaatggtt atttgcagag  28740
ttagagaagg catgttttac agtttggatg gcaggtatgg atgtagacaa taaagagcaa  28800
ccagagtcca tgggttcaga aatccccatg tgtttctgtt tgaatgagac gcttgcataa  28860
acagcacaag gagtttgggg tggggttaaa gagaatggtg tggtataggg agagctgaat  28920
gaggaactga gagagcaaaa tcctgtgttt ggttcaatca ctgattacaa cctccctgag  28980
gctcggtctc ctaatctgta aaatgggggg aaataatacc tgccttgcag gtcctcacac  29040
acagggcatg atgtgaatcc actgaggcat atagcactgt gtaacatgag ttattgctat  29100
tccaaggccc gtaaaaggct cttgccttgg aatatatctg ccacaccaat gcctgcagtc  29160
cattaatgac acataaagga cactggagat aacgatgtcc cttgttctat gcatccctcc  29220
cacccatgcc agaaaagaaa acacagtcac ctgaagtcat tctaaagagt atgcctgcct  29280
cttttcctgc acagacacat atacacagac acgcacatac acagaccatg cacatacaca  29340
cacatgggaa aacatgagga aaagtggaga caagaggcac caaaggacaa agtcactttt  29400
gtcgcctgtc ccttccccag cagggctggg cctgggctgc ttctcctgcc tcctccctga  29460
agccccctcc tcatcatatt ccagtgcgtg tccaccactt tggggccagg tctacacaac  29520
tgcagtgatt caggtcacgg gagaaaaccc aaacaagcac aaaacatgct tcaacctata  29580
ttttctaaat tgtttttctt taaaggtgaa gacttctgag cttgaattat ccccttgtca  29640
gtgggctttc catgctgtcc aagtgaccta agtgataatc aacctccatt tcattttgag  29700
aatggttgtg gtattttaga gctatggtga ataagaaaat catttaaaat aaaatgattt  29760
ttatttattt attgttttta tttattttat cttaaatgaa ttttaaatca tttaaaataa  29820
aataatggga taaaagagga tgctaaaaat aataaatata tatgtatcaa agtgtgcttg  29880
taataccagg caaagaatta ataagagata atattatggt tggtgaaatg ttatgtatgg  29940
ctacatcctt tcaatgagca tttatagttc ctttaaaata tgcctactga agaaatattt  30000
acatgctaat taacatgtgc atagtaccac taggtattat agaggatacc agatgtttgt  30060
agtagacaca gaccttgccc taagtcctgg tcttgatgta gtcacttttt agtcactaca  30120
ggtgactaca tttagtcact acaagtgacc ttccttcaat ggggaaataa aggactttac  30180
aaaagacgta gaagacaatt cttaatataa aagtgattta gatcttcaca agtttgtgaa  30240
gagaagcaga tgagtgaaat agaacactat caatgtaaaa tattattctg aggcctctgt  30300
aatgactggg aagcaacaag agggaggtca tttcagagag agaggctcta ggttccaagc  30360
tggatgctca ggtcagtgac tgcaggtccc ctccacaccc atcaccccac accctaaccc  30420
tcttcagttg ctcacaaagg tagataaata cccacatttt tgccctcttc catcttgaaa  30480
ccctggaaac ccttgcttcc gccaggggag gttacttagt atctgtcacc ccaagggaac  30540
caacgtcgaa gcccaagaat aagagtcaat actcctacca gaggtttaca tttttcccag  30600
```

```
gggtctaggt ggatattcct gggaaccccc gtcaacacag gcatctacag tacaatccag  30660
gcctcctgtt ttcagcaggg gctgcaagag cactgcagcc ttttccccag aggtgtcagt  30720
ttggcccagt aaagattgcc cctgagaaaa cacatgggca attagagcaa agttcctatg  30780
ttctggtaac atttaattgt gctatttctc aacctcctct gcacccacac actcacacac  30840
aacatttatt ccactgactt caaaggaagc tcaacgtgtt aaaaatatgt gtgggaacaa  30900
agaagggagt ttgaaattgg tctaaactct gtataactgg gtttgacacg tacattagga  30960
ttttacaagt atgtatttaa tctttttta aaaaaagcgt ttacataggg ttcagaataa  31020
tgacaataaa tcaacatttc tattgtccat ttgtgtgttt tcatagtaaa taatgctcat  31080
ttatccttaa ccagtaatac atacttatgg gcttaaatta gcaaaagcct ctcaaaaagt  31140
agctccactc atttatccac cagtgtccag atgccatcca gcacatgagg agctcccaga  31200
aaggagcagg gaacaaacta gggctgtcag gagtggagga gaaagaatgg catatgcaaa  31260
aaggagctgt aattaaatcc aagggaacat ggcacactct agtcttttgc acgagacaaa  31320
gggcaatcct ggtaaaaata cagatcccca ggccccaccc caaagagtct gatctgattc  31380
tgaaatgggg ccggagaatc tgcattttaa caagcacctt caccaggtga tccttttgct  31440
gagaacccct gagaaatgag aaccctgtgc tagtgctgaa tggagcatta tattccagag  31500
ttgaagtttg gtgatcagtt ttccagatgg agctggtcct tggtgcatac ctgggtataa  31560
atccaagcca attcaggtat atgagctgat atttcaaccg aaacactatc tatagcctaa  31620
attttttcta atattctgtt tggtatgaat tctagaaagt tgtaaatgct atatttcctt  31680
ctcatctatt tctggacttt gtcccaagac caaatcccag ggcatctgat agacattcat  31740
tgcatacatt tttctgtaaa catgaaaact gaattgtcta atagaaaagg gcaaggaagt  31800
agaaaataag aaatcatcat cagaagtggt ttgttttgga attatattgt ccagctgcat  31860
aacaaatcac ccccaaaatt gagtcgctta gaacaacaaa cattgatcct ccacagtttc  31920
tgtgtgttag gaatcaaagt gatttaattt aatggttctg ctcagggtct ctcgggggct  31980
gcaatccagg tctcaggctg ggatcctttc aaggctgagc tggggaaaga tccatgtcta  32040
agctcactca catggccgat ggcgggattc agttcctctt aggctgtcag actgagggcc  32100
tccgtgtctc agtggtttta gccagagccc tctctcagtt cctttccaca tgggcctctc  32160
cacagggcaa ctcacaacat ggcagctggt ttccagtaga gcaagcgagt gagagaacaa  32220
gaaaggcaag caaggtgaat gtcccagtct tttgtaacct catctcagaa gtgttaaccc  32280
atcacttttg ccatgtttta ttatttagaa gcaaatcact aagtccagcc cacaattaga  32340
gggatggcat tacacaaggg aatgaacacc agcagacagg gtcattgaaa gccatcttag  32400
atgctgtcta tcgcatctaa gtgtgatttt tccagatgaa aagaatatat taatttgttt  32460
cagtcttagt cgatgtgcca tcccatttgt gctttgctaa aacttgtatc aatgtaaagc  32520
aaacattttc tgatacaatt taggtagtgt attgtggtaa tagagaccag tagtgttgaa  32580
aagatatgtt gaggtcagaa attaagctca tgtttctaaa agaggagata tgtacaacta  32640
ctatgcaagc caacaggaaa gagtgtttta agaatgcttt ctgctacagg taactaaaaa  32700
cctaaacagc tgtggcttta aaataaaggt atatctaagt cacataagca aaagtctagg  32760
ggtgggcagc tgctggcatt gcttcagtag cttgataatg gcaaaagcag catctcttct  32820
atttccttgg ccttctaatc atgcatgtca cctcacaatc acaacatagg caacacctca  32880
tattctaagc aagatgaaaa gggcaaagag tcatgccata tgcctctgtc tcttttcata  32940
```

```
aggaagacaa agcttccctg gaagtcccct ctagcagatt tcacttagat ctcattggcc  33000
agaactgagt cacatgcctg ccttaaacca atcactcacc aagaagacta acattatcat  33060
ggcaagtcta aaccaactgt gactcatctc tgaaatcaaa ggattattac cattacccga  33120
atccatcagg atcctgttgg cagagaagtg ggactgtaaa ttttgagcag gcaacaaaca  33180
agtcttctgt aaacttctta tgtgttgttt tttatgtgtt ctatatatcc agtagaatca  33240
caatttccaa taacagtcta aaaagatatt ttccaataga aacagaatgt gtaagatcat  33300
tacttatgaa atcccaaatg tacttaaggt ttccttcttg aaaattcctt attcaaaata  33360
aaatgtccag attttgaaac ccagaaaaga ttctatattt taaaaatcct gtgcacatgt  33420
aaactgtttt tcaaatattg ccttcagata cattgaacag aatgaaatct tctgagattt  33480
actacatcag ccaagtatta tcaaaacaaa caggacagat tgcttttctt gacgtctgct  33540
gcttgatttg tgttaactca tgtttctgaa attgtagtat cataagccaa tgctgcacaa  33600
aggtatttca tgtcatttat aaaaatctag taatgtaaac tgttaactcc ttataaagca  33660
tctgttgaca cacaaaaata tcactgaagt gcatttatgc ctttcttctt taggtctgca  33720
taatacttcc ctccagaagg ccaagttgtt ccataaatta cagaacagaa agttggttgt  33780
gggaggaata gctcaacctc atctgaggca tcccactcta agaaactaat ggcacctaca  33840
cctcttgggc attgagtttt taagcccatt tttaattctt gttctgctca tattctaagt  33900
gagcacataa agtgctgctc caagcaagac cagcccttgt agaagggcaa gtgcagtcag  33960
tcccctagga aacgggactg gggagtgatc gtttcaatga gagataaatc aaactgatgc  34020
taaacatgaa caatgagccc attagagatt gtgagaaaga ggcatcatca tccactcaac  34080
aataggcctg tgggacctct tgatagcctg aggatgttta atttcaggtg caggtatcca  34140
gaatgtagca gctagactga tcaaggatgt gtgatgacag caagcagtag tggaagagcc  34200
caggagagtt cctaagcctg aattgcaatc ctgtgctgcc ataaaatggg aagatatact  34260
tggtccagtc atctgacagc tttggtcatc aatttctcta tctcatatgt gactctattg  34320
ctttaagaat ccctttagct ttaaatatct atgaatctgc tgaagcagct gtgctttgat  34380
tgatgtggat ctctgaactc ccttaaatac aaagaccaat tatttagccg agctttgttg  34440
gattcagtgc attctgaata catgtcaaaa tatacttgga tttgtaaaaa atattccttc  34500
ctgttttttt caccatagat agatgtacaa aaatgtccgt gttcacaccg tggaaaggac  34560
atttctcata aactcacaca gagatacctt tcaagtcaat gccttagaaa gcaatgagag  34620
atttaaagga gacctagaga tatgaatgga gtaggcagag aaggtatgtg aggagaatga  34680
tgtaacttcc tagggaaaaa gtatgaagca caaggctgga catagacctg ggaatcagga  34740
aattagagtt ctaattgcag cttttccatt gattcacttg ggatcttgag aatatctgtc  34800
tcattttaat cattctgggc cacagtttcc atatctgtca attagagtaa gagtccctgg  34860
ctgggtgccc aggattgtga gaacatacca ttcagagcca taaaaatgca atcagtacca  34920
ataatgtact agtaccagta cctaggatgc aaaacatcct agatactagg tgtcctaact  34980
taaagtggaa acattaacaa gagtaattct ttgaatcatc aaactgggaa tattttagga  35040
agcatatcta tctgggtgaa aactaagcaa ataagacaat tgtaaaggct tgtgatctca  35100
ggaatacaaa ggcaaaaatg cgcagacttg aaatatgaca agttctagtt ttgtcactta  35160
gcatctctgt gaccttggat aatttcttaa cccccggcag tattctcatc tgtaaaatgg  35220
gaataatgac atgcacttca gtggtttgtg gtgaagatta ttacaaatag aaattagctc  35280
ttttgagcca ctggtggggt ttaaattccc agcccttatg tgctttgcag ctgttagttc  35340
```

```
ctcttattac aattgtctat ttaaaaacct agtcacagcc cggtgcagta gctcacgtct  35400
gtaatcccaa cactttggga ggccaaggca ggagaactgc ttgagctcag gcgttcaaca  35460
tcagcctagg caacatagtg agaccctctc atctctacaa aaagcaaaaa attagccagt  35520
gatgcatggc tgtagtccca gctattctga gggctgaagt tggaggattg cttgagccca  35580
ggaggtcaag gctgcagtgg gcagtgatca tgccgctgca ctctagcctg gatgacagag  35640
caagaacctg tctccaaaaa aagaaaggaa ggaaggaagg aaggaaggaa ggaggaaaga  35700
aaagaaagaa agaaagaaag aaagaaagaa agaaagagag agagagagag agagagagag  35760
aaagaaagaa agaaagaaag aaagaaagaa agaaagaaag aaagaaagaa agaaagaaag  35820
agaaagaaag aaagaaggga gggagggagg gagaggagag aaagaaaaag gaaggaagga  35880
aggaagagag agagagagag agaaagacct agtcaccaaa agcaagagat tttttaaatg  35940
ctactatttt ttgggcattt actaatcata ttgctatgct ctgcacccaa gctaagtaat  36000
ttaaataaat tatctcatgt actcctctaa aactaattac tgctgtgtaa atggaggtag  36060
aaagaaacta agctttattt ctgcctctat tgtttcttta acctgccttg cttccttttt  36120
cagttgcacc taattggctg tacttttagt tttctttaaa actgccttaa atttcaaaga  36180
ctaaagcagc aataactaac tgaatatatt tatataacat gttatttttg tcatgttgct  36240
ttccacccct ggagacctgc tctaaattca cttggacgtt tgaggataaa tcatgctcac  36300
tagcagtttc tgaaaatgca gtttcactga aaatgcaggc atccagaaat ttagtaagca  36360
acttaaaaga aagtgtaaga atctcctatg tattcattga aaaataattt gaatttatgc  36420
ttagaaaaat agaattatta ttaagaaatc ttacacactc atgtttttaa atatcttcac  36480
taaggaccaa ttgtgtatat ggtgtaacac tgtcctcaaa gaacatgccg ggagaattgt  36540
tgcagttacc agagggttaa atttggcaaa ctctttttta ttaacgtgcc ttttaattat  36600
gaaatagcat actcacctta gataaaattt gaaaaccatt tttgtaaagt ggtacaatat  36660
tgaagaaagt tgataacttt cagaccagat ttaagcctca aatctacctc tcttttacct  36720
ggacaactca ttagcatttc tgaacctcac attttttcta taaagtgaga atactatatt  36780
atagagttgt tgtcagttaa atgagaacag tgtctgatca caactagtca acaaatgttc  36840
acaactcttc ccctcctagg aaaagaatct caaggcagac ctgcttcggg tctgctctgt  36900
aaagaggtag gaatcctctg ctcccggtaa attgcttcct aaccttcttt ggtaatagac  36960
tattttttaa taaaggtgat ggatcatttc ccattataca ctcaaaatgt gtgtccattt  37020
cagggcagtc atggatgacc attgcccatc ttttgacccc agattaagaa cacctgctgt  37080
agtattttaa ttctgccttc aaatcctctt acaaaacaaa gacatcttta aaaaataaaa  37140
ttctttaggt gtcttgcagt tgaatgcagg aaaaccagag ccccttattt ttgatagttt  37200
tgggaagaat gcagtgtcag aacacaaacc cataatagac aaataatttg cacagaaact  37260
tcataaaagt attgacctga tttgccatgt atttgccacc ttttaaaaca cacaactaaa  37320
tgtttaccct gtgtctagat ccaaatgggt gaagaaaaat gagtgacaat acatctactt  37380
aagctcactt acataattgt ggccatgccg tttttttcac attacattat tagaacattg  37440
gacaataagt caagaaacag aatgttctac aaaataaact ttaaaaattg gtaagcatca  37500
tgtgcttttt ccagaagaca ttttattttg ttgaatcaaa ggtggctctt tggcactgag  37560
tagctccgtg gagtcatggc agtcctcatt ccctaatcct gagcctgcct gagtcgctgc  37620
tgtcagtcat ccacttgttg ggatttcaaa ctgcattaaa tcccctccta tagctgtcac  37680
```

```
tgccaagcag ttgcactggc tctgtcctac ctttctgttg gtaattctgt ttttaatcct  37740
gtgcttcagt gtagtttata taaatcttta cagagggata aaacttcctg taattaattg  37800
tttgggtgaa catgtacctg ggagagctat tgggaaaggg gccaaatttg cattccagct  37860
cctttcatcc ccacccttga gctaaccaag tcctgtggat tcttccctta gcatctctgg  37920
aaccttcttt tcttttcttt tttttatgac cacctttcca gtcctggccc ttcaaacttg  37980
agtgacagca acagtctccc tgccttgagt ctctttcctc cttctcccag tgtgcatacg  38040
gttgtcaaac tcatcttgat aaactactgc atcgattgtg gctacactcc cctgctccca  38100
catcttccat agaccccact gtctgtaaaa taatattcag tctggcctca acctgtcttt  38160
ccagcctcgg tgacacaggt ctattctgcc tgagacactt actatgacac ccttgcttgt  38220
tcctggggct ttgacacatt tccaacgtcc cattgttctt cctctccaaa tcagccaatt  38280
gcccaagccc tgctcaaatc tcccacctca tgaagccttc ttgatgcctc ccagcacacc  38340
atgatctaat ttcctgaagt aattatgcta attgggcatt tgaagaattg ttaaccgatt  38400
atcaactaac tgccccttaa cattgcatgt gtagttgtct tcaaaggcag ttaaattatg  38460
tcatgttcct tacattgtac tgagtgcctc gtatccttat ccatgtttgg gggttttact  38520
ttaagtcaag aaatttaatc acatccattt ggtttttctct agagctgtag ttctcaacct  38580
tttgtgtggt agagaaacac ctagagaaca tgtttaaaaa tatcctgggt tccacccttg  38640
agagataata aggtccaagg ggaacccaaa tatctgtgtt tcaggtcagc ttattggctc  38700
atcctattat accaactcct cagaaggcca aggtgggtgg attccttgat ctcaggcgtt  38760
caagaccagc ctgggcaata tcgtgagact ccatctctta aaaaaaaaaa aaaaaaggat  38820
tagccaagtg tggtggcatg aacctgtggt cccagctact taagaggctg aggcagacag  38880
attgcttgag cctgggaagt cgaagctgca gtgagccatg atcatgccac tgcactccag  38940
cctgggtgac agagcaagac cctgtctcaa aaaaataaaa atgaaaaaaa tctgtgttcc  39000
caagttccaa gtgatgctga tgctgctggt tgcctttaag catctcacaa agaacgaact  39060
cataaatgct aatacagtat atgtctatgg atactgaata gtgggttttt tttctctttt  39120
cttctattct gtgctcatgt tgtgtcactt cttcctttta gattgacttt gaagatgtga  39180
ttgcagaacc agaagggaca cacagttttg acggcatttg gaaggccagc ttcaccacct  39240
tcactgtgac gaaatactgg ttttaccgct tgctgtctgc cctctttggc atcccgatgg  39300
cactcatctg ggcatttac ttcgccattc tctctttcct gcacatctgg gcagttgtac  39360
catgcattaa gagcttcctg attgagattc agtgcatcag ccgtgtctat tccatctacg  39420
tccacaccgt ctgtgaccca ctctttgaag ctgttgggaa aatattcagc aatgtccgca  39480
tcaacttgca gaaagaaata taaatgacat ttcaaggata gaagtatacc tgattttttt  39540
tccttttaat tttcctggtg ccaatttcaa gttccaagtt gctaatacag caacaattta  39600
tgaattgaat tatcttggtt gaaaataaaa agatcacttt ctcagttttc ataagtatta  39660
tgtctcttct gagctatttc atctattttt ggcagtctga atttttaaaa cccatttaaa  39720
tttttttcct taccttttta tttgcatgtg gatcaaccat cgctttattg gctgagatat  39780
gaacatattg ttgaaaggta atttgagaga aatatgaaga actgaggagg aaaaaaaaaa  39840
aaaagaaaag aaccaacaac ctcaactgcc tactccaaaa tgttggtcat tttatgttaa  39900
gggaagaatt ccagggtatg gccatggagt gtacaagtat gtgggcagat tttcagcaaa  39960
ctcttttccc actgtttaag gagttagtgg attactgcca ttcacttcat aatccagtag  40020
gatccagtga tccttacaag ttagaaaaca taatcttctg ccttctcatg atccaactaa  40080
```

```
tgccttactc ttcttgaaat tttaacctat gatattttct gtgcctgaat atttgttatg  40140
tagataacaa gacctcagtg ccttcctgtt tttcacattt tccttttcaa atagggtcta  40200
actcagcaac tcgctttagg tcagcagcct ccctgaagac caaaattaga atatccatga  40260
cctagttttc catgcgtgtt tctgactctg agctacagag tctggtgaag ctcacttctg  40320
ggcttcatct ggcaacatct ttatccgtag tgggtatggt tgacactagc ccaatgaaat  40380
gaattaaagt ggaccaatag ggctgagctc tctgtgggct ggcagtcctg gaagccagct  40440
ttccctgcct ctcatcaact gaatgaggtc agcatgtcta ttcagcttcg tttattttca  40500
agaataatca cgctttcctg aatccaaact aatccatcac cggggtggtt tagtggctca  40560
acattgtgtt cccatttcag ctgatcagtg ggcctccaag gaggggctgt aaaatggagg  40620
ccattgtgtg agcctatcag agttgctgca aacctgaccc ctgctcagta aagcacttgc  40680
aaccgtctgt tatgctgtga cacatggccc ctccccctgc caggagcttt ggacctaatc  40740
caagcatccc tttgcccaga aagaagatgg gggaggaggc agtaataaaa agattgaagt  40800
attttgctgg aataagttca aattcttctg aactcaaact gaggaatttc acctgtaaac  40860
ctgagtcgta cagaaagctg cctggtatat ccaaaagctt tttattcctc ctgctcatat  40920
tgtgattctg cctttgggga cttttcttaa accttcagtt atgatttttt tttcatacac  40980
ttattggaac tctgcttgat ttttgcctct tccagtcttc ctgacacttt aattaccaac  41040
ctgttaccta ctttgacttt ttgcatttaa aacagacact ggcatggata tagttttact  41100
tttaaactgt gtacataact gaaaatgtgc tatactgcat actttttaaa tgtaaagata  41160
tttttatctt tatatgaaga aaatcactta ggaaatggct ttgtgattca atctgtaaac  41220
tgtgtattcc aagacatgtc tgttctacat agatgcttag tccctcatgc aaatcaatta  41280
ctggtccaaa agattgctga aattttatat gcttactgat atattttaca attttttatc  41340
atgcatgtcc tgtaaaggtt acaagcctgc acaataaaaa tgtttaacgg ttaaacagtc  41400
agctttatta tttttttccca aaacaggtgt ttatgtgtca gagtctgtgt atgtctatgt  41460
atttgtatgt aatgagcatg tgcatagtgt gtgtatgtgt ttgtatgtgt ttgtgggggg  41520
taatggtctc ccactttaaa attattacaa agtcacttag gatatttctg ctaaggtcat  41580
caccatttat gagttgcttc agataaaagt tataattaat aacaaagttt ttttagcaat  41640
ttgcccaatg ttttatatgt catctaattt gagcccccag caagcttgtg tgatggatat  41700
taatactctt aacttagcga aagacacaat ttgcattcgg ggccaatgcc ttcaactttg  41760
ccatgcctta actgggtttt aaagaggtat attgcagtct caatttatgt ttgttgcttg  41820
gctaagttta ccttcaggac tcctatatta gggttctcca gagaaacaaa accaatagga  41880
gatagttgga gatagataga tagatgatag atgatagata gatagatgat agatagatag  41940
atagatagac agatgataga tagatgatag atagatgata gatacataga tagatagaat  42000
agagatgata aagatagaga gatgaagata gagatagaga tggacatgga gatggagata  42060
gagagatgaa aatatatata tagagagaga gatggagata gagatatata gggacagata  42120
gacacagaga tagaaataga gatagagata gatggagata gagatagaga tatatagaga  42180
cagatagaaa tagagatata tagagatgga gctacagata gagatagatg gagatgatga  42240
gaaagaggta gatggaggga taaagatata gatggagatg acaggggtag agatagagat  42300
agatggagat gatagagata cagagcaaga gctttattac aaggaactgg cttacacgat  42360
tatggaggct gacaagttcc caaatctgca gggtgagtca gcaagctggg aacccaggag  42420
```

agctgatgat gtagttccag tccaacatca gcaggctcaa gagccaggaa aagctgctat 42480
tttagaccaa gtccaaaggc aggaaaaaaa ttcaatgttc cagtttgaag gcagtcaagc 42540
agaaggaatt ctctcttagt tggtggtcag ggtcagggtc agcttattct atgcaagcct 42600
tcaactgatt agatgaggcc cacccagatt agggagggca atctgcctta ctccgtctat 42660
cagtttaaat gttaatctta tccaaaagca ccctcaaaga aacgttcaga ataatatgtg 42720
accaaacata tggacacccc atgacccagt caagttgaca caaaaagtca atcatcacag 42780
cttccagttc catctacaaa aataactata tggctttgga caacttttat tccatattgg 42840
taataaatag cttcatacat cacacattta gcctgtagtc ctagcagttt ggaagcccaa 42900
ggctgagact gggggatcaa ttgaggccag gagttcagac cagccttgac aacgtagtga 42960
gaccatcaga aaaaagaaaa gaaaggaaag gaaagaaagg aaaggaagaa agaaagaaag 43020
aaaaagaaag aaagaaaaga aagaaagaaa ggaagaaaga aagagagaaa gaaagaaaga 43080
aaaagaaaga aaagagagaa agaaagagga aggaagagaa agaggaagga aggaagagga 43140
aggaagagaa agaaagagga aggaaggaag gaaggaagga aggaaggaag gaaggaagga 43200
aggaaggtag gtctcatacc ttccctgatg tgggtgctaa tggtcaagca ttctatgttt 43260
taatttataa tccatatttt taacattggg tggaggggag aagtaaagag agacactctt 43320
aacacagaag gctgaaatca taaaataaaa aggtcatggc aataaacaca caaaatatca 43380
aacttctata tg 43392

<210> SEQ ID NO 16
<211> LENGTH: 2338
<212> TYPE: DNA
<213> ORGANISM: Homo sapiens

<400> SEQUENCE: 16
ggcgcgcggg aggcgcgcag agctttcggg ctgcaggcgc tcgctgcgcc tggggaattg 60
ggctgtgggc gaggcggtcc gggctggcct ttatcgctcg ctgggcccat cgtttgaaac 120
tttatcagcg agtctcgcca ctcgtcgcag acgcgagcgg ggggcggggg cgcggcgagg 180
cgccggcggc cgtgacgagg cgctcccgga gctgagcgct tctgctctgg gcacgcatgg 240
cgcccgcaca cggagtctga cctgatgcag acgcaagggg gttaatatga acgcccctct 300
cggtggaatc tggctctggc tccctctgct cttgacctgg ctcacccccg aggtcaactc 360
ttcatggtgg tacatgagag ctacaggtgg ctcctccagg gtgatgtgcg ataatgtgcc 420
aggcctggtg agcagccagc ggcagctgtg tcaccgacat ccagatgtga tgcgtgccat 480
tagccagggc gtggccgagt ggacagcaga atgccagcac cagttccgcc agcaccgctg 540
gaattgcaac accctggaca gggatcacag cctttttggc agggtcctac tccgaagtag 600
tcgggaatct gcctttgttt atgccatctc ctcagctgga gttgtatttg ccatcaccag 660
ggcctgtagc caaggagaag taaaatcctg ttcctgtgat ccaaagaaga tgggaagcgc 720
caaggacagc aaaggcattt ttgattgggg tggctgcagt gataacattg actatgggat 780
caaatttgcc cgcgcatttg tggatgcaaa ggaaaggaaa ggaaaggatg ccagagccct 840
gatgaatctt cacaacaaca gagctggcag gaaggctgta aagcggttct tgaaacaaga 900
gtgcaagtgc cacggggtga gcggctcatg tactctcagg acatgctggc tggccatggc 960
cgacttcagg aaaacgggcg attatctctg gaggaagtac aatggggcca tccaggtggt 1020
catgaaccag gatggcacag gtttcactgt ggctaacgag aggtttaaga agccaacgaa 1080
aaatgacctc gtgtattttg agaattctcc agactactgt atcagggacc gagaggcagg 1140

```
ctccctgggt acagcaggcc gtgtgtgcaa cctgacttcc cggggcatgg acagctgtga   1200

agtcatgtgc tgtgggagag gctacgacac ctcccatgtc acccggatga ccaagtgtgg   1260

gtgtaagttc cactggtgct gcgccgtgcg ctgtcaggac tgcctggaag ctctggatgt   1320

gcacacatgc aaggccccca agaacgctga ctggacaacc gctacatgac cccagcaggc   1380

gtcaccatcc accttccctt ctacaaggac tccattggat ctgcaagaac actggacctt   1440

tgggttcttt ctggggggat atttcctaag gcatgtggcc tttatctcaa cggaagcccc   1500

ctcttcctcc ctgggggccc caggatgggg gggccacacg ctgcacctaa agcctaccct   1560

attctatcca tctcctggtg ttctgcagtc atctcccctc ctggcgagtt ctctttggaa   1620

atagcatgac aggctgttca gccgggaggg tggtgggccc agaccactgt ctccacccac   1680

cttgacgttt cttctttcta gagcagttgg ccaagcagaa aaaaaagtgt ctcaaaggag   1740

ctttctcaat gtcttcccac aaatggtccc aattaagaaa ttccatactt ctctcagatg   1800

ggaacagtaa agaaagcaga atcaactgcc cctgacttaa ctttaacttt tgaaaagacc   1860

aagacttttg tctgatcaag tggttttaca gctaccaccc ttaggggtaa ttggtaatta   1920

cctggagaag aatggctttc aataccottt taagtttaaa atgtgtattt ttcaaggcat   1980

ttattgccat attaaaatct gatgtaacaa ggtggggacg tgtgtccttt ggtactatgg   2040

tgtgttgtat ctttgtaaga gcaaaagcct cagaaaggga ttgctttgca ttactgtccc   2100

cttgatataa aaaatcttta gggaatgaga gttccttctc acttagaatc cgaagggaat   2160

taaaaagaag atgaatggtc tggcaatatt ctgtaactat tgggtgaata tggtggaaaa   2220

taatttagtg gatggaatat cagaagtata tctgtacaga tcaagaaaaa aagggagaat   2280

aaaattccta tctcatatta aaaaaaaaaa aaaaaaaaaa aaaaaaaaaa aaaaaaaa     2338
```

<210> SEQ ID NO 17
<211> LENGTH: 3572
<212> TYPE: DNA
<213> ORGANISM: Homo sapiens

<400> SEQUENCE: 17

```
gaataattct gctacaaggc tgatttcaag gacatgaatt gttgacctca tcccaacatc     60

agaacctcag atgttctaat ttttgcacca ttccaggcaa gttgatctta taaggaaata    120

aaattgaacc ttaggggtct gatggaaatt cactgtgaca ttcaaatcaa gaaaacttgc    180

taatgcccac agagcctttt ccccatgggc cctgatggta gcctccagaa ggtgcagcct    240

caggtggtgc cctttcttct gtggcaagaa taaactttgg gtcttggatt gcaataccac    300

ctgtggagaa aatggtatgc gagggaaagc gatcagcctc ttgcccttgt ttcttcctct    360

tgaccgccaa gttctactgg atcctcacaa tgatgcaaag aactcacagc caggagtatg    420

cccattccat acgggtggat ggggacatta ttttgggggg tctcttccct gtccacgcaa    480

agggagagag aggggtgcct tgtggggagc tgaagaagga aaaggggatt cacagactgg    540

aggccatgct ttatgcaatt gaccagatta acaaggaccc tgatctcctt tccaacatca    600

ctctgggtgt ccgcatcctc gacacgtgct ctagggacac ctatgctttg gagcagtctc    660

taacattcgt gcaggcatta atagagaaag atgcttcgga tgtgaagtgt gctaatggag    720

atccacccat tttcaccaag cccgacaaga tttctggcgt cataggtgct gcagcaagct    780

ccgtgtccat catggttgct aacattttaa gactttttaa gatacctcaa atcagctatg    840

catccacagc cccagagcta agtgataaca ccaggtatga ctttttctct cgagtggttc    900
```

```
cgcctgactc ctaccaagcc caagccatgg tggacatcgt gacagcactg ggatggaatt    960
atgtttcgac actggcttct gaggggaact atggtgagag cggtgtggag gccttcaccc   1020
agatctcgag ggagattggt ggtgtttgca ttgctcagtc acagaaaatc ccacgtgaac   1080
caagacctgg agaatttgaa aaaattatca aacgcctgct agaaacacct aatgctcgag   1140
cagtgattat gtttgccaat gaggatgaca tcaggaggat attggaagca gcaaaaaaac   1200
taaaccaaag tgggcatttt ctctggattg gctcagatag ttggggatcc aaaatagcac   1260
ctgtctatca gcaagaggag attgcagaag ggctgtgac aattttgccc aaacgagcat    1320
caattgatgg atttgatcga tactttagaa gccgaactct tgccaataat cgaagaaatg   1380
tgtggtttgc agaattctgg gaggagaatt ttggctgcaa gttaggatca catgggaaaa   1440
ggaacagtca tataaagaaa tgcacagggc tggagcgaat tgctcgggat tcatcttatg   1500
aacaggaagg aaaggtccaa tttgtaattg atgctgtata ttccatggct tacgccctgc   1560
acaatatgca caaagatctc tgccctggat acattggcct ttgtccacga atgagtacca   1620
ttgatgggaa agagctactt ggttatattc gggctgtaaa ttttaatggc agtgctggca   1680
ctcctgtcac ttttaatgaa aacggagatg ctcctggacg ttatgatatc ttccagtatc   1740
aaataaccaa caaaagcaca gagtacaaag tcatcggcca ctggaccaat cagcttcatc   1800
taaaagtgga agacatgcag tgggctcata gagaacatac tcacccggcg tctgtctgca   1860
gcctgccgtg taagccaggg gagaggaaga aaacggtgaa aggggtccct tgctgctggc   1920
actgtgaacg ctgtgaaggt tacaactacc aggtggatga gctgtcctgt gaactttgcc   1980
ctctggatca gagacccaac atgaaccgca caggctgcca gcttatcccc atcatcaaat   2040
tggagtggca ttctccctgg gctgtggtgc ctgtgtttgt tgcaatattg ggaatcatcg   2100
ccaccacctt tgtgatcgtg acctttgtcc gctataatga cacacctatc gtgagggctt   2160
caggacgcga acttagttac gtgctcctaa cggggatttt tctctgttat tcaatcacgt   2220
ttttaatgat tgcagcacca gatacaatca tatgctcctt ccgacgggtc ttcctaggac   2280
ttggcatgtg tttcagctat gcagcccttc tgaccaaaac aaaccgtatc caccgaatat   2340
ttgagcaggg gaagaaatct gtcacagcgc ccaagttcat tagtccagca tctcagctgg   2400
tgatcacctt cagcctcatc tccgtccagc tccttggagt gtttgtctgg tttgttgtgg   2460
atcccccccca catcatcatt gactatggag agcagcggac actagatcca gagaaggcca   2520
ggggagtgct caagtgtgac atttctgatc tctcactcat ttgttcactt ggatacagta   2580
tcctcttgat ggtcacttgt actgtttatg ccattaaaac gagaggtgtc ccagagactt   2640
tcaatgaagc caaacctatt ggatttacca tgtataccac ctgcatcatt tggttagctt   2700
tcatccccat ctttttttggt acagcccagt cagcagaaaa gatgtacatc cagacaacaa   2760
cacttactgt ctccatgagt ttaagtgctt cagtatctct gggcatgctc tatatgccca   2820
aggtttatat tataattttt catccagaac agaatgttca aaaacgcaag aggagcttca   2880
aggctgtggt gacagctgcc accatgcaaa gcaaactgat ccaaaaagga aatgacagac   2940
caaatggcga ggtgaaaagt gaactctgtg agagtcttga aaccaacact tcctctacca   3000
agacaacata tatcagttac agcaatcatt caatctgaaa cagggaaatg gcacaatctg   3060
aagagatgtg gtatatgatc ttaaatgatg aacatgagac cgcaaaaatt cactcctgga   3120
gatctccgta gactacaatc aatcaaatca atagtcagtc ttgtaaggaa caaaaaattag   3180
ccatgagcca aaagtatcaa taaacgggga gtgaagaaac ccgttttata caataaaacc   3240
aatgagtgtc aagctaaagt attgcttatt catgagcagt taaaacaaat cacaaaagga   3300
```

aaactaatgt tagctcgtga aaaaaaatgc tgttgaaata aataatgtct gatgttattc 3360
ttgtattttt ctgtgattgt gagaactccc gttcctgtcc cacattgttt aacttgtata 3420
agacaatgag tctgtttctt gtaatggctg accagattga agccctgggt tgtgctaaaa 3480
ataaatgcaa tgattgatgc atgcaatttt ttatacaaat aatttatttc taataataaa 3540
ggaatgtttt gcaaatgtta aaaaaaaaaa aa 3572

<210> SEQ ID NO 18
<211> LENGTH: 1310
<212> TYPE: DNA
<213> ORGANISM: Homo sapiens

<400> SEQUENCE: 18
catctttttg agtattgttt attgtaatgt aagaaccagt catgcctggg gtacactcaa 60
gctggatcct tgccataagg gcaggctggg gtgaatggtg gtacactctt ggtaaatgtg 120
acatgataag aaatatatat ttgggccagg cacattgtcc tgcacctgta atcacagaac 180
ttggggaggc taaggcaggc aaattgcttc aggccaggag ttagagacca gcctggccaa 240
catggtgaaa acctcctctc aactaaaaat acgaagatta gctgggcgtg gtggctcctg 300
cccgtagtcc cagctactcg ggaggttgag gcatgagaat cgcttgaacc cgggaggtgg 360
aggttgcagt gagctgagat cacaccactg ctttccagcc tgggcaacag agtgagactc 420
tgtctcaaaa atttggtctc tgccccttga cacccaactg ctaaaaccct tgtaatttcc 480
tgagtgatag aggtgataag aatgtcttcc acagaattcc caaatccctt ggaatttcct 540
gggtgataaa cctttttgttc taatgaggtg attcttagtg ggttcctgga tagcttcaaa 600
gtggtgatgt catcagaaag actaaactgt cattagaagc ttggaacttc taacccaccc 660 taccccctatt ctccagggag gagagagggg ctggaaattg tttaattatc tatcatgcct 720
atgtgatgaa accccctcaa aatttctaaa ctatgaggtt tggagagcct ccaggttgat 780
aaccatatcc acatgccggg aggatggtgc accccgactc catggggata gaagcctctg 840
tgtttgggac ttttctggac atcacacagt gtacctcttc atctggctgt tcatgtgtat 900
ccattatgtc ctttttaata aatcagtaat agtaagctgt tttcttgagt tctgtgaccc 960
cttctagcaa acgattgaac ttgaggaggg agtcatgaga tcccctgact tgtaggcagt 1020
tggtgagaag tataggagac ccagacttgt gattggcatt tgaagtgagg gataatcttg 1080
tggctctgag cccctaacct gtggtgtctg cattaactct gggtaattac tgtcagaatt 1140
gaattcaatc attagatatc aagtaggttt ccaggaagtt ggagaacttg ttgttggtgt 1200
gaggggaaga aacccataag tttggtgtca gagcattgcc agtagagaaa caggtccccc 1260
ccacatatga gttggatggt gttatgctct tggtagggca tttgttttga 1310

<210> SEQ ID NO 19
<211> LENGTH: 2724
<212> TYPE: DNA
<213> ORGANISM: Homo sapiens

<400> SEQUENCE: 19
actcattgct ttggcgccgt ctggggagcg cgagcccgcg ggtggcgcgc ggcgcatggt 60
ggcggctcct ttcggagcgc agccgaacct ctgacccgga ctccgttacc cctgcccggc 120
gcgccccggc ggccggctgg aggcagaaac agcagaagcg ttaacagcag cagcggcggc 180
ggctgctccg ccgccgtctc cgcgggagca tggagtgcgc cctggacgcc cagagcctga 240

```
tcagcatctc cctgcgcaag atccacagct cccgaaccca gcgcggcggc atcaagctgc    300
acaagaacct cctggtgtcc tacgtgctcc gcaacgcgcg ccagctctac ctgagcgagc    360
gctacgccga gctctaccgg cgccagcagc agcagcaaca gcagcagccg ccccaccacc    420
agcaccagca cctagcgtac gcggcgccgg gcatgccggc cagcgcggcc gacttcggcc    480
cgctccaact tggcggcggc ggggacgcgg aggcgcgcga gccggccgcc cggcaccagc    540
tgcaccagct ccaccagctc caccagctgc acctccagca gcagctgcac cagcaccagc    600
acccggcgcc caggggctgc gcggcggcgg cggcggccgg agcgcccgcg ggcggcgcgg    660
gggcgctctc ggagctgccc gggtgcgccg cgctccagcc gccgcacggc gcgccccacc    720
gcgggcagcc cttggagcct ctgcagccgg gtcctgcgcc gctgccgctg ccgctgccgc    780
cgcccgcgcc cgctgcgctc tgcccgcggg accctcgcgc cccggccgcc tgctccgcgc    840
ccccaggggc cgcccctccg gccgccgccg cttctccgcc cgcctccccg gcccccgcct    900
cctcccccgg cttctaccgg ggcgcatacc ctaccccttc ggacttcggc ttgcactgca    960
gcagccagac caccgtgctg gacctagaca ctcacgtggt gaccacggtg gagaacggct   1020
acttgcacca ggactgctgc gcctccgccc actgcccctg ctgtggccag ggcgctccgg   1080
gaccgggcct ggcgtccgcc gccggctgca agcgcaagta ttaccctggc caggaggagg   1140
aggaagacga cgaggaggat gcgggcgggc tgggggccga gcccccgggg ggcgccccgt   1200
tcgcccccctg caagcgcgcc cgcttcgagg acttctgccc ggactcgtcc ccggacgcgt  1260
ccaacatctc aaacttgatc tccatctttg gctccggctt ctcggggctg gtgagccgac   1320
agccggactc ctcggagcag ccgccgccgc tcaacgggca gctgtgcgcc aagcaggcgc   1380
tcgccagcct cggcgcctgg actcgagcca ttgtcgcctt ctagggaccc ccgagggcac   1440
agggacccgg ggccccgcgg ggctggggcc agacaaagac tcggcaaagg ggcgagagga   1500
gggaacgagc gggcgccggg ccactcgggg ctgagctggg ggcgagcggg ggcaggcggc   1560
tgatgtttta taaattgtaa aataaaaaaa aaagaaatct aaaatcttgg actttatttt   1620
tgcagagaga aaaagcgcct atttaagtat gctttgtgtt tctcctactc cttttttttct  1680
ttttattgta gtgattgcag tggtgtttag cgaggagcct accacgtgag ggagggctgc   1740
tgcccggagg aggtgccggg cagccggggg cgaggcaggg cgccctggcc gccggggcgc   1800
gccgggggcg cagctcagga gggcgccgga cctgggaagc cgattccaat cagttgtcag   1860
acccgggaag cccgacgttc cgctctcccg agtccctctg tggggtgagg aatgggtctt   1920
gtgaaattct gagcaaaaac aaaggcaaac tctatctccg aaagggacgt ttgggtcaca   1980
tttcctctct gggggcggac tccaaagttc tcaaaatgag aaggcagaaa tgaaaacact   2040
tcaacttttt ttttcttttc ttcccggggc gggtgtcttg aacccctctt ctccccgccc   2100
ctctggctcc gttctcctcc cctcctccac ccgtctcccg gactcggggg tggcgcctga   2160
caccccgaca ctctcggaca ctgggtaagg ggtgggggggc gggcacggcg gactacattt  2220
cccatcatgc ctagcactgc ggtcctcact aaacaaaaaa ggaagtcaat tccttcacct   2280
ggatccccgg cggccccggg ggagggaggg gccgggaccg ccgactgcgt tggagacttt   2340
gcactaagtt cctggtcagc tgtggtgttt gtgtgtgtgc ttctaagttg cactgccttg   2400
gttcagcctt cggttgcatt tcatgaaacc agcattgttc gagcctgtga gaaccccgtc   2460
ctgtgtcttc agctcgatag atttgtttaa tttaaaagcc ttttgttgta aaaaggtggg   2520
gttcgtctgc agcccctctg gttctctgcc atcagcaccg tgtggactcc aaaacgagtt   2580
gccaatcctt cctttctcgg ccctttttccc tcattaccct gtatttttgt gcatactgaa  2640
```

ttgtatatca ccgggtaaaa ctgttcagat tgtttaaatt tataatctta ataaaaagtc 2700
gattacagaa aaaaaaaaaa aaaa 2724

<210> SEQ ID NO 20
<211> LENGTH: 3535
<212> TYPE: DNA
<213> ORGANISM: Homo sapiens

<400> SEQUENCE: 20
ggcagcagcg gcgcggccgg ccccagtcgc cgtcggtctc ccgccttcgg gggaaccagg 60
tctccgtccc tcttctctcc tccagcccgc accgccccgc tccccagctc ggtttttccg 120
caggatttcc ctcgctctcc cctccctgct tggcccccgc gctcccctcc ctctccactc 180
ggcaccatgc cccctccccc gggcgctccc ccgggtttct gacggccctc tgcgccgctc 240
cgaccccgcc gggatgcaga gagaccccta gctcctcgcg atggacccag gcatcctgga 300
ccttggcgtt gccgctccgc ggacccccga tttcccggcg ggatccagtt gattttgttg 360
gctccggacc gaggcttggg ccctggttta cctccgcttc atccctaccc cgctcccgga 420
gctcggagcc ggaggggggc ttcgcggggc tgcgcagccc cgcgtccccg cccccggcca 480
tggggctgtg aggcggtcgc ccccgggccg aaatgccccc cggggggagc gggccggggg 540
ggtgcccgcg ccgccccccg gccctggctg ggcccctgcc gccgcctcca ccgccgccgc 600
cgccacctct gctgccgctg ttgccgctgt tgctgctgtt gctgctgggg gcggccgagg 660
gggcccgggt ctcctccagc ctcagcacca cccaccacgt ccaccacttc cacagcaagc 720
acggcaccgt gcccatcgcc atcaaccgca tgcccttcct cacccgcggc ggccacgccg 780
ggaccacata catctttggg aaggggggag cgctcatcac ctacacgtgg ccccccaatg 840
acaggcccag cacgaggatg gatcgcctgg ccgtgggctt cagcacccac cagcggagcg 900
ctgtgctggt gcgggtggac agcgcctccg gccttggaga ctacctgcag ctgcacatcg 960
accagggcac cgtgggggtg atctttaacg tgggcacgga cgacattacc atcgacgagc 1020
ccaacgccat agtaagcgac ggcaaatacc acgtggtgcg cttcactcga agcggcggca 1080
acgccaccct gcaggtggac agctggccgg tcaacgagcg gtacccggca ggaaactttg 1140
ataacgagcg cctggcgatt gctagacaga gaatccccta ccggcttggt cgagtagtag 1200
atgagtggct gctcgacaaa ggccgccagc tgaccatctt caacagccag gctgccatca 1260
agatcggggg ccgggatcag ggccgcccct tccagggcca ggtgtccggc ctctactaca 1320
atgggctcaa ggtgctggcg ctggccgccg agagcgaccc caatgtgcgg actgagggtc 1380
acctgcgcct ggtgggggag ggccgtccg tgctgctcag tgcggagacc acggccacca 1440
ccctgctggc tgacatggcc accaccatca tggagactac caccaccatg gccactacca 1500
ccacgcgccg gggccgctcc cccacactga gggacagcac cacccagaac acagatgacc 1560
tgctggtggc ctctgctgag tgtccaagcg atgatgagga cctggaggag tgtgagccca 1620
gtactggagg agagttaata ttgcccatta tcacggagga ctccttagac ccccctcccg 1680
tggccacccg atccccttc gtgcccccgc cccctacctt ctacccttc ctcacgggag 1740 tgggcgccac ccaagacacg ctgcccccgc ccgccgcgcg ccgcccgccc tctgggggcc 1800
cgtgccaggc cgagcgggac gacagcgact gcgaggagcc catcgaggcc tcgggcttcg 1860
cctccgggga ggtctttgac tccagcctcc cccccacgga cgacgaggac ttttacacca 1920
cctttcccct ggtcacggac cgcaccaccc tcctgtcacc ccgcaaaccc gctccccggc 1980

```
ccaacctcag gacagatggg gccacgggcg cccctggggt gctgtttgcc ccctccgccc   2040

cggcccccaa cctgccggcg ggcaaaatga accaccgaga cccgcttcag cccttgctgg   2100

agaacccgcc cttggggccc ggggccccca cgtcctttga gccgcggagg ccccctcccc   2160

tgcgccccgg cgtgacctca gcccccggct tcccccatct gcccacagcc aaccccacag   2220

ggcctgggga gcggggcccg ccgggcgcag tggaggtgat ccgggagtcc agcagcacca   2280

cgggcatggt ggtgggcatt gtggcggcgg cggcgctctg catcctcatc ctcctctacg   2340

ccatgtataa gtaccgcaat cgtgatgagg gctcctacca ggtggaccag agccgaaact   2400

acatcagtaa ctcggcccag agcaatgggg cggtggtgaa agagaaggcc ccggctgccc   2460

ccaagacgcc cagcaaggcc aagaagaaca aagacaagga gtattatgtc tgagcccccg   2520

gcactgcgcc ccactgccag ctgcccctcc tgggagggcc cgggaggagg gtgccaccct   2580

ctccctgcca ggggcctggg gaccctctcc ctggctgcct caggcttctc ttacgaagag   2640

gaaacgcaaa aaaagaaaag gaaaaacccc gtgctcgccc ccttcctcct gccgtccact   2700

gcgcggcctc gtcagtcccg ggctgactg tccctctcag ctctgcgcct gccaggcagg   2760

gcacgtgctc acagccctgg gttgatttat tttttaagg gggtagtttt attttggtgg   2820

ggttgggtgg gaaggaaggc tgggggtttt gtaaagtgtc cactgctcgt cctgttaatt   2880

ttcctcaatt tttcttcttc ttccttctgt ccctcctgcc ttccttctct tcccaagccc   2940

tccaatcccc atcccaggct tgctgtgtct cactgtcccc accctccttc cctacttctt   3000

tttttgtgtg tctggtttct cccttccttt cctccctttg ggtttccaga gtcggtggga   3060

gaagggcggg agggtgggcc cgagtggccc agtgggtggg tggggtgggg tggggcaagt   3120

gccccaactc ccctcaccag gagaggcacc tgcttggtgc cgcccaggga aggggctcag   3180

gcctgacgga aggcctgttc tgtgtgtgcc gccgggcgac gtgcattgat ggggaagctg   3240

ctggaggagc aggggtgggg ggtgggaggg aggggaaagg caaatgcaga tatatattac   3300

agacaaatac tctagattcc acgagcagca gcctgtggca cccgctgggc gcgggcagca   3360

gggaagaggg agcaaggcat tgtccacaga ctgctggggt cacttctttg cccacgggct   3420

ccctgctccc ccagtttttt ttctctcttt gttaacaaat gtgtctgagt cttggaaaac   3480

accccaaccc cggaaatgtg tgggaaaaag aaaacaaaaa ctttccaaat tccaa        3535
```

<210> SEQ ID NO 21
<211> LENGTH: 6456
<212> TYPE: DNA
<213> ORGANISM: Homo sapiens

<400> SEQUENCE: 21

```
agggacatcg aatcggaggc cctgggagga gcagccggct ggctgccctg cagaggccag     60

gtctgcccag caaacccagg aaggtgtggc gtccccgctt cgcggccaag atggtgctgg    120

tgctgcgcca tcctttgtgt gcccgggaag ggcgttccgg gagccgggtc gggggctcct    180

gactcgcact gggcagcatg acggtgcgcc ggctgtcact gctgtgccgg gacctctggg    240

cgctgtggct gctgctgaag gccggcgcag atgaaatcat gcaccaggac atcgtcccgc    300

tctgtgctgc cgacatccag gaccagctaa agaagcgctt tgcttacctg tccggtgggc    360

gggggcagga cggaagcccg gttatcacct tccctgacta cccggccttc agcgagattc    420

cggacaagga gttccagaat gtcatgacct acctcaccag catccccagc ctgcaggacg    480

ctggcatcgg attcatcctg gtgatagacc ggcgacggga caaatggacc tccgtgaagg    540

cgtccgtcct gcgcatcgca gcatctttcc cggcaaacct gcagctcgtc ctcgtgcttc    600
```

```
gcccgacggg ttttttccaa aggactctct ccgacatcgc tttcaaattc aatagagatg    660
actttaagat gaaggtgccg gtcataatgc tgagctccgt accagactta cacggttaca    720
tcgataagtc gcagctgacc gaggacctgg gtgggaccct ggactactgc cactcccggt    780
ggctgtgcca gcgcacggcc atcgaaagtt tcgccctcat ggtgaagcag acggctcaga    840
tgctgcagtc cttcgggacc gagctggctg aaacagagct gcccaatgac gtccagtcga    900
caagctcagt gctgtgtgcg cacacagaga agaaggacaa ggcgaaggag gatttgaggc    960
tggcactgaa agaggggcac agtgtcctgg agagcctcag ggagctgcag gctgagggct   1020
cagagcccag tgtgaaccag gaccagcttg acaaccaggc caccgtgcag aggctcctgg   1080
cccagctgaa cgaaaccgag gctgccttcg atgagttctg ggcaaagcat cagcagaaac   1140
tggagcagtg tctgcagctc cggcactttg agcagggctt ccgggaggtc aaagccatct   1200
tggacgcagc gtcccagaag atagcaacct tcacagacat cggcaacagc ctggcgcatg   1260
tggagcacct gctgagggac ctggccagct tcgaggagaa atcaggcgtg gccgtggaga   1320
gggcccgggc cctgtctctg gacggcgagc agctcattgg gaacaagcac tacgcggtag   1380
actccatccg cccaaagtgc caggagctcc ggcacctctg tgaccagttc tctgcggaga   1440
tcgcaaggag gagggggctg ctcagcaagt ccctggagct gcaccgccgc ctggagacgt   1500
ccatgaagtg gtgtgatgaa gggatttacc tgctggcctc acaacctgtg gacaagtgcc   1560
agtcccagga cggcgcggag gctgccctcc aggaaatcga gaagtttttg gagaccggtg   1620
cggaaaataa gatccaggag ctcaacgcga tttacaagga atacgaatcc atcctcaacc   1680
aagatctcat ggagcacgtg cgaaaggtct tccagaagca ggcaagcatg gaggaggtgt   1740
tccaccgcag gcaggccagc ctgaagaagc tggcggccag gcagacgcgg cccgtgcagc   1800
cggtggcccc cagacccgag gcactggcaa agtcgccctg cccctcccca ggcattcggc   1860
gaggctctga gaactccagc tccgagggcg gtgcgctccg gagagggccc taccggaggg   1920
ccaagagtga gatgagtgag agccggcagg gccgcggctc agcgggggag gaggaggaaa   1980
gcctggccat cctgcgcagg cacgtgatga gcgagctcct ggacacagaa cgggcctacg   2040
tggaggagct gctgtgcgtc ctggagggct acgccgcgga gatggataac ccactgatgg   2100
ctcacctcct gtcaacaggc cttcacaaca agaaggatgt tttgtttgga aacatggagg   2160
aaatctatca cttccacaac aggatattcc tcagggagct ggaaaactac actgactgcc   2220
cagaactggt tggaagatgc tttctggaga ggatggaaga tttccagatc tatgagaagt   2280
actgtcagaa caagccccgc tctgagagcc tgtggagaca gtgctccgac tgcccgtttt   2340
tccaggaatg ccagagaaag ctggaccaca agctgagcct ggactcctac ctgctgaagc   2400
cagtgcagag gatcaccaag taccagctgc tgctcaagga aatgctgaaa tacagcagga   2460
actgcgaggg ggctgaggac ctgcaggagg cgctgagctc catcctgggc atcctgaagg   2520
ccgtgaacga ctccatgcac ctcatcgcta tcaccggcta tgacgggaat ctcggcgacc   2580
tgggcaagct gctgatgcag ggctcgttca gcgtctggac cgaccacaag aggggccaca   2640
ccaaggtgaa ggagctggcc aggttcaagc ccatgcagcg gcacctgttc ctgcacgaga   2700
aggcagtgct cttctgcaag aagagggagg agaatgggga ggggtatgag aaagctccct   2760
cctacagcta caagcagtcc ttaaacatgg ctgccgttgg cattacggag aacgtgaagg   2820
gagatgctaa gaagttcgag atctggtaca acgcgcgcga ggaggtctac atcgtccagg   2880
cgccaactcc tgagattaaa gccgcgtggg tgaatgaaat tcggaaagtg ctgaccagcc   2940
```

```
agctgcaggc ttgtagagaa gccagccagc accgggcgct ggagcagtca cagagcctgc   3000
ccctgccggc cccgaccagc accagtccct caagaggaaa ctcaaggaac atcaagaagc   3060
tggaagaaag gaaaacagac cccctaagcc tggagggata cgtcagctca gcgccactga   3120
caaagccccc cgaaaagggc aaaggttgga gcaaaacgtc ccactcactg gaggcacctg   3180
aggacgacgg gggctggtca agtgcagagg agcagattaa ctcgtccgac gcagaggagg   3240
acggcgggtt gggccccaag aagctggttc caggtaaata cacggtcgtg gcggaccacg   3300
agaagggagg ccccgatgcg ctgcgcgtga ggagcgggga cgtggtggag ctggtgcagg   3360
agggcgacga gggcctctgg tacgtcaggg acccgaccac tggcaaggag ggctgggtgc   3420
cggccagcag cctgtccgtc cggctcggcc cgtccggctc ggcccagtgc ctgagcagct   3480
cagagtcgag cccggggtcg gccgtgctga gcaactcgtc cagctgcagc gagggcggcc   3540
aggccccctt ctccgacctg caggggtagc gcggcctcgg cgccggagac ccgcgcgctg   3600
tctggggctg cggtggcgtg gggagggcgc ggcccccgga cgccccgagg aaggggcacc   3660
tcaccgcccc cacccagagc gcctggccgt gcgggctgca gaggacccct ccggggcaga   3720
ggcaggttcc acggaagacc ccggcccgct ggggcttccc cggagactcc agagcccaca   3780
gaggaggggc cgcagggaac agccccgggc ggcaggcgcc gggcagcggc atctcgtcct   3840
ggctccaccg tgctgcttct gcctctggac ggtgctttca ggggacgcgc ggaccgtggt   3900
ggagctgctt ccggagaagt ggaggatcct ctggccaacg gcctgaggag agcggggcac   3960
ggggtctctt tagcttttac aagttttagg attttttcaa gcagggatca atcccgtggc   4020
catttttgt ggtactttgg cctcaattct tcaccaggaa tcactgtgtt tacatgaaat    4080
gacaatttga tactgtattt gatagaaaac tattttttg ttaccggggt ttacatagaa    4140
gcacgttgtt tataccacta agtgactttg ggggggctct cccatggaaa cggatggcac   4200
tccctgaagc tccctggtca caggtggatg aaaacgtgtc cgtgggtgac atcaggtggt   4260
gtctccacca ccaaaagcag ttagaagcca aggagattcc tttatctacc tagggttcat   4320
tttcaaaaga aaatttaaac tataatttaa acaattaacg ttcttttcta caaaaaaaat   4380
gcagggactt gattttttta aagagcttca ctgaattagg atatttttat tgcttttaaa   4440
gaaaatacaa agatgcagtt tctgcagggt gtggcgtgga ccagtgctgc cgaccatagc   4500
tcagagagcc ctgcccctgc ctcactgcac tgcagcctcc tcggaggccg cacctccact   4560
ccactcccca cgcgccccct gcctcccacc caggtccacc tgccacctgg tgaccacctt   4620
gagtacagaa gtgaaagtgg ggagagtatt ttattcaagt cacagcagaa ctggaaaaaa   4680
actcttctgt tttaccaact tcttgtgttt cagaaacata ttctgttcaa aacttttgaa   4740
gccctttcgg tgtctagtct gcagatgttt ttgtatgtgt gcacctctga ccatgtgtgt   4800
acatatgtgt cttgctggaa aggacatatt cgctgtcccc gtgctgctgg gagggccgcc   4860
tcacagcctc acggttccca gccccagcac agtggaggca ggcgtggctg cattcccctc   4920
acgctaccct cccagcggct tgtagccgtc actggccaga cctccagggt gcggaatcaa   4980
ataggaagca tgcagagact cggcagcttt tcctctgatg tgtaagttat ttggaacgcg   5040
tgctgtgtcc cgcgatgtcc ctgatgtact gtgcaggcgc ggtgcctccg tctcgtcgca   5100
cagctgcgcg cccttgtgtg accctcccca taaaggcact ttacagcttc atgtttcatc   5160
cactgtcact tttttttaac tgctgatgta aatggaattt taaaagcaga gttctttatt   5220
gtatggatga cgtttgaata aatatcagca actcctgcca tctgcctttg tctgtcaaga   5280
cacagaacgt ctcagcagtc ggggtttcca gggccgcagt gcactgtgct tgcacatggt   5340
```

```
aagtcattgt tgggacggaa aagaagccgg cagtgggcag ggcccagcgt gcggctcagg   5400
caccgagcaa ccgctttgct ttcttctgtc agacggcgat gatgacaaaa tagcaacaag   5460
gttgtgcgtg tcagaaacgc aaaggcagca gaggaagcgt agtggaacca ttacagaatc   5520
acaatgcagc cgacactctc cagaccagaa aagggagcat aaagaaaggg tattgatcca   5580
atagaagaag ggaagggtgg agaaagggga aagcatggtt aacaggaaac aacatgtaac   5640
ggaagagaca gcccagatgt gtctggctca caacagacgt gatcatgtta tgctggcctg   5700
gaagagcatc ggatcagacg tgacaagtca ctgcttagag accatcaagc aaatttatat   5760
atagattgga gatttaaaat aaaagaagac agaacagaca aacaccataa gaaagctggt   5820
gtagcagtat cgatgacctg aaatgggatt caggacagtt catagagtaa agggggctgc   5880
gtggcaatca ggaactcata agccactgac tataaagctc aaaacacagc aaagttggca   5940
gtcggcagac agcaatgttg actgtcatga aaagtgatcc ctgtttgccc ctaaacgtag   6000
agaaatctgc gttattttcc agcacacatg gagcacaaac aaaatatttg caaaacaatg   6060
ggaagatcat tgaaacactg tttggcaatt taaaagcttg tttctaactc acgggatgcg   6120
ggcagtctgc tctctagaac tggacagcgt gcacagagcc acgggaggga gcagccacgg   6180
ccagctcaga ttggtgtcga cagcttagtg gtgtctgatt ttatacatga caaaatgaac   6240
gagttaacca tttaagccaa aaaaataaga ctagcgtaac ccaaagaaag tatttaaata   6300
cttctgtcaa ttaggacagt tgagaaaaga gaataacaaa atcaaaagca aaactcaaac   6360
tttgtacctg aaaaatctaa taaaactgac taatttatag aaaacctaag aaactccata   6420
tcaaataaaa aattttaaat atgagagaaa aaaaaa                             6456
```

<210> SEQ ID NO 22
<211> LENGTH: 3075
<212> TYPE: DNA
<213> ORGANISM: Homo sapiens

<400> SEQUENCE: 22

```
agtcccatgg ggaatgtcaa caggcagggg cagcactgca gagatttcat catggtctcc     60
caggccctca ggctcctctg ccttctgctt gggcttcagg gctgcctggc tgcagtcttc    120
gtaacccagg aggaagccca cggcgtcctg caccggcgcc ggcgcgccaa cgcgttcctg    180
gaggagctgc ggccgggctc cctggagagg gagtgcaagg aggagcagtg ctccttcgag    240
gaggcccggg agatcttcaa ggacgcggag aggacgaagc tgttctggat ttcttacagt    300
gatggggacc agtgtgcctc aagtccatgc cagaatgggg gctcctgcaa ggaccagctc    360
cagtcctata tctgcttctg cctccctgcc ttcgagggcc ggaactgtga gacgcacaag    420
gatgaccagc tgatctgtgt gaacgagaac ggcggctgtg agcagtactg cagtgaccac    480
acgggcacca agcgctcctg tcggtgccac gaggggtact ctctgctggc agacggggtg    540
tcctgcacac ccacagttga atatccatgt ggaaaaatac ctattctaga aaaaagaaat    600
gccagcaaac cccaaggccg aattgtgggg ggcaaggtgt gccccaaagg ggagtgtcca    660
tggcaggtcc tgttgttggt gaatggagct cagttgtgtg gggggaccct gatcaacacc    720
atctgggtgg tctccgcggc ccactgtttc gacaaaatca agaactggag gaacctgatc    780
gcggtgctgg gcgagcacga cctcagcgag cacgacgggg atgagcagag ccggcgggtg    840
gcgcaggtca tcatccccag cacgtacgtc ccgggcacca ccaaccacga catcgcgctg    900
ctccgcctgc accagcccgt ggtcctcact gaccatgtgg tgcccctctg cctgcccgaa    960
```

```
cggacgttct ctgagaggac gctggccttc gtgcgcttct cattggtcag cggctggggc   1020
cagctgctgg accgtggcgc cacggccctg gagctcatgg tcctcaacgt gccccggctg   1080
atgacccagg actgcctgca gcagtcacgg aaggtgggag actccccaaa tatcacggag   1140
tacatgttct gtgccggcta ctcggatggc agcaaggact cctgcaaggg ggacagtgga   1200
ggcccacatg ccacccacta ccggggcacg tggtacctga cgggcatcgt cagctggggc   1260
cagggctgcg caaccgtggg ccactttggg gtgtacacca gggtctccca gtacatcgag   1320
tggctgcaaa agctcatgcg ctcagagcca cgcccaggag tcctcctgcg agccccattt   1380
ccctagccca gcagccctgg cctgtggaga gaaagccaag gctgcgtcga actgtcctgg   1440
caccaaatcc catatattct tctgcagtta atggggtaga ggagggcatg ggagggaggg   1500
agaggtgggg agggagacag agacagaaac agagagagac agagacagag agagactgag   1560
ggagagactc tgaggacatg gagagagact caaagagact ccaagattca aagagactaa   1620
tagagacaca gagatggaat agaaaagatg agaggcagag gcagacaggc gctggacaga   1680
ggggcagggg agtgccaagg ttgtcctgga ggcagacagc ccagctgagc ctccttacct   1740
cccttcagcc aagcccacct gcacgtgatc tgctggcctc aggctgctgc tctgccttca   1800
ttgctggaga cagtagaggc atgaacacac atggatgcac acacacacac gccaatgcac   1860
acacacagag atatgcacac acacggatgc acacacagat ggtcacacag agatacgcaa   1920
acacaccgat gcacacgcac atagagatat gcacacacag atgcacacac agatatacac   1980
atggatgcac gcacatgcca atgcacgcac acatcagtgc acacggatgc acagagatat   2040
gcacacaccg atgtgcgcac acacagatat gcacacacat ggatgagcac acacacacca   2100
atgcgcacac acaccgatgt acacacacag atgcacacac agatgcacac acaccgatgc   2160
tgactccatg tgtgctgtcc tctgaaggcg gttgtttagc tctcactttt ctggttctta   2220
tccattatca tcttcacttc agacaattca gaagcatcac catgcatggt ggcgaatgcc   2280
cccaaactct cccccaaatg tatttctccc ttcgctgggt gccgggctgc acagactatt   2340
ccccacctgc ttcccagctt cacaataaac ggctgcgtct cctccgcaca cctgtggtgc   2400
ctgccaccca ctgggttgcc catgattcat ttttggagcc cccggtgctc atcctctgag   2460
atgctctttt ctttcacaat tttcaacatc actgaaatga accctcacat ggaagctatt   2520
ttttaaaaac aaaagctgtt tgatagatgt ttgaggctgt agctcccagg atcctgtgga   2580
attggatgtt ctctccctgc cacagccctt gtcaatgata tttcacagag accctgggag   2640
cacctgctca agagtcaggg acacacgcat cactaaatgc aagttcccag gccctggctg   2700
cagtgggagg acctggcaag ctgcactctt gctgagtccc cagggtggtg gaagaagaat   2760
gagaaacaca tgaacagaga aatggggagg tgacaaacag tgcccccact cagactccgg   2820
caagcacggc tcagagagtg gactcgatgc catccctgca gggccgtcct gggcaccact   2880
ggcactcaca gcagcaaggt gggcaccatt ggcactcaca gcagcaaggc aggcaccagc   2940
aacccacctc gggggcactc aggcatcatc tacttcagag cagacagggt ctatgaacta   3000
cagccgtggg ctgcttccaa ggcaccctgc tcttgtaaat aaagttttat gggaacacaa   3060
aaaaaaaaaa aaaaa                                                   3075
```

<210> SEQ ID NO 23
<211> LENGTH: 6236
<212> TYPE: DNA
<213> ORGANISM: Homo sapiens

<400> SEQUENCE: 23

```
gtttttgtc actgcctgcc tgggtcctgc ccgaggtctc catcctcggt ttccctgtcc     60
ttgccccggg ccctgggagt gctctggaag gctgcgcagt attggagggg acagaatgac    120
cttccggcct tgagtccctg gggagcagat ggaccctact ggaagtcagt tggattcaga    180
tttctctcag caagatactc cttgcctgat aattgaagat tctcagcctg aaagccaggt    240
tctagaggat gattctggtt ctcacttcag tatgctatct cgacaccttc ctaatctcca    300
gacgcacaaa gaaaatcctg tgttggatgt tgtgtccaat cctgaacaaa cagctggaga    360
agaacgagga gacggtaata gtgggttcaa tgaacatttg aaagaaaaca aggttgcaga    420
ccctgtggat tcttctaact tggacacatg tggttccatc agtcaggtca ttgagcagtt    480
acctcagcca aacaggacaa gcagtgttct gggaatgtca gtggaatctg ctcctgctgt    540
ggaggaagag aagggagaag agttggaaca gaaggagaaa gagaaggaag aagatacttc    600
aggcaatact acacattccc ttggtgctga agatactgcc tcatcacagt tgggttttgg    660
ggttctggaa ctctcccaga gccaggatgt tgaggaaaat actgtgccat atgaagtgga    720
caaagagcag ctacaatcag taaccaccaa ctctggttat accaggctgt ctgatgtgga    780
tgctaatact gcaattaagc atgaagaaca gtccaacgaa gatatcccca tagcagaaca    840
gtccagcaag gacatccctg tgacagcaca gcccagtaag gatgtacatg ttgtaaaaga    900
gcaaaatcca ccacctgcaa ggtcagagga catgcctttt agccccaaag catctgttgc    960
tgctatggaa gcaaaagaac agttgtctgc acaagaactt atggaaagtg gactgcagat   1020
tcagaagtca ccagagcctg aggttttgtc aactcaggaa gacttgtttg accagagcaa   1080
taaaacagta tcttctgatg gttgctctac tccttcaagg gaggaaggtg ggtgttcttt   1140
ggcttccact cctgccacca ctctgcatct cctgcagctc tctggtcaga ggtcccttgt   1200
tcaggacagt ctttccacga attcttcaga tcttgttgct ccttctcctg atgctttccg   1260
atctactcct tttatcgttc ctagcagtcc cacagagcaa gaagggagac aagataagcc   1320
aatggacacg tcagtgttat ctgaagaagg aggagagcct tttcagaaga aacttcaaag   1380
tggtgaacca gtggagttag aaaacccccc tctcctgcct gagtccactg tatcaccaca   1440
agcctcaaca ccaatatctc agagcacacc agtcttccct cctgggtcac ttcctatccc   1500
atcccagcct cagttttctc atgacatttt tattccttcc ccaagtctgg aagaacaatc   1560
aaatgatggg aagaaagatg gagatatgca tagttcatct ttgacagttg agtgttctaa   1620
aacttcagag attgaaccaa agaattcccc tgaggatctt gggctatctt tgacaggga    1680
ttcttgcaag ttgatgcttt ctacaagtga atatagtcag tccccaaaga tggagagctt   1740
gagttctcac agaattgatg aagatggaga aaacacacag attgaggata cggaacccat   1800
gtctccagtt ctcaattcta aatttgttcc tgctgaaaat gatagtatcc tgatgaatcc   1860
agcacaggat ggtgaagtac aactgagtca gaatgatgac aaaacaaagg gagatgatac   1920
agacaccagg gatgacatta gtattttagc cactggttgc aagggcagag aagaaacggt   1980
agcagaagat gtttgtattg atctcacttg tgattcgggg agtcaggcag ttccgtcacc   2040
agctactcga tctgaggcac tttctagtgt gttagatcag gaggaagcta tggaaattaa   2100
agaacaccat ccagaggagg ggtcttcagg gtctgaggtg gaagaaatcc ctgagacacc   2160
ttgtgaaagt caaggagagg aactcaaaga agaaaatatg gagagtgttc cgttgcacct   2220
ttctctgact gaaactcagt cccaagggtt gtgtcttcaa aaggaaatgc caaaaaaaga   2280
atgctcagaa gctatggaag ttgaaaccag tgtgattagt attgattccc ctcaaaagtt   2340
```

-continued

```
ggcaatactt gaccaagaat tggaacataa ggaacaggaa gcttgggaag aagctacttc   2400
agaggactcc agtgttgtca ttgtagatgt gaaagagcca tctcccagag ttgatgtttc   2460
ttgtgaacct ttggagggag tggagaagtg ctcagattcc cagtcatggg aggatattgc   2520
tccagaaata gaaccatgtg ctgagaatag attagacacc aaggaagaaa agagtgtaga   2580
atatgaagga gatctgaaat cagggactgc agaaacagaa cctgtagagc aagattcttc   2640
acagccttcc ttacctttag tgagagcaga tgatccttta agacttgacc aggagttgca   2700
gcagccccaa actcaggaga aaacaagtaa ttcattaaca gaagactcaa aaatggctaa   2760
tgcaaagcag ctaagctcag atgcagaggc ccagaagctg ggaagccct ctgcccatgc    2820
ctcacaaagc ttctgtgaaa gttctagtga aaccccattt catttcactt tgcctaaaga   2880
aggtgatatc atcccaccat tgactggtgc aaccccacct cttattgggc acctaaaatt   2940
ggagcccaag agacacagta ctcctattgg tattagcaac tatccagaaa gcaccatagc   3000
aaccagtgat gtcatgtctg aaagcatggt ggagacccat gatcccatac ttgggagtgg   3060
aaaaggggat tctggggctg ccccagacgt ggatgataaa ttatgtctaa gaatgaaact   3120
ggttagtcct gagactgagg cgagtgaaga gtctttgcag ttcaacctgg aaaagcctgc   3180
aactggtgaa agaaaaaatg gatctactgc tgttgctgag tctgttgcca gtccccagaa   3240
gaccatgtct gtgttgagct gtatctgtga agccaggcaa gagaatgagg ctcgaagtga   3300
ggatcccccc accacaccca tcagggggaa cttgctccac tttccaagtt ctcaaggaga   3360
agaggagaaa gaaaaattgg agggtgacca tacaatcagg cagagtcaac agcctatgaa   3420
gcccattagt cctgtcaagg accctgtttc tcctgcttcc cagaagatgg tcatacaagg   3480
gccatccagt cctcaaggag aggcaatggt gacagatgtg ctagaagacc agaaagaagg   3540
acggagtact aataaggaaa atcctagtaa ggccttgatt gaaaggccca gccaaaataa   3600
cataggaatc caaaccatgg agtgttcctt gagggtccca gaaactgttt cagcagcaac   3660
ccagactata aagaatgtgt gtgagcaggg gaccagtaca gtggaccaga actttggaaa   3720
gcaagatgcc acagttcaga ctgagagggg gagtggtgag aaaccagtca gtgctcctgg   3780
ggatgataca gagtcgctcc atagccaggg agaagaagag tttgatatgc ctcagcctcc   3840
acatggccat gtcttacatc gtcacatgag aacaatccgg gaagtacgca cacttgtcac   3900
tcgtgtcatt acagatgtgt attatgtgga tggaacagaa gtagaaagaa aagtaactga   3960
ggagactgaa gagccaattg tagagtgtca ggagtgtgaa actgaagttt ccccttcaca   4020
gactggggc tcctcaggtg acctggggga tatcagctcc ttctcctcca aggcatccag    4080
cttacaccgc acatcaagtg ggacaagtct ctcagctatg cacagcagtg gaagctcagg   4140
gaaaggagcc ggaccactca gagggaaaac cagcgggaca gaacccgcag attttgcctt   4200
acccagctcc cgaggaggcc caggaaaact gagtcctaga aaaggggtca gtcagacagg   4260
gacgccagtg tgtgaggagg atggtgatgc aggccttggc atcagacagg gagggaaggc   4320
tccagtcacg cctcgtgggc gtgggcgaag ggccgcccca ccttctcgga ccactggaac   4380
cagagaaaca gctgtgcctg gcccccttggg catagaggac atttcaccta acttgtcacc  4440
agatgataaa tccttcagcc gtgtcgtgcc ccgagtgcca gactccacca gacgaacaga   4500
tgtgggtgct ggtgctttgc gtcgtagtga ctctccagaa attcctttcc aggctgctgc   4560
tggcccttct gatggcttag atgcctcctc tccaggaaat agctttgtag ggctccgtgt   4620
tgtagccaag tggtcatcca atggctactt ttactctggg aaaatcacac gagatgtcgg   4680
agctgggaag tataaattgc tctttgatga tgggtacgaa tgtgatgtgt tgggcaaaga   4740
```

cattctgtta tgtgacccca tcccgctgga cactgaagtg acggccctct cggaggatga 4800
gtatttcagt gcaggagtgg tgaaaggaca taggaaggag tctggggaac tgtactacag 4860
cattgaaaaa gaaggccaaa gaaagtggta taagcgaatg gctgtcatcc tgtccttgga 4920
gcaaggaaac agactgagag agcagtatgg gcttggcccc tatgaagcag taacacctct 4980
tacaaaggca gcagatatca gcttagacaa tttggtggaa gggaagcgga aacggcgcag 5040
taacgtcagc tccccagcca cccctactgc ctccagtagc agcagcacaa cccctacccg 5100
aaagatcaca gaaagtcctc gtgcctccat gggagttctc tcaggcaaaa gaaaacttat 5160
cacttctgaa gaggaacggt cccctgccaa gcgaggtcgc aagtctgcca cagtaaaacc 5220
tggtgcagta ggggcaggag agtttgtgag cccctgtgag agtggagaca acaccggtga 5280
accctctgcc ctggaagagc agagagggcc tttgcctctc aacaagacct tgtttctggg 5340
ctacgcattt ctccttacca tggccacaac cagtgacaag ttggccagcc gctccaaact 5400
gccagatggt cctacaggaa gcagtgaaga agaggaggaa tttttggaaa ttcctccttt 5460
caacaagcag tatacagaat cccagcttcg agcaggagct ggctatatcc ttgaagattt 5520
caatgaagcc cagtgtaaca cagcttacca gtgtcttcta attgcggatc agcattgtcg 5580
aacccggaag tacttcctgt gccttgccag tgggattcct tgtgtgtctc atgtctgggt 5640
ccatgatagt tgccatgcca accagctcca gaactaccgt aattatctgt tgccagctgg 5700
gtacagcctt gaggagcaaa gaattctgga ctggcaaccc cgtgaaaatc ctttccagaa 5760
tctgaaggta ctcttggtat cagaccaaca gcagaacttc ctggagctct ggtctgagat 5820
cctcatgact ggtggtgcag cctctgtgaa gcagcaccat tcaagtgccc ataacaaaga 5880
tattgcttta ggggtatttg atgtggtggt gacggacccc tcatgcccag cctcggtgct 5940
gaagtgtgct gaagcattgc agctgcctgt ggtgtcacaa gagtgggtga tccagtgcct 6000
cattgttggg gagagaattg gattcaagca gcatccaaaa tataaacacg attatgtttc 6060
tcactaaaga tacttggtct tactggtttt attccctgct atcgtggaga ttgtgtttta 6120
accaggtttt aaatgtgtct tgtgtgtaac tggattcctt gcatggatct tgtatatagt 6180
tttatttgct gaacttttat gataaaataa atgttgaatc tctttggttg tagtaa 6236

<210> SEQ ID NO 24
<211> LENGTH: 10275
<212> TYPE: DNA
<213> ORGANISM: Homo sapiens

<400> SEQUENCE: 24
actcccaccc taagtgctgc agactcttcc ctgaagctgc cggctgaggc cggagctgcc 60
gcctccatga gaggcttcct cctacacccc agggccagag gaccctttgc caccagagtg 120
agatcctaga gaccatcatc ctggtaaatc ccagtgcaga cagcatcagc tctgaggttc 180
atcatcttct tagcagctca tcagcttata aactactaat cttgagtggg caaagtttag 240
agcctggggg agacctcatc ctacagagtg gcacctactc atatgaaaac tttgcccagg 300
tccttcacaa ccccgagatt tcccaattgc tcagcaatag agaccctggg atacaggcct 360
tccttaccgt gtcctgctta ggggaaggtg attggagcca cctgggatta tccagttccc 420
aagagaccct gcacctccgg ctaaaccctg agcccactct gcccaccatg gacggcgtgg 480
ctgagttctc cgagtatgtc tctgagactg tggacgtgcc atccccattt gacctactag 540
agccccccac ctcagggggc ttcctcaagc tctccaagcc ttgttgctac atcttcccag 600

-continued

```
gtggtcgtgg ggactctgcc ctctttgctg tcaatggttt caacatcctg gtggatggtg    660
gctctgatcg caagtcctgt tttggaagc tggtacggca cttggaccgc attgactcgg    720
tgctactcac acacattggg gcagacaacc tgccaggcat caatggacta ctgcagcgca    780
aagtggcaga gctagaggag gagcagtccc agggctctag cagttacagc gactgggtga    840
agaaccttat ctctcctgag cttggagttg tctttttcaa cgtgcctgag aagctgcggc    900
ttcctgatgc ctcccggaaa gccaagcgta gcattgagga ggcctgcctc actctgcagc    960
acttaaaccg cctgggcatc caggctgagc ctctatatcg tgtggtcagc aataccattg   1020
agccactgac cctcttccac aaaatgggtg tgggccggct ggacatgtat gtcctcaacc   1080
ctgtcaagga cagcaaggag atgcagttcc tcatgcaaaa gtgggcaggc aatagtaaag   1140
ccaagacagg catcgtgctg cccaatggga aggaggctga gatctccgtg ccctacctta   1200
cctctatcac tgctctggtg gtctggctac cagccaatcc cactgagaag attgtgcgtg   1260
tgctttttcc aggaaatgct ccccaaaaca agatcttgga gggcctagaa aagcttcggc   1320
atctggactt cctgcgttac cctgtggcca cgcagaagga cctggcttct ggggctgtgc   1380
ctaccaacct caagcccagc aaaatcaaac agcgggctga tagcaaggag agcctcaaag   1440
ccactaccaa gacggccgtg agcaagttgg ccaaacggga ggaggtggta gaagagggag   1500
ccaaggaggc acgttcagag ctggccaagg agttagccaa gacagagaag aaggcaaaag   1560
agtcatctga gaagcccccca gagaagcctg ccaagcctga gagggtgaag acagagtcaa   1620
gtgaggcact gaaggcagag aagcgaaagc tgatcaaaga caaggtaggg aaaaagcacc   1680
ttaaagaaaa gatatcaaag ctggaagaaa aaaaagacaa ggagaaaaaa gagatcaaaa   1740
aggagaggaa agagctcaag aaggatgaag gaaggaagga ggagaagaag gatgccaaga   1800
aggaggagaa gaggaaagat accaaacctg agctcaagaa gatttccaag ccagacctaa   1860
agccctttac tcctgaggta cgtaagaccc tctataaagc caaggtccct ggaagagtca   1920
aaatagacag gagccgtgct atccgtgggg agaaggagct gtcttctgag ccccagacac   1980
ccccagccca gaagggaact gtaccactcc caaccatcag tgggcacagg gagctggtcc   2040
tatcctcacc agaggacctc acacaggact ttgaggagat gaagcgtgag gagagggctt   2100
tgctggctga acaaagggac acaggactag gagataagcc attccctcta gacactgcag   2160
aggagggacc cccaagtaca gctatccagg gaacaccacc ctctgttcca gggctgggac   2220
aagaagaaca tgtgatgaag gagaaagagc ttgtcccaga ggtccctgag gaacaaggca   2280
gcaaggacag aggcctagac tctggggctg aaacagagga agagaaagat acctgggagg   2340
aaaagaagca gagggaagca gagaggctcc cagacagaac agaagccaga gaggaaagtg   2400
aacctgaagt aaaggaggat gtgatagaaa aggctgagtt agaagaaatg gaggaggtac   2460
acccttcaga tgaggaggaa gaggacgcga caaaagctga gggtttttac caaaaacata   2520
tgcaggaacc cttgaaggta actccaagga gccgggaggc ttttgggggt cgggaattgg   2580
gactccaggg caaggcccct gagaaggaga cctcgttatt cctaagcagc ctgaccacac   2640
ctgcaggagc cactgagcat gtctcttaca tccaggatga gacaatccct ggctactcag   2700
agactgagca gaccatctca gatgaggaga tccatgatga gccggaggag cgcccagctc   2760
cacccagatt tcatacaagt acatatgacc tgcccgggcc tgaaggtgct ggcccattcg   2820
aagccagcca acctgccgat agtgctgttc ctgctacctc tggcaaagtc tatggaacgc   2880
cagagactga actcacctac cccactaaca tagtggctgc ccctttggct gaagaggaac   2940
atgtgtcctc ggccacttca atcactgagt gtgacaaact ttcttccttt gccacatcag   3000
```

```
tggctgagga ccaatctgtg gcctcactta cagctcccca gacagaggag acaggcaaga   3060
gctccctgct gcttgacaca gtcacaagca tcccttcctc ccgtactgaa gctacgcagg   3120
gcttggacta tgtgccatca gctggtacca tctcacccac ctcctcactg gaagaagaca   3180
agggcttcaa atcaccaccc tgtgaggact tctctgtgac tggggagtca gagaagagag   3240
gagagatcat agggaaaggc ttgtctggag agagagctgt ggaagaggaa gaggaggaga   3300
cagcaaacgt agagatgtct gagaaacttt gcagtcaata tggaactcca gtgtttagtg   3360
cccctgggca tgccctacat ccaggagaac cagcccttgg agaagcagag gagcggtgcc   3420
ttagcccaga tgacagcaca gtgaagatgg cttctcctcc accatctggc ccacccagtg   3480
ccacccacac accctttcat cagtccccag tggaagaaaa gtctgagccc caagactttc   3540
aggaggcaga ctcctgggga gacactaagc gcacaccagg tgtgggcaaa gaagatgctg   3600
ctgaggagac agtcaagcca gggcctgaag agggcacact agagaaggaa gagaaagttc   3660
ctcctcccag gagcccccag gcccaggaag cacctgtcaa cattgatgag gggcttacag   3720
gctgtaccat tcaactgttg ccagcacagg ataaagcaat agtctttgag attatggagg   3780
caggagagcc cacaggccca attctgggag cagaagccct tcccggaggt ttgaggactt   3840
taccccaaga acctggcaaa cctcagaaag atgaggtgct cagatatcct gaccgaagcc   3900
tctctcctga agatgcagaa tccctctctg tcctcagcgt gccctcccca gacactgcca   3960
accaagagcc taccccccaag tctccctgtg gcctgacaga acagtaccta cacaaagacc   4020
gttggccaga ggtatctcca gaagacaccc agtcactttc tctgtcagaa gagagtccca   4080
gcaaggagac ctccctggat gtctcttcta agcagctctc tccagaaagc cttggcaccc   4140
tccagtttgg ggaactaaac cttgggaagg aagaaatggg gcatctgatg caggccgagg   4200
atacctctca ccacacagct cccatgtctg ttccagagcc ccatgcagcc acagcgtcac   4260
ctcccacaga tgggacaact cgatactctg cacagacaga catcacagat gacagccttg   4320
acaggaagtc acctgccagc tcattctctc actctacacc ttcaggaaat gggaagtact   4380
tacctggggc gatcacaagc cctgatgaac acattctgac acctgatagc tccttctcca   4440
agagtcctga gtctttgcca ggccctgcct tggaggacat tgccataaag tgggaagata   4500
aagttccagg gttgaaagac agaacctcag aacagaagaa ggaacctgag ccaaaggatg   4560
aagttttaca gcagaaagac aaaactctgg agcacaagga ggtggtagag ccgaaggata   4620
cagccatcta tcagaaagat gaggctctgc atgtaaagaa tgaggctgtg aaacagcagg   4680
ataaggcttt agaacaaaag ggcagagact tagagcaaaa agacacagcc ctagaacaga   4740
aggacaaggc cctggaacca aaagacaaag acttagaaga aaaagacaag gccctggaac   4800
agaaggataa gattccagaa gagaaagaca aagccttaga acaaaaggat acagccctgg   4860
aacagaagga caaggccctg gaaccaaaag ataaagactt ggaacaaaag gacagggtcc   4920
tagaacagaa ggagaagatc ccagaagaga aagacaaagc cttagatcaa aaagtcagaa   4980
gtgttgaaca taaggctccg gaggacacgg tcgctgaaat gaaggacaga gacctagaac   5040
agacagacaa agcccctgaa cagaaacacc aggcccagga acaaaaggat aaagtctcag   5100
aaaagaagga tcaggcctta gaacaaaaat actgggcttt gggacagaag gatgaagccc   5160
tggaacaaaa cattcaggct ctggaagaga accaccaaac tcaggagcag gagagcctag   5220
tgcaggagga taaaaccagg aaaccaaaga tgctagagga aaaatcccca gaaaaggtca   5280
aggccatgga agagaagtta gaagctcttc tggagaagac caaagctctg ggcctggaag   5340
```

agagcctagt gcaggagggc agggccagag agcaggaaga aaagtactgg agggggcagg
atgtggtcca ggagtggcaa gaaacatctc ctaccagaga ggagccggct ggagaacaga
aagagcttgc cccggcatgg gaggacacat ctcctgagca ggacaatagg tattggaggg
gcagagagga tgtggccttg gaacaggaca catactggag ggagctaagc tgtgagcgga
aggtctggtt ccctcacgag ctggatggcc agggggcccg cccacactac actgaggaac
gggaaagcac tttcctagat gagggcccag atgatgagca agaagtaccc ctgcgggaac
acgcaacccg gagcccctgg gcctcagact tcaaggattt ccaggaatcc tcaccacaga
aggggctaga ggtggagcgc tggcttgctg aatcaccagt tgggttgcca ccagaggaag
aggacaaact gacccgctct ccctttgaga tcatctcccc tccagcttcc ccacctgaga
tggttggaca aagggttcct tcagccccag gacaagagag tcctatccca gaccctaagc
tcatgccaca catgaagaat gaacccacta ctccctcatg gctggctgac atcccaccct
gggtgcccaa ggacagaccc ctcccccctg caccccctctc cccagctcct ggtcccccca
cacctgcccc ggaatcccat actcctgcac ccttctcttg ggcacagcc gagtatgaca
gtgtggtggc tgcagtgcag gagggggcag ctgagttgga aggtgggcca tactcccccc
tggggaagga ctaccgcaag gctgaagggg aaagggaaga agaaggtagg gctgaggctc
ctgacaaaag ctcacacagc tcaaaggtac cagaggccag caaaagccat gccaccacgg
agcctgagca gactgagccg gagcagagag agcccacacc ctatcctgat gagagaagct
ttcagtatgc agacatctat gagcagatga tgcttactgg gcttggccct gcatgcccca
ctagagagcc tccacttgga gcagctgggg attggccccc atgcctctca accaaggagg
cagctgccgg ccgaaacaca tctgcagaga aggagctttc atctcctatc tcacccaaga
gcctccagtc tgacactcca accttcagct atgcagccct ggcaggaccc actgtacccc
caaggccaga gccagggcca agtatggagc ccagcctcac ccccacctgca gttccccccc
gtgctcctat cctgagcaaa ggcccaagcc cccctcttaa tggtaacatc ctgagctgca
gcccagatag gaggtcccca tcccccaagg aatcaggccg gagtcactgg gatgacagca
ctagtgactc agaactggag aagggggctc gggaacagcc agaaaaagag gcccaatccc
caagtcctcc tcaccccatt cctatggggt cccccacatt atggccagaa actgaggcac
atgttagccc tcccttggac tcacacctgg ggcctgcccg acccagtctg gacttccctg
cttcagcctt tggcttctcc tcattgcagc cagctccccc acagctgccc tctccagctg
aaccccgctc ggcaccctgt ggctcccttg ccttctctgg ggatcgagct ctggctctgg
ctccaggacc ccccaccaga acccggcatg atgaatacct ggaagtgacc aaggccccca
gcctggattc ctcactgccc cagctcccat cacccagttc tcctggggcc cctctcctct
ccaatctgcc acgacctgcc tcaccagccc tgtctgaggg ctcctcctct gaggctacca
cgcctgtgat ttcaagtgtg gcggagcgct tctctccaag ccttgaggct gcagaacagg
agtctggaga gctggaccca ggaatggaac cagctgccca cagcctctgg gacctcactc
ctctgagccc agcaccccca gcttcactgg acttggccct agctccagct ccaagcctgc
ctggagacat gggtgatggc atcctgccgt gccacctgga gtgctcagag gcagccacgg
agaagccaag cccctccag gttccctctg aggattgtgc agccaatggc ccaactgaaa
ccagccctaa ccccccaggc cctgccccag ccaaggctga aaatgaagag gctgcggctt
gccctgcctg ggaacgtggg gcctggcctg aaggagctga gaggagctcc cggcctgaca
cattgctctc ccctgagcag ccagtgtgtc ctgcaggggg ctccgggggc ccacccagca

```
gtgcctctcc tgaggtcgaa gctgggcccc agggatgtgc cactgagcct cggccccatc   7800
gtggggagct ctccccatcc ttcctgaacc cacctctgcc cccatccata gatgataggg   7860
acctctcaac tgaggaagtt cggctagtag gaagaggggg gcggcgccgg gtagggggc   7920
cagggaccac tgggggccca tgccctgtga ctgatgagac accccctaca tcagccagtg   7980
actcaggctc ctcacagtca gattctgatg tcccgccaga aactgaggag tgtccgtcca   8040
tcacagctga ggcagccctc gactcagatg aagatggaga cttcctacct gtggacaaag   8100
ctgggggtgt cagtggtact caccacccca ggcctggcca tgacccacct cctctcccac   8160
agccagaccc ccgcccatcc cctccccgcc ctgatgtgtg catggctgac cccgaggggc   8220
tcagctcaga gtctgggaga gtagagaggc tacgggagaa ggaaaaggtt caggggcgag   8280
tagggcgcag ggccccaggc aaggccaagc cagcgtcccc tgcacggcgt ctggatcttc   8340
ggggaaaacg ctcacccacc cctggtaaag ggcctgcaga tcgagcatcc cgggccccac   8400
ctcgaccacg cagcaccaca agccaggtca ccccagcaga ggaaaaggat ggacacagcc   8460
ccatgtccaa aggcctagtc aatggactca aggcaggacc aatggccttg agttccaagg   8520
gcagctctgg tgcccctgta tatgtggatc tcgcctacat cccgaatcat tgcagtggca   8580
agactgctga ccttgacttc ttccgtcgag tgcgtgcatc ctactatgtg gtcagtggga   8640
atgaccctgc caatggcgag ccaagccggg ctgtgctgga tgccctgctg gagggcaagg   8700
cccagtgggg ggagaatctt caggtgactc tgatccctac tcatgacacg gaggtgactc   8760
gtgagtggta ccaacaaact catgagcagc agcaacaact gaatgtcctg gtcctggcta   8820
gcagcagcac cgtggtgatg caggatgagt ccttccctgc ctgcaagatt gagttctgaa   8880
agagccgccc tcccttcccc aaggatccac tcccccagct cctttagaga atggctactg   8940
ctgagtcctt tggggttgag ggagatggga gctaggggga ggggagggag atgtcttgtt   9000
gtggggactt gggctgggct aaatgggagg ggttgtccct ccccatcatc cattcctgtg   9060
aggtgtctca aaccaaagtt aacagggaga ggatggggga ggggacaaat tagaatagga   9120
tagcatctga tgcctgagaa ccctctccta gcactgtcaa atgctggtat tgaatgggga   9180
ctgaggatgg gtctcagaga gcaacctcct ccctcgtaga gggagattat atccccaact   9240
ccagggacct ctttatctca atctatttat ttggcatcct gggagggatt tccaatagta   9300
atttatgtga cctggggcag gataccgtca gtgaggtgcc cagagctgca ccctttcctc   9360
catttcccat cccccatctc ctcaaccacc agggtctgag ttctagcagg gtcctggggg   9420
tatcccactg ctatactgtt ctactgcttc cctcagtatc tgaatgtctc aatttaaaac   9480
ttgaagctct ttagaccaat agactggtga gaggagaaag gagcttatcc cccagaccct   9540
gctttatacc attcacatcc cagggctgtg tccagacagc acaaaaacggc aaggagagcc   9600
caagccccaa tgccagaatt cttccaaact ccctgactct ttgaagtttt tactcacccc   9660
atttcaatta tcctgatccc ttctcatccc ctgcttggct tctctgcatg tggtcatctg   9720
ctgtggcttg gtgtttaatg ggttaaaaat aagccactgc ctgacatccc aacatttgac   9780
accccagcaa tgtgtgactc ccccaacatt ccactatgcc atcctgcagc tgaaatggga   9840
acactggctg cctctccaaa cccgctcttg gacagaggat ctgggaggtg gaagccaggc   9900
cagaggactt ggggaaaatg agatggagga aggaaaaagg gagaagctga gccacagctt   9960
aactcctaca gagtgaaatg aaaacgggct gaaaatacca ccccaggaga ggacctcgcc  10020
ccaagcaagc cagtgagcag ccctgccaga ctactgccag actgagaaac ccagaagctg  10080
```

```
gtagtcatgt gggcttgcct tctctgccaa acgactggga aaccaaaatg agcccacctt  10140

gtgttcttcc tagctccacc ctccccgtgc tgctgtgttc tgctcctccc cacgcttccc  10200

tgctatagtt cccagctgct gtaacggagc cacctccaac tctaacaata aaccaagttc  10260

attgcagata gtgta                                                    10275
```

<210> SEQ ID NO 25
<211> LENGTH: 568
<212> TYPE: DNA
<213> ORGANISM: Homo sapiens

<400> SEQUENCE: 25

```
aacggaggca ggttggagcc gctgccgtcg ccatgacccg cggtaaccag cgtgagctcg     60

cccgccagaa gaatatgaaa aagcagagcg actcggttaa gggaaagcgc cgagatgacg    120

ggctttctgc tgccgcccgc aagcagaggg actcggagat catgcagcag aagcagaaaa    180

aggcaaacga gaagaaggag gaacccaagt agctttgtgg cttcgtgtcc aaccctcttg    240

cccttcgcct gtgtgcctgg agccagtccc accacgctcg cgtttcctcc tgtagtgctc    300

acaggtccca gcaccgatgg cattcccttt gccctgagtc tgcagcgggt cccttttgtg    360

cttccttccc ctcaggtagc ctctctcccc ctgggccact cccgggggtg agggggttac    420

cccttcccag tgtttttat tcctgtgggg ctcaccccaa agtattaaaa gtagctttgt    480

aattcaaaaa aaaaaaaaaa aaaaaaaaaa aaaaaaaaaa aaaaaaaaaa aaaaaaaaaa    540

aaaaaaaaaa aaaaaaaaaa aaaaaaaa                                       568
```

<210> SEQ ID NO 26
<211> LENGTH: 2261
<212> TYPE: DNA
<213> ORGANISM: Homo sapiens

<400> SEQUENCE: 26

```
ggctgaggga aggaggagga taaggaggag gaacgaggcc agcaggaggc aacggcagcg     60

acggggccgg ggtgatggtg caggtgcctg ggtcggtgc ggagctgccg ggctgaggga    120

cgcctggtcc agggtccgca gcgccgccgc gtcgctcccg ggcgggcggg cgggaagatg    180

ctgagcaggt tgatgagcgg cagcagcagg agcctggagc gcgagtacag ctgcaccgtg    240

cggctgctgg acgacagcga gtacacctgc accatccaga gagatgccaa aggccagtac    300

ctgtttgacc ttctttgcca ccatctgaac ctacttgaga aagactattt tggtatccgc    360

tttgtagacc cagataagca gcggcattgg ctggaattta caaagtctgt ggtgaaacaa    420

ttgagatccc agcctccatt caccatgtgc ttccgtgtga agttttatcc tgcagaccct    480

gctgctctga aagaagaaat aaccaggtat ttagtcttcc tgcagatcaa aagggatctc    540

taccatggcc gactcctctg taaaacatcg gatgctgcct tgttagcagc ttacatcctt    600

caagcggaga ttggggatta tgactcaggg aaacaccctg aaggctacag ctccaagttc    660

cagtttttcc ctaaacattc agagaagctg gaaaggaaaa ttgctgagat tcacaagacg    720

gaactgagtg gtcaaacacc agcaacatca gagctgaact tcttaagaaa agcacagaca    780

ttggaaacat atggagtgga tcctcaccca tgtaaggacg tgtcaggaaa tgctgcattt    840

ctggccttca ctcctttgg gtttgttgtt cttcaaggaa acaagagggt ccacttcatt    900

aaatggaatg aggtgaccaa gctgaaattt gaaggaaaga ctttctattt atacgtaagt    960

cagaaagagg aaaagaaaat tattcttaca tattttgctc caactcctga agcgtgtaag   1020

cacctctgga aatgtggaat cgagaaccaa gccttctaca agctggagaa gtcaagccaa   1080
```

```
gtccgcacag tgtccagcag caatttattc tttaaaggga gccggttccg atacagtggc   1140
cgagttgcaa aggaagtcat ggaatcaagt gctaagatca aacgggagcc accggaaata   1200
cacagagcag ggatggttcc cagccggagc tgtccctcca taacccatgg cccaaggctg   1260
agcagcgtcc ccaggacccg cagaagagct gttcacatct ccatcatgga aggcctagag   1320
tccttacggg acagtgccca ttccacacca gtgcgttcca cttcccatgg ggacaccttc   1380
ctgcctcacg tgagaagcag ccggacagat agcaatgagc gagtagctgt gattgcagac   1440
gaggcctaca gccctgcaga cagcgtgctg cccacccctg tggctgagca cagcctggag   1500
ctgatgttgc tttcccggca gatcaatgga gccacctgca gcattgagga ggagaaggaa   1560
tctgaagcca gcaccccaac tgctacagag gtggaggccc ttgggggaga gctgagggcc   1620
ctgtgtcagg ggcacagcgg gcccgaggag gaacaggtga ataagtttgt tctaagtgtc   1680
ctccgtttgc tccttgtgac catgggactc ctctttgttt tgctcctcct cctgatcatc   1740
cttaccgagt ctgaccttga cattgccttt ttccgtgata tccgccagac ccccgagttt   1800
gaacaattcc actatcaata cttttgtccc ctcaggcgat ggtttgcctg caaaatccgc   1860
tcagtggtga gcctgctcat tgacacctga gaaggcatga ctcctcccaa aaactagcca   1920
ggtggaccaa ggaacccggc tacccattcc cagcaatggg acccatcgcg gaaccatcgg   1980
cacatatacc aagtcctcct ctcatgactc aaagtccact gcagcctagg agggtgtttc   2040
ccagaagaag aaagggatag gctcatgccc tgtctaaaca aactgggaaa actcattttc   2100
ttcagaagtt atttcaagaa aggctcagcg actctgtttc tcatctttcc aatttgcagg   2160
ataattttg gttttgaatt ttgatttttc atagatgtat attattttga agtatcaaat   2220
aaaaataatt tattttacta ttaaaaaaaa aaaaaaaaaa a                        2261
```

<210> SEQ ID NO 27
<211> LENGTH: 1618
<212> TYPE: DNA
<213> ORGANISM: Homo sapiens

<400> SEQUENCE: 27

```
agctgcgcgc cgggtcctgg aggccgaggc cgctcccgcc cgttgtcccc gcagtccccg     60
acgggagcgc catggcccag ccgccgcccg acgtggaggg ggacgactgt ctccccgcgt    120
accgccacct cttctgcccg gacctgctgc gggacaaagt ggccttcatc acaggaggcg    180
gctctgggat tgggttccgg attgctgaga ttttcatgcg ggcatctgag gaccagatgg    240
gacattgcag ctccagtggg acctgcctag caggggtagc tacctttatg gttattgtgg    300
gcaagcaacc cccgaaccag aagagccgag aaaccaaaga acaaggcaga cagatcccgt    360
ttgtctgtgt caggcacggc tgccatacgg tgattgccag taggagcctg ccgcgagtgc    420
tgacggccgc caggaagctg gctggggcca ccggccggcg ctgcctccct ctctctatgg    480
acgtccgagc gcccccagct gtcatggccg ccgtggacca ggctctgaag gagtttggca    540
gaatcgacat tctcattaac tgctccagca gctcctgcgg tctcccattc tgcaggtgcg    600
gccgggaact tcctgtgccc cgctggcgcc ttgtccttca acgccttcaa gaccgtgatg    660
gacatcgata ccagcggcac cttcaatgtg tctcgtgtgc tctatgagaa gttcttccgg    720
gaccacggag ggtgatcgt gaacatcact gccaccctgg ggaaccgggg gcaggcgctc      780
caggtgcatg caggctccgc caaggccgct gtggacgcga tgacgcggca cttggctgtg    840
gagtggggtc cccaaaacat ccgcgtcaac agcctcgccc ctggccccat cagtggcaca    900
```

```
gaggggctcc ggcgactggg tggccctcag gccagcctga gcaccaaggt cactgccagc    960

ccgctgcaga ggctggggaa caagaccgag atcgcccaca gcgtgctcta cctggccagc   1020

cctctggctt cctacgtgac gggggccgtg ctggtggccg atggcggggc atggttgacg   1080

ttcccaaacg gtgtcaaagg gctgccggat ttcgcatcct tctctgctaa gctctaggaa   1140

tcttccggcc gctgcttcct gccgcctcac tcagccaggt ggagagcacc aatctgaacc   1200

agcaatgcct gcagcccagc ccctcctctg aacactcagc tattactgcg ctttccctcc   1260

ccacggcccc aactccaggg caggagcaac tggacagtgg gcctggcccg tggagctgcc   1320

acgcaggtgc ctgagggcca ggtgccacgc aggtgtctga ggaccaggtg ccacgcaggt   1380

ggtgggggta cagacaagat gctgggatgt cccctgcccc atggtcaagg gtgtcctgcc   1440

tgcctgggtc cagggcctga gggagccaca tggatcccga gacttgtgtt ctcttggctg   1500

aaaacactga ggtgctccca tctgtgcgtg gcccatgagc tgggatggtc ctccagctgc   1560

ccacaaggtc cgcccctctg tctctgcacc acctgtttgc ataaacacac tttgctac     1618
```

<210> SEQ ID NO 28
<211> LENGTH: 4273
<212> TYPE: DNA
<213> ORGANISM: Homo sapiens

<400> SEQUENCE: 28

```
tcctgcttca caggctccgc ggcctccggc ctcctcggcc cccgtccccc ggcctcctcg     60

gcccccgtcc cccgccatcc gccgcccgga tcctcgccgc cctccctagg ccgccccgcc    120

gccatgggcc tgcgcccgcc gcgccgccgg gccgagggca gctgaggcgc ggtgcgaaga    180

tgggcgagga cagagcaggg cccgagcgcc agccccagca gcccgggcgc cccgcgcgcg    240

cccgcccgcg ccgccgaggg gatgcccgcg cccgccgccg cgccctgagc gcctttgtct    300

gccgcccgcg cccttccgca ccactagcct ctcgggagca tggcgtcggc cccgccggcc    360

tcgcccccgg gctcggagcc gccggggccc gacccggagc cgggcgggcc ggacgggccg    420

ggggcggcac aactggctcc gggccctgcg gagctacgcc tcggagcgcc cgtcggcggc    480

cccgacccgc agtccccggg cctggatgag cctgcgcccg gggccgctgc agatggcggg    540

gcgcgttgga gcgccgggcc ggccccgggg ctggagggag gcccgcgaga ccccgggccg    600

tccgccccgc cgccgcgctc cggcccgcgg gggcagcttg cgagccccga cgccccgggc    660

ccagggccgc gctccgaagc gccgcttcca gaactcgacc cgttgttctc ctggactgag    720

gagcccgagg agtgtggccc cgcgagctgc ccggagagcg cgcctttccg cttgcagggg    780

tccagcagca gccaccgagc gcggggcgag gtcgacgtct tctctccctt ccccgcgccc    840

acggcgggcg agctggcgct ggagcaaggt cccgggtccc cgccgcagcc ctcggacctc    900

agccagaccc acccccttcc gagcgagccc gtggggagtc aggaggacgg cccccgcctc    960

cgagccgtgt tcgatgccct ggacggggat ggggacggtt tcgtccgcat cgaggacttc   1020

atccagtttg ctacggtcta cggggcagag caggtgaagg acttaactaa gtacttggat   1080

cccagtgggc tcggcgtgat cagctttgaa gacttctacc aagggatcac agccatcaga   1140

aacggagatc ctgatggcca gtgctacggt ggtgtcgctt ctgcccaaga tgaggagccc   1200

ctggcctgcc cggacgagtt cgatgacttc gtcacctatg aggccaacga ggtgacggac   1260

agcgcgtaca tgggctccga gagcacctac agtgagtgtg agaccttcac ggacgaggac   1320

accagcaccc tggtgcaccc tgagctgcaa cctgaagggg acgcagacag tgccggcggc   1380

tcggccgtgc cctctgagtg cctggacgcc atggaggagc ccgaccatgg tgccctgctg   1440
```

```
ctgctcccag gcaggcctca cccccatggc cagtctgtca tcacggtgat cgggggcgag   1500
gagcactttg aggactacgg tgaaggcagt gaggcggagc tgtccccaga gaccctatgc   1560
aacgggcagc tgggctgcag tgaccccgct ttcctcacgc ccagtccgac aaagcggctc   1620
tccagcaaga aggtggcaag gtacctgcac cagtcagggg ccctgaccat ggaggccctg   1680
gaggaccctt cccccgagct catggagggc ccagaggagg acattgctga caaggttgtc   1740
ttcctggaaa ggcgtgtgct ggagctggaa aaggacacgg cagccaccgg tgagcaacac   1800
agccgcctga ggcaggagaa cctgcagctg gtgcacagag caaacgccct ggaggagcag   1860
ctgaaggagc aggagctgag agcctgcgag atggtcctgg aagagacccg gcgtcagaag   1920
gagctcctgt gcaagatgga gagggagaag agcattgaga tcgagaacct gcagaccagg   1980
ctacagcaac tggacgagga gaacagtgaa ctccggtcct gcacgccctg tctgaaggcc   2040
aacattgagc gtctggagga ggagaagcag aagctgttgg atgagataga gtcgctgacg   2100
ctgcggctca gtgaagagca ggagaacaag aggagaatgg gggacaggct gagtcacgag   2160
aggcaccagt tccagaggga caaggaggcc acccaggagc tgatcgagga cctccgaaag   2220
cagctggagc acctgcagct cctcaagctg gaggccgagc agcggcgggg ccgcagcagc   2280
agcatgggcc tgcaggagta ccacagccgc gcccgggaga gcgagctgga gcaggaggtc   2340
cgcaggctga agcaggacaa ccgcaacctg aaggagcaga acgaggagct gaacgggcag   2400
atcattaccc tcagcatcca gggcgccaag agcctcttct ccacagcctt ctctgagtcc   2460
ctggctgcag agatcagctc cgtctcccga gatgagctca tggaggcgat tcagaagcag   2520
gaggagatca acttccgcct gcaggactac atcgacagga tcatcgtggc catcatggag   2580
accaacccgt ccatcctgga ggtcaagtag aggcaggaag gtccagcctg agctggattc   2640
gggactccaa caccctggag tggttccgtc agaccatgag gagccaagac cagcaggtcc   2700
cacagccgac agtgcccaga gcatgcaggg aaccctcgtg cagctgagct ggggccgcca   2760
aagaccgggg ctgccaaagg ggcagagggt ggtggagagg agagggagaa agggaagtcc   2820
cagggcccgg ggtccacaga ggatgagggt tgtggcaggg ccgtccatca gcgctgacct   2880
tccgggggcc cagagcttcc cagccctgag tcaagctggc catgaacgcg tacacttcag   2940
ttcagcagga tgggctggag agcctctctg tgcagcggtg tggggtgagc cctgctgtgg   3000
cctccttgtg gtggtccctc ttcccacgtg cagccctgtt gggaagaaag gaagaaaaca   3060
ggtccctcca ggggtgctgc tgcctaagcc acccacataa gtacgctggt gccgtgtcac   3120
ccatgttgag ccgctcctga tggctgacgg gctcccagac cctcacctcg gacatggtgg   3180
tgggggaagg acgggtgggc aaggctggtg cgttccccag ctctccctac gctgctcggg   3240
ccattgccca gccagatgtg gtcacctcag tccagctctg ggcctccag gccatgtggc   3300
tgttcccacg gcccagtcct cgctgcagta acccctgggg gctctgacca cctatggggg   3360
ccgggcagga gcctctgggg cctccactcc gacatcagga cctgagatga ccgctgtgtg   3420
gcgctctctc cctgggcagg gtggatgcca caggcccctc tggctcccag gtgctgcttc   3480
tccacaggtg cggcctggcc cggcctccta aaggccacac cctccccacg cacttcccag   3540
gccagaatcc aaacatcggg aaccctgttt tcttctgggt gtgtctcact tagaaatcgt   3600
ggttcttccc cgagggtgca tgttgcagga gggagagggc agggaagact cacagcagag   3660
caggaggggg cctgtgcttc tcggggtctg caccccaggc acagcggtgt caccccgcag   3720
gaccgcgggc ctgccccaac cccagcatt cccgggtggg cccagacccc atcaccaaga   3780
```

```
ctggccaccc gctgcgtgtg tgtgcgcgcg cgtgtacgtg tggccccaca tccgccgcct   3840

tccacgctag gatgtaagag gtcgcctcct attgtacatt tggggaaagc cttgggtgta   3900

aatcagtgta aacttggagg agagattttt ctatcatgta gagtaggtat tttttataga   3960

ttgaaggttg atcaattttt taatactttc aagagaaaac tgtgtataca catgaaatat   4020

atatatatat atatatatat atatgtataa tatataaaga ctggcaccct gcctctctgt   4080

gcccaggccc agccctggtg acatggcacc actcagcagt gctgtcactg taagcatgga   4140

ctcccaggag acagtgtggg aaacgctcct gctttaattc cccgagaaac ggctcttcct   4200

gcctggatgc aggagggcag gggccaccac agattaaagc tgttactgca caaaaaaaaa   4260

aaaaaaaaaa aaa                                                      4273
```

<210> SEQ ID NO 29
<211> LENGTH: 1922
<212> TYPE: DNA
<213> ORGANISM: Homo sapiens

<400> SEQUENCE: 29

```
gtaacaactc tcagaggagc attgcccgtc agacagcaac tcagagaata accagagaac     60

aaccagattg aaacaatgga ggatctttgt gtggcaaaca cactctttgc cctcaattta    120

ttcaagcatc tggcaaaagc aagccccacc cagaacctct tcctctcccc atggagcatc    180

tcgtccacca tggccatggt ctacatgggc tccaggggca gcaccgaaga ccagatggcc    240

aaggtgcttc agtttaatga agtgggagcc aatgcagtta cccccatgac tccagagaac    300

tttaccagct gtgggttcat gcagcagatc cagaagggta gttatcctga tgcgattttg    360

caggcacaag ctgcagataa aatccattca tccttccgct ctctcagctc tgcaatcaat    420

gcatccacag ggaattattt actggaaagt gtcaataagc tgtttggtga gaagtctgcg    480

agcttccggg aagaatatat tcgactctgt cagaaatatt actcctcaga accccaggca    540

gtagacttcc tagaatgtgc agaagaagct agaaaaaaga ttaattcctg ggtcaagact    600

caaaccaaag gcaaaatccc aaacttgtta cctgaaggtt ctgtagatgg ggataccagg    660

atggtcctgg tgaatgctgt ctacttcaaa ggaaagtgga aaactccatt tgagaagaaa    720

ctaaatgggc tttatccttt ccgtgtaaac tcggctcagc gcacacctgt acagatgatg    780

tacttgcgtg aaaagctaaa cattggatac atagaagacc taaaggctca gattctagaa    840

ctcccatatg ctggagatgt tagcatgttc ttgttgcttc cagatgaaat tgccgatgtg    900

tccactggct tggagctgct ggaaagtgaa ataacctatg acaaactcaa caagtggacc    960

agcaaagaca aaatggctga agatgaagtt gaggtataca taccccagtt caaattagaa   1020

gagcattatg aactcagatc cattctgaga agcatgggca tggaggacgc cttcaacaag   1080

ggacgggcca atttctcagg gatgtcggag aggaatgacc tgtttctttc tgaagtgttc   1140

caccaagcca tggtggatgt gaatgaggag ggcactgaag cagccgctgg cacaggaggt   1200

gttatgacag ggagaactgg acatggaggc ccacagtttg tggcagatca tccttttctt   1260

tttcttatta tgcataagat aaccaactgc attttatttt tcggcagatt ttcctcaccc   1320

taaaactaag cgtgctgctt ctgcaaaaga tttttgtaga tgagctgtgt gcctcagaat   1380

tgctatttca aattgccaaa aatttagaga tgttttctac atatttctgc tcttctgaac   1440

aacttctgct acccactaaa taaaaacaca gaaataatta gacaattgtc tattataaca   1500

tgacaaccct attaatcatt tggtcttcta aaatgggatc atgcccattt agattttcct   1560

tactatcagt ttattttat aacattaact tttactttgt tatttattat tttatataat   1620
```

ggtgagtttt taaattattg ctcactgcct atttaatgta gctaataaag ttatagaagc 1680
agatgatctg ttaatttcct atctaataaa tgcctttaat tgttctcata atgaagaata 1740
agtaggtatc cctccatgcc cttctgtaat aaatatctgg aaaaaacatt aaacaatagg 1800
caaatatatg ttatgtgcat ttctagaaat acataacaca tatatatgtc tgtatcttat 1860
attcaattgc aagtatataa taaataaacc tgcttccaaa caacaataaa aaaaaaaaaa 1920
aa 1922

<210> SEQ ID NO 30
<211> LENGTH: 1319
<212> TYPE: DNA
<213> ORGANISM: Homo sapiens

<400> SEQUENCE: 30
gtcaaagcag cagcggcggc ggcggcggcg gcagcagcag cagcagcagg agaccttctc 60
tgatggatga cctctgtgaa gcaaatggca cttttgccat cagcttattt aaaatattgg 120
gggaagagga caactcaaga aacgtattct tctctcccat gagcatctcc tctgccctgg 180
ccatggtctt catgggggca aagggaagca ctgcagccca gatgtcccag gcactttgtt 240
tatacaaaga cggagatatt caccgaggtt tccagtcact tctcagtgaa gttaacagaa 300
ctggcactca gtacttgctt agaactgcca acagactctt tggagaaaag acgtgtgatt 360
tccttccaga ctttaaagaa tactgtcaga agttctatca ggcagagctg gaggagttgt 420
cctttgctga agacactgaa gagtgcagga agcatataaa tgactgggtg gcagagaaga 480
ctgaaggtaa gatttcagag gtactggatg ctgggacagt cgatcccctg acaaagctag 540
tccttgtgaa tgccatttat ttcaagggaa agtggaatga gcaatttgac agaaagtaca 600
caaggggaat gctctttaaa accaacgagg aaaaaaagac agtgcagatg atgtttaagg 660
aagctaagtt taaaatgggg tatgcggatg aggtacacac ccaggtcctg gagctgccct 720
atgtggaaga ggagctgagc atggtcattc tgcttcccga tgacaacacg gacctcgccg 780
tgaaagagtg atggatcttg aagaatttga agctaactcc aggacaggca gaggacaaac 840
aaggatgctg atgaagtctt cttgcattcc ccatttctcg tctcatgctc ccttctcatg 900
cctcccttca tcttcagatg aaacacaatt ccctctcttt tactctgagt tgccctctga 960
tttaaccctg aatagtcccc tcattagact cagaagcaga gttctgagcc atgctctttg 1020
tcttttgtca aacaatctct cccactcaca gtagtatgta ttgcatgaag attaatgtaa 1080
tgaattggtt agaattttct aaactgttaa aaaatgtttt taacatttga aaggagttag 1140
gtacaaattg tttttattaa aaatttctgc ctgtctcaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaa 1319

<210> SEQ ID NO 31
<211> LENGTH: 2831
<212> TYPE: DNA
<213> ORGANISM: Homo sapiens

<400> SEQUENCE: 31
ggaccgggcc cggtcagctt ccgcggagcc attggcagac gccgtggcct cccttgagcc 60
ccgacccccg tcgtcagaac aaccccgggc ccactccccc aaccccactt ccgcttcgcg 120
ccgctatcgc gatagcgccc gggcccgggg cgcgagaaaa aggcggcggg cgctcgcctc 180

```
ccccgcctgt cgcgatacgc tcctcagcgg cggcgccagc tcctgtgcgt ccgtctccaa    240
gagagtatga agagagtgcg tctgtagggc agggaagatg gcggacaagc gcaaactcca    300
aggtgagatt gatcgctgcc tcaagaaggt gtccgagggc gtggagcagt ttgaagatat    360
ttggcagaag ctccacaatg cagccaacgc gaaccagaaa gaaaagtatg aggctgacct    420
aaagaaggag attaagaagc tacaacggct gagggaccaa atcaagacat gggtagcgtc    480
caacgagatc aaggacaaga ggcagcttat agacaaccgc aagctcattg agacgcaaat    540
ggaacggttc aaagttgtgg aacgagagac caaaaccaaa gcttacagca aagagggcct    600
gggcctggcc cagaaggtag atcctgccca gaaggagaag gaagaggttg gccagtggct    660
cacgaatacc atcgacacgc tcaacatgca ggtggaccag tttgagagtg aagtggagtc    720
actgtcagtg cagacacgca agaagaaggg cgacaaggat aagcaggacc ggattgaggg    780
cttgaagcgg cacatcgaga agcaccgcta ccacgtgcgc atgctagaga ccatcctgcg    840
catgctggac aatgactcca tcctcgttga cgccatccgc aagatcaagg acgacgttga    900
gtactatgtt gactcatccc aggaccccga cttcgaggag aacgagtttc tctacgatga    960
cctggacctc gaggacattc cacaggcgct ggtcgccacc tcccccccca gccacagcca   1020
catggaggat gagatcttca accagtccag cagcacgccc acctcaacca cctccagctc   1080
tcccatcccg cccagcccag ccaactgtac cacggaaaac tctgaagatg ataagaagag   1140
gggacgttcc acagacagtg aagtcagcca gtctccagcc aaaaacggct ccaagcctgt   1200
ccacagcaac cagcaccctc agtccccagc tgtgccgccc acctacccct ccggcccccc   1260
gcctgctgcc tctgccttga gcaccactcc tggcaacaat ggggtccccg cccccgcagc   1320
acccccaagt gccctgggcc ccaaggccag tccagctccc agccacaact cgggcacccc   1380
tgctccctat gcccaggcgg tggccccacc agctcccagt gggcccagca cgacccagcc   1440
ccggcccccc agcgtccagc ctagcggagg cggaggcggc ggcagcggag gcggagggag   1500
cagcagcagt agtaacagca gtgccggtgg aggggctggc aagcagaatg gcgccaccag   1560
ttacagctca gttgtggcag acagcccggc agaggtggct ttgagcagca gtgggggcaa   1620
caatgccagc agccaggcct tgggcccccc ttccggcccc cacaacccac ctcccagcac   1680
ctcgaaggaa cccagtgcgg cagccccaac gggggctggg ggcgtggccc caggctcagg   1740
gaacaactca gggggaccca gcctcctggt gccactgcct gtgaatcctc ccagctcccc   1800
aacgcccagc ttcagtgatg ccaaggcagc cggtgccctg ctcaatgggc ctccacagtt   1860
cagcaccgcc ccagaaatca aggcccctga gcctctgagc tccttgaagt ccatggcgga   1920
acgggcagcc atcagctctg gcattgagga ccctgtgcca acgctgcacc tgaccgagcg   1980
agacatcatc ctgagcagta catcagcacc tccggcctca gcccagccgc ccctgcagct   2040
gtcagaggtg aacataccgc tgtcgctggg tgtctgtcca ctgggccctg tgcccctcac   2100
caaggagcag ctctatcagc aggccatgga agaggccgcc tggcaccaca tgcctcaccc   2160
ctctgactct gagcgtattc ggcagtacct cccccggaac cctgtccgga cgccccccta   2220
ccaccaccag atgccacccc cacactcgga cactgtggaa ttctaccagc gcctgtcgac   2280
cgagacactc ttcttcatct tctactatct ggagggcact aaggcacagt atctggcagc   2340
caaggcccta aagaagcagt catggcgatt ccacaccaag tacatgatgt ggttccagag   2400
gcacgaggag cccaagacca tcactgacga gtttgagcag ggcacctaca tctactttga   2460
ctacgagaag tggggccagc ggaagaagga aggcttcacc tttgagtacc gctacctgga   2520
ggaccgggac ctccagtgac accggcccct ccctctaccc accccccttcc ccttgcatgc   2580
```

```
tgatcccccct gcccaggtga gggccctgcc ctggaagact ggagggaggc cccaagccac   2640

ggggcatccc cctctcccag gaagcaggga gggggccggg aggttttcct ctcagcccca   2700

ccctgggggc ccgggggcga gggctgcccc ctcctcccct ccccagtgag ggacattttt   2760

tggtaaacct attttcattt tggaaaatat ttatgaataa atagttttat atgaaaaaaa   2820

aaaaaaaaaa a                                                        2831
```

<210> SEQ ID NO 32
<211> LENGTH: 1329
<212> TYPE: DNA
<213> ORGANISM: Homo sapiens

<400> SEQUENCE: 32

```
atgcagctca gcctgggcta cacagccagg tgtcagatgt gtctctgctg atctgagtct     60

gcctgtggca tggacctgca tcttccctga agcatctcca gggctgaaaa atcactgacc    120

atggcaccat ggtctcatcc atctgcacag ctgcagccag tgggaggaga cgccgtgagc    180

cctgccctca tggttctgct ctgcctcggg aacctctcca aagccaccct ctgggctgag    240

ccaggctctg tgatcagccg gggggaactct gtgaccatcc ggtgtcaggg gaccctggag    300

gcccaggaat accgtctggt taaagaggga agcccagaac cctgggacac acagaaccca    360

ctggagccca agaacaaggc cagattctcc atcccatcca tgacagagca ccatgcaggg    420

agataccgct gttactacta cagccctgca ggctggtcag agcccagcga cccccctggag    480

ctggtggtga caggattcta caacaaaccc accctctcag ccctgcccag tcctgtggtg    540

acctcaggag agaacgtgac cctccagtgt ggctcacggc tgagattcga caggttcatt    600

ctgactgagg aaggagacca caagctctcc tggaccttgg actcacagct gacccccagt    660

gggcagttcc aggccctgtt ccctgtgggc cctgtgaccc ccagccacag gtggatgctc    720

agatgctatg gctctcgcag gcatatcctg caggtatggt cagaacccag tgacctcctg    780

gagattccgg tctcaggagc agctgataac ctcagtccgt cacaaaaacaa gtctgactct    840

gggactgcct cacaccttca ggattacgca gtagagaatc tcatccgcat gggcatggcc    900

ggcttgatcc tggtggtcct tgggattctg atatttcagg attggcacag ccagagaagc    960

ccccaagctg cagctggaag gtgaacagaa gagagaacaa tgcaccattg aatgctggag   1020

ccttggaagc gaatctgatg gtcctaggag gttcgggaag accatctgag gcctatgcca   1080

tctggactgt ctgctggcaa tttctttttt tctttctttt cttttctttc tttttttttt   1140

tttttttttt ttttttgaga tggagtcttg ctctgtcacc aggctggaat gcagtggcgc   1200

aatctgggct cactgcaacc tccgcctctc gggttcaagt gattctcctg cctcagcctc   1260

tggcaatttc tagagggagg aatgggtgtt tgagtgcaga gacactggtc tggggtgatc   1320

catggagga                                                           1329
```

<210> SEQ ID NO 33
<211> LENGTH: 2553
<212> TYPE: DNA
<213> ORGANISM: Homo sapiens

<400> SEQUENCE: 33

```
ctgaaatctc atttgaccag taccatctgt tcagacacgg ggttgctcat ggacagtggc     60

tcagtggagg gcagagacac agggaagcat tccaggccaa tttttctgtg ggccgtgcaa    120

cgccagtccc tggcgggacc tatagatgct atggttcctt caatgactct ccctataagc    180
```

```
ccccagtgac ccgctgcaac tttacaccac aggaaacact aagagtactc ctctgtcatt    240
cacagaatcc acccctgaat ctgacaccac catggcaaac acagagccca cggaaggcca    300
acggacggat gaagaggagc ctgcagcaga agagacacag gagatcatat atgcccagtt    360
aaaccaccag gccctctcac agacaggatt ccctcctgcc tcccagtgtc cccactacct    420
ctcggaggat cctagtatct acatcactgt ccaccaagcc caggctgagg ccagagctgc    480
ccccagtctt tggcacaaag ggcattaata cgcaaggacc tggatctatt cctaggagga    540
tttttttcc acggacattc ttcctccttc tggtaccatc ttgacacctc gaagctggca    600
acagcagtgt ctgaatgctt gtgggattat cttaaaattc cagcactgct gaacagacaa    660
ctagccattc tacaattcta ttttgagcat ccaaccattt caggtgattt gactctaccc    720
acacactcat cctggatatc tcattaatat catctgagtt atcctgaaac tctacagaca    780
tgcttctgga aagccgatgt atatgctcag ccagtttaat ctctaaatta ctcaataagg    840
ttttttaaa aaaatttttt taaagttctg ggtacatgc tcaggatgtg caggtttgtt    900
acgtaggtaa acgtgtgcca tggtggtttg ctgcacctat caaaccgtca cctaggtatt    960
aagcccagca ggcattagct ctcttcccta atgctctcca tacccccctgc cctcctctga   1020
caggccccag tgaatgtgtt cccctccctg tgtccatgtg ttctcattgt tcagctccca   1080
cttataagtg aaaacatgcg gtgtctggtt ttctgttcct gcattagttt gctgaggata   1140
atgtcttcta gcttcattca tgtctctgca aatgatatga tctcattcct ttttatgact   1200
gcgtagtatt ccgtggtgta tatgtacaac tttattttta tccagtctat cattgatggg   1260
catttgggtt gattccacgt ctttgctgtt actcaacaaa attttgcaga gatgaagtgt   1320
attctatatc tgagtcatct aatatggtag ccactagcca aatatggctt tttaacttag   1380
aattagaata gatcaaattc catgaagttt aaaattcagt tcctcagcca catggccaca   1440
atttgagttc tcagagccac gtgtggctgc tggctgtggg agagaatagc atgaacacaa   1500
aatgttttcc ttgtcagagg aagttctagc tgttctagat taaaggtgca aatttgaaga   1560
tgcagagcct attttctcat gcagtgcagg ctcctggaag agacctaatg taacaaaacg   1620
ataatatttc acatcaatgg tgacatgtct ttatcttacg aaatgcgggg aacaagcaga   1680
gttctcttgt ggagtgtctt atcacctctt atcctcatgc aaatttctgc catagagatt   1740
ttctcccaaa ctttgagaag gtcacctctg tcaggcctct gagcccaagc taagccatcc   1800
tatcccctgt gacctgcacg tacacatcca gatggcctga agcaactgaa gattcacaaa   1860
agaagtgaaa atagccttaa ctgatgacat tccaccactg tgacttgttc ccgccccact   1920
aactgatacc atatattctg ccccgcccaa gaaggtactt tgtaatattc ctcgccccct   1980
tacccccccac cgccctgccc ccgctcgccc gccttaagaa ggtactttgt aatattctcc   2040
cccacaactt tagaaggtac tttgtaatat tctcccccac aactttagaa ggtactttgt   2100
aatattctcc cccacaactt tagaaggtac tttgtaatat tctcccctcc ccttaagaag   2160
gtactttgta atattctccc ccacaacttt agaaggtact ttgtaatatt ctcccctccc   2220
cttaagaagg tacttcgagg ctgggtgcgg tggctcatgt ctgtaatccc agcactctgg   2280
ggggccgagg tgggtggatc acgaggtcag gagatcgaga ccatcctggc taatgtggtg   2340
aaaccccgtc tctactaaaa aaatacaaaa caattggctg ggcatggtgg cgggtgcctg   2400
tggtcccagc cacttgggag tctgaggcag gagaatggcg tgaacccagg aggcagagct   2460
tgcagtgagc tgaggtcgcg ccactgcact ccagcctggg cgatagagca agactctgtc   2520
tcaaaaaaaa aaaaaaaaaa aaaaaaaaaa aaa                                2553
```

<210> SEQ ID NO 34
<211> LENGTH: 3191
<212> TYPE: DNA
<213> ORGANISM: Homo sapiens

<400> SEQUENCE: 34

```
acacacacag cgagcgggcg ggcagaaggc ggttctgctg gtctcctctt cctgctgcag     60
ccagcccagc gtgcgggcca tgggccctgc cggcgggtga ggcagccgcg tggcaggcat    120
gttcggaggc ccggggcctg gggtcctggg agcccagggc atggcgggac ccctgcgggg    180
ccgggtggaa gagctgaagc tgccgtggtg gcgggagagc tcaccgctgg tgctgcggca    240
cagcgaggcg gctcggctgg cggccgacgc cctcctggag cggggtgagg ctgcctacct    300
gcgggtcatc tccgaggagc gggagctgcc cttcctgagc gccctggatg tggactacat    360
gaccagccat gtgcgcgggg gccctgagct cagcgaggct caggggcagg aggcctccgg    420
gccagaccgc ctcagcctgc tctctgaagt cacctcaggg acttacttcc ccatggcctc    480
tgacatagac cccccagacc tggacctggg ctggcccgag gtgccacagg ccacaggctt    540
cagccccacc caggctgtgg tccacttcca gagggacaag gccaagaaca tcaaggacct    600
gctgcgcttc cttttcagcc aggcccacac ggtggtggct gtggtgatgg acatattcac    660
tgacatggag cttctgtgtg acctcatgga ggcctcaagc cggcgtggtg tccctgtgta    720
cctgctcctt gcccaggagc acctgaggca cttcctggag atgtgctaca agatggacct    780
caatggggag cacctgccga acatgcgtgt gcggagcacg tgtggggaca catactgcag    840
caaggctggc cgccgcttca cgggggcagc cctggagaag ttcgtcctca ttgactgtga    900
gcaagtggtg gcgggcagtt acagcttcac ctggctttgc agccaggccc acactagcat    960
ggtgctgcag ctgaggggcc gcatcgtgga agactttgac cgggagttcc gctgtctgta   1020
cgctgagtcg cagcctgtgg agggcttctg tggcggtgag gacccgctgt ctccccgggc   1080
actgcgtcct cccccctgtgg ccctagcctt caggcctgat gtcccaagcc ccacgtcgtc   1140
cctgccctcc agcaccagcc tcagcagcat caagcagtca ccgcttatgg gtcgctcctc   1200
ctacctcgct ctaccaggag gtggtgattg cagtgatacg ggtgtggtgt cctcgtccct   1260
gggtcctgcc cgccgtgagg ccagtggcca gccctcccta catcgccaac tgtcagaccc   1320
taaccacggc tcccctcctg ggctctatag ggccaatctc ggcaagctag ggcataccc    1380
atggtcccag tcctcccctg ccctcaacca taatagtacc agccccttaa ccttggcagt   1440
ggggtcacct ctgcttcctc gctcccggcc cctcctccag ttccatcggg gtgccccagc   1500
tctgtcccgg ttcccagaga atgggctccc aggaagccaa gagcccagcc ccctgcgggg   1560
tcgatgggta cctggcacaa ccctggagac agtggaggag aaggagaaga aggcatctcc   1620
aagtcagagc cgtggccagc tggatctcct tgtccccttc cccagagccc gagaagtggg   1680
agaccctgac tctggggtta cccccaactc aggccccctt cggcctggcg agcaggcccc   1740
agaggacagg aggttgtccc caagccaggc cgacagccag ctggatctcc tgtcccgagc   1800
cctgggtact gggggtgccc ctgagttggg ttccctcaga cctggtgatc gggccctgga   1860
ggacaggagg ctgtccctaa accaaagccg tggccaatca gacctcctga tgcagtaccc   1920
caaggcccag ggttccagag tgccccttga aaccaactcc tcagccagac ctgccagacg   1980
ggcaccagat gagcggcggc agaccctggg gcacagccag ctggacctca tcacaaagtt   2040
cggcccattc cgtggtgagg ggcctgggcc caatggtctc ccgatatcaa gccctgctcg   2100
```

```
cacggctgga gctgggtctg gggatgagaa acggctaacc ctgggccaca gcaagctgga   2160

cctcatcacc aagtatcatc agttgcacgg ggccaggcag ggaactgagc ctgggggtcc   2220

caagggtggc catctcaatg gtggtaacag tgacctggtc agggatgaga aacggctgac   2280

cctgggtcac agcaaactgg acctcatcac taagtacaac aagtccaagt tcaagcagct   2340

ccgaagccgc tttgagtcct agccaaagga ctggcatcgg gggtgcactg gcaagggcag   2400

gcccctcctc tgtccaccga gactctggac ttgctcaggt cccagactgg ggaagggagg   2460

tgtctagaaa cccaggtcag acacactctc tgggctcaag attcttgtgt acacacacac   2520

acacacacac acacacacac accctaacta gtatcttctt gaatctaggc tgtgtttcca   2580

gccctgtgct gggcctgtag agctgacagg tgggtcacac tcagacctgg ggacagaggt   2640

gaaatgcaca agctgctgga gaaggggtca gagccatatc aagttaaagg ttaaccagtt   2700

acagagggtg ttagaaaaca aagggcagag agtcctggag aaggtggagt agtcagaaaa   2760

ctttcttaga ggagatggag gtggcctttg agccaggccc tgaaggatgg ggaggttttg   2820

gacagaggga ggagagagtt agaaaaattt ttggtagaga gaatcaggtg aaagagatgc   2880

cctaaagagg actgagtggg tctgaggtga atgagtgagg aagagcagag tatgtggata   2940

cccggaaaca cacacacaca cacatcatca ttatcatcat catcattgtc gtcgtcatca   3000

tcttgctgag tcatcatcat catcatcatc attgtcgtcg tcatcatctt gctgagtgtc   3060

tcttgaagta caggctgtga caggttgtgg gccattttcc tgaactcacc acttacccgg   3120

gatagtaaac atgatacaca tcaataaagg cagactttat tgtgaaaaaa aaaaaaaaaa   3180

aaaaaaaaaa g                                                        3191
```

<210> SEQ ID NO 35
<211> LENGTH: 2383
<212> TYPE: DNA
<213> ORGANISM: Homo sapiens

<400> SEQUENCE: 35

```
ctccttcaag ccctcagtca gttgtgcagg agaaaggggg cggttggctt tctcctttca     60

agaacgagtt attttcagct gctgactgga gacggtgcac gtctggatac gagagcattt    120

ccactatggg actggataca aacacacacc cggcagactt caagagtctc agactgagga    180

gaaagccttt ccttctgctg ctactgctgc tgccgctgct tttgaaagtc cactcctttc    240

atggtttttc ctgccaaacc agaggcacct ttgctgctgc cgctgttctc tttggtgtca    300

ttcagcggct ggccagagga tgagactccc caaactcctc actttcttgc tttggtacct    360

ggcttggctg gacctggaat tcatctgcac tgtgttgggt gcccctgact tgggccagag    420

accccagggg accaggccag gattggccaa agcagaggcc aaggagaggc ccccccctggc    480

ccggaacgtc ttcaggccag ggggtcacag ctatggtggg ggggccacca atgccaatgc    540

cagggcaaag ggaggcaccg ggcagacagg aggcctgaca cagcccaaga aggatgaacc    600

caaaaagctg ccccccagac cgggcggccc tgaacccaag ccaggacacc ctccccaaac    660

aaggcaggct acagcccgga ctgtgacccc aaaaggacag cttcccggag gcaaggcacc    720

cccaaaagca ggatctgtcc ccagctcctt cctgctgaag aaggccaggg agcccgggcc    780

cccacgagag cccaaggagc cgtttcgccc acccccccatc acaccccacg agtacatgct    840

ctcgctgtac aggacgctgt ccgatgctga cagaaaggga ggcaacagca gcgtgaagtt    900

ggaggctggc ctggccaaca ccatcaccag ctttattgac aaagggcaag atgaccgagg    960

tcccgtggtc aggaagcaga ggtacgtgtt tgacattagt gccctggaga aggatgggct   1020
```

```
gctgggggcc gagctgcgga tcttgcggaa gaagccctcg gacacggcca agccagcggc   1080

ccccggaggc gggcgggctg cccagctgaa gctgtccagc tgccccagcg gccggcagcc   1140

ggcctccttg ctggatgtgc gctccgtgcc aggcctggac ggatctggct gggaggtgtt   1200

cgacatctgg aagctcttcc gaaactttaa gaactcggcc cagctgtgcc tggagctgga   1260

ggcctgggaa cggggcaggg ccgtggacct ccgtggcctg ggcttcgacc gcgccgcccg   1320

gcaggtccac gagaaggccc tgttcctggt gtttggccgc accaagaaac gggacctgtt   1380

ctttaatgag attaaggccc gctctggcca ggacgataag accgtgtatg agtacctgtt   1440

cagccagcgg cgaaaacggc gggcccccact ggccactcgc cagggcaagc gacccagcaa   1500

gaaccttaag gctcgctgca gtcggaaggc actgcatgtc aacttcaagg acatgggctg   1560

ggacgactgg atcatcgcac cccttgagta cgaggctttc cactgcgagg ggctgtgcga   1620

gttcccattg cgctcccacc tggagcccac gaatcatgca gtcatccaga ccctgatgaa   1680

ctccatggac cccgagtcca caccacccac ctgctgtgtg cccacgcggc tgagtcccat   1740

cagcatcctc ttcattgact ctgccaacaa cgtggtgtat aagcagtatg aggacatggt   1800

cgtggagtcg tgtggctgca ggtagcagca ctggccctct gtcttcctgg gtggcacatc   1860

ccaagagccc cttcctgcac tcctggaatc acagaggggt caggaagctg tggcaggagc   1920

atctacacag cttgggtgaa aggggattcc aataagcttg ctcgctctct gagtgtgact   1980

tgggctaaag gcccccttt atccacaagt tcccctggct gaggattgct gcccgtctgc   2040

tgatgtgacc agtggcaggc acaggtccag ggagacagac tctgaatggg actgagtccc   2100

aggaaacagt gctttccgat gagactcagc ccaccatttc tcctcacctg ggccttctca   2160

gcctctggac tctcctaagc acctctcagg agagccacag gtgccactgc ctcctcaaat   2220

cacatttgtg cctggtgact tcctgtccct gggacagttg agaagctgac tgggcaagag   2280

tgggagagaa gaggagaggg cttggataga gttgaggagt gtgaggctgt tagactgtta   2340

gatttaaatg tatattgatg agataaaaag caaaactgtg cct                     2383
```

<210> SEQ ID NO 36
<211> LENGTH: 7814
<212> TYPE: DNA
<213> ORGANISM: Homo sapiens

<400> SEQUENCE: 36

```
ggaattccgg gaaatcctgg gataagagaa tagtttcctg gaagatctgt gcctccaacc     60

agcagagagg gattgagctt cattgaactc aacagagcca acatttcata gcaccatgtt    120

caagaggagg ttgaagtggc atggcaatgg ttagagaccc tgctgggcgt gaacaccctc    180

tggctaccta gggacctgtg ggcctaccac ctggtgccct catggagaca agaagccctg    240

ggttgaacaa catgaagccc cagtcactgc agctggtact ggaagagcag gtgctggcac    300

tacagcagca gatggcagag aatcaggcag cctcctggcg gaagctgaag aactcccagg    360

aggcccagca gagacaagca acccttgtga ggaagctgca ggccaaggtg ctgcagtacc    420

gaagctggtg ccaagagctg gagaagcggc tagaagccac tggaggacca atcccccaga    480

ggtgggaaaa tgtggaggag ccaaacctgg atgagctgct ggtccgattg gaggaggagc    540

aacagaggtg tgagagtcta gcagaggtga acacccagat tcgactgcac atggaaaaag    600

ctgacgtggt gaataaagcc cttagggcag atgtggaaaa actgacagtg gactggagcc    660

gggcccggga tgagctaatg aggaaggaga gccagtggca gatggagcag gagttcttca    720
```

```
agggctacct gaaaggggag cacggtcgcc ttctcagtct atggcgggag gttgtgacat    780
tccgacgcca cttcctggaa atgaagtcag ctactgacag agatctgatg gagctaaaag    840
ctgagcatgt gaggctttca gggtctctgt tgacctgttg tctgcgcttg actgtgggag    900
cacagtctcg ggaacccaac ggatctggaa gaatggatgg gcgggagccg gcccagctgc    960
tgctgctact agccaagacc caggagctgg agaaggaagc ccatgaaagg agccaggagt   1020
taatacagct gaagagtcaa ggggatctgg agaaggctga acttcaggac cgggtgaccg   1080
agctctctgc tctgttgacc cagtctcaga agcaaaatga agattatgaa aagatgataa   1140
aggctctgag agagacagtg gagatcctgg agacaaatca cacagaatta atggaacatg   1200
aagcatctct tagtaggaat gcgcaagagg agaagttgtc tttacagcag gtgatcaagg   1260
atataaccca ggtcatggtg gaagaagggg acaatatagc ccaaggctct ggtcttgaga   1320
actctttgga attggagtct agtatcttct cccagtttga ttaccaagat gcagacaagg   1380
ctcttactct ggtgcgttca gtgctgactc ggagacgcca ggctgtgcag gacctaaggc   1440
agcagcttgc aggctgtcaa gaggctgtga acttgttgca acagcagcat gatcagtggg   1500
aggaagaggg caaagccttg agacagcggc tgcagaagct cactggggag cgggacactc   1560
tggcagggca gactgtggac ctccagggag aggtggactc tctcagcaag gagcgagagc   1620
tgctgcagaa ggccagggaa gagctgcggc agcagctgga ggtgctagag caggaggcat   1680
ggcgcctgcg aagggtaaat gtggagcttc agctgcaggg ggactctgcc cagggccaga   1740
aggaggaaca gcaggaggag ctgcacctgg ctgtccggga gagggagcgt cttcaggaga   1800
tgctgatggg cctggaagcc aaacagtcag aatcactcag tgaactgatc actcttcggg   1860
aagccctgga gtcaattcac ctggaagggg agttactgag gcaagagcaa acggaagtga   1920
ccgcagcgct ggctagggca gagcagtcaa ttgcagagct gtcgagttct gaaaacaccc   1980
tgaagacaga agtagctgat cttcgggctg cagctgtcaa gctcagtgcc ttaaatgagg   2040
ctttggcgtt agataaagtt gggctgaacc agcagcttct ccagttagag gaggagaacc   2100
agtctgtgtg cagcagaatg gaggccgcag agcaggcgag aaatgctttg caggtcgacc   2160
tggcggaggc agagaagagg agggaagccc tgtgggaaaa gaacactcac ctggaggctc   2220
agctgcagaa agctgaggag gctggggctg agctgcaggc agatctcagg gacatccaag   2280
aagagaagga agaaattcaa aagaaactaa gtgagtcacg tcaccagcag gaggcagcca   2340
cgactcagct ggagcagcta catcaggagg caaagcgaca ggaagaagtg cttgccaggg   2400
cagtccagga gaaggaggcc ctagtacgag agaaagcggc tctagaggtg cggctgcagg   2460
ccgtggagcg tgaccggcag gacctcgctg cacaactaca ggggctcagc tcagccaagg   2520
agctactgga gagcagtctg tttgaagccc aacaacaaaa ttctgtgata gacgagccgc   2580
aggggcagct ggaggtccag attcaaactg tcactcaagc caaggaagta atccaagggg   2640
aagtgaggtg cctgaagctg gaactggaca ctgaacggag tcaggcagag caggagcggg   2700
atgctgcagc cagacagctg gcccaggctg agcaagaagg gaagactgcc ttggagcagc   2760
agaaggcagc ccatgagaaa gaggtgaacc agctccggga gaaatgggag aaggagcgct   2820
cctggcacca gcaggagctg gcaaaggctc tggagagctt agaaagggaa aaaatggagc   2880
tggaaatgag gctaaaggag cagcagacag aaatggaggc catccaggcc cagagggaag   2940
aagaacggac ccaggcagag agtgccctat gccagatgca gctggaaaca gagaaggaga   3000
gagtatccct cctggagaca ctgctgcaga cgcagaagga gctagcagat gccagccaac   3060
aactggaacg actgaggcag gacatgaaag tccagaaatt aaaggagcag gagaccactg   3120
```

```
ggatactaca gacccagctc caggaggctc aacgggagct gaaggaggca gcccggcagc   3180
acagagatga ccttgctgcc ctccaagaag agagcagctc cctgctgcag gataagatgg   3240
acctgcagaa gcaggtggag gacttgaagt ctcagctggt ggcccaggat gactcccaga   3300
ggctggtgga gcaggaggtt caggagaagc tgagagagac ccaggagtat aaccgaattc   3360
agaaggagct ggagagagag aaagccagcc tgactctgtc actgatggaa aaggaacaga   3420
gactccttgt tttacaagaa gctgactcta ttcgacaaca agagctgagt gccctgcgcc   3480
aggacatgca ggaggcccag ggagaacaga aagagctcag tgctcagatg gaattactaa   3540
ggcaagaggt gaaggaaaag gaggctgact ttctggccca ggaagcacag ctgctggagg   3600
agctggaggc gtctcatatc acggagcagc agctgcgagc ctccttgtgg gcccaggaag   3660
ccaaggcagc ccaactacac ctgcgactgc gcagcacaga gagccagcta gaagcgctgg   3720
ccgcagagca gcagcccggg aaccaggccc aggcccaggc ccagctggcc agcctctact   3780
ctgccctgca gcaggccctg ggtctgtttt gtgagagcag gcctgagctg agtggtgggg   3840
gagactctgc tccttccgtc tggggccttg agccagacca gaatggagct aggagcctct   3900
ttaagagagg gcccctgctg actgctctct ccgctgaggc agtagcatct gccctcctca   3960
agcttcatca agacctgtgg aagactcaac agacccggga tgttctgagg gatcaggtcc   4020
agaaactgga agagcgtcta actgatactg aggctgagaa gagccaggtc cacacagagt   4080
tgcaggatct gcagagacag ctctcccaga atcaggaaga gaaatccaag tgggaaggaa   4140
agcagaactc cctagaatct gagctgatgg aactacatga aactatggca tccttacaga   4200
gtcgcctgcg gagagcagag ctacagcgaa tggaagccca gggtgagcga gagttacttc   4260
aggcagccaa ggagaacctg acagcccagg tggaacacct gcaagcagct gtcgtagaag   4320
ccagggctca ggcaagtgct gctggcatcc tggaagaaga cctgagaacg gctcgctcag   4380
cactgaagct gaaaaatgag gaagtagaga gtgagcgtga gagagcccag gctctgcaag   4440
agcagggcga actgaaggtg gcccaaggga aggctctgca agagaatttg gccctcctga   4500
cccagaccct agctgaaaga gaagaggagg tggagactct gcggggacaa atccaggaac   4560
tggagaagca acgggaaatg cagaaggctg ctttggaatt gctgtctctg gacctgaaga   4620
agaggaacca agaggtagat ctgcagcaag aacagattca ggagctagag aagtgtaggt   4680
ctgttttaga gcatctgccc atggccgtcc aggagcgaga gcagaagctg actgtgcaga   4740
gggagcagat cagagagccc gagaaggatc gggagactca gaggaacgtc ttggagcatc   4800
agcttctaga acttgagaag aaagaccaaa tgattgagtc ccagagagga caggttcagg   4860
acctgaaaaa gcagttggtt actctggaat gcctggccct ggaactggag gaaaaccatc   4920
acaagatgga gtgccagcaa aaactgatca aggagctgga gggccagagg gaaacccaga   4980
gagtggcttt gacccacctt acgctggacc tagaagaaag gagccaggag ctgcaggcac   5040
aaagcagcca gatccatgac ctggagagcc acagcaccgt tctggcaaga gagctgcagg   5100
agagggacca ggaggtgaag tctcagcgag aacagatcga ggagctgcag aggcagaaag   5160
agcatctgac tcaggatctc gagaggagag accaggagct gatgctgcag aaggagagga   5220
ttcaggttct cgaggatcag aggacccggc agaccaagat cctggaggag gacctggaac   5280
agatcaagct gtccttgaga gagcgaggcc gggagctgac cactcagagg cagctgatgc   5340
aggaacgggc agaggaaggg aagggcccaa gtaaagcaca gcgcgggagc ctagagcaca   5400
tgaagctgat cctgcgtgat aaggagaagg aggtggaatg tcagcaggag catatccatg   5460
```

-continued

```
aactccagga gctcaaagac cagctggagc agcagctcca gggcctgcac aggaaggtag   5520
gtgagaccag cctcctcctg tcccagcgag agcaggaaat agtggtcctg cagcagcaac   5580
tgcaggaagc cagggaacaa ggggagctga aggagcagtc acttcagagt caactggatg   5640
aggcccagag agccctagcc cagagggacc aggaactgga ggctctgcag caagaacagc   5700
agcaggccca gggacaggag gagagggtga aggaaaaggc agacgccctc cagggagctc   5760
tggagcaagc ccatatgaca ctgaaggagc gtcatggaga gcttcaggac cacaaggaac   5820
aggcacgaag gctggaggaa gagctggcag tggagggacg gcgggtccaa gccctggagg   5880
aggtgctggg agacctaagg gctgagtctc gggaacagga gaaagctctg ttggccctcc   5940
agcagcagtg tgctgagcag gcacaggagc atgaggtgga gaccagggcc ctgcaggaca   6000
gctggctgca ggcccaggca gtgctcaagg aacgggacca ggagctggaa gctctgcggg   6060
cagaaagtca gtcctcccgg catcaggagg aggctgcccg ggcccgggct gaggctctgc   6120
aggaggccct tggcaaggct catgctgccc tgcaggggaa agagcagcat ctcctcgagc   6180
aggcagaatt gagccgcagt ctggaggcca gcactgcaac cctgcaagcc tccctggatg   6240
cctgccaggc acacagtcgg cagctggagg aggctctgag gatacaagaa ggtgagatcc   6300
aggaccagga tctccgatac caggaggatg tgcagcagct gcagcaggca cttgcccaga   6360
gggatgaaga gctgagacat cagcaggaac gggagcagct gctggagaag tctctggccc   6420
agagggtcca agagaatatg atccaagaga agcagaatct ggggctagag agagaagagg   6480
aggagataag ggccttcat cagagtgtaa gggagctaca gctgactcta gcccaaaagg   6540
aacaggagat tctggagctg agggagaccc agcaaaggaa caacctggaa gccttacccc   6600
acagccacaa aacctcccca atggaggaac aatctctaaa acttgattct ttagagccca   6660
ggctgcagcg ggagctggag cggctacagg cagccctgag acagacagaa gccagggaga   6720
ttgagtggag ggagaaggcc caggacttgg cactctccct agcgcagacc aaggccagtg   6780
tcagcagtct gcaggaggtt gccatgttcc tacaagcctc tgtcctggag cgggactcag   6840
aacagcaaag gctgcaggat gaactggagc tcaccagacg ggctctggag aaggagcggc   6900
tacacagccc aggtgcaacc agcacagcag aactggggtc cagaggggag cagggtgtgc   6960
agctgggaga ggtctcagga gtggaggctg agcctagtcc tgatggaatg gagaagcagt   7020
catggagaca aaggcttgaa cacctgcagc aagcagtggc ccggctggag attgacagga   7080
gcaggctgca gcgccacaat gtccagctgc ggagtacctt ggagcaggtg gagcgagaac   7140
ggaggaagct gaagagggag gccatgcgtg cggcccaggc agggtcccta gagatcagca   7200
aggccacggc ttcttcaccc acacagcagg atgggagagg acagaagaac tcaaatgcca   7260
agtgtgtggc tgaactgcag aaagaggtgg tcctgctgca agctcagctg actttggagc   7320
ggaagcagaa gcaggactac atcacccgct cagcacagac cagccgtgag ctagcaggcc   7380
tgcaccacag cctctcacac tcacttcttg ccgtggccca ggcccctgag gccactgtcc   7440
tggaggcaga gacccgcagg ctggatgagt ccctgactca aagtctgaca tccccagggc   7500
cagtcctgct acaccccagc cccagcacta cccaagccgc ctccaggtag cagccacagc   7560
caggagcaca cagacagaag actgtgtcat gggtcatggc ccctccgcac acctacaggt   7620
ttgccaaagg aaaagcctgg ctctgttagg cacccaggag ccccaggtcg gcgggtgttc   7680
ccaggaagag gaagtaaatc tgcaaccctg gggaggaccc caactcacct gggaatgagg   7740
caaattgcat ttgcttgctc cctatggaat cacccagagg ggtgccttgc cctggctgag   7800
ggacccggaa ttcc                                                     7814
```

<210> SEQ ID NO 37
<211> LENGTH: 1368
<212> TYPE: DNA
<213> ORGANISM: Homo sapiens

<400> SEQUENCE: 37
gtggctccag gccggaagag ggagtctgta ggggcgggcc ggctggcgtc ccctttccgg 60
ccggtcccca tggaggcgct ggggaagctg aagcagttcg atgcctaccc caagactttg 120
gaggacttcc gggtcaagac ctgcgggggc gccaccgtga ccattgtcag tggccttctc 180
atgctgctac tgttcctgtc cgagctgcag tattacctca ccacggaggt gcatcctgag 240
ctctacgtgg acaagtcgcg gggagataaa ctgaagatca acatcgatgt actttttccg 300
cacatgcctt gtgcctatct gagtattgat gccatggatg tggccggaga acagcagctg 360
gatgtggaac acaacctgtt caagcaacga ctagataaag atggcatccc cgtgagctca 420
gaggctgagc ggcatgagct tgggaaagtc gaggtgacgg tgtttgaccc tgactccctg 480
gaccctgatc gctgtgagag ctgctatggt gctgaggcag aagatatcaa gtgctgtaac 540
acctgtgaag atgtgcggga ggcatatcgc cgtagaggct gggccttcaa gaacccagat 600
actattgagc agtgccggcg agagggcttc agccagaaga tgcaggagca gaagaatgaa 660
ggctgccagg tgtatggctt cttggaagtc aataaggtgg ccggaaactt ccactttgcc 720
cctgggaaga gcttccagca gtcccatgtg cacgtccatg acttgcagag ctttggcctt 780
gacaacatca acatgaccca ctacatccag cacctgtcat ttggggagga ctatccaggc 840
attgtgaacc ccctggacca caccaatgtc actgcgcccc aagcctccat gatgttccag 900
tactttgtga aggtggtgcc cactgtgtac atgaaggtgg acggagaggt actgaggaca 960
aatcagttct ctgtgaccag acatgagaag gttgccaatg ggctgttggg cgaccaaggc 1020
cttcccggag tcttcgtcct ctatgagctc tcgcccatga tggtgaagct gacggagaag 1080
cacaggtcct tcacccactt cctgacaggt gtgtgcgcca tcattggggg catgttcaca 1140
gtggctggac tcatcgattc gctcatctac cactcagcac gagccatcca gaagaaaatt 1200
gatctaggga agacaacgta gtcaccctcg gtgcttcctc tgtctcctct ttctccctgg 1260
cctgtggttg tcccccagcc tctgccaccc tccacctcct cggtcagccc cagccccagg 1320
ttgataaatc tattgattga ttgtgatagt aaaaaaaaaa aaaaaaaa 1368

<210> SEQ ID NO 38
<211> LENGTH: 6598
<212> TYPE: DNA
<213> ORGANISM: Homo sapiens

<400> SEQUENCE: 38
gattcaggtg ggcgggctgg tgggcagaag ggcagacggg cagaggaagt gccagtgcca 60
ctgggaccat ggctctgacg gtaacgcgtg caacgactaa cagggctgac cggcacccac 120
gaccgacaag tgaagctcac ctttcgaggc tttacccaga aaacaagaaa aattcactgt 180
ggtccagaag cagatatcgg tgagctgttc cgatggcccc actatggggc tccactggct 240
ggggagtgtc tgtctgtgca ggtggtcaac tgcagccgtg tattcagcct taggcctcta 300
gggaccctgg tgatctccct gcagcagcta cagaatgctg ggcatttggt gctacgggaa 360
gccctagtgg atgagaatct tcaagtgtcc ccgatccagg tggagcttga cctgaagtac 420
cagcccccag agggcgctac tggagcctgg tcagaggagg actttggggc acccatccag 480

```
gacagcttcg agttaatcat ccccaatgtg ggcttccagg aactggagcc tggggaggcc    540
cagctggagc ggcgggcagt ggctctaggc cgcaggctag ctcgaagtct aggccagcag    600
gacgatgaag agaatgagct ggagcttgag ctggagcagg acctggatga tgagcctgac    660
gtggaacttt ctggtgttat gttcagcccc ctcaagagcc gcgccagggc cctggcccat    720
ggggatccct tccaggtgtc cagagctcaa gacttccagg tgggagtcac tgtgctggaa    780
gcccagaaac tggtgggagt caacattaac ccctatgtgg ccgtgcaagt gggggggcag    840
cgccgtgtga ccgccacaca gcgtgggacc agttgcccct tctacaatga gtacttcttg    900
ttcgaatttc atgacacgcg gcttcgtctc caagacttgc tgctggagat cacggctttc    960
cattcgcaga ccctcccctt tatggccacc cggataggca ccttcaggat ggacctgggc   1020
atcatcttgg accagccaga tggccagttc taccaaagat gggttccgct gcatgatccc   1080
cgagacaccc gcgccgggac caagggtttc attaaggtca ccttgtccgt gagggcgcgc   1140
ggggacctgc cccctccaat gctacccccg gccccagggc actgttcgga catcgagaag   1200
aacctgctcc tgccgcgcgg ggtgcccgcc gagaggccat gggcgcggct ccgcgtgcgc   1260
ctgtaccgcg ccgaggggct tcccgcgctg cgcctggggc tgctgggcag cctggtccgc   1320
gccctgcacg accagcgcgt cctggtggag ccctatgtgc gggtgtcttt cctggggcag   1380
gagggcgaga cgtcggtgag cgccgaggcg gcggcgcccg aatggaacga gcagctgagc   1440
ttcgtggagc tcttcccgcc gctgacgcgc agcctccgcc tgcagctgcg ggacgacgcg   1500
cccctggtcg acgcggcact cgctacgcac gtgccggacc tgaggcggat ctcccatccg   1560
ggccgcgcgg cggggtttaa ccctaccttc ggcccggcct gggtgcccct ctatggctcg   1620
ccccccggcg cggggctccg ggatagtctt caaggtctca acgaaggcgt tggccaaggc   1680
atttggttcc gcggccgcct tctgctggct gtgtccatgc aggtgttgga agggagagct   1740
gaacctgagc ctccccaggc ccagcagggg tccacgttgt cccggctcac ccgaaagaag   1800
aaaaagaaag ccagaaggga tcagacccca aaggcggttc cgcagcactt ggacgccagc   1860
cccggtgccg aggggcctga gatccccgt gccatggagg tggaggtgga ggagctgctg   1920
ccgctgccag agaatgtcct ggcgccctgt gaagatttcc tgcttttcgg tgtgctcttc   1980
gaggccacca tgatcgaccc caccgtggcc tcccagccca tcagcttcga gatctccatt   2040
ggtcgcgcag gccgtctgga ggagcaattg ggccgagggt ccagggctgg ggagggaact   2100
gagggtgcag ccgtggaggc tcagcctctg ctgggagcca ggccagagga ggagaaagag   2160
gaggaagaac tggggaccca tgctcagcgg cctgagccca tggacggcag tgggccatac   2220
ttctgcttgc cctctgtca ctgcaagcca tgcatgcatg tgtggagttg ctgggaggac    2280
cacacctggc gcctgcagag cagcaactgc gtgcgcaaag tggccgagag gctggaccag   2340
gggctgcagg aggttgagag actgcagcgc aagccggggc ctggcgcctg tgcacagctc   2400
aagcaggcac tggaagtact ggtggctggg agcagacagt tttgccacgg tgccgagcgc   2460
aggacgatga cccggcccaa tgccctggat cgatgccgag ggaaactcct ggtgcacagc   2520
ctgaaccttt tggctaagca aggactgcga cttctacgcg gcctgagacg gcgcaatgtg   2580
caaaagaagg tggcactggc caagaagctc ctggcaaaac tgcgctttct ggctgaggag   2640
ccccagccac ccctccccga tgtgctggtc tggatgctca gcgggcagcg ccgtgtggcc   2700
tgggcccgga tccctgccca ggatgtgctg ttctctgtgg ttgaggagga acggggccga   2760
gactgtggga agatccagag tctaatgctc acggcacccg gggcagcccc tggtgaggtc   2820
tgtgccaagc tggagctctt cctgcggctg ggcctgggca agcaagccaa ggcctgcacc   2880
```

```
tctgagctgc cccggattt gctgcccgag ccctcagccg ggctgccctc cagcctacac   2940
cgggacggtc ctggagcaga cgctgagccc tctgtgggat gaactcctgg tatttgagca   3000
gttgatcgtg gatgggagga gggagcacct gcaggaggag cctccattag tgatcatcaa   3060
tgtatttgac cacaataagt ttccctcagt gcccagtgag gtggagcccc aggatctggc   3120
acccctggtt gagccccact ctggacgcct gtcccttcca cccaacgtgt gcccagtgct   3180
cagggagttc cgtgttgagg tgctgttctg ggtcttagg ggacttggtc gtgtgcatct   3240
gctcgaggtg gagcagcccc aggttgtact ggaggtggct gggcaaggtg tggagtctga   3300
ggtcctggcc agctaccgtg agagccccaa tttcactgag cttgtcaggc atctgacagt   3360
ggacttgccg gagcagcctt acttgcagcc tccactcagc atcttggtga ttgagcgccg   3420
ggcctttggc cacacagtcc ttgtgggttc ccacattgtc cccacatgc tgcgattcac   3480
atttcggggt catgaggatc ctcctgagga ggaaggagag atggaggaga caggggatat   3540
gatgcccaag ggacctcaag gacagaagtc cctggatccc ttcttggctg aagcgggtat   3600
atccagacag ctcctgaagc ctcctctgaa gaagctccca ctaggaggcc tcctaaatca   3660
aggccctggg ctggaggaag acatcccaga tccagaggag ctcgactggg ggtccaagta   3720
ctatgcgtcg ctgcaggagc tccaggggca gcacaacttt gatgaagatg aaatggatga   3780
tcctggagat tcagatgggg tcaacctcat ttctatggtt ggggagatcc aagaccaggg   3840
tgaggctgaa gtcaaaggca ctgtgtcccc aaaaaaagca gttgccaccc tgaagatcta   3900
caacaggtcc ctgaaggaag aatttaacca ctttgaagac tggctgaatg tgtttcctct   3960
gtaccgaggg caagggggcc aggatggagg tggagaagag gaaggatctg gacaccttgt   4020
gggcaagttc aagggctcct tcctcattta ccctgaatca gaggcagtgt tgttctctga   4080
gccccagatc tcccggggga tcccacagaa ccggcccatc aagctcctgg tcagagtgta   4140
tgttgtaaag gctaccaacc tggctcctgc agaccccaat ggcaaagcag acccttacgt   4200
ggtggtgagc gctggccggg agcggcagga caccaaggaa cgctacatcc ccaagcagct   4260
caaccccatc tttggagaga tcctggagct aagcatctct ctcccagctg agacggagct   4320
gacggtcgcc gtatttgatc atgacctcgt gggttctgac gacctcatcg gggagaccca   4380
cattgatctg gaaaaccgat tctatagcca ccacagagca aactgtgggc tggcctccca   4440
gtatgaagtg tgggtccagc agggcccaca ggagccattc tgagtttctg gccaaacaca   4500
ttcaagctca cattcccttt tgtgtctcca gatcctatga tttcatggaa ggggaccctc   4560
ccacccaccg ccactgccaa ccaagacata gctcagtggt caagacttgg gcttgggagt   4620
cgggatcctg taacgaatgt cacttgaccg ctttcttttt ttatgaaaca gtctcgctct   4680
gtctcccagg ttggagtgca gtggcacgat ctcggctgac tgcaacctcc acctcctggg   4740
ttcaagcgat tctcctgcct cagcctcccc agtagctggg attacaggcg tgggccccca   4800
tgtccagcta atttttatat tttcgctctg tctcccaggt tggagtgcag tggcacgatc   4860
tcggctgact gcaacctcca cctcctgggt tcaagcgatt ctcctgcctc agcctcccca   4920
gtagctggga ttacaggcgt gggcccccat gtccagctaa tttttatatt tttagtagag   4980
acagggtttc accatgttgt ccaggctggt cttgaacccc tgacctcaag tgatccaccc   5040
acctctgcct cccaaagtgc tgggattaca ggtgtgagcc accatgccag gccctcttaa   5100
cctcttcaag tctgttttct catctgcaaa acagaggtaa taagatcagt atcttcttaa   5160
tggaagcacc tggactacat ttttttcatt cattgttatc ataaatgagg actaacctgt   5220
```

```
ctcccgttgg gagttttgaa cctagacctc atgtcttcat gacgtcatca ctgccccagg   5280
cccagctgtg tccctacacc agccccagct gacgcatctt ctttttctgc ctgtagagat   5340
ggttacaatg cctggcgtga tgcattctgg ccttcgcaga tcctggcggg gctgtgccaa   5400
cgctgtggcc tccctgcccc tgaataccga gccggtgctg tcaaggtggg cagcaaagtc   5460
ttcctgacac caccggagac cctgccccca gggatctctt cacatgtgga ttgacatctt   5520
tcctcaagat gtgcctgctc cacccccagt tgacatcaag cctcggcagc caatcagcta   5580
tgagctcaga gttgtcatct ggaacacgga ggatgtggtt ctggatgacg agaatccact   5640
caccggagag atgtcgagtg acatctatgt gaagagctgg gtgaaggggt tggagcatga   5700
caagcaggag acagacgttc acttcaactc cctgactggg gaggggaact tcaattggcg   5760
ctttgtgttc cgctttgact acctgcccac ggagcgggag gtgagcgtct ggcgcaggtc   5820
tggacccttt gccctggagg aggcggagtt ccggcagcct gcagtgctgg tcctgcagga   5880
tccctggagt tgcagctacc agacatggtg cgtggggccc ggggccccga gctctgctct   5940
gtgcagctgg cccgcaatgg ggccgggccg aggtgcaatc tgtttcgctg ccgccgcctg   6000
aggggctggt ggccggtagt gaagctgaag gaggcagagg acgtggagcg ggaggcgcag   6060
gaggctcagg ctggcaagaa gaagcgaaag cagaggagga ggaagggccg gccagaagac   6120
ctggagttca cagacatggg tggcaatgtg tacatcctca cgggcaaggt ggaggcagag   6180
tttgagctgc tgactgtgga ggaggccgag aaacggccag tggggaaggg gcggaagcag   6240
ccagagcctc tggagaaacc cagccgcccc aaaacttcct tcaactggtt tgtgaacccg   6300
ctgaagacct ttgtcttctt catctggcgc cggtactggc gcaccctggt gctgctgcta   6360
ctggtgctgc tcaccgtctt cctcctcctg gtcttctaca ccatccctgg ccagatcagc   6420
caggtcatct tccgtcccct ccacaagtga ctctcgctga ccttggacac tcacccaggg   6480
tgccaaccct tcaatgcctg ctcctggaag tctttcttac ccatgtgagc taccccagag   6540
tctagtgctt cctctgaata aacctatcac agccactgaa aaaaaaaaaa aaaaaaaa     6598
```

<210> SEQ ID NO 39
<211> LENGTH: 1050
<212> TYPE: DNA
<213> ORGANISM: Homo sapiens

<400> SEQUENCE: 39

```
tctcccgacc ctggatctga ggcaggagat gcctcccccg cgggtgttca agagctttct     60
gagtacgggc caggccagct gcgatcccct ctgaccctcg ggttcccctc tccgaactcc    120
agttctctct gagcccccgg cccccgtttg agtatcgagc ccctctccga gcctcaactc    180
attcctagcc cccatccaat tatcctagcc gaccctctct tcctgagccc caggcccacc    240
cccggcccct cccaagcccc ttctgaaccc ggacaccacg caggctgagc cccgcctctc    300
cctgccgtgg gcccctctct gaccctctgt cctggcctca ggcctgctct tccaggggct    360
gagcgtgttg ttatccctgg caggagacgt gctggtcagc atgtacaggt cagaggaagg    420
gacgctggcg ccccaggaac agctctttgg agggggtggg gagcagggcc ggaaccttgc    480
tggcgcttga gccgattcag atctgattga gtcatgttgg caagagctgg gtctaggacc    540
ctggggtggg gactggaggg ttgagcaggt cggggcctca gcctccctcc ggttccccag    600
ggaggtctgt tccatccgct tcctgttcac ggctgtgtcg ctgctgagcc tctttctgtc    660
aggtgagggg cagtgaattc cctggagccc ctgccctggg tgctttggag gcaaacccag    720
cacattttct cctacatcct cggtcctgca gctcctggca ttcccctgca gaacccccta    780
```

attcccccctc agactcccac ggtcctcccc aggcttaacc ccctcaagcc tctttccact 840
gtccccctat gccggggaaa cccattctct tccttttcct tctgagaccc ctccctctct 900
ttctccagca ttctggctgg ggcttctgta cctggtctct cctttggaga atgtgagttg 960
gggagactgt cttggggtag ggggttggca ggttgtgaac ccggagattg tgggggtccc 1020
ctggactgtc ggtctgctgg ggtgggggta 1050

<210> SEQ ID NO 40
<211> LENGTH: 1455
<212> TYPE: DNA
<213> ORGANISM: Homo sapiens

<400> SEQUENCE: 40
cgattgatgg cgacgtccgt ggggcaccga tgtctgggat tactgcacgg ggtcgcgccg 60
tggcggagca gcctccatcc ctgtgagatc actgccctga gccaatccct acagccctta 120
cggaagctgc cttttagagc ctttcgcaca gatgccagaa aaatccacac tgcccctgcc 180
cgaaccatgt tcctgctgcg tcccctgccc attctgttgg tgacaggcgg cgggtatgca 240
gggtaccggc agtatgagaa gtacagggag cgagagctgg agaagctggg attggagatt 300
ccacccaaac ttgctggtca ctgggaggtg gctttgtaca agtcagtgcc aacgcgcttg 360
ctgtcacggg cctggggtcg cctcaatcag gtggagctgc cacactggct gcgcaggccc 420
gtctacagcc tgtacatctg gacgtttggg gtgaacatga aagaggccgc tgtggaggac 480
ctgcatcact accgcaacct cagcgagttc ttccggcgca agctgaagcc gcaggcccgg 540
cctgtctgtg gcctgcacag cgtgattagc ccatcggatg gaaggatcct caactttggg 600
caggtgaaga actgtgaggt ggagcaggta aagggggtca cctactccct ggagtcgttc 660
ctgggcccgc gtatgtgcac agaggacctg cccttcccac cagccgcgtc gtgtgactcc 720
ttcaagaacc agctggtcac ccgggaaggg aatgagctct atcactgtgt catctacctg 780
gcccctgggg actaccactg cttccactcc cccaccgact ggactgtgtc ccaccggcgc 840
cacttcccag gctccctgat gtcagtgaac cctggcatgg ctcgctggat caaagagctc 900
ttctgccata acgagcgggt ggtcctgacg gggggactgga aacatggctt cttctcactg 960
acagctgtgg gggccaccaa cgtgggctcc attcgcatct actttgaccg ggacctgcac 1020
acaaacagcc caaggcacag caagggctcc tacaatgact tcagcttcgt gacgcacacc 1080
aatagagagg gcgtccccat gcgtaagggc gagcacctgg gcgagttcaa cctgggctcc 1140
accatcgtgc tcatcttcga ggcccccaag gacttcaatt tccagctgaa aacaggacag 1200
aaaatccgct ttggggaagc cctgggctcg ctctagagtc tctttcctga ttatggctgc 1260
taagggatct tttccaaaca gagtgagggt cttttcaaga gggaggccca tgaggccatc 1320
caggtaaggg cctgcctcag cgtggttggg agtctgacca ggtaggactt gaatgattcg 1380
gctaccacct gttccagagg tgcagacaag aggtggcgag agcccccatc atgcccctca 1440
accctatccc gttcc 1455

<210> SEQ ID NO 41
<211> LENGTH: 4683
<212> TYPE: DNA
<213> ORGANISM: Homo sapiens

<400> SEQUENCE: 41
caagatgact tctctgcccc aagcttggaa cagctaaagg gaaaaacagt gcaagatgag 60

```
aacaacaaag gtctacaaac tcgtcatcca caagaagggc tttgggggca gtgatgatga    120
gctagttgtg aaccccaaag tgttccctca catcaagctt ggagacattg tagagattgc    180
acaccccaac gatgaataca gccctctgct tttgcaggtc aagtctctta aggaagattt    240
acagaaggaa actatcagtg tggaccagac tgtgactcaa gtgttccggc tgagacctta    300
tcaggatgtc tatgttaatg tcgtagaccc taaggatgtg acccttgacc tagtggaatt    360
aacttttaag gatcagtata ttggccgtgg ggatatgtgg cgactaaaga aaagtttggt    420
cagcacatgt gcctatatca cccagaaggt ggagtttgct ggcatcagag cacaggctgg    480
tgaactgtgg gttaagaatg agaaggtcat gtgtggctac atcagtgaag ataccagggt    540
ggtgtttcgt tctacgtcgg ctatggttta catatttatt cagatgagct gtgaaatgtg    600
ggattttgat atttatgggg atttgtattt tgagaaagct gtgaatggtt tccttgctga    660
tctatttacc aagtggaagg agaagaactg tagtcatgaa gtgacagtgg tcctgttttc    720
tagaactttc tatgatgcaa aatctgttga tgaatttcct gaaataaacc gagcctcaat    780
tcgacaggat cacaagggga gattctatga agacttttac aaagtggtgg tgcagaatga    840
gagaagagaa gaatggactt cacttctcgt aaccattaaa aaactcttca tccagtatcc    900
agtgttggtg cgactggaac aggcagaggg ctttcctcaa ggagataatt ctacctcagc    960
acaaggaaac tacctggagg ccatcaatct gtcattcaat gtgtttgata agcactacat   1020
caaccgcaac tttgaccgaa ctgggcagat gtcagtggtg atcacgcccg ggtgggtgt    1080
ctttgaagtg gaccgcctac tcatgatcct gaccaagcag cggatgatag ataatggaat   1140
tggtgtggat ttggtgtgca tgggagagca accgttacat gctgtcccat tgttcaagct   1200
ccataatcgg agtgctcccc gtgattctcg tctgggcgat gactataata tccctcactg   1260
gataaaccac agtttctaca catccaaaag ccagctcttt tgtaatagtt tcaccccacg   1320
aataaaactg gcaggaaaga agcccgcctc tgagaaagca aaaaatggcc gtgatacatc   1380
tctcgggagt ccaaaagaat ctgagaacgc ccttcccatc caagtagatt atgacgccta   1440
tgacgctcaa gtgttcaggc tgcccggccc atcccgggcc cagtgcctca ccacctgcag   1500
atctgtgcga gagcgagaga gtcacagtcg aaagagtgcc agctcctgtg atgtttcatc   1560
cagcccttcc ctaccaagcc gcacactgcc cactgaggaa gtgaggagcc aggcttctga   1620
cgacagctcc ctaggcaaga gtgccaacat cctgatgatc cccacacccc acctgcacca   1680
gtatgaagtc agcagctcct tgggatacac cagcactcga gatgtcctgg agaacatgat   1740
ggagccacca cagcgagact ccagtgcacc agggaggttt cacgttggca gtgcagaatc   1800
catgctgcat gttcgacctg gtggatacac gccccagaga gcactgatta accccttcgc   1860
tccctctcgg atgcccatga agcttacgtc caacagaagg cgctggatgc acacttttcc   1920
tgtggagaca agctgttttt atctttccat aggtatgaat cctaggaccc agaataagga   1980
ttctctagag gacagtgttt ctacctctcc agacccaatg ccaggcttct gttgcacagt   2040
tggagtggac tggaagtctc tcactactcc ggcgtgcctc cccccttacca ccgactactt   2100
ccctgaccgc cagggcctgc agaatgacta cacagagggc tgttatgatc tccttccaga   2160
agcagacatc gacaggaggg acgaagatgg tgtgcagatg acagcccagc aggtatttga   2220
agagtttatt tgccaacgtc tcatgcaggg ctaccaaatc atagtgcagc ccaagacaca   2280
gaaacccaat cctgctgtcc cgcccccgct gagcagtagc ccactctata gccgaggcct   2340
tgtgtcccga aaccgccctg aggaggagga ccagtattgg ctgagtatgg gcagaacgtt   2400
ccacaaagtg acgctgaagg ataagatgat cacagtgacg cgataccttc ccaagtatcc   2460
```

```
ttatgaatct gcccagatcc actacaccta cagcctctgt ccttcccact cagactcaga   2520
gttcgtctcc tgctgggtgg aattctccca cgaacggctg gaggagtaca agtggaatta   2580
cttagatcag tatatctgtt ctgccggctc tgaagacttc agcttaattg agtccctgaa   2640
gttctggagg acccgcttcc tgctgctgcc agcctgtgtc accgccacca agcgcatcac   2700
ggagggggag gcccactgcg acatctatgg ggacaggccc cgtgcagacg aggacgagtg   2760
gcaactcctg gatggttttg tccgctttgt ggagggcttg aatcgcattc gcaggcggca   2820
tcgctcggat cgcatgatgc ggaaagggac cgccatgaaa ggcttgcaga tgactgggcc   2880
catttccacg cattctctgg agtcaactgc acccccagtg gggaagaagg gaacctcagc   2940
tctctctgcc ctgttggaga tggaggccag tcagaagtgc ctgggagaac agcaggcagc   3000
tgtgcatggt gggaagagct ccgcccagtc agccgagagc agcagcgttg ccatgactcc   3060
cacctacatg gacagcccac gaaaggtatc tgtggaccaa acagccactc ctatgttgga   3120
cggcaccagt ttgggcatat gcacaggcca atccatggac agaggcaaca gccagacctt   3180
tgggaactcc cagaacatag gagaacaggg ctactcctcc acaaactcca gtgacagcag   3240
ctctcagcag ctggtggcaa gctccttgac ctcatcctct accctgacag agatcctgga   3300
agccatgaag caccccctcga caggagtcca gctgctctct gaacagaagg gcctctcacc   3360
gtactgcttc atcagcgcgg aggtggtaca ctggttggtg aaccacgtgg aggggatcca   3420
gacacaggcg atggccattg acatcatgca gaaaatgctg gaagagcagc tcatcacaca   3480
tgcatctggc gaagcctggc ggaccttcat ctacggcttc tatttctaca agatagtaac   3540
ggacaaagag cccgaccgag tggccatgca gcagcccgcc accacctggc acacagcagg   3600
agtggacgac ttcgccagct tccagcgcaa gtggtttgag gtggcctttg tggcagaaga   3660
gctcgtgcac tctgagattc ctgcctttct cctgccctgg ctgcctagcc ggccagcctc   3720
ctatgcaagt aggcacagct cctttagccg aagttttgga ggacggagcc aggcggcagc   3780
acttttagct gccactgtcc cagagcagag gactgtgacc ctggatgttg acgtgaacaa   3840
ccgcacagac cggctggagt ggtgcagctg ttattaccat ggcaactttt ctctgaatgc   3900
agcctttgag atcaagctgc actggatggc ggtgaccgca gcagtactct tcgagatggt   3960
ccaaggttgg catcggaaag ccacctcctg tggcttcttg ttagtcccag ttttggaggg   4020
gccttttgca ctgcccagtt acctgtatgg cgaccccctt cgtgcccagc tcttcatccc   4080
actcaacatc agctgcttgc tcaaggaggg cagcgagcac ctgtttgata gctttgaacc   4140
cgaaacgtac tgggatcgaa tgcacctctt ccaggaagcc attgcacaca ggtttgggtt   4200
tgtacaagat aaatattctg cctctgcttt taacttccct gctgagaaca agcctcagta   4260
tatccacgtt acaggaacag tgtttctgca gctgccctac tccaagcgca agttctcagg   4320
gcagcagcgg cggcggcgga actccaccag ctccaccaac cagaacatgt tctgcgagga   4380
gcgggtcggc tacaactggg cctacaacac catgctcacc aaaacatggc gctccagcgc   4440
cacaggggat gaaaagtttg ctgatcggct gctgaaggac ttcacggact tctgcatcaa   4500
ccgtgacaac cggctggtca cgttctggac aagttgcctg gagaagatgc atgccagtgc   4560
cccgtgaggc caggctgcac ctgtgctggg ggaaggtggg tgagccactg ccctcaaacc   4620
cggggcggag gattccaggc aggctctagg agtcaggtgt ccgtttgctg ctatcagtga   4680
gtg                                                                 4683
```

<210> SEQ ID NO 42

<211> LENGTH: 3047
<212> TYPE: DNA
<213> ORGANISM: Homo sapiens

<400> SEQUENCE: 42

```
gtaaataaag gcagctaaag ctgactgctg gttgcgcaaa atccccctgg ctcttctggc     60
taaagtccta ccactccctg tacctggcag cagcctgtct tctgggcctc acctacacac    120
gtctgggtag gagccagtca tctccatcca tccacagcca tgaatttcct ccggcgacgt    180
ctctctgaca gcagcttcat ggccaacctg cctaatggct atatgacgga cctgcaacgc    240
ccagatagct ccaccagctc acctgcttcc cccgccatgg agaggaggca cccccagccc    300
ctggctgcct ccttctcctc tccaggatcc agccttttta gctccctctc cagtgccatg    360
aagcaggccc ctcaggccac ctcaggactg atggagcctc caggtccctc cacgcccatt    420
gttcaaagac ccaggatcct gttggtgatc gatgatgccc atacagactg gtcgaagtat    480
ttccatggga agaaggtgaa tggagagatt gagatccgag tggagcaggc tgaattctca    540
gagttgaacc tagctgccta tgtgaccggg ggctgcatgg tggacatgca ggtcgtgaga    600
aatgggacca aagtggtgag cagatccttc aagccagact tcatcctggt ccgccagcat    660
gcctacagca tggccctggg ggaagactac cgcagcctgg tcatcggcct gcagtatgga    720
gggctgcctg ctgtcaactc tctctactcc gtctacaact tctgcagcaa gccctgggtg    780
ttctctcagc tcattaagat cttccattcc ctgggtcctg agaagttccc gcttgtggag    840
caaacatttt tccccaacca taagccaatg gtcacagccc cacacttccc ggtggtagtc    900
aagctgggac atgcccacgc tggaatggga aagatcaaag tggaaaacca gcttgacttc    960
caggacatca ccagcgtggt cgccatggcc aaaacctacg ccaccaccga ggccttcatc   1020
gactccaagt acgacatccg catccagaaa attggatcca actacaaggc ttacatgaga   1080
acctccatct ctgggaactg gaaggccaac acaggctctg ccatgctgga gcaggtggcc   1140
atgacagaga ggtacaggct gtgggtggac agctgctcgg aaatgtttgg cggcctggac   1200
atctgtgccg tcaaggctgt ccacagcaag gatggcagag attacatcat cgaggtaatg   1260
gacagctcaa tgccgctgat tggagagcat gtggaagagg acagacagct gatggccgac   1320
cttgttgtct ccaaaatgag ccagctcccg atgccaggag gcacagcgcc ctcccccctc   1380
agaccttggg ctccacagat taaatcagcg aaatccccag ggcaagccca gctggggcct   1440
cagctaggcc agccccagcc acgcccacct ccgcaaggag gccctcgcca agctcagtct   1500
cctcagcccc agagatctgg aagcccctcc caacagaggc tctccccaca aggccagcag   1560
cccctgagcc cccagtccgg atctccacag cagcaaaggt caccaggctc tccgcagcta   1620
tcccgggcat ccagtggcag ctccccaaac caggcctcca agccaggtgc caccctcgcc   1680
tcacagcccc ggccccctgt gcagggccgt agtacctccc agcagggtga agagtccaag   1740
aagccagcac caccccatcc gcatctcaac aaatctcagt ccctgactaa cagcctcagc   1800
acatccgaca cctcccagcg tgggacccca agtgaagacg aggccaaggc tgaaaccatc   1860
cgcaacctga ggaagtcttt tgccagcctg ttctctgact aacgccatcc aggctgggag   1920
gggaagagtg ctctgctaca ctcgtccccc tcctgcctca tcttccttct cagccttggt   1980
tcctgatggg aacagaatgg agggcctgag aacatacttt ctaaatgcct ttgacccagg   2040
aaccgattat ctatatttgt tcccattttc cttcaccgtg acattccagc attgtctgac   2100
tgtgaggtgg gcctttgaga gcctccaggt tcctcaaaac aggcctgagc gatgggcatc   2160
acaccctctg cctacccacg tgcctgctta cctgccagat aaccaagtga gatgtctgcg   2220
```

```
agtggctagt tttcacattc ttactagtgt ttggctcacc tttgggcaaa ggccccctct   2280

aggccttgcc ccacctccat caaacgcaga cactgtagtc agacctcagc aatataggag   2340

gcaataatct tttaacagtg ttttgcaaac aaacaaaaag agaaaaatcc cagccagggg   2400

aactcgccac ctgcccacgc tagttccatc cacgctcaag acccgccctt agaccaggca   2460

ggcaaaggcc cccatcacac tcggccacta gtggggtcct gaggccaaga aagaaaccag   2520

accctgtatg acaagtgggg tctttcagaa cacgacagaa acagggggc ccttgtaatg    2580

ccactcatac tcagagcatt attcttattt ggacagccaa gggcagatca caggttattg   2640

taggaataaa gactagttta caaaggagaa agaggccctg gacttcccaa ggaaagggtc   2700

aggttagggc tcctgtaccc attctgttcc accactgttt gatctctctg gcctcccacc   2760

aggaatgccg tttccttttt atggatctgt tgggaaccag agagaatcaa cagatcaatg   2820

acataggatc cgaagtgcaa tgatagtcac ttctagtttg gcatttcaca aactctgtac   2880

agcaaggtat tggtaggtta ctcaatttca aaagggcccc atggccaaat atgtttagga   2940

accgctgttt gtatttcttt ttttggagac gcattgtata taatatatgt caaaggcttt   3000

cggaattcct gcaggaaaga aatcagcttt gttaaatcca aaaaaaa                 3047
```

<210> SEQ ID NO 43
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 43
gggtaatatt tataagttta ataataaggt 30

<210> SEQ ID NO 44
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 44
taaaaactat cccaaccctt c 21

<210> SEQ ID NO 45
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 45
aagtttaata ataaggttat ggtag 25

<210> SEQ ID NO 46
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 46
ggaggagagg aagttaggag tttataaagg a 31

<210> SEQ ID NO 47

<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 47
caaatacaac ccaaaaccaa aaacaat 27

<210> SEQ ID NO 48
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 48
gaagttacga gtttataaag gat 23

<210> SEQ ID NO 49
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 49
ggatgggata gtgaagataa gagt 24

<210> SEQ ID NO 50
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 50
ttcaacatac tatcatctaa tcctttacac 30

<210> SEQ ID NO 51
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 51 ttttttaag gttatgtgat aa 22

<210> SEQ ID NO 52
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 52
gagttgagtt ttattttggg tattttgaag 30

<210> SEQ ID NO 53
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 53
acccccaaat tactaaacta atatattcc 29

<210> SEQ ID NO 54
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 54
caaattacta aactaatata ttcca 25

<210> SEQ ID NO 55
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 55
gttgtgggag agtaaggttt ggaaataa 28

<210> SEQ ID NO 56
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 56
ctcatctcca ccccttcat ttt 23

<210> SEQ ID NO 57
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 57 ccccttcat tttct 15

<210> SEQ ID NO 58
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 58
ttttggaggt atagggtagg aaataa 26

<210> SEQ ID NO 59
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 59
aattcaaaat catccaaacc caaa 24

<210> SEQ ID NO 60
<211> LENGTH: 23
<212> TYPE: DNA

<213> ORGANISM: Artificial Sequence
<220> FEATURE:
<223> OTHER INFORMATION: synthetic oligonucleotide

<400> SEQUENCE: 60
aggaaataat ttttaattga ata 23

<210> SEQ ID NO 61
<211> LENGTH: 200
<212> TYPE: DNA
<213> ORGANISM: Homo sapiens

<400> SEQUENCE: 61
catgtgtttt aaggcagaga tggaacttgg gcgatgggcg gggggtgggg gaggtgggaa 60
gggacggctt aggacagggc aggattgtgg attgtttctg ccgccttggt tgcccatact 120
gggcatctct gcaggcgcgt cggctccctc cacccctgct gagatgatgc actgcgaaaa 180
cattcgctct ccccgggacg 200

<210> SEQ ID NO 62
<211> LENGTH: 802
<212> TYPE: DNA
<213> ORGANISM: Homo sapiens

<400> SEQUENCE: 62
agctgccaag gcagaagggg gaagcgggtc ccagaaccac ccacctccgg ctgtccccac 60
cgcgaggacc cagcagtctg gcgcccccac cacggcctgg aagatgacgg agggcccaag 120
actaatattc acgacagcca gaccacgctt attgtttaga aggaagctcc ctttgttctt 180
actttttaac caaagagaag cgaaaacatt tttttcctga tcacattttc accgacacct 240
gagccgacaa gccagctcct ggcccccggc tcaggactcc tcgctctctc ccttctcggg 300
gccctgtcgc cgttgaaagg cccgctgcag gctggggagg gtgatcgggg ccgcgggcca 360
tctcccccga gccgggcggg cagactgcgg aggcaggccc cacacgcgcc gcttttccga 420
gcccggtttt cttcaggagc gaagctgttc cagctgaccc gcgcgtctgg gggcctatgc 480
ccggcttccg attccattta aaacgacccg cgcatcttat ctccgtcgcc tccccggggt 540
tcccacccac ccccctccgg cccgggccag gccagcccag ccccggcgga agccaagctg 600
ggagcttttg aagtccggag aatttcaatc cgagaggagc cggctggacc ggagcccgtc 660
gccccagcgg gggaagggac ggggggcctg ccgtgtggca ggtgggggat gggtgtcccc 720
cgccgcgaga aatgagaagc cgccgggcct ggagcggcct ccacctcagc tgctatcacc 780
ccctctccgc tgtcatggga tt 802

<210> SEQ ID NO 63
<211> LENGTH: 200
<212> TYPE: DNA
<213> ORGANISM: Homo sapiens

<400> SEQUENCE: 63 tttttgtct tctttccttt aaaaacccaa ccgctcttaa tgtgaggttg atgaaaggat 60
gcttttggaa gaagtgacat ttggttaaaa cgttttcccc ctaatgcgcc ggtggaaagg 120
ggcgggggtg ggtgtggttc cctaggctcc taagactggc cagtcagctt tgaaagagcg 180
gggcagaagt cgggagaggg 200

<210> SEQ ID NO 64
<211> LENGTH: 200

<212> TYPE: DNA
<213> ORGANISM: Homo sapiens

<400> SEQUENCE: 64
cttatgagtc aaacctctat gaaccccaac ctttttgtac tcggggaggc tgaacccctg 60
cccaaaatag cgcggtgaaa gctactgcct tctcccaagt aggggcctcc agtactgcca 120
cagcaggggc cgcattcctg gcgcctcttc attcgaaaaa cctctttcca ggagacttcg 180
ctgattctga acgaatactt 200

<210> SEQ ID NO 65
<211> LENGTH: 400
<212> TYPE: DNA
<213> ORGANISM: Homo sapiens

<400> SEQUENCE: 65
actataaggg ggagtactgc gtcaccttca tctttttatc cctttggcct tgctccgtgc 60
ctgaaagctc accacactgg aacgtccagg tgcacatgtg ccactggaca ccgggatgtt 120
gccggatgct cttttggacg ctggaatgct ggtgcattgt tgccggatgc tggaatggtg 180
cacgcacgct ctgttggacg ctggaatgct ggtgcattgt tgccggatgc tggaatggtg 240
cacgcatgcc ctgttggact ctggaatgct ggtgcattgt tgccaaatgc cggaatggta 300
cacggatgct ctgttggacg ctggaatgct ggtgcattgt tgccggatgc tggaatggtg 360
cacgcatgct ctgttggacg ctggaatgct ggcgcatgtg 400

<210> SEQ ID NO 66
<211> LENGTH: 1000
<212> TYPE: DNA
<213> ORGANISM: Homo sapiens

<400> SEQUENCE: 66
aaccacaaaa ggatagctgc ggttttgggc gaggagagct cagagagttt cttgcatatg 60
gccctgtgat ggcggccatg gccctgcata gacacgagct ggaatctgca ggtggcagcc 120
aggacgctgc gtgtgtcgag tgcacagtgt ggcttggtgc caaccatggc gagggtggag 180
agccccgtgc ctgcagcgcg cgcttccctc actgggtcct gcgtccttgg gcaggcgatg 240
cccctgcggg gaggggctgg tccatccccg gccagccacg gacccacgca tggacccagc 300
gacccacgga cctgcttacc tgggcgcggc gcgggtggca tgcggccaca cggaaggggc 360
gcgctgggct gctgcggcct ctgcagcttc tacacctgcc acggggcggc cggaggtaaa 420
gggaggcggc ggccaggcgc ggccccgcgg aggcagctgc actcgctcgg tccactcgcg 480
gcttcgcggc tgcccgcaaa ccaggagggc gtggagaccc ggaaccgggg ggaagggcgg 540
gggcacttgt gcggcacccg cggggctccc aggggacctc ggcggtgaca cgaatttcta 600
ggtgaccttg gcggtgacac gaatttctag gtgacctgtg tgatacacta ggtgacctag 660
tgacacaggt gacacttcca ggtgaccgcg gcggtgaccc gcggggctcc caggtgacct 720
cgttggtgag ccccggggct ccccgacgac cgcggcggtg acacgcgggg ctcccaggtg 780
accccggcgg tgcactcaca ggactcccag gtgacccgcg gtggtgacac accggggcgg 840
gcgcgcgccg cttccgcttc cgccgagccg ccccccgccc cccgcggcgc agcgcgcgcc 900
cccctcccgg tggcgcggaa ccaatcctgg gcagggaggc ggcggctgga ggctgaaagc 960
gctgccgtgg ccccctcccc gcctccgccg cgccccctcc 1000

<210> SEQ ID NO 67

<211> LENGTH: 210
<212> TYPE: DNA
<213> ORGANISM: Homo sapiens

<400> SEQUENCE: 67
gcttctcctg tgcctgcctc atattctggg ttctctccag agctcgcgtc cactgcctgc 60
cagtcagcag atggatgact ctgttcacct cagccgcgac acgccccaca gcgagtgcag 120
cagtcgtcct gccagatggg ctgctcctgg ctgcgtccat tctctcagta aatagcctct 180
ccattcatcc ttccggtccc tctatgcccg 210

<210> SEQ ID NO 68
<211> LENGTH: 566
<212> TYPE: DNA
<213> ORGANISM: Homo sapiens

<400> SEQUENCE: 68
agccgctcct gtcatcttcc ctttctctct ccccatcagc ctgcgaggga ctaaaagccg 60
gcgatttttc cttgctgtat ttctttcttt tttttttttt ttttttgaga cggagtctcg 120
ctctgtcccc caggctggag tgcagtggcc cgatctcagc tcactgcaag ctccgcctcc 180
caggttcaca cctttctcct gcctcagcct cccaagtagc tgggactaca ggcgcccgcc 240
accgcgccca gctaattttt tgtattttta gtagagacgg ggtttcaccg agttagccag 300
gatggtctcg atctcctgac ctcatgaccc gcccacctcg gcctcccaaa gtgctgggat 360
tacaggcgtg agccaccgcg cccggcctgt ttctttctct tttttcttga gaccgagtct 420
cgctctgttg cccaggctgg agtacagtgg catgatctca gctcactgca acctctgtct 480
cccaggttca agcaattctc ctgcctcagc cttccgagta gctgggacta aaggctcccg 540
tcaccaccgt tgcccagcta attttt 566

<210> SEQ ID NO 69
<211> LENGTH: 200
<212> TYPE: DNA
<213> ORGANISM: Homo sapiens

<400> SEQUENCE: 69
gattattttg gaatagcaca gggttttgtt tttttttcgt tttttggttt ttcttgagac 60
ggagtttcgc tgttgttgct caggctggag tgcaatgcca caatctcagc tcatcacaac 120
ctccgcctcc cgggttcaag cgattctcct gcctcagcct cctgagtagc tgggattaca 180
ggcatgcgcc accatgcccg 200

<210> SEQ ID NO 70
<211> LENGTH: 340
<212> TYPE: DNA
<213> ORGANISM: Homo sapiens

<400> SEQUENCE: 70
cctccttcat gggtattcca cattgcttac acagtgacag ggattaaaaa caaaactaaa 60
ggctgggcgt ggtggctcac gcctgtaatc ccagcacttt gggaggctga ggcgggtgga 120
tcacgaggtc aggagatcga gaccatcttg gctaacacgg tgaaaccccg tctctactaa 180
aaatacaaaa aattagccgg gcgcggtggc aggcgcctgt agtcccagct actcaggagg 240
ctgaggcagg agaatggcgt gaacctggga ggcggagctt gcagtgagcc gagattgtgc 300
cactgcaatc cggcctgggc taaagagcgg gactccgtct 340

<210> SEQ ID NO 71
<211> LENGTH: 200
<212> TYPE: DNA
<213> ORGANISM: Homo sapiens

<400> SEQUENCE: 71
atgtattgat gatcacattc actactcaca cttacaaagt acagctccca ggccgggcgc 60
ggtggcttac gcctgtaatc ccagcacttt gggaggccga ggcaggcgga tcacgaggtc 120
atgagttcaa gaccagcctg gccaacatgg tgaaacccca tctctactaa aaatataaaa 180
attagcctgg tgtggtggcg 200

<210> SEQ ID NO 72
<211> LENGTH: 200
<212> TYPE: DNA
<213> ORGANISM: Homo sapiens

<400> SEQUENCE: 72
gttgtgaact tgtgtttttc cgttttatat gtatatgcca cttgtttttt tgttttgttt 60
tatttcgttt tgaggcggag tctcgctctg tctggagtgc agtggtgcaa tctcggctca 120
ctgcaacctc cacctccagg gttcaagcga ttctcctgcc tcagcctccg gtgtagctgg 180
gactacaggc gcctgccacc 200

<210> SEQ ID NO 73
<211> LENGTH: 200
<212> TYPE: DNA
<213> ORGANISM: Homo sapiens

<400> SEQUENCE: 73
aagtagctgg gattacaggc gcctgctacc acgcctggct aattttttgt attttagtag 60
agacgtggtc tcaccatgtt ggccaggctg gtctcaaact cctgacctca agtgatccac 120
ctgcctcggc ctccaaaact gccgggatta caggcgtgag ccaccacgcc tggccgctaa 180
caagtaattt taaagtatca 200

<210> SEQ ID NO 74
<211> LENGTH: 200
<212> TYPE: DNA
<213> ORGANISM: Homo sapiens

<400> SEQUENCE: 74
tttaactttt gaacttttcc gaagctttcc atattttcta tgtcctccaa gtgcccatca 60
tatcttttat tttctccttt cattgacctc tgtctttctt cagagctttc tggaaacctt 120
tgccgcttct cggccaccca cttgcttaga agccccatgc gggccgcggg gtgctgtggg 180
ctccaggcgg attgggcggg 200

<210> SEQ ID NO 75
<211> LENGTH: 200
<212> TYPE: DNA
<213> ORGANISM: Homo sapiens

<400> SEQUENCE: 75
ccagaatccc aactcagtaa gaccttgtaa atccatgaca ttagccccaa ttcccactcg 60
tcccaaatcc cataaccttt ccaccctgca cctgaagtgc gcagtcatca gcacaagctc 120
ctgtatgctc agcttctctg aacgtcaccg cggtactctc cctgacatct gcctgttctc 180
cgaggacaat gctttctccg 200

<210> SEQ ID NO 76
<211> LENGTH: 1002
<212> TYPE: DNA
<213> ORGANISM: Homo sapiens

<400> SEQUENCE: 76
gccaaccacc ttttctttcc taagtgtctg gatttacttc aagaaaatgc gggacaaaga 60
agggtggagg taagctttcg tttattcccc tgcttcacgg gggaaggagg tttgtgagca 120
taagcatgta agtacatgag aggcgtgttg ctctttggtg cctatcatac cctccccatg 180
gccggcgtgc acacacggcg agcagaaacg ctcccccgcc ccgctgcctg ccgccccacg 240
cgccctccct gcacctcccg cccgaccgac gcagaccaag cagaacttcc ctgggtcgcg 300
gcccagcgat acggagcggc cctggcgagg agccctgctc ttcccgagtc gtgggtggcg 360
cggtgcttgt ttccctcccc tccctttccg gacccaaacg gggatgtatc tgggtcagcc 420
tgggaggggc cggacctgcc agggaccagc gtgggggaag gggtggcga tgacagcatc 480 tttcaggttt ttggcgtctc tgagcttcgc ctcgtccagc ctctcaccgc gctcgctgcc 540
ggcgagggct gacgctctgg ccagtccagg cccgagggtg ggctggagag agggagagcc 600
cgtccttccg atctgggcgg caccccctcc cccacgccct gcgaacaatt cgcctcccac 660
acatacacac aggcgcatac tctattcccc agagcacgct cctcgggcgg gcagtgagtc 720
cctccgcccc aggaaaagag caatggaaca gttcacggcc gccacgagtt cctggtcttc 780
cttcctttcc ggtgataaac ggcgcggcta caagccagct actgctcaaa atgctccacc 840
cgcgggccca agcccctctc tcttggctgg gcgggggccc aggtccagga ccgagggtcc 900
cttaacctcc acaaggcgca caggctgagc gcccaggcgg caggaggtgc aagggcgcac 960
acccccggcg aacgcctggc tgcctcggtt cctctctatg tg 1002

<210> SEQ ID NO 77
<211> LENGTH: 400
<212> TYPE: DNA
<213> ORGANISM: Homo sapiens

<400> SEQUENCE: 77
atagacgcgg cagctccaaa tttacaagtg ctagctcttc atcccagctt cagggagaga 60
agcgaagcaa tgagttgaga atcatctctg gattcttgta tcccatgcat agtaatctcc 120
ttatcccctg gcccccttcc tcgtttcctc acattgcacg ctcagggact tgtttgccag 180
cggatggcct cggcaatccg gaacgcacgc tccgagagcc cacggatgct ctttggcctg 240
gagcttccct aaaggttcct gtattcgcgt gtgctcgtaa ccatgcagcg atgttccccc 300
ttccccgcct cacctcatcc ccagacatct cttgccatca tttcatgcac ccgtgtctaa 360
aaccccgcgt ttctccccac ccccgccagg cgcagcaccc 400

<210> SEQ ID NO 78
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 78
atcgacctgg tcaaccgcga ccctaaacac ctcaacgatg acgtggtcaa 50

<210> SEQ ID NO 79
<211> LENGTH: 50

<212> TYPE: DNA
<213> ORGANISM: Artificial Sequence
<220> FEATURE:
<223> OTHER INFORMATION: synthetic oligonucleotide

<400> SEQUENCE: 79
ttgtcacttc ccgggcttcg cggcgccagg tcggaaatgg tcccaatggt 50

<210> SEQ ID NO 80
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 80
tcttctcctg gggaggaggc gtggctcgga gcagacgtga cttctgtttt 50

<210> SEQ ID NO 81
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 81
acaagctatg ataagtgctg tgaaggttgt gccaagggct ggggggatgg 50

<210> SEQ ID NO 82
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 82
gtttcctcac ctgtagagag agaaatatta tatcacactg ttgcaaggac taagataagc 60
ga 62

<210> SEQ ID NO 83
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 83
gtttcctaag tttccttcaa actctgtctg catccgcaca tttgatctct ag 52

<210> SEQ ID NO 84
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 84
ttataatcag ggaagggcac tgtacacaag cccagtgagt agaaaggctg 50

<210> SEQ ID NO 85
<211> LENGTH: 57
<212> TYPE: DNA
<213> ORGANISM: Artificial Sequence
<220> FEATURE:
<223> OTHER INFORMATION: synthetic oligonucleotide

<400> SEQUENCE: 85
cggcagaagc tggcattaca tttctaagaa cggggaaatc gttattcaat tagagat 57

<210> SEQ ID NO 86
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 86
caccatcctc ccggcatgtg gatatggtta tcaacctgga ggctctccaa 50

<210> SEQ ID NO 87
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 87
atctgattga gtcatgttgg caagagctgg gtctaggacc ctggggtggg 50

<210> SEQ ID NO 88
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 88
taggagttag agattagttt ggttaatatg 30

<210> SEQ ID NO 89
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 89
ccaaattttt aaaacaaaat ctcactctat 30

<210> SEQ ID NO 90
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 90
caactcacta caacctcca 19

<210> SEQ ID NO 91
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 91
ggtaggagaa gtgttggtta gtatgt 26

<210> SEQ ID NO 92
<211> LENGTH: 20

<212> TYPE: DNA
<213> ORGANISM: Artificial Sequence
<220> FEATURE:
<223> OTHER INFORMATION: synthetic oligonucleotide

<400> SEQUENCE: 92
cctaaaccca actcttacca 20

<210> SEQ ID NO 93
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 93
ttagtatgta taggttagag gaag 24

<210> SEQ ID NO 94
<211> LENGTH: 458
<212> TYPE: DNA
<213> ORGANISM: Artificial Sequence
<220> FEATURE:
<223> OTHER INFORMATION: synthetic oligonucleotide

<400> SEQUENCE: 94
cgtcctcccc gcgggcagtg ccggccccga gcagcgcttc gcaggccccc gcgcgaacgc 60
tgccgaccgc cgcgttcggt cgccgaatgt tacccggttc tgaatgttac acttacacat 120
tccattcccg acacgacagc gctgacctca tccatccacg cagcccgcgc tgccattggc 180
cgagcgtcac gtccgggggg ggcggtgctt ccgctgcgcc cattcataac ccccggccgc 240
gggccgaggc gccggcgcgg cgttgggggc gtagggggcg cagggagccg gggctcccgg 300
gttgcaagct gccggcgggc tgccgggcag gtggagcgcg ggacggcccg gtgcgagccc 360
cgcggcccct cggcgcgccc aggcccggat ctcggcctgc gccgtgccgg ggaccagagg 420
cgcctgcgga aacgcggcgg ccggggaagg aggcaccg 458

<210> SEQ ID NO 95
<211> LENGTH: 2190
<212> TYPE: DNA
<213> ORGANISM: Artificial Sequence
<220> FEATURE:
<223> OTHER INFORMATION: synthetic oligonucleotide

<400> SEQUENCE: 95
gaggtcagga gttcacgacc agcctggcca acatggtaaa accccgtctc tacaaaaata 60
caaaaattag ccaggcatga tggcgggtgt ctgtaatccc aactactcgg gaggctgagg 120
caggagaatc gcttgaaccc gggaggcgga ggttgcactg agccgagatt gcactactgc 180
cctccagcct gggcgacaca gcaggactct gtctcaaaaa ataaaaataa aataaaaata 240
aaaatgctgg gcgcagtggc tcatgcctgt aatcccagca ctttaggagg ccggggcggg 300
tggatcacct gagatcggga gttcaagacc agcctgacta acatggagaa accccgtctc 360
tactaaaaat acaaaattag ccaggcatgg tggtgcatgt ctgtaatccc agccactcag 420
gaggctgagg cgggagaatc gcttgaaccc gggaggcgga ggttgcagtg gaccaagatc 480
gcgccattgc actccagcct gggcaacaga atgagactcc atctcaaaaa aaaaaaaaaa 540
agaaagaaag aaagaaagaa agaaagaaag aaagaaagaa agaaagaaag aaagaaagaa 600
agaaaaaaac tgttatagac tgagtgccat tttagatggg gttttctggg aagtgctgtg 660

```
acatcatcgc ttgctgtaaa agaggccggg cgcggtggct gacgcctgta ctcccagcgc    720
tttgggaggc cgaggcggga ggatcgcttg agcctaggag ttcgaagtta caatgagcta    780
tgatcaggcc actgcactcc agcctgggca atgagaaaga ccctgtctct taaacaacaa    840
caaagtcaga aggagaggct gccatggcta cggctccagg tgacgtcacg gccagctccg    900
tgacgcgcgg ccagggcagc ccgcggagac cgaggctcct ctgtgacgtc agcagccggc    960
cgggacacag cgggagggca ggtgcggccg cggggcctgc cgacttcacg cagggtccgt   1020
ggggtccccg cggcgcgcag cggctgaagg aggccccagg gccttggcga ccgcagcggc   1080
ggctttagcg tcagtgacta ggcagcaggg ggtcaggatg cggcgaagct cccgcccggg   1140
ctcggcctcg tcctcgcgca agcacacgcc caactttttc agcgagaaca gctcaatgag   1200
catcacctcg gaggacagca aagggctccg gtcagcggag cccgggcctg ggagcccga    1260
gggcagaaga gcccggggcc cgagctgcgg tgagcccgcc ttgagcgcgg gagtgcccgg   1320
aggaaccaca tgggcaggaa gctctcagca gaagccagcg cctcggagcc acaactggca   1380
gacagcctgt ggcgcggcaa ccgtgagggg cggggcctcg ggtgcgggcg gggtcgaccc   1440
cgggtgagcc agtggagggg gcggggccta aagggcggtg ctgggcgggg acggggctaa   1500
gatgatatct gggcacctcc tacaaggtgg gtcctgtagg gtaaagggat ggtgctaaat   1560
gagatccctt aaggggcgga gcctcggtgt cctggacggt tatgggaagg ggcggggaaa   1620
atcttgtggt tgggtgccac tgaggggggcg cggcctcaat gttagcgtga gtggctccca  1680
ggacaattgg gttccaccaa gatctaaggc tgggggcggg tcatccgttt gggggaggga   1740
ccaactcttt tttttttttt tttgcaacgg agtttcgctc ctgttgccca tgccatgcaa   1800
tggcatgatc tcggctcacc gcaacctccg cctcccgggt tcaaacgatt ctcccgcctc   1860
agcctcccga gtagctggga ttacaggcgt gcgccaccat gcccggccaa tttttgtgtt   1920
tttagtagag acggggtttc tccgtgttaa tcaggctggc ctcgaactcc cgacctcagg   1980
tgatccgccc gcctcggcct cccaaatcgc tgggattaca ggcgtgagcc accgcgcccg   2040
gccaggagac caactcttga cggagcctcc ctgaggggcg gggcttcaga gggcggagct   2100
ggagccggga tagggctgcg gtgggaccaa agcctgtgag agacttccca gctgtctggc   2160
ttgtggactg agcaatctgc ggcccggtct                                    2190
```

<210> SEQ ID NO 96
<211> LENGTH: 282
<212> TYPE: DNA
<213> ORGANISM: Artificial Sequence
<220> FEATURE:
<223> OTHER INFORMATION: synthetic oligonucleotide

<400> SEQUENCE: 96

```
cggcccggtc tcgaggggaa aataggtctg tggtccgcaa ggccccagtg gagcccttgg     60
gttcccgcag aaccgactgg gtctccagta gtctctgagg agccgctcga ccttctcccg    120
accctggatc tgaggcagga gatgcctccc ccgcgggtgt tcaagagctt tctgagtacg    180
ggccaggcca gctgcgatcc cctctgaccc tcgggttccc ctctccgaac tccagttctc    240
tctgagcccc cggcccccgt ttgagtatcg agcccctctc cg                       282
```

<210> SEQ ID NO 97
<211> LENGTH: 234
<212> TYPE: DNA
<213> ORGANISM: Artificial Sequence
<220> FEATURE:
<223> OTHER INFORMATION: synthetic oligonucleotide -continued

<400> SEQUENCE: 97

```
cggcagcagt cgctctgtcc gacggttccg atggtccctc cgcccgcctg cagccccacg     60
tgttccctgg gaattgctgg gcttttgaag gcgaccaagg ccaggtggtg atccaactgc    120
cgggccgagt gcagctgagc gacatcactc tgcagcatcc accgcccagc gtggagcaca    180
ccggaggagc caacagcgcc ccccgcgatt tcgcggtctt tgtgagtgcg gacg          234
```

UNBIASED DNA METHYLATION MARKERS DEFINE AN EXTENSIVE FIELD DEFECT IN HISTOLOGICALLY NORMAL PROSTATE TISSUES ASSOCIATED WITH PROSTATE CANCER: NEW BIOMARKERS FOR MEN WITH PROSTATE CANCER

CROSS-REFERENCE TO RELATED APPLICATION

This application claims the benefit of U.S. Provisional Patent Application Ser. No. 61/806,218 filed on Mar. 28, 2013; U.S. Provisional Patent Application Ser. No. 61/806,566 filed on Mar. 29, 2013; and is a continuation-in-part of U.S. application Ser. No. 13/288,607 filed on Nov. 13, 2011. All of these applications are incorporated by reference in their entirety.

STATEMENT REGARDING FEDERALLY SPONSORED RESEARCH OR DEVELOPMENT

Not applicable.

BACKGROUND

It is estimated that 198,280 men were diagnosed with prostate cancer and 27,360 men died from prostate cancer (PCa) in 2009 in the USA (Jemal et al., (2009) *CA Cancer J Clin* 59, 225-249). The predominant tools for early detection of prostate cancer are prostate specific antigen (PSA) testing and digital rectal exam (DRE). However, 65% to 70% of men with total PSA ranging between 4.0-10.0 ng/ml have a negative prostate biopsy result. In addition, 15% of PCa patients have PSA levels <4.0 ng/ml, indicating a weak predictive ability (Thompson et al., (2004) *N Engl J Med* 350, 2239-2246). PSA-based screening also detects non-significant cancers leading to an estimated 50% of overdiagnosis (Fritz et al., (2009) *The New England Journal of Medicine* 360). A urine-based test examining an RNA molecule termed PCA-3 is currently undergoing FDA trials. Prostate biopsy is used to confirm disease. However, because of sampling errors repeated sets of samples are commonly required to make a diagnosis (Gann et al., (2010) *JCO* 28, 7). Typical biopsy schemes include 10-12 or more tissue cores removed under local anesthetic. Re-biopsy is often required two to three times in order to rule out cancer because of sampling errors. Cancers can also be missed because of sampling problems.

There is a clear need for biomarkers that allow easier and more accurate diagnosis and prognosis of prostate cancer.

SUMMARY OF THE INVENTION

In one embodiment, the present invention is a method of detecting the presence of a prostate cancer field defect in a human subject comprising the steps of obtaining genomic DNA from the human subject, amplifying at least one target region, and preferably at least two, three or four regions, selected from the group consisting of CAV1, EVX1, MCF2L, FGF1, NCR2, WNT2, EXT1 and SPAG4 target regions, purifying the amplification product; and quantitating the methylation in the target regions, wherein significant methylation changes indicate the presence of prostate cancer field defect, wherein the change is relative to tissue from a second human subject who does not have prostate cancer.

Preferably, the significant methylation change is $p<0.05$ or at least ±50% of the pyrosequencing percentages or fold-changes shown in Table 1.

In another embodiment, the present invention is the amplification product described above.

In another embodiment, the present invention is a combination of the amplification product described above and materials useful to determine methylation status.

In another embodiment, the genomic DNA is obtained from prostate tissue. In another embodiment, the genomic DNA is obtained from body fluid preferably selected from the group consisting of urine and semen. Most preferably the bodily fluid is urine.

In a preferred embodiment, primer sets are used for amplification of the target region and at least one primer within each set of primers is biotinylated.

In yet another preferred embodiment, the methylation is quantified via pyrosequencing.

In another embodiment, the quantitation of methylation comprises analyzing whether the CAV1, EVX1 or MCF2L regions are hypermethylated or FGF1, WNT2 or NCR2 regions are hypomethylated as a positive correlation to prostate cancer field defect. Preferably, the target loci comprise sequences selected from the group consisting of SEQ ID Nos:1-6. Preferably, the target loci are amplified using at least one set of primers in FIG. 12.

In another embodiment, the quantitation of methylation comprises analyzing whether the SPAG4 regions are hypermethylated or EXT1 regions are hypomethylated as a positive correlation to prostate cancer field defect. Preferably, the target loci comprise sequences selected from the group consisting of SEQ ID Nos:18 and 39. Preferably, the target loci are amplified using at least one set of primers in FIG. 25.

In another embodiment, the quantitation of methylation comprises analyzing whether the CAV1, EVX1, MCF2L or SPAG4 regions are hypermethylated or FGF1, WNT2, NCR2 or EXT1 regions are hypomethylated as a positive correlation to prostate cancer field defect. Preferably, the target loci comprise sequences selected from the group consisting of SEQ ID Nos:1-6, 18 and 39. Preferably, the target loci are amplified using at least one set of primers in FIGS. 12 and 25.

In another embodiment, the human subject is a prostate cancer patient.

In another embodiment, the invention is a method of diagnosing high grade prostate cancer field defect in a human subject comprising the steps of: (a) obtaining genomic DNA from the human subject; and (b) quantitating the methylation in at least one target region selected from the group consisting of NCR2 and WNT2 target, wherein significant methylation changes indicate the presence of high grade prostate cancer field defect or prostate cancer, wherein the change is relative to tissue from a second human subject who does not have prostate cancer; and (c) treating the human subject for high grade prostate cancer field defect based the results of steps (a) and (b).

In another embodiment, the invention is a method of screening biomarkers for prostate cancer comprising the steps of: (a) obtaining genomic DNA from a human subject; and (b) quantitating the methylation in at least one target region selected from the group consisting of SEQ ID NOs: 1-6 and 18, 39; wherein significant methylation changes indicate the presence of prostate cancer field defect or prostate cancer, wherein the change is relative to tissue from a second human subject who does not have prostate cancer.

In another embodiment, the invention is a method of screening biomarkers for prostate cancer comprising the steps of (a) obtaining genomic DNA from a human subject; and (b) quantitating the methylation in at least one target region selected from the group consisting of SEQ ID NOs: 61-77 and 94-97; wherein significant methylation changes indicate the presence of prostate cancer field defect or prostate cancer, wherein the change is relative to tissue from a second human subject who does not have prostate cancer.

Other objects, advantages and features of the present invention will become apparent from the following specification taken in conjunction with the accompanying drawings.

BRIEF DESCRIPTION OF DRAWINGS

The invention will be better understood and features, aspects and advantages other than those set forth above will become apparent when consideration is given to the following detailed description thereof. Such detailed description makes reference to the following drawings, wherein:

FIG. 1 shows the sequence of the target region for CAV1 (SEQ ID NO:1).

FIG. 2 shows the sequence of the target region for EVX1 (SEQ ID NO:2).

FIG. 3 shows the sequence of the target region for MCF2L (SEQ ID NO:3).

FIG. 4 shows the sequence of the target region for FGF1 (SEQ ID NO:4).

FIG. 5 shows the sequence of the target region for NCR2 (SEQ ID NO:5).

FIG. 6 shows the sequence of the target region for WNT2 (SEQ ID NO:6).

FIG. 7 shows probe sequences used in the methylation array for the genes CAV1, EVX1, MCF2L, FGF1, NCR2 and WNT2.

FIG. 11A-D shows CAV1, EVX1, MCF2L and FGF1 methylations. To analyze CAV1 methylation, we analyzed methylation of ten CpGs and eight out of the ten CpGs showed significantly increased methylation in T (tumor), TAA (tumor-associated adjacent) and TAD (tumor-associated distant) prostate tissue compared to NTA (non-tumor-associated normal prostate tissue). The figure shows methylation percentages of the sixth CpG and they are 14%, 45%, 27% and 26% for NTA, T, TAA and TAD prostate tissues, respectively. *t-test. $P<0.05$ was used for all figures below. To analyze EVX1 methylation, we tested six CpGs for EVX1 and four out of the six showed significantly increased methylation in T, TAA and TAD compared to NTA prostate tissues. This figure shows methylation percentage of the third CpG and they are 22%, 45%, 31% and 28% for NTA, T, TAA and TAD prostate tissues, respectively. For MCF2L, the region detected contains nine CpGs and three out of the nine CpGs showed significantly increased methylation in T, TAA and TAD compared to NTA prostate tissue. This figure shows the methylation for the first CpG and they are 80%, 88%, 85% and 85% for NTA, T, TAA and TAD prostate tissues, respectively. For FGF1, all four CpGs we analyzed showed significantly decreased methylation in TAA and TAD compared to NTA prostate tissue, but no significant change in T prostate tissue. This figure shows methylation percentage of the third CpG and they are 71%, 73%, 60% and 61% for NTA, T, TAA and TAD prostate tissues, respectively.

FIG. 12 shows the sequences of primers used for pyrosequencing.

FIG. 14 shows the sequence of the expanded region of CAV1 to screen for methylation changes associated with PCa.

FIG. 15 shows the sequence of the expanded region of EVX1 to screen for methylation changes associated with PCa.

FIG. 16 shows the sequence of the expanded region of MCF2L to screen for methylation changes associated with PCa.

FIG. 17 shows the sequence of the expanded region of FGF1 to screen for methylation changes associated with PCa. Since there is no CPG island within the promoter region, all the regions shown are within introns between exons one and three.

FIG. 18 shows the sequence of the expanded region of NCR2 to screen for methylation changes associated with PCa.

FIG. 19 shows the sequence of the expanded region of WNT2 to screen for methylation changes associated with PCa.

FIG. 20 shows the sequence of the target region for EXT1 (SEQ ID NO:18).

FIG. 21 shows the sequence of the target region for SPAG4 (SEQ ID NO:39).

FIG. 22 shows probe sequences used in the methylation array for the genes EXT1 and SPAG4 (SEQ ID NOs:86-87).

FIG. 25 shows the sequences of primers used for target amplification and pyrosequencing (SEQ ID NOs:88-93).

FIG. 26 shows the sequence of the expanded region of EXT1 to screen for methylation changes associated with PCa (SEQ ID NO:94).

FIG. 27 shows the sequence of the expanded region of SPAG4 to screen for methylation changes associated with PCa (SEQ ID NOs:95-97).

DESCRIPTION OF THE PRESENT INVENTION

In General

Figure 8:
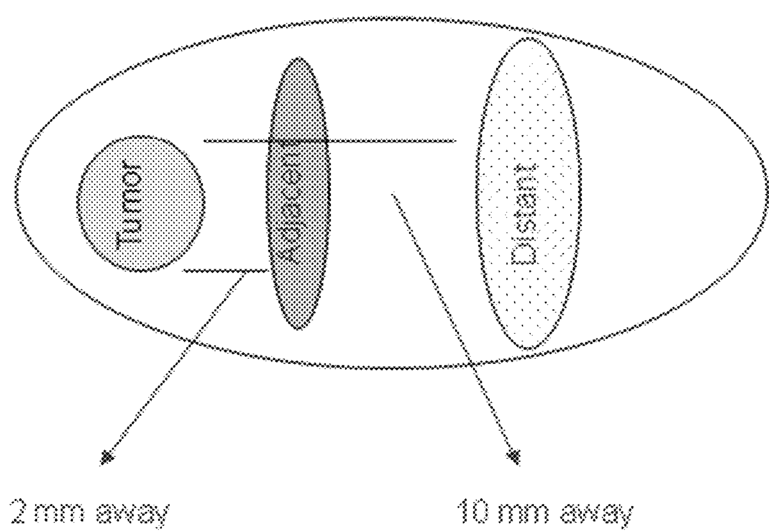
FIG. 8 is a diagram demonstrating microdissection of prostate tissue.

Like other human cancers, prostate cancer development and progression is driven by the interplay of genetic and epigenetic changes (Schulz et al., (2009) *Semin Cancer Biol* 19, 172-180). Changes in somatic DNA methylation constitute a superb source of cancer biomarkers for several reasons. These changes can be detected using PCR methods at single-copy sensitivity and small DNA fragments are more stable in blood and body fluids than RNA or protein species. In addition, acquired DNA methylation differences have been reported for nearly every human cancer. Finally, somatic hypermethylation of CpG island sequences may be more consistent for a given cancer than genetic changes (Nelson et al., (2009) *Endocrinology* 150, 3991-4002). Patterns of DNA methylation in tumors may also discriminate aggressive vs. nonaggressive disease and predict responsiveness to specific treatments (Nelson et al., (2009) *Endocrinology* 150, 3991-4002).

Genetic and epigenetic alterations do not appear to be limited to the cancerous cells, as recent data indicates tissue adjacent or distant to the tumor is also abnormal (Norm et al., (2009) *Prostate* 69, 1470-1479). This field defect (also termed field effect) has been identified in colon and head and neck cancer, as well as prostate based on alterations in gene expression (YP, Y. (2004) *Journal of Clinical Oncology* 22; Chandran et al., (2005) *BMC Cancer* 5, 45) and genomic loss of imprinting (Agnieszka et al., (2009) *International Journal Of Oncology* 35, 87-96). Aberrant methylation patterns in the GSTP1, RARb2, APC and RASSF1A promoters have been detected in normal epithelial or stromal tissue adjacent to cancer (Aitchison et al., (2007) *Prostate* 67, 638-644; Hanson et al., (2006) *J. Natl. Cancer Inst.* 98, 255-261; Henrique et al., (2006) *Mol Cancer Res* 4, 1-8). These genes are altered in the tumor and represent a single gene approach to analyzing the field effect. Results vary as to whether this field effect is limited to the tissue adjacent to the tumor or whether it is found in distant 'normal' tissue.

By use of the present invention, one can reassure men who have a negative biopsy that no cancer is present by testing for the presence of the field defect without additional future biopsies and avoid the complications directly associated with increasing the biopsy number and frequency. If methylation changes associated with a biopsy field defect are detected, more detailed imaging with an MRI and endorectal probe and a more aggressive detection strategy requiring anesthesia and 30-50 biopsies will typically be undertaken to detect and/or characterize the disease. This approach is associated with additional risks associated with anesthesia, infection, bleeding and others, and is not performed routinely. In addition, it is likely these patients would be monitored much more closely.

In developing the present invention, the inventors have analyzed histologically normal tissues from men with and without prostate cancer utilizing a high-throughput technique that simultaneously scans 385,000 regions of the genome. Using a human ENCODE methylation array (Roche Nimblegen), the inventors have found distinct alterations in methylation at specific loci or "target regions". The inventors associated methylation changes at these loci with the presence of prostate cancer. Analysis of these loci in tissue samples from patients will enhance the detection of prostate cancer.

By "histologically normal", we mean prostate tissue that has no evidence of disease in the specimen itself, based on standard morphologic and histochemical criteria used by pathology. By "normal" or "non-tumor associated (NTA)", we mean prostate specimen which not only does not contain cancer itself, as defined by a pathologist, but also does not contain cancer elsewhere in the prostate. By "tumor associated (TA)", we mean a prostate specimen which does not show evidence of cancer, but is taken from a prostate with evidence of cancer in another location. One would appreciate that both "non-tumor associated" and "tumor associated" prostate specimens in this application are "histologically normal" prostate specimens.

Standard PCR methods generally entail amplification of a target region using a pair of forward and reverse primers that are designed to be complementary to sequences flanking the target region. The size of a fragment that can be amplified using PCR can range from less than 50 base pairs (bp) to greater than 10,000 base pairs. Similarly, sequencing of a target region can be accomplished by designing sequencing primers that are complimentary to a sequence less than 50 bp upstream of the target gene or more than 1000 bp upstream depending on the sequencing technology selected. Therefore it is possible to design many permutations of sequencing primers or PCR primer sets that are capable of amplifying a given target region. For example, given a sample containing genomic DNA comprising a 500 bp target gene or region, a primer set can be designed to amplify i) the explicit target region; or ii) a region encompassing the target region including upstream and downstream sequence. If the minimum requirement is a 20 bp primer and the amplified fragment size can range from 500 to 10,000 bp, the number of potential primer sets that can be used to amplify the target region is on the order of $10^4$.

This invention discloses a number of preferred primers for amplification of specific target regions. However, one skilled in the art will appreciate that the target regions disclosed in the present invention can be amplified by other than the described primers, which have been presented for purposes of illustration. A number of PCR amplification and sequencing schemes are contemplated and therefore, the scope of the appended claims should not be limited to the description of the embodiments contained herein.

Biomarker Candidates

The inventors identified eight biomarker candidates associated with the genes CAV1, EVX1, MCF2L, FGF1, WNT2, NCR2, EXT1 and SPAG4 which showed significant changes ($p<0.05$) in methylation in target regions when normal and tumor-associated tissues are compared (Table 1). The CAV1, EVX1, MCF2L and SPAG4 regions showed hypermethylation, and the FGF1, WNT2, NCR2 and EXT1 regions showed hypomethylation.

TABLE 1

| Gene | Location | Function | Fold Change Microarray | Pyrosequencing |
|---|---|---|---|---|
| CAV1 | 7q31.1 | Tumor suppressor gene candidate<br>A negative regulator of the Ras-p42/44 MAP kinase cascade<br>Negative regulation of JAK-STAT cascade<br>A scaffolding protein within caveolar membranes | 7.6 | 30% increased in tumor, 12% in tumor-associated, adjacent and distant |
| EVX1 | 7p15-p14 | Sequence-specific DNA binding, transcription factor<br>A role in the specification of neuronal cell types. | 7.1 | 23% increased in tumor, 6-13% in tumor-associate, adjacent and distant |
| FGF1 | 5q31 | Fibroblast growth factor receptor signaling pathway<br>Positive regulation of epithelial cell proliferation<br>Embryonic development, cell growth, tumor growth and invasion | 0.77 | 11-15% decreased in tumor-associated, adjacent and distant |
| MCF2L | 13q34 | Rho guanine nucleotide exchange factor activity | 4.5 | 8% increased in tumor, 5% in tumor-associated, adjacent and distant |
| NCR2 | 6p21.1 | Increases efficiency of activated NK cells<br>To mediate tumor cell lysis | 0.6 | 11% decreased in tumor, adjacent and distant for high grade<br>5% decreased in tumor for intermediate grade |
| WNT2 | 7q31.2 | Wnt receptor signaling pathway, calcium modulating pathway<br>Implicated in oncogenesis and in several developmental processes (embryogenesis) | 0.7 | 16% decreased in tumor, 5% in adjacent and distant for high grade<br>8% decreased in tumor for intermediate grade |
| EXT1 | 8q24.11 | exostosin glycosyltransferase<br>It is a putative tumor suppressor protein, involved in glycosaminoglycan biosynthesis, signal transduction, negative regulation of cell cycle, as well as skeletal development. | 0.6 | 5% decreased in tumor, adjacent and distant histologically normal prostate tissue. |
| SPAG4 | 20q11.21 | sperm associated antigen 4<br>Structural molecule activity,<br>Spermatogenesis. | 2.1 | 9% increased in tumor, 8% in adjacent and 12% distant histologically normal prostate tissue |

By "gene loci" or "target region", we mean the gene regions described in FIGS. 1-6 and 20-21. These are the gene regions in which we correlated either hypermethylation or hypomethylation with a prostate cancer field defect. FIG. 12 describes preferred primer sequences for determining methylation perturbations in these selected target regions. FIGS. 12 and 25 describes preferred primer sequences for determining methylation perturbations in these selected target regions.

In a second embodiment, by "gene loci" or "target region", we mean the gene regions described in FIGS. 20-21. These are the gene regions in which we correlated either hypermethylation or hypomethylation with a prostate cancer field defect. FIG. 25 describes preferred primer sequences for determining methylation perturbations in these selected target regions.

EMBODIMENTS OF THE PRESENT INVENTION

In one embodiment, one can diagnose and/or treat prostate cancer in a human subject by detecting a prostate cancer field defect in histologically normal tissue biopsy specimens taken from men who may have prostate cancer. Based on the results of the detection methods described herein, the subject may be diagnosed with prostate cancer and/or treated for prostate cancer via conventional therapies. It is an advantage of the present invention that fewer biopsies are needed for the detection of prostate cancer. In a preferred embodiment, the presence of prostate cancer field defect can be detected based on only 1-2 core biopsy specimens taken from anywhere in the prostate. Preferably, one would examine one, two, three, four, five, six, seven or eight targets disclosed in Table 1. In addition, in individuals who have had a negative biopsy but whose PSAs continue to rise, analysis of the previously obtained specimens for methylation status in the target regions will direct whether additional evaluation needs to be performed. For example, if the methylation status in any of the target regions is abnormal, a more intensive biopsy set requiring anesthesia would be performed. If not, the patient can be reassured.

In one typical embodiment, prostate tissue samples are obtained via standard transrectal ultrasound and biopsy protocols using an 18 gauge needle (Brooks et al. (2010) *J. Natl. Med. Assoc.* 102(5), 423-429). In another embodiment, prostate tissues are obtained from paraffin blocks of prostate biopsy samples that have already been obtained and examined.

Figure 29:
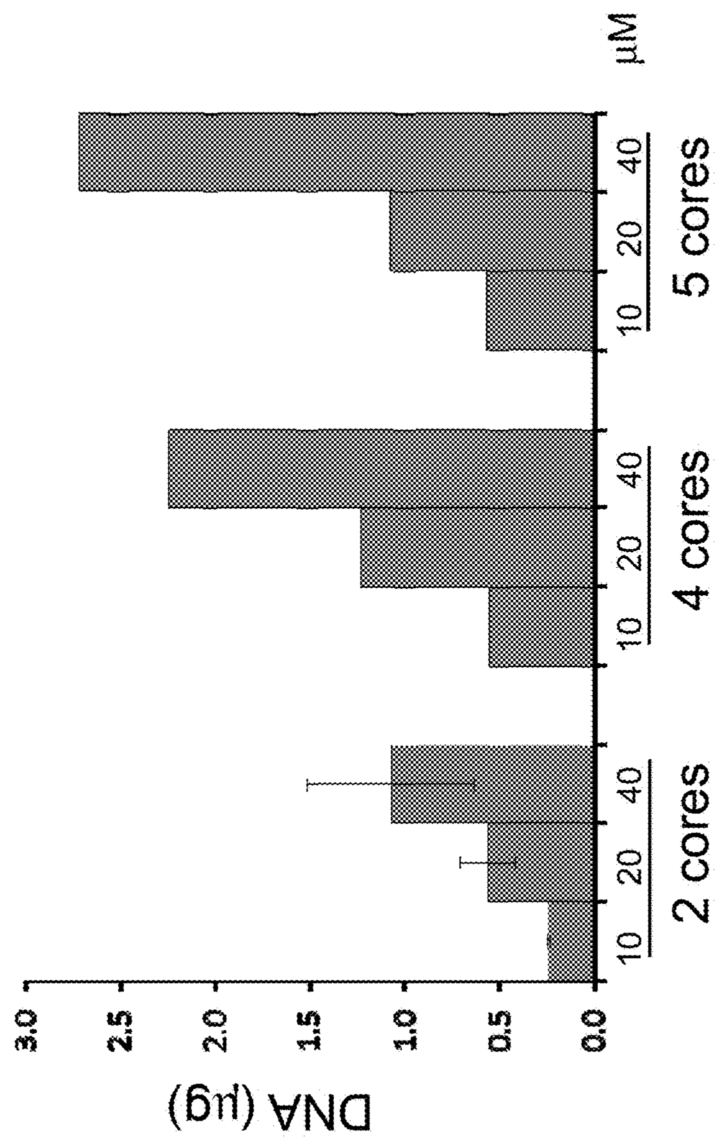
FIG. 29 shows DNA isolation from paraffin-embedded prostate biopsies.

To examine the methylation status of the target regions, one would typically wish to obtain genomic DNA from the tissue samples. The purified genomic DNA is then typically subject to sodium bisulfite modification. We present data demonstrating the ability to obtain enough DNA for analysis using prostate tissue either fresh or paraffin-embedded (See FIG. 29).

In general, bisulfite modified DNA is subjected to PCR reaction containing a single or multiple pair(s) of primers and probes at specific gene loci of at least one of the CAV1, EVX1, MCF2L, FGF1, WNT2, NCR2, EXT1 and SPAG4 loci detailed in FIGS. 1-6 and 20-21. The DNA amplification and methylation quantification will be evaluated in one or multiple tubes included as part of a kit. In one embodiment, one would then subject the bisulfite DNA to Methylation-Specific-Quantitative PCR (MS-QPCR) such as MethyLight (WO 00/70090) or HeavyMethyl WO 02/072880). A typical kit for the Mehtylight assay of this embodiment would contain primers and probes of target regions detailed in FIGS. 1-6, and 20-21, and wild type reference gene primers such as Beta-Actin, PCR buffer, dNTP, $MgCl_2$, polymerase, positive and negative methylation controls and a dilution reference. In another embodiment, the present invention is the amplification product described above. In a typical embodiment, the DNA targets are bisulfate-modified DNA. In another typical embodiment, the amplification product comprises the amplification product of 2, 3, 4, 5, 6, 7, or 8 of the targets combined in a vessel, such as a tube or well. Preferably, the DNA amplification product is at least 90% target DNA, most preferably 95% or 99%.

In another embodiment, the present invention is a combination of the bisulfite-treated DNA described above and materials useful to determine methylation status.

In another embodiment, one would subject the bisulfite DNA to PCR amplification to amplify at least one of the target regions detailed in FIGS. 1-6 and 20-21. The PCR products would be subject to pyrosequencing for detection of methylation. The kit for this assay would contain at least one pair of primers for target regions detailed in FIGS. 1-6 and 20-21, either forward or reverse primer is biotinylated, PCR buffer, dNTPs, $MgCl_2$, Taq polymerase for bisulfite DNA amplification. A sequencing primer and controls, which typically include positive and negative methylation controls and a dilution reference are typically also included.

In another embodiment, bisulfite treated DNA (initial PCR amplification is needed if bisulfited DNA is less than 20 ng) is subjected to an Invader® assay to detect changes in methylation. The Invader® assay entails the use of Invader® chemistry (Hologic Inc.; invaderchemistry.com; Day, S., and Mast, A. Invader assay, 2004; Chapter in Encyclopedia of Diagnostic Genomics and Proteomics. Marcel Dekker, Inc., U.S. Pat. Nos. 7,011,944; 6,913,881; 6,875,572 and 6,872,816). In the Invader® assay, one would use a structure-specific flap endonuclease (FEN) to cleave a three-dimensional complex formed by hybridization of C/T specific overlapping oligonucleotides to target DNA containing a CG site.

The kit for this assay would typically contain the primers and probes of single or multiple target regions detailed in FIGS. 1-6 and 20-21, and controls, which typically include a reference gene such as Beta-Actin, positive and negative methylation controls and a dilution reference.

In another embodiment, the PCR products are purified, denatured to single-strand and annealed to a sequencing primer for methylation quantification by pyrosequencing at the specific gene loci of at least one of the loci described above.

In all embodiments, one would examine the amplification products for a significant change in methylation pattern. One may examine several criteria to evaluate significant change. For example, a finding of ±50% of the fold-change listed in Table 1 in methylation values of at least one gene loci at one site selected from the group consisting of CAV1, EVX1, MCF2L, FGF1, WNT2, NCR2, EXT1 and SPAG4 would indicate the presence of a prostate cancer field effect. Significant change can also be any statistically meaningful change in methylation pattern relative to normal tissue from men with no history of prostate cancer. For example, significant change may be characterized by a p value less than 0.05. As described below, one may wish to use pyrosequencing as a quantitation method and evaluate the sample for the pyrosequencing percentage, as indicated in Table 1.

One may also wish to examine the change in methylation at specific CpG islands. (The Example below discloses specific characterization of CpG islands for the eight target regions.) Preferably, one would determine the methylation status of two, three, four, five, six, seven or eight of the gene loci detailed in FIGS. 1-6 and 20-21.

As described above, there are many techniques for measuring DNA methylation. For example, one can use Methylation-Specific-Quantitative PCR (MS-QPCR) or to measure DNA Methylation. (See: Eads C. A., MethyLight: a high-throughput assay to measure DNA methylation. *Nucleic Acids Res.* 2000 Apr. 15; 28(8):E32; 2. Darst R. P., Bisulfite sequencing of DNA. *Curr Protoc Mol Biol.* 2010 July; Chapter 7: Unit 7.9.1-17, and Cottrell S. E., et al., A real-time PCR assay for DNA-methylation using methylation specific blockers, *Nucleic Acids Res.* 2004; 32(1): e10.).

The Examples focus on a preferred method, but one of skill in the art would understand that other methods would be suitable. One simply needs to evaluate the methylation status of CpG islands within the target regions. Examples 1 and 2 below disclose methylation changes at specific CG rich regions, and we anticipate seeing similar changes in adjacent CpG islands not necessarily measured in Examples 1 and 2. Any change in CpG island methylation at one or multiple CG dinucleotides within this island, is considered a positive marker for prostate cancer field defect. One may wish to start with the expanded regions disclosed in Example 3 below.

Preferably, one primer within each set of primers is biotinylated, and the biotinylated PCR products are purified, or captured, with Streptavidin sepharose beads. In a preferred embodiment, one would use the primers detailed in FIGS. 12-25.

Preferably, the methylation is quantified with PyroMark™MD Pyrosequencing System (Qiagen) using PyroPyroMark® Gold Q96 Reagents (Qiagen, Cat#972804) (QIAGEN PyroMark Gold Q96 Reagents Handbook 08/2009, (36-38)). Other approaches for methylation quantification include, for example, methylation specific QPCR or quantitative bisulfite sequencing of methylation.

It is an advantage of the present invention that markers for prostate cancer can be detected noninvasively in bodily fluids, such as urine or semen. The bodily fluid screening method currently used is based on PSA levels in serum and has very poor specificity. Biopsies are more specific, but can produce significant clinical complications, including infection, bleeding and urinary retention. Therefore, in one preferred embodiment of the present invention, the methylation status of the target regions is determined from a urine sample.

In another embodiment, the present invention is a method of identifying biomarkers whose DNA methylation changes associate with high grade PCa, using the protocol described above and in the Examples below. By "high grade", we mean PCa with a Gleason Score 8-10 and a tumor volume of 25-80%. For example, a finding of ±50% of the fold-change in methylation values of at least one gene loci selected from WNT2 and NCR2 would indicate the presence of a high grade PCa field effect. Additional biomarkers for high grade PCa may be identified using the protocol described above and in the Examples below and may also be included in kits.

Generally, patient urine can be obtained, spun and the cell pellet utilized for DNA extraction using protocols as published (Yoshida et al., *International Journal of Cancer*, n/a-n/a; Mehrotra et al., (2008) *Prostate* 68, 152-160). One may wish to use DNA methylation urine-based screen for PCa disclosed below in Example 4. One would then analyze the genomic DNA samples as described above for solid tissue samples. Presence of methylation changes correlating to field effect diagnosis would be analyzed in the same manner as described above.

Generally, when pyrosequencing primers (such as the preferred primers in FIG. 12) are used, significant methylation changes of at least one of the eight target regions would indicate a prostate cancer field defect. In various embodiments, significant change is indicated by a value of at least ±50% of the pyrosequencing percentages shown in Table 1 or ±50% of the fold-level change in Table 1 or a $p<0.05$ change in specific CpG island methylation patterns.

In a second embodiment, when pyrosequencing primers (such as the preferred primers in FIG. 12 or 25) are used, significant methylation changes of at least one of the two target regions according to SEQ ID NOs:18 and 39 would indicate a prostate cancer field defect. In various embodiments, significant change is indicated by a value of at least ±50% of the pyrosequencing percentages shown in Table 1 or ±50% of the fold-level change in Table 1 or a $p<0.05$ change in specific CpG island methylation patterns.

In a third embodiment, when pyrosequencing primers (such as the preferred primers in FIG. 12 and/or FIG. 25) are used, significant methylation changes of at least one of the eight target regions according to SEQ ID NOs:1-6, 18 and 39 would indicate a prostate cancer field defect. In various embodiments, significant change is indicated by a value of at least ±50% of the pyrosequencing percentages shown in Table 1 or ±50% of the fold-level change in Table 1 or a $p<0.05$ change in specific CpG island methylation patterns.

It is another advantage of the present invention that changes in methylation levels of the disclosed markers for prostate cancer can be detected in histologically normal prostate tissue or bodily fluid from men with no history of prostate cancer.

Yet another embodiment of the invention recognizes that the markers can also be used to monitor changes to the prostate as a result of future drug treatments that modify methylation or to assess the clinical severity of an at-risk or cancer patient.

In another embodiment of the present invention, one may wish to use evaluation of methylation status of at least one of the eight target regions for the diagnosis of other cancers, such as breast or colon cancer.

In another embodiment, the present invention is a method of amplifying on of the eight target DNA sequences comprising (a) providing a reaction mixture comprising a double-stranded bisulfite converted target DNA and (i) at least one pair of primers selected from the group designed to amplify at least one gene selected from the group consisting of CAV1, EVX1, MCF2L, FGF1, WNT2, NCR2, EXT1 and SPAG4, wherein the primer pair comprises a first and a second primer that are complementary to the target DNA sequence, (ii) a polymerase and (iii) a plurality of free nucleotides comprising adenine, thymine, cytosine and guanine; (iv) PCR reaction buffer; (v) $MgCl_2$ (b) heating the reaction mixture to a first predetermined temperature for a first predetermined time to separate the strands of the target DNA from each other;

(c) cooling the reaction mixture to a second predetermined temperature for a second predetermined time under conditions to allow the first and second primers to hybridize with their complementary sequences on the target DNA and to allow the polymerase to extend the primers; and (d) Repeating steps (b) and (c) at least 10 times.

In one embodiment, the primers are methylated. In another embodiment, the primers are not methylated. In one embodiment, one would use a primer pair designed to amplify one target. In another embodiment, one would use primer pairs designed to amplify 2, 3, 4, 5, 6, 7, or 8 target regions.

Kit Claims

In another embodiment, the present invention is a kit designed for PCa field defect detection. Typically, the kit comprises at least a set of primers, wherein the primers preferably comprise forward and reverse primers designed to amplify a target region selected from the group consisting of CAV1, EVX1, MCF2L, FGF1, NCR2, WNT2, EXT1 and SPAG4 target (SEQ ID NOs: 1-6, 18 and 39), or selected from the group consisting of SEQ ID NOs: 61-77 and 94-97, and other components essential for DNA amplification, preferably, polymerase, dNTP, buffer and a magnesium salt which can release $Mg^{2+}$. Typically, one can use $MgCl_2$ or $MgSO_4$. In other embodiments, the kit comprises primers designed to amplify two, three, four, five, six, seven or eight targets.

In one embodiment, the primers preferably comprise a forward primer selected from the group consisting of SEQ ID NOs:43, 46, 49, 52, 55 and 58, and a reverse primer selected from the group consisting of SEQ ID NOs:44, 47, 50, 53, 56 and 59, and other components essential for DNA amplification, preferably, polymerase, dNTP, buffer and a Magnesium salt which can release $Mg^{2+}$. Typically, one can use $MgCl_2$ or $MgSO_4$.

In a second embodiment, the aforementioned kit comprises an alternative set of primers, wherein the primers preferably comprise a forward primer selected from the group consisting of SEQ ID NOs:88 and 91, and a reverse primer selected from the group consisting of SEQ ID NOs:89 and 92.

In a third embodiment, the aforementioned kit comprises a combined set of primers, wherein the primers preferably comprise a forward primer selected from the group consisting of SEQ ID NOs: 43, 46, 49, 52, 55, 58, 88 and 91, and a reverse primer selected from the group consisting of SEQ ID NOs: 44, 47, 50, 53, 56, 59, 89 and 92.

In one preferred embodiment, the kit further comprises FAM or Hex fluorophore-labled methylation and unmethylation-specific probes and is suitable for a closed tube assay for MS-QPCR. In another preferred embodiment, the kit further comprises sequencing primers and is suitable for bisulfite pyrosequencing-based assay. Preferably, the sequencing primers are selected from the group consisting of SEQ ID NOs:45, 48, 51, 54, 57 and 60. Even more preferably, the kit further comprises Streptavidin sepharose beads, enzyme mixture, substrate mixture and dinucleotides.

In a second preferred embodiment, the kit further comprises sequencing primers selected from the group consisting of SEQ ID NOs: 90 and 93.

In a third preferred embodiment, the kit further comprises sequencing primers selected from the group consisting of SEQ ID NOs: 45, 48, 51, 54, 57, 60, 90 and 93.

In another embodiment, the kit comprises components for an Invader® assay to detect changes in methylation. The Invader® assay entails the use of Invader® chemistry (Hologic Inc.) which is composed of two simultaneous isothermal reactions. A primary reaction specifically and accurately detects single-base pair changes measuring methylation. A second reaction is used for signal amplification and result readout.

EXAMPLES

Example 1

Prostate cancer (PCa) is typically found as a multifocal disease suggesting the potential for molecular defects within the morphologically normal tissue. In Example 1, the inventors compared non-tumor associated (NTA) prostate to histologically indistinguishable tumor-associated (TA) prostate tissues and detected a distinct profile of DNA methylation alterations (0.2%) using genome-wide DNA arrays. Hypomethylation (87%) occurred more frequently than hypermethylation (13%). Analysis of TA tissues adjacent and distant from tumor foci revealed a persistence of this methylation defect. Further evaluation and validation of six loci distinguished TA from NTA patients. Still further evaluation and validation of two additional loci distinguished TA from NTA patients. The inventors found a subset of markers which were solely associated with the presence of high grade disease. These findings demonstrate a widespread methylation defect occurs in the peripheral prostate tissues of men with PCa that may be utilized to identify the presence of the disease.

Introduction

'Field cancerization', 'field effect' or 'field defect' were terms first utilized in head and neck tumors to describe an increased frequency of cancer development found outside the visible boundaries of the primary tumor[1]. These genetically or epigenetically compromised cells in histologically normal appearing tissues have the potential to give rise to not only multifocal tumors, but additional cancers after therapy. Although described in colorectal, bladder and esophageal cancer (Jothy et al. (1996) Field effect of human colon carcinoma on normal mucosa: relevance of carcinoembryonic antigen expression. *Tumour Biol* 17, 7; Takahashi, T., et al. (1998) Clonal and Chronological Genetic Analysis of Multifocal Cancers of the Bladder and Upper Urinary Tract, *Cancer Research* 58, 5835-5841; Miyazato, et al. (1999) Microsatellite instability in double cancers of the esophagus and head and neck, *Diseases of the Esophagus* 12, 132-136; Ushijima, T. (2007) Epigenetic Field for Cancerization, *Journal of Biochemistry and Molecular Biology*, Vol. 40, No. 2, March 2007, pp. 142-150 40, 9), a field effect has not been clearly defined for prostate cancer (PCa). Features suggesting the presence of a field effect in PCa include regional multifocality at diagnosis, as well as the increased incidence with aging (Eastham, J. A., et al. (2007) Prognostic Significance of Location of Positive Margins in Radical Prostatectomy Specimens, *Urology* 70, 965-969). Defining an epigenetic field defect associated with PCa would have important clinical ramifications with regard to recurrence and recent interest in focal ablative therapies (Mouraviev, V., et al. Prostate cancer laterality as a rationale of focal ablative therapy for the treatment of clinically localized prostate cancer, *Cancer* 110, 906-910 (2007)).

PCa development and progression is driven by the interplay of genetic and epigenetic changes (Schulz, W. A. & Hoffmann, M. J. Epigenetic mechanisms in the biology of prostate cancer, *Semin Cancer Biol* 19, 172-180 (2009)). One important epigenetic process is the reversible methylation of cytosine at CpG dinucleotides, a sequence underrepresented in the genome except at CpG islands (Brid, A. DNA methylation patterns and epigenetic memory, *Genes Dev* 16, 16 (2002)). DNA methylation regulates gene expression and participates in the nuclear organization of higher organisms. Alterations in DNA methylation are a hallmark of cancer. Typically, adjacent histologically normal tissues are the standard against which many genomic and epigenetic alterations in cancers are identified. In light of the relevance of a potential field defect to both molecular and clinical studies, little is known regarding its distribution and extent in PCa. In part, this has reflected a limitation of techniques for assessing DNA methylation at specific sequences throughout the genome, as well as a lack of specimens without histological evidence of PCa.

In the Example below, the inventors utilized an immunocapture approach to enrich methylated DNA and combine this with DNA microarrays. During an evaluation of control tissues for genome-wide methylation profiles in cancer, the inventors found marked methylation changes in tumor associated (TA) histologically normal appearing prostate tissues extending across susceptible prostate tissues.

Results

Figure 13:
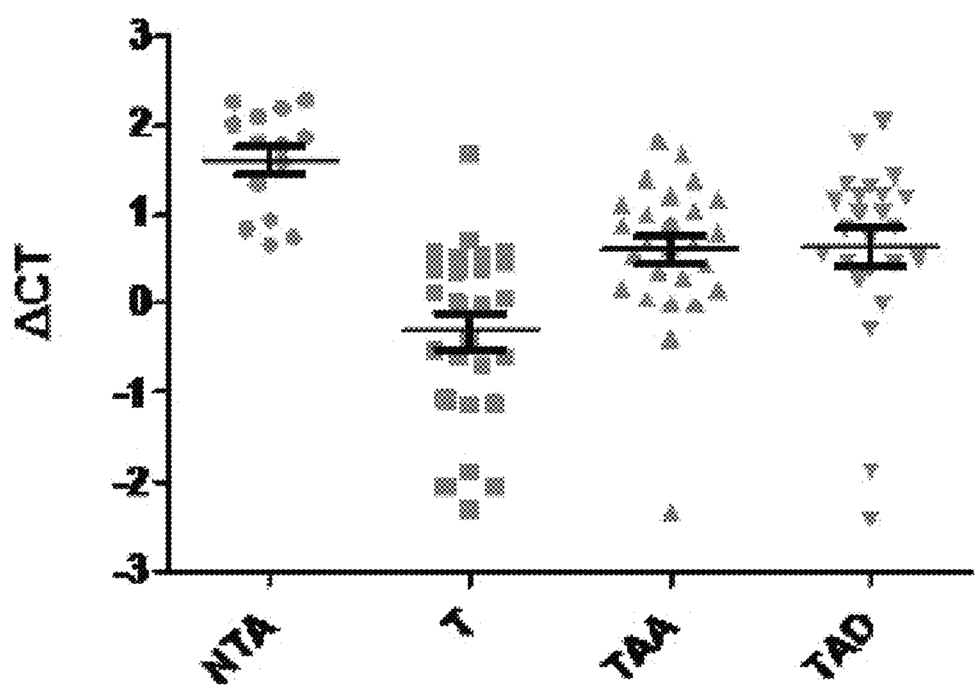
FIG. 13 shows AMACR expression in NTA, T, TAA and TAD prostate tissues which will be used in quantitative methylation Pyrosequencing. AMACR expression was assayed with quantitative RT-PCR, the data are shown as ΔCT. Two NTA and three TA (T,TAA,TAD) specimens were excluded from experiential group due to higher AMACR expression.

Distinct Patterns of DNA Methylation Define Tumor Associated (TA) and Non-Tumor Associated (NTA) Prostate Tissues As an initial study of the proper controls for cancer analyses, the inventors undertook an analysis of genome-wide methylation changes in histologically normal prostate tissues from men with cancer and compared those to men without cancer. We utilized 385,000 locus arrays based on the Encyclopedia of DNA Elements (ENCODE) 18 sequence that tiles a series of biologically significant regions in the human genome and includes all chromosomes except chromosomes 3 and 17. DNA was initially prepared from four TA and five NTA prostate specimens, digested with restriction enzymes and enriched for methylated DNA by immunoprecipitation (IP) with an antibody against 5-methylcytidine as described (User's, N.S.P.I.i.N. & Guide: DNA Methylation Analysis). Peripheral zone prostate tissues were utilized for these studies as PCa demonstrates a predilection for this region. We carefully evaluated all NTA specimens to confirm the lack of PCa within the prostate by both H&E staining in three dimensions and α-methylacyl-Coa racemase (AMACR) expression (FIG. 13). Furthermore, the proportion of epithelium to stroma was similar between tissue groups. After labeling, differential hybridization and scanning, we used a probe score cut-off of $-\log_{10}$ [p] range 2-10 to generate about 1,000 probes for each chromosome and a total of 18,101 probes. We then compared the $\log_2$-ratios at individual probes for TA and NTA tissues to evaluate methylation.

Figure 9A:
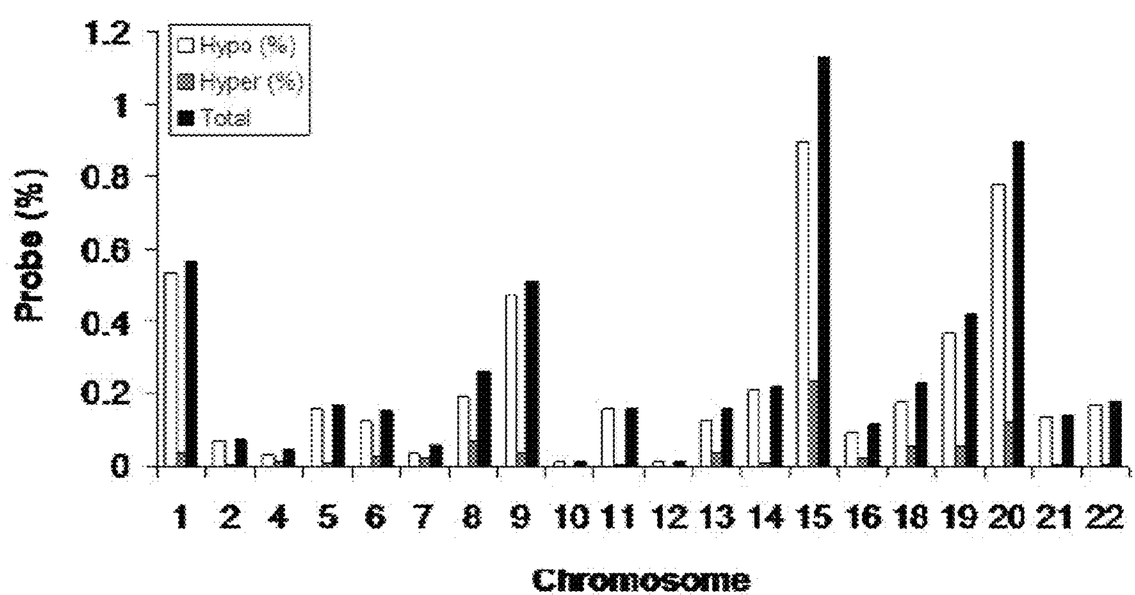
FIG. 9A shows genome-wide distribution of DNA methylation array differences at 385,000 loci in histologically normal tumor-associated (TA) prostate tissues compared to non-tumor associated (NTA) tissues. Significant differences in methylation between TA and NTA prostate tissues were generated using a cut-off of probe score of −log 10 [p] that ranged from 2 to 10 resulting in around 1,000 probes on each chromosome and 18,101 probes in total. After statistical analysis comparing the $log_2$-ratios between the NTA and TA groups, significant methylation differences between groups were determined using a t-test ($P<0.05$). A total of 615 probes were differentially methylated in TA tissues with 537 demonstrating hypomethylation and 78 hypermethylation. The percentage (axis) is the significantly altered probe number versus the total probe number analyzed for each chromosome. Chromosomes 15 and 20 were differentially methylated to a greater extent than other chromosomes.
Figure 9B:
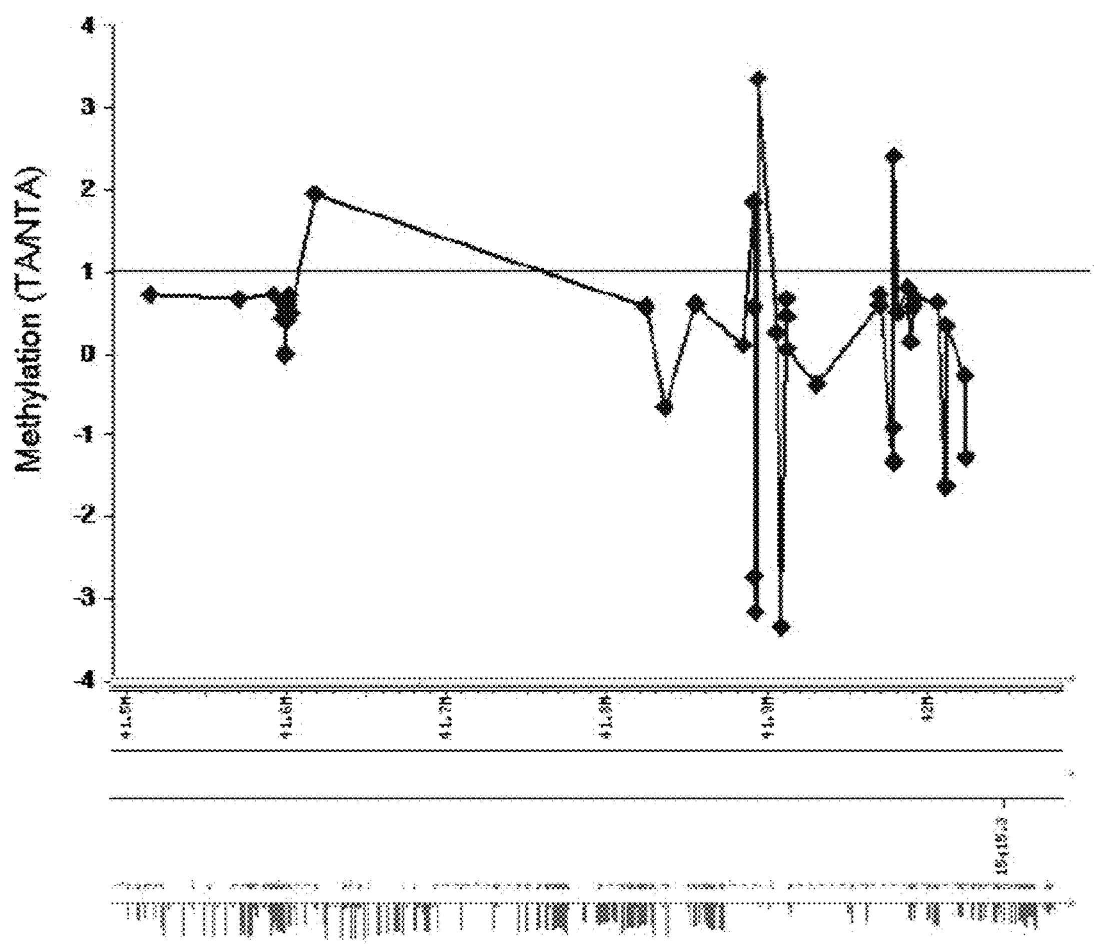
FIG. 9B shows the significant methylation changes across 41,522,036-4,2004,151 on chromosome 15p. The data are represented as a ratio of Mean TA/NTA.
Figure 9C:
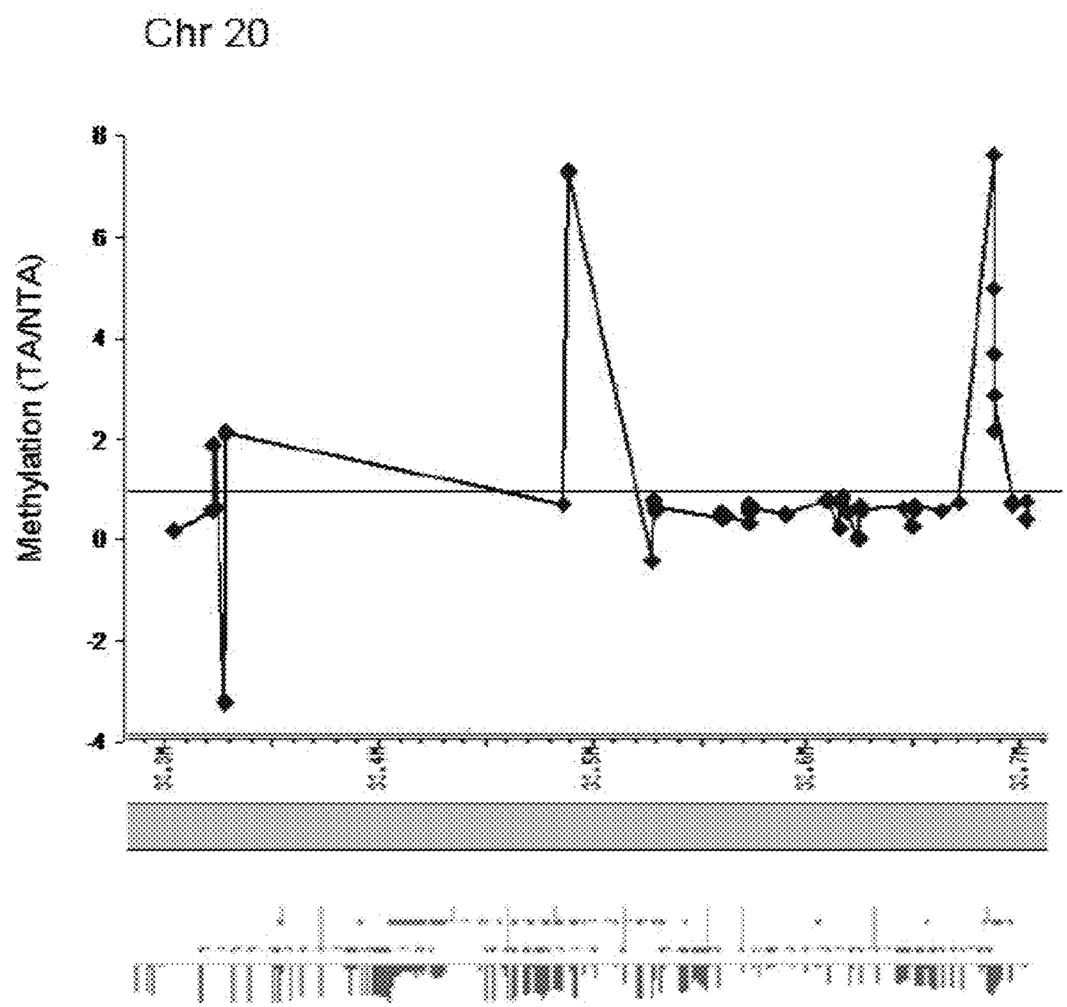
FIG. 9C shows the significant methylation changes across 33,343,402-33,565,080 on chromosome 20p. The data are represented as ratio of Mean TA/NTA.

Striking differences in methylation were noted when TA and NTA tissues were compared. With P<0.05, 615 loci were identified to be differentially methylated in TA tissues, with 537 (87%) hypomethylated and 78 (13%) hypermethylated (FIG. 9A). Chromosome 15 demonstrated the greatest number of differentially methylated loci (1.13%) in TA tissues, followed by chromosome 20 (0.9%), 1 (0.57%) and 9 (0.51%). Across genomic regions specific areas demonstrated either hyper- or hypomethylation (FIG. 9B and FIG. 9C). Fold changes in methylation for TA vs. NTA prostate specimens ranged from 0.02-7.59 (data not shown).

Figure 9D:
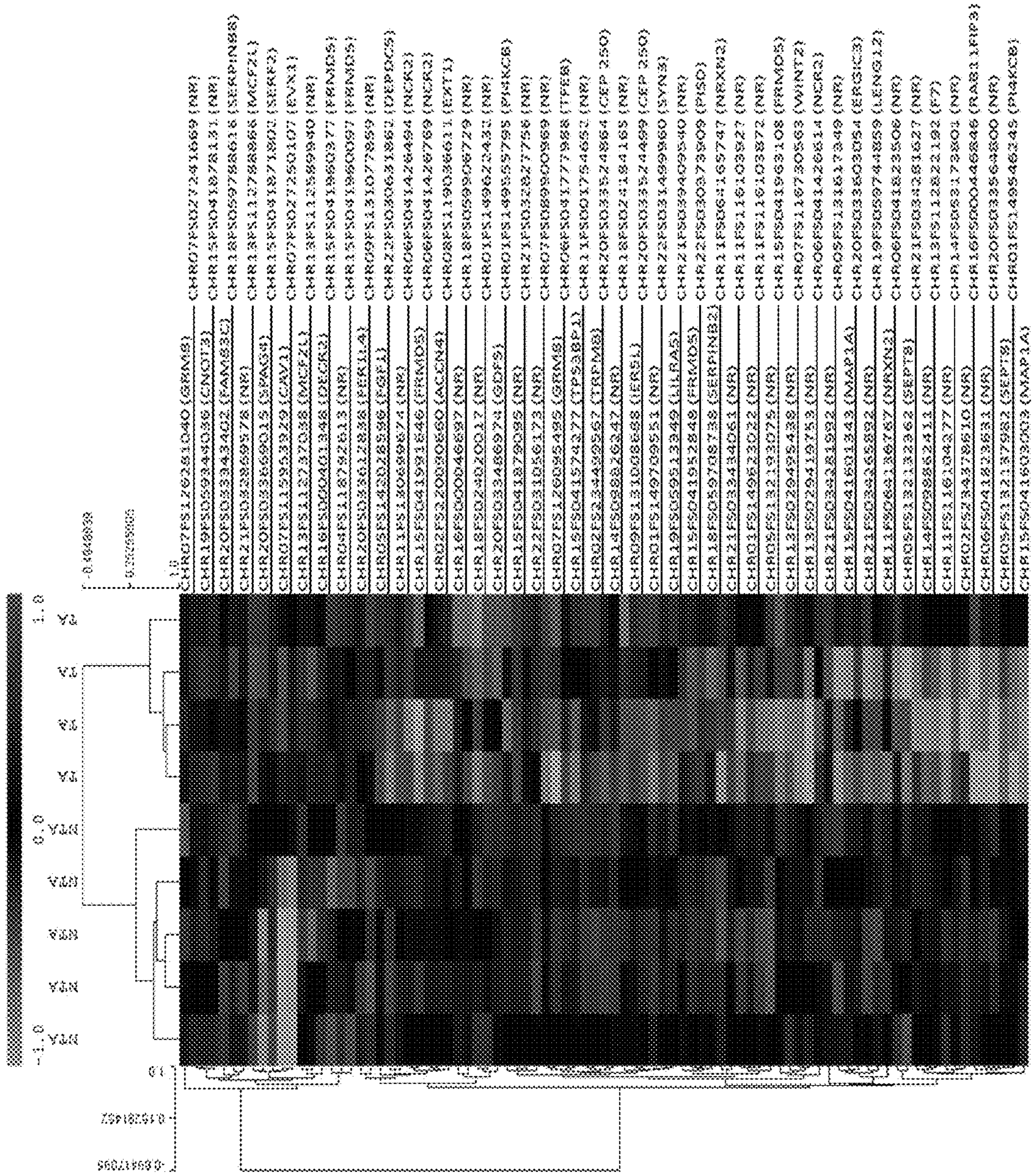
FIG. 9D is a heat map of significant DNA methylation array changes using unsupervised hierarchical clustering. Using more stringent criteria (t-test, $p<0.01$), 87 probes are shown comparing sets of NTA (left) to TA (right) and hierarchically ordered from top to bottom by relatively hypermethylation to hypomethylation. Green indicates relative hypomethylation whereas the red shaded areas demonstrate hypermethylation. The heat map was generated with JAVA TMEV™ (MultiExperiment View).

Using more stringent statistical parameters (P<0.01), the inventors identified 87 loci which showed significantly differential methylation in TA prostates. These loci were subject to unsupervised hierarchical clustering using TMEV software to generate a heat map. This global view of methylation profile clearly distinguishes TA from NTA prostate tissues (FIG. 9D). Among the 87 loci, 69 were hypomethylated and 18 hypermethylated in TA tissues (Table 2). Of these, 49 probes were associated with 38 genes and 38 probes were non-gene related. Accession numbers for these genes are listed in Table 3.

TABLE 2

Location of Differentially Methylated Probes

| Chromosome location | Total Probe No. | Tumor-Associated vs Normal: Hypomethylation | Hypermethylation |
|---|---|---|---|
| 1 | 5 | P14KB (2), NR (3) | |
| 2 | 3 | ACCN4 (1), TRPM8 (1), NR (1) | |
| 4 | 1 | | NR (1) |
| 5 | 5 | SEPT8 (2), FGF1 (1), NR (2) | |
| 6 | 6 | NCR2 (3), TFEB (1), NR (2) | |
| 7 | 7 | WINT2 (1), GRM8 (1), NR (1) | EVX1 (1), GRM8 (1) CAV1 (1), NR (1) |
| 8 | 1 | EXT1 (1) | |
| 9 | 2 | IER5L (1), NR (1) | |
| 11 | 7 | NRXN2 (2), NR (5) | |
| 13 | 6 | F7 (1), NR (2) | MCF2L (2), NR (1) |
| 14 | 3 | NR (3) | |
| 15 | 11 | TP53BP1 (1), MAP1A (2), FRMD5 (3), NR (1) | FRMD5 (2), SERF2 (1), NR (1) |
| 16 | 3 | RAB11FIP3 (1), NR (1) | DECR2 (1) |
| 18 | 5 | SERPINB2 (1), NR (3) | SERPINB8 (1) |
| 19 | 3 | LILRA5 (1), LENG12 (1) | CNOT3 (1) |
| 20 | 8 | GDF5 (1), CEP250 (2), ERGIC3 (1), FER1L4 (1), NR (1) | FAM83C (1), SPAG4 (1) |
| 21 | 7 | NR (6) | NR (1) |
| 22 | 4 | DEPDC5 (1), SYN3 (1), PISD (1), NR (1) | |
| Total | 87 | 69 | 18 |

Significant methylated probes between normal and tumor-associated prostate were generated from Methylation array using a cut-off probes score-log10 [p] ranged from 2-10 to generate 18,101 probes in total, and then log2ratio for these probes were compared between TA and NTA, t-test P < 0.01. Sixty-nine probes were hypomethylated, 36 probes related to 27 non-gene regions. NR represents not related to any gene.

TABLE 3

| Gene Symbol | Gene Name | Accession # |
|---|---|---|
| P14KCB | Phosphatidylinosol 4-kinase, catalytic, beta | NM_002651 (SEQ ID NO: 7) |
| ACCN4 | Amiloride-sensitive cation channel, pituitary | NM_182847 (SEQ ID NO: 8) |
| TRPM8 | Transient receptor potential cation channel, subfamily M, member 8 | NM_024080 (SEQ ID NO: 9) |
| SEPT8 | Septin | AF440762 (SEQ ID NO: 10) |
| FGF1 | Fibroblast growth factor 1 (acidic) | NM_000800 (SEQ ID NO: 11) |
| NCR2 | Natural cytotoxicity triggering receptor 2 | AJ010100 (SEQ ID NO: 12) |
| TFEB | Transcription factor EB | NM_007162 (SEQ ID NO: 13) |
| EVX1 | Even-skipped homeobox 1 | NM_001989 (SEQ ID NO: 14) |
| CAV1 | Caveolin 1 | NG_012051.1 (SEQ ID NO: 15) |
| WNT2 | Wingless-type MMTV integration site family member 2 | BC078170 (SEQ ID NO: 16) |
| GRM8 | Glutamate receptor, metabotropic 8 | NM_000845 (SEQ ID NO: 17) |
| EXT1 | Exosloses (multiple) 1 | BC001174 (SEQ ID NO: 18) |
| IER5L | Immediate early response 5-like | NM_203434 (SEQ ID NO: 19) |
| NRXN2 | Neurexin 2 | NM_138734 (SEQ ID NO: 20) |

TABLE 3-continued

| Gene Symbol | Gene Name | Accession # |
|---|---|---|
| MCF2L | Cell line derived transforming sequence-like | NM_024979 (SEQ ID NO: 21) |
| F7 | Coagulation factor VII | NM_019616 (SEQ ID NO: 22) |
| TP53BP1 | Tumor protein p53 binding protein 1 | NM_005657 (SEQ ID NO: 23) |
| MAP1A | Microtubule-associated protein 1A | NM_002373 (SEQ ID NO: 24) |
| SERF2 | Small EDRK-rich factor 2 | BC015491 (SEQ ID NO: 25) |
| FRMD5 | FERM domain containing 5 | NM_032892 (SEQ ID NO: 26) |
| DECR2 | 2,4-dienoyl CoA reductase 2, peroxisomal | AK128012 (SEQ ID NO: 27) |
| RAB11FIP3 | RAB11 family interacting protein 3 (class III) | NM_014700 (SEQ ID NO: 28) |
| SERPINB2 | Serpin peptidase inhibitor, clade B (ovalbumin), member 2 | NM_002575 (SEQ ID NO: 29) |
| SERPINB8 | Serpin peptidase inhibitor, clade B (ovalbumin), member 8 | BC034528 (SEQ ID NO: 30) |
| CNOT3 | CCR4-NOT transcription complex, subunit 3 | BC016474 (SEQ ID NO: 31) |
| LILRA5 | Leukocyte immunoglobulin-like receptor, subfamily A (with TM domain), member 5 | NM_181985 (SEQ ID NO: 32) |
| LENG12 | Leukocyte receptor cluster (LRC) member 12 | NM_033206 (SEQ ID NO: 33) |
| FAM83C | Family with sequence similarity 83, member C | NM_178468 (SEQ ID NO: 34) |
| GDF5 | Growth differentiation factor 5 | NM_000557 (SEQ ID NO: 35) |
| CEP250 | Centrosomal protein | AF022655 (SEQ ID NO: 36) |
| ERGIC3 | ERGIC and golgi 3 | NM_015966 (SEQ ID NO: 37) |
| FER1L4 | Fer-1-like 4 | NR_024377.1 (SEQ ID NO: 38) |
| SPAG4 | Sperm associated antigen | NM_003116 (SEQ ID NO: 39) |
| PISD | Phosphatetidylserine decarboxylase | CR456540 (SEQ ID NO: 40) |
| DEPDC5 | DEP domain containing 5 | AJ698951 (SEQ ID NO: 41) |
| SYN3 | Synapsin III | NM_003490 (SEQ ID NO: 42) |

Figure 10:
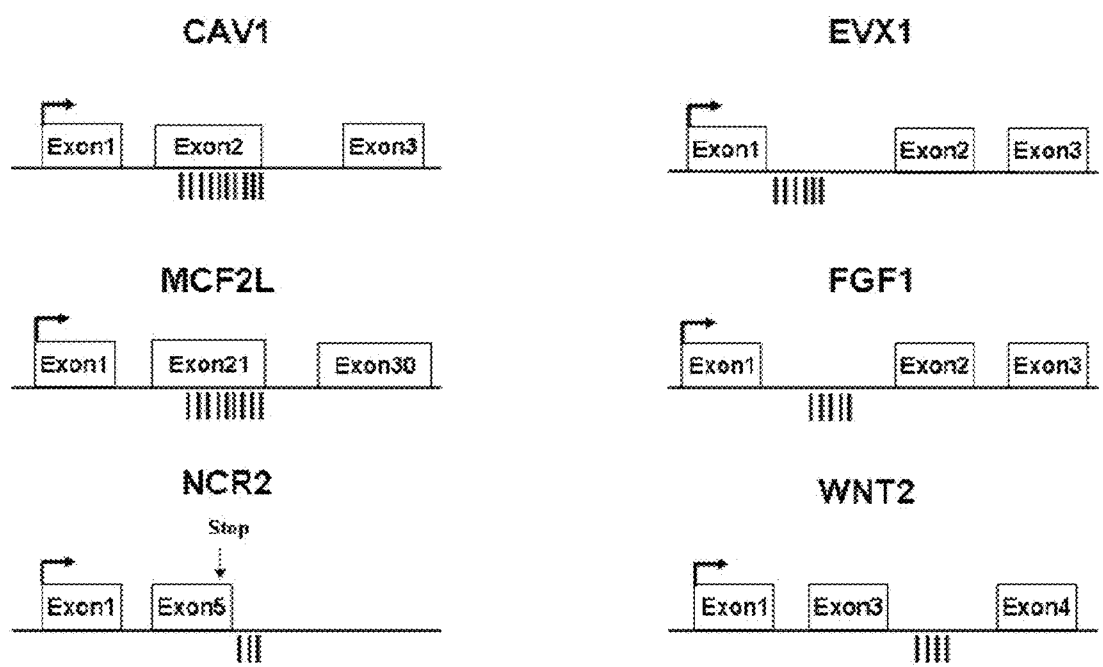
FIG. 10 is a schematic representation of CpGs analyzed by Pyrosequencing. The ratio of ObsCpG/ExpCpG and GC percentage for all regions are: CAV1 1.2, 60%; EVX1 0.8, 60%; FGF1 1.0, 50%; MCF2L 1.0, 60%; NCR2 0.5, 50%; WNT2 1.0, 50%.

A subset of the 20 genes were chosen for further evaluation, based on genomic location, putative biological function, extent of methylation and primer success in a separate validation using a set of 24 TA and NTA prostate specimens. Quantitative Pyrosequencing was employed to allow a more accurate evaluation of the extent of DNA methylation[11,12]. Internal controls for the adequacy of bisulfite conversion were performed. Six loci, which were associated with the genes CAV1, EVX1, MCF2L, FGF1, NCR2 and WNT2, showed significant methylation changes ($P<0.05$). The three loci associated with CAV1, EVX and MCF2L were hypermethylated and the three loci associated with FGF1, NCR2 and WNT2 were hypomethylated. The location of the probes and CG's assessed by Quantitative Pyrosequencing are shown in FIGS. 10 and 12. The six loci in pyrosequencing are close or overlap the methylation array regions but sequences are different. The sequences listed in FIG. 1-6 have covered both array region (FIG. 7) and pyrosequencing regions. These data demonstrate that TA tissues have a methylation profile distinct from men without cancer (NTA) and that these changes alter specific regions of the genome.

Identification of a Widespread Methylation Field Defect in the Peripheral Prostate.

Preferential alteration in tissues adjacent to PCa tumor foci, i.e., field defect, suggests a peritumoral response. To evaluate whether tissues adjacent to PCa tumor foci are preferentially altered, the extent of field defect was assessed in 26 additional histologically normal tissues by looking at the methylation status of these six differentially methylated markers. The inventors micro-dissected normal tissues adjacent (TAA, 2 mm) and distant (TAD, >10 mm) from the main tumor focus for each of the specimens (FIG. 8). Histological 3-dimensional H&E staining and AMACR expression determined by qPCR were applied to rule out any contamination by tumor cells or the presence of high grade prostatic intraepithelial neoplasia (HGPIN), a putative cancer precursor (Ayala, A. G. & Ro, J. Y. Prostatic Intraepithelial Neoplasia: Recent Advances, *Archives of Pathology & Laboratory Medicine* 131, 1257-1266 (2007)). Increased AMACR expression was found in 2 NTA and 3 TA tissues that were subsequently excluded from further analysis (FIG. 13).

When compared to NTA tissues, hypermethylation of probes associated with CAV1, EVX1, MCF2L and hypomethylation of FGF1 demonstrated significant changes in both TAA, as well as TAD tissues (FIG. 11A-D and Table 4). Notably, there was no difference in the extent of methylation seen at different distances from the tumor when TAA and TAD tissue sets were compared. Significant methylation changes were also seen in tumor samples when compared to NTA tissues for CAV1, EVX1, MCF2L, NCR2 and WNT2, revealing a persistence of these changes in the associated cancer. These data indicate that the epigenetic field defect in the prostate is widespread and not solely localized to the immediate peritumor environment.

TABLE 4

Methylation Percentage Of All Analyzed CpGs For Each Gene

| | CAV1 | | | EVX1 | | | MCF2L | | | FGF1 | | | NCR2[1] | | | WNT2[1] | | |
|---|---|---|---|---|---|---|---|---|---|---|---|---|---|---|---|---|---|---|
| | NTA | TAA | TAD | NTA | TAA | TAD | NTA | TAA | TAD | NTA | TAA | TAD | NTA | TAA | TAD | NTA | TAA | TAD |
| CG1 | 4.5 | 8.8* | 9.6* | 30.5 | 38.8* | 32.6 | 80.2 | 85.2* | 85.3* | 80.4 | 70.7* | 70.8* | 54.3 | 50.8 | 52.1 | 95.4 | 89.8* | 89.8* |
| CG2 | 14.6 | 22.4* | 21.3* | 28.2 | 36.9* | 29.9 | 77.0 | 85.3* | 85.1 | 71.7 | 60.7* | 59.8* | 30.5 | 30.6 | 30.9 | 94.9 | 91.0* | 91.5* |
| CG3 | 17.8 | 27.7* | 25.8* | 22.7 | 30.8* | 27.8* | 96.3 | 97.4 | 96.5 | 71.2 | 60.2* | 60.9* | 74.7 | 68.6* | 70.7 | 100 | 99.5 | 100 |
| CG4 | 13.8 | 24.3* | 23.0* | 50.4 | 55.4 | 48.3 | 84.8 | 82.1 | 80.7 | 81.1 | 72.9* | 71.1* | | | | 99.8 | 99.5 | 100 |
| CG5 | 15.3 | 25.0* | 21.9* | 46.5 | 51.7 | 47.2 | 79.9 | 86.1 | 87.5 | | | | | | | | | |

TABLE 4-continued

| Methylation Percentage Of All Analyzed CpGs For Each Gene | | | | | | | | | | | | | | | | | | |
|---|---|---|---|---|---|---|---|---|---|---|---|---|---|---|---|---|---|---|
| | CAV1 | | | EVX1 | | | MCF2L | | | FGF1 | | | NCR2[1] | | | WNT2[1] | | |
| | NTA | TAA | TAD | NTA | TAA | TAD | NTA | TAA | TAD | NTA | TAA | TAD | NTA | TAA | TAD | NTA | TAA | TAD |
| CG6 | 14.9 | 27.2* | 26.4* | 36.7 | 44.8* | 40.6* | 75.3 | 81.0 | 82.1 | | | | | | | | | |
| CG7 | 18.9 | 28.0* | 26.0 | | | | 89.6 | 94.3 | 93.6 | | | | | | | | | |
| CG8 | 8.25 | 15.4* | 14.7* | | | | 57.8 | 57.2 | 55.8 | | | | | | | | | |
| CG9 | 15.8 | 22.7 | 19.5 | | | | 39.8 | 31.4 | 38.1 | | | | | | | | | |
| CG10 | 17.9 | 26.7* | 28.6* | | | | | | | | | | | | | | | |

*P < 0.05

[1]High grade tumor only

Specific Methylation Loci are Associated with a High-Grade PCa Field Defect.

Figure 11E:
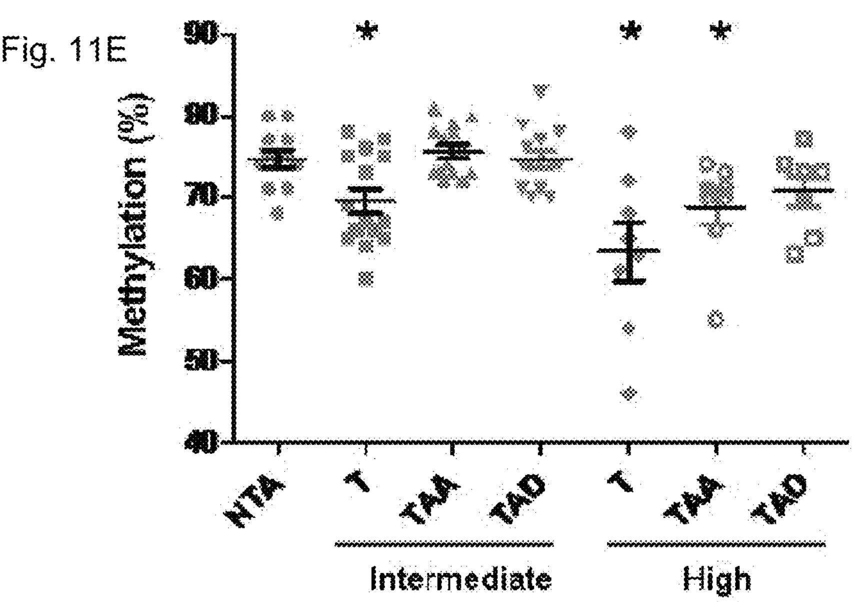
FIG. 11E-F shows NCR2 and WNT2 methylations. For NCR2, three CpGs were analyzed within the target region. In the prostate with high grade (Gleason grade ≥8, H) the third CpG showed significantly decreased methylation in T and TAA prostate compared to NTA prostate tissue. However, in the prostate with intermediate grade (Gleason grade 6 & 7, Int), the methylation change of this CpG was only significant in T prostate. This figure shows methylation of the third CpG and they are 75%, 69%, 63%, 68% and 70% for NTA, T (Int), T (H), TAA(H) and TAD(H), respectively. For WNT2, we detected methylation of four CpGs. In the prostate with high grade, two of them showed significantly decreased methylation in all T, TAA and TAD prostate tissues compared to NTA prostate tissue. However, in the prostate with intermediate grade, methylation change was only significant in T prostate tissue. This figure shows methylation of the first CpG and they are 95%, 87%, 79%, 89% and 89% for NTA, T (Int), T (H), TAA (H) and TAD (H), respectively.
Figure 11F:
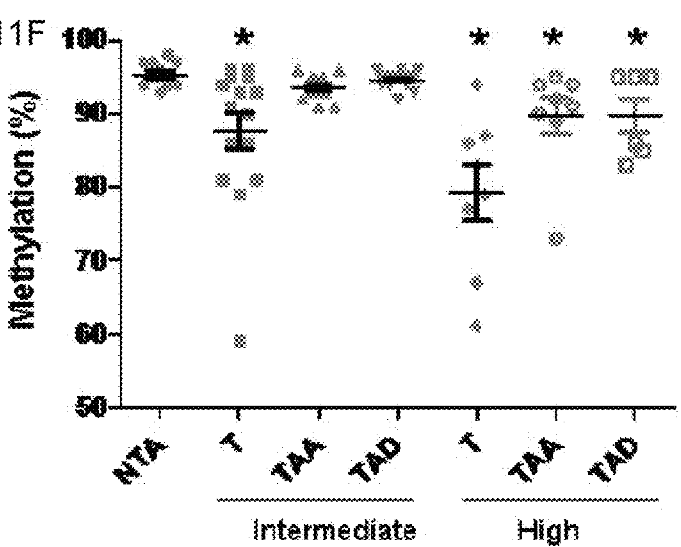

An important issue in PCa is the early identification and treatment of lethal high grade PCa. The inventors Analyzed a subset of TA tissues that were associated with either intermediate or high grade cancer using pyrosequencing. When compared to NTA tissues, an analysis of NCR2 and WNT2 demonstrated significant hypermethylation and hypomethylation, respectively, in TA tissues associated with high-grade specimens (FIG. 11E-F). This was not seen in TA tissues associated with intermediate grade PCa.

Discussion

Research has theorized that a field defect may underlie the development of multifocal cancers (Slaughter D. P., Southwick H. W., Smejkal, W.; Field cancerization in oral stratified squamous epithelium; Clinical implications of multicentric origin, *Cancer* 6, 6 (1953)). Initial efforts in characterizing this process focused on genetic alterations (Braakhuis, B. J. M., Tabor, M. P., Kummer, J. A., Leemans, C. R. & Brakenhoff, R. H., A Genetic Explanation of Slaughter's Concept of Field Cancerization, *Cancer Research* 63, 1727-1730 (2003); Garcia, S. B., Park, H. S., Novelli, M. & Wright, N. A. Field cancerization, clonality, and epithelial stem cells: the spread of mutated clones in epithelial sheets, *The Journal of Pathology* 187, 61-81 (1999)), but more recently epigenetic changes have been proposed as a etiology (Hu, M., et al. Distinct epigenetic changes in the stromal cells of breast cancers, *Nat Genet* 37, 899-905 (2005); Wolff, E. M., et al., Unique DNA Methylation Patterns Distinguish Noninvasive and Invasive Urothelial Cancers and Establish an Epigenetic Field Defect in Premalignant Tissue, *Cancer Research* 70, 8169-8178). In the present study, we conclusively demonstrate, using unbiased methylation arrays, that significant changes in DNA methylation occur at specific loci within histologically normal tissues associated with PCa. Furthermore, these changes are widespread and not restricted to the immediate peritumor environment. These changes also permit a clear distinction between tumor associated and non-tumor associated prostate tissue.

To date, epigenetic profiling of tumor-associated histologically normal tissues has not been performed in solid tumors. Our genome-wide assessment of specific loci demonstrates that hypomethylation was seen more commonly than hypermethylation in TA prostate tissues. These changes occurred in 0.2% of the 385,000 loci studied. DNA hypomethylation may occur early in solid tumor carcinogenesis based on its identification in precancerous lesions, including prostatic intraepithelial neoplasia (Feinberg, A. P., Ohlsson, R. & Henikoff, S., The epigenetic progenitor origin of human cancer, *Nat Rev Genet* 7, 21-33 (2006); Suzuki, K., et al. Global DNA demethylation in gastrointestinal cancer is age dependent and precedes genomic damage, *Cancer Cell* 9, 199-207 (2006)). This may lead to chromatin instability and contribute to the neoplastic phenotype. Our data extend these findings and suggest that epigenetic alterations may precede even the histologic changes identified with these precursor lesions. These DNA methylation changes may reflect diet and other environmental exposures (Richardson, B. C., Role of DNA Methylation in the Regulation of Cell Function: Autoimmunity, Aging and Cancer, *The Journal of Nutrition* 132, 2401S-2405S (2002); Mathers J C, S. G., Relton C L, Induction of epigenetic alterations by dietary and other environmental factors, *Adv Genet.* 71, 37 (2010)) and represent a potential avenue for prevention.

Epigenetic alterations limited solely to the immediate peritumor environment suggest a response of the surrounding tissue to the primary cancer. Single gene epigenetic studies have identified these changes in a subset of specimens adjacent to the primary PCa (Mehrotra, J., et al., Quantitative, spatial resolution of the epigenetic field effect in prostate cancer, *Prostate* 68, 152-160 (2008); Aitchison, A., Warren, A., Neal, D. & Rabbitts, P. RASSF1A promoter methylation is frequently detected in both pre-malignant and non-malignant microdissected prostatic epithelial tissues, *Prostate* 67, 638-644 (2007); Hanson, J. A., et al., Gene Promoter Methylation in Prostate Tumor-Associated Stromal Cells, *J. Natl. Cancer Inst.* 98, 255-261 (2006); Henrique, R., et al., Epigenetic heterogeneity of high-grade prostatic intraepithelial neoplasia: clues for clonal progression in prostate carcinogenesis, *Mol Cancer Res* 4, 1-8 (2006)). In contrast, in the present epigenomic profiling study, we found that these alterations consistently extended to regions distant from tumor foci. In bladder cancer, a disease also characterized by multifocality and recurrence, there is no dependence on distance from the primary tumor (Wolff, E. M., et al., Unique DNA Methylation Patterns Distinguish Noninvasive and Invasive Urothelial Cancers and Establish an Epigenetic Field Defect in Premalignant Tissue, *Cancer Research* 70, 8169-8178). A similar widespread field defect was demonstrated during evaluation of Insulin-like Growth Factor 2 (IGF2) loss of imprinting in peripheral prostate tissues (Bhusari, S., Yang, B., Kueck, J., Huang, W. & Jarrard, D. F., Insulin-like growth factor-2 (IGF2) loss of imprinting marks a field defect within human prostates containing cancer, *The Prostate,* 2011 Mar. 22). There has been recent interest in the treatment of PCa using focal ablative therapy (Mouraviev, V., et al., Prostate cancer laterality as a rationale of focal ablative therapy for the treatment of clinically localized prostate cancer, *Cancer* 110, 906-910 (2007)). The current findings suggest a field of susceptibility that might be utilized to help select patients who would be poor candidates for this approach.

In the current study, we focused on a high-resolution genome-wide analysis of methylation status rather than on specific gene promoter regions. The ENCODE18 human genome project includes gene-enriched areas thought to be biologically significant, a fact that potentially may generate a bias in our analyses. The majority of probes fell within CpG islands (Saxonov, S., Berg, P. & Brutlag, D. L., A genome-wide analysis of CpG dinucleotides in the human genome distinguishes two distinct classes of promoters, *Proceedings of the National Academy of Sciences of the United States of America* 103, 1412-1417 (2006); Fatemi, M., et al., Footprinting of mammalian promoters: use of a CpG DNA methyltransferase revealing nucleosome positions at a single molecule level, *Nucleic Acids Research* 33, e176), but none fell into defined gene promoter regions. Hypermethylation within promoters has been linked to decreased gene expression (J Y, P., Promoter hypermethylation in prostate cancer, *Cancer Control* 17, 11; Cooper, C. S. & Foster, C. S., Concepts of epigenetics in prostate cancer development, *Br J Cancer* 100, 240-245 (2008)), but the function of CpG islands outside these regions remains uncertain. Given the potential for long-range epigenetic silencing, these changes may herald alterations in gene expression affecting distant regions (Clark, S. J., Action at a distance: Epigenetic silencing of large chromosomal regions in carcinogenesis, *Human Molecular Genetics* 16, R88-R95 (2007)), or, alternatively, reflect altered nuclear structure.

The current findings have several additional implications. PSA-based screening has been widely criticized for its failure to specifically identify lethal PCa (Adami, H.-O., The prostate cancer pseudo-epidemic, *Acta Oncologica* 49, 298-304). This study raises the possibility of using a tissue test, or potentially urine-based test, for the detection of disease (and specifically high-grade disease) based on abnormalities found in not only the tumor but in the associated TA tissues. This would be expected to demonstrate increased sensitivity by increasing the percentage of affected cells able to be detected. In addition, the assessment of alterations that occur in PCa have typically compared tumor to 'normal' tissues within the same prostate gland. The current study indicates that the histologically normal tissue from men who have PCa already contains methylation abnormalities, which may lead to an underestimation of epigenetic changes that exist in the associated cancers.

Example 2

Material and Methods

Tissue Samples

Samples termed non-tumor associated (NTA, mean 63, age range 55-81 years old) were obtained from organ donation or cystoprostatectomy. The presence of any associated PCa was ruled out by extensive histological evaluation. Tumor-associated (TA, mean 61, age range 57-64 years old) prostate tissues were obtained from patients who underwent radical prostatectomy for PCa (Table 5). This study was approved by the institutional review boards at the University Pittsburgh and the University of Wisconsin-Madison. A separate validation group of 14 NTA (mean 60, age range 55-70 years old) and 12 TA (mean 58, age range 53-64 years old) samples were also assessed.

TABLE 5

Subject clinical and pathological characteristics

| | Methylation Array | | Pyrosequencing | | |
|---|---|---|---|---|---|
| | NTA | TA | NTA | TA | T, TAA, TAD |
| Number | 5 | 4 | 14 | 11 | 26 |
| Age (yr) | 63 (55~81) | 61 (57~64) | 60 (55~70) | 59 (51~67) | 58 (44~69) |
| Tumor Volume (%) | | 6.3 | | 5.1 | 27.1 |
| Gleason grade | | | | | |
| Intermediate | | 4 | | 6 | 16 |
| High | | | | | 10 |
| Pathological stage | | | | | |
| T2 | | | | 3 | |
| T2a | | | | 1 | 1 |
| T2b | | | | | 2 |
| T2c | | 3 | | 6 | 14 |
| T3a | | 1 | | 1 | 2 |
| T3b | | | | | 4 |
| PSA (ng/ml) | | 7.7 | | 5.9 | 6.9 |

NTA: non-tumor-associated normal,
TA: tumor-associate,
T: tumor,
TAA: tumor-associated adjacent,
TAD: tumor-associated distant.
Stages for three patients are unavailable.
Intermediate: 3 + 3, 3 + 4;
High: 4 + 4, 4 + 5, 5 + 5.

To define the relationship of methylation to tumor foci, histological sections containing both cancer and normal regions were generated from 26 (mean 58, age range 44-69 years old) radical prostatectomy specimens under the direction of a genitourinary pathologist. Microdissection was performed to obtain tumor (T), normal tissue adjacent (2 mm) to tumor foci (TAA) and at a greater distance (10 mm, TAD) as previously described (FIG. 8) (Bhusari, S., Yang, B., Kueck, J., Huang, W. & Jarrard, D. F., Insulin-like growth factor-2 (IGF2) loss of imprinting marks a field defect within human prostates containing cancer, *The Prostate,* 2011 Mar. 22). The clinical and pathological characteristics of the PCa study population are presented in Table 5. Of these patients, 16 had an intermediate grade cancer (Gleason score between 6 and 7; tumor volumes 5-70%) and 10 had high grade cancer (Gleason score 8-10; tumor volumes 25-80%). Prostate specimens were confirmed to have no tumor by both H&E staining in three dimensions and AMACR expression. For AMACR analysis, RNA was extracted using an RNeasy Mini Kit (Qiagen, CA), and 300 ng RNA was reverse transcribed with Ominscript® (Qiagen, CA). Quantitative real time PCR for total AMACR was performed using primer sequences as reported[33] (incorporated herein by reference).

DNA Methylation Microarrays

Genomic DNA was isolated using the DNeasy Blood & Tissue kit (Qiagen, CA). DNA used for microarray analysis was additionally incubated with RNaseA for 30 mins at 37° C. to prevent any RNA contamination. Roche NimbleGen ENCODE HG18 DNA methylation arrays were utilized. These arrays contain 385,000 50-75mer oligonucleotides (probes) that cover biologically significant pilot regions of the human genome at 60-bp spacing.

Sample preparation for the microarray was performed following the manufacturer's protocol. Briefly, up to 6 micrograms of high-quality genomic DNA was digested with MseI (New England Biolabs, Ipswich, Mass.) to produce 200-1,000 bp fragments while keeping CpG islands intact, and was then heat denatured to single strand DNA fragments. Methylated DNA fragments were immunoprecipitated (IP) overnight at 4° C. with 1 μg of antibody against 5-methyl cytidine (Abcam, Cambridge, Mass.) and incubated with agarose beads for two hours. The DNA: antibody:bead mixture was digested with Proteinase K overnight at 55° C. before purified with phenol-chloroform. Methylated immunoprecipited (MeDIP) DNA and flowthrough were validated with PCR primers specific for methylated and un-methylated regions as described by Weber et al (Weber, M., et al. Chromosome-wide and promoter-specific analyses identify sites of differential DNA methylation in normal and transformed human cells. Nat Genet 37, 853-862 (2005)). Enriched DNA was amplified with the WGA2 Kit (Promega, Madison, Wis.). The labeling of IP and input DNA, microarray hybridization and scanning were performed by NimbleGen (Reykjavik, Iceland) as described (Roche. NimbleGen Arrays User's Guide DNA Methylation Arrays Version 7.2, (2010). Data were extracted from scanned images using NimbleScan 2.4 extraction software (NimbleGen Systems, Inc.). The samples were assayed in duplicate.

Sodium Bisulfite Modification and Quantitative Pyrosequencing

Sodium bisulfite modification of genomic DNA was carried out using the EpiTect Bisulfite Kit (Qiagen, CA) according to the manufacturer's protocol. Bisulfite modified DNA was then amplified using PCR with either the forward or reverse biotinylated primer in preparation for Pyrosequencing (Jörg Tost, El Abdalaoui, H., and Ivo Glynne Gut., Serial pyrosequencing for quantitative DNA methylation, *BioTechniques,* 40, 6 (2006)). The PCR and sequence primers for Pyrosequencing were designed using PyroMark Assay Design 2.0 (Qiagen), and positioned on or adjacent to the probe sites which showed significant ($p<0.01$) methylation changes. The analyzed regions for specific loci are listed in FIG. 10, while primer sequences are listed in FIG. 12. The biotinylated PCR products were captured with Streptavidin sepharose beads, denatured to single strand and then annealed to the sequencing primer for the Pyrosequencing assay. SssI methylase-treated bisulfite-converted DNA from HPEC (human prostate epithelial cell) and PPC1 cells were used as positive controls, and water substituted for DNA was used as a negative control. The methylation was quantified with the PyroMark™MD Pyrosequencing System (Qiagen, CA) within the linear range of the assay. All the samples were analyzed in at least two independent experiments, both in duplicate.

Data Analysis

Scaled $\log_2$-ratio GFF file and P-value GFF file were used for microarray analysis. These were extracted from scanned images provided by Nimblegen (NimbleGen Systems, Inc.). The scaled $\log_2$-ratio data is the ratio of the test sample and input signals co-hybridized to the array. Scaling was performed by subtracting the bi-weight mean for all features of the array. From the scaled $\log_2$-ratio data, a fixed-length window was placed around each consecutive probe and the one-sided Kolmogorov-Smirnov (KS) test was applied to determine whether the probes were drawn from a significantly more positive distribution of intensity log-ratios than those in the rest of array. The resulting score for each probe is the $-\log_{10}$ p-value. The probe IDs were first chosen based on a p-value $-\log_{10}$ [p] that ranged from 2 to 10 resulting in around 1,000 probes on each chromosome and 18,101 probes in total. After statistical analysis comparing the $\log_2$-ratios between the NTA and TA groups, significant methylation differences between groups were determined using t-test ($P<0.05$). Significantly changed probes were clustered by Java MultiExperiment View (MEV 4.6.2) with unsupervised Hierarchical Clustering (Saeed Al, B. N., Braisted J C, Liang W, Sharov V, Howe E A, et al., TM4 microarray software suite, *Methods in Enzymology* 411, 60 (2006)).

For quantitative Pyrosequencing, the methylation at each CpG site was expressed as a percentage. A t-test was used to test for differences between groups, $P<0.05$ was considered statistically significant. The Spearman test was used to determine correlations, with significance set at $P<0.05$; r represents the measure of the relationship between two variables, and varies from −1 to +1.

Example 3

CpG Islands

Based on the teachings of Examples 1 and 2, one can also check the CpG islands that are located in the promoter regions of the genes showing significant methylation changes correlating with PCa, preferably the region within about 5 kb upstream of the transcription start site (TSS), because the methylation of these CpG islands will change the gene expressions and affect gene functions. The inventors' primary research (data not shown) showed that one may wish to start with genes CAV1, EVX1, MCF2L and WNT2. The expanded regions of each of the six genes for preferred screening of methylation changes are detailed in FIGS. 14-19.

FGF1 and NCR2 do not have CpG islands within the promoter regions. For FGF1, the expanded regions for preferred screening of methylation changes would be 300 bps upstream and 1 kb downstream of the target region reported in Example 1, as well as about 5 Kb upstream of the translation start site ATG (detailed in FIG. 17). For NCR2 the expanded regions for preferred screening of methylation changes would be the region between exon two and three and the two CpG islands between exon four and five (detailed in FIG. 18).

Example 4

Development of a DNA Methylation Urine-Based Screen for Lethal PCa

As disclosed in Example 1, specific loci associated with field defect appear to be preferentially altered in lethal, high grade PCa, which is responsible for the majority of PCa deaths. Establishing the role epigenetic changes play in the development of lethal PCa can lead to better diagnosis and treatment of high grade PCa. We envision that epigenetic field defect characterized by changes in DNA methylation in histologically normal appearing cells within the prostate can be utilized to identify patients with lethal disease.

Introduction

In 2010, PCa was the most commonly diagnosed cancer in Wisconsin men (Fu V X, Dobosy J R, Desotelle J A, Almassi N, Ewald J A, Srinivasan R, Berres M, Svaren J, Weindruch R, Jarrard D F., Aging and cancer-related loss of insulin-like growth factor 2 imprinting in the mouse and human prostate, *Cancer Res.* 2008 Aug. 15; 68(16):6797-802), and is the second most common cause of cancer death (after lung cancer), with over 600 men succumbing to the disease (Jemal A, Siegel R, Xu J, Ward E., Cancer statistics, 2010. 1. *CA Cancer J. Clin.* 2010 September; 60(5):277-300). Over 70% of PCa deaths occur in men diagnosed with high grade (Gleason Score 8-10) disease or high volume intermediate grade disease (Gleason Score 6-7), making the detection of these variants at an earlier time point critical (Stephenson A. J., Kattan M. W., Eastham J. A., Bianco F. J., Jr., Yossepowitch O., Vickers A. J., Klein E. A., Wood D. P., Scardino P. T., Prostate cancer-specific mortality after radical prostatectomy for patients treated in the prostate-specific antigen era, *J. Clin. Oncol.* 2009 Sep. 10; 27(26): 4300-5). Low volume (<10%) intermediate and lower grade cancers have a much more indolent natural history. Several striking features of PCa include its multifocality and marked increase in incidence with aging. These characteristics suggest a 'field defect' may be an important component in the etiology of PCa. To date, cancer diagnosis has focused on the finding of cancer cells, typically by biopsy, yet the presence of alterations associated with histologically normal prostate tissue is as yet an untapped resource in both the diagnosis and understanding of the etiology of this disease.

Over 600,000 diagnostic prostate biopsies are performed annually in the United States. The false negative rate is as high as 34%, and roughly 20-35% of patients sent for repeat biopsy are ultimately diagnosed with cancer (Djavan B, Zlotta A, Remzi M, Ghawidel K, Basharkhah A, Schulman C C, Marberger M. Optimal predictors of prostate cancer on repeat prostate biopsy: A prospective study of 1,051 men, *J. Urol.* 2000 April; 163(4):1144-8). Prostate biopsy is associated with risk of bleeding, urinary distress and hospitalization for infection that increases with each subsequent biopsy. Alternatively, patients whose biopsies are initially negative with an elevated PSA represent a serious clinical dilemma, and are at risk for additional evaluation costs and procedures, including saturation biopsy that is performed in the operating room under anesthesia. Men in this situation experience significant anxiety as well (Katz D A, Jarrard D F, McHorney C A, Hillis S L, Wiebe D A, Fryback D G., Health perceptions in patients who undergo screening and workup for prostate cancer, *Urology* 2007 February; 69(2): 215-20). The development of a non-invasive test to augment PSA screening would be of enormous benefit to society.

Currently utilized screening tests (serum prostate specific antigen (PSA) and digital rectal exam have only a modest predictive value (Strope S A, Andriole G L, Prostate cancer screening: Current status and future perspectives, *Nat. Rev. Urol.* 2010 September; 7(9):487-93). PSA isoforms add little specificity. Body fluids including semen and urine may contain molecular information regarding the presence of PCa. PCa and prostate epithelial cells are shed into biologic fluids, particularly when the prostate is subjected to physical manipulation, thus creating the potential for their noninvasive detection in either urine or expressed prostatic fluid. Attempts at detecting PC cells in urine by traditional cytology are thwarted by unacceptably low sensitivities, although specificities were consistently high (Fujita K., Pavlovich C. P., Netto G. J., Konishi Y., Isaacs W. B., Ali S., DeMarco A., Meeker A. K., Specific detection of prostate cancer cells in urine by multiplex immunofluorescence cytology, *Hum. Pathol.* 2009 July; 40(7):924-33). This is due primarily to low numbers of PC cells present in urine cytology preparations. Analyzing cells shed from the abnormal prostate bypasses this important hurdle and represents the first effort of its kind in prostate and many other cancers.

To date, one of the few field defect alterations found in both non-cancerous peripheral prostate tissue and in associated prostate tumors is our finding of a loss in the typical imprint of the IGF2 gene (Fu V. X., Dobosy J. R., Desotelle J. A., Almassi N., Ewald J. A., Srinivasan R., Berres M., Svaren J., Weindruch R., Jarrard D. F., Aging and cancer-related loss of insulin-like growth factor 2 imprinting in the mouse and human prostate, *Cancer Res.* 2008 Aug. 15; 68(16):6797-802). We have demonstrated that this is not a peritumor phenomenon (i.e. adjacent response to the cancer), but is widely prevalent even in distant areas within the peripheral prostate (Bhusari S., Yang B., Kueck J., Huang W., Jarrard D. F., Insulin-like growth factor-2 (IGF2) loss of imprinting marks a field defect within human prostates containing cancer, *Prostate* 2011 Mar. 22). Our lab has expanded these studies to other epigenetic phenomenon and recently using a series of Nimblegen™ ENCODE18 Methylation Arrays, which survey the whole human genome, have identified 87 loci (out of 385,000 loci surveyed) that exhibit altered methylation ($p<0.01$) in the peripheral prostate tissue of men who have the disease when compared to those that do not (FIG. 9D). Interestingly these methylation defects are found both in gene and relatively gene-free areas of the genome. To date, we have screened 16 of these loci and validated 6 (CAV1, EVX1, MCF2L, FGF1, WNT2 and NCR2) using quantitative bisulfite Pyrosequencing in an additional cohort of 40 patients (FIG. 11). Notably, we found that methylation at the WNT2 and NCR2 were associated with the field defect in high grade, but not intermediate grade, cancers (FIG. 11E-F). This striking finding suggests these high grade cancers may have a molecular fingerprint present in the adjacent normal tissues that could assist in the earlier diagnosis of the disease. Finally, analyses of associations between tumor volume, PSA, and the extent of methylation demonstrated a significant association between FGF1 and increased tumor volume ($P=0.036$, $r=0.4616$) (see Example 1). In addition to histological confirmation of the absence of cancer in these prostate tissues, we also performed AMACR expression analysis, a specific marker for the presence of PCa (Ananthanarayanan V., Deaton R. J., Yang X. J., Pins M. R, Gann P. H., Alpha-methylacyl-CoA racemase (AMACR) expression in normal prostatic glands and high-grade prostatic intraepithelial neoplasia (HGPIN): association with diagnosis of prostate cancer, *Prostate* 2005 Jun. 1; 63(4):341-6), to rule out contamination with cancer cells (data not shown). In sum, these data demonstrate that particular methylation changes occur at specific loci in tumor associated tissues and that several of these markers are altered preferentially in high grade cancers.

Significance

By defining these epigenetic changes one can leverage this information to improve diagnosis and cure of high grade PCa. This analysis has the potential to provide an assay that will decrease the morbidity associated with PCa diagnosis and improve prognostication. This panel of markers can be used on non-cancer prostate biopsy tissue to validate negative findings and decrease in the near term the number and frequency of biopsies being performed in men with elevated PSAs. In addition, we envision the application of these markers to develop a non-invasive urine test that can be used as an adjunct to further identify men with a higher risk lethal PCa. The approaches to achieve these goals are described in detail below.

Confirm that Methylation Alterations Associated with a Field Defect in High Grade/High Volume PCa can be Detected in the Urine (Prophetic Example)

Prostate cells are shed into the urine. Previous small studies have focused on cancer-specific methylation alterations in the urine (Fujita K., Pavlovich C. P., Netto G. J., Konishi Y., Isaacs W. B., Ali S., De Marco A., Meeker A. K., Specific detection of prostate cancer cells in urine by multiplex immunofluorescence cytology, *Hum. Pathol.* 2009 July; 40(7):924-33; Rogers C. G., Gonzalgo M. L., Yan G., Bastian P. J., Chan D. Y., Nelson W. G., Pavlovich C. P., High concordance of gene methylation in post-digital rectal examination and post-biopsy urine samples for prostate cancer detection, *J. Urol.* 2006 November; 176(5):2280-4) and have demonstrated feasibility, but lower sensitivity because of the presence of rare cancer cells. In contrast, normal prostate epithelial cells are found within the urine at a much higher rate (Fujita K., Pavlovich C. P., Netto G. J., Konishi Y., Isaacs W. B., Ali S., De Marco A., Meeker A. K., Specific detection of prostate cancer cells in urine by multiplex immunofluorescence cytology, *Hum. Pathol.* 2009 July; 40(7):924-33). We seek to evaluate methylation changes found in normal cells associated with prostate cancer to determine if these changes predict the presence of cancer within this biofluid. Notably, our markers are also abnormal in cancer cells.

We will take validated tissue markers (six markers disclosed in Example 1 and others validated from the above described experiments in this Example) and apply them to urine specimens from men undergoing prostate biopsy throughout Wisconsin. We will confirm that methylation differences can be detected in the urine from men with cancer versus those without.

We envision that prospective urine samples from 250 men with high PSA values undergoing prostate biopsy will be obtained after an 'attentive' digital rectal examination. Of these samples 100 will be obtained through the Wisconsin Network for Health Research (WNHR). A further control group of 50 age-matched controls seen in the urology clinic with normal PSA values will be consented, obtained and tested. Briefly, after prostate examination, 20 ml of the initial stream will be collected, mixed with EDTA and stored on ice as described (Rogers C. G., Gonzalgo M. L., Yan G., Bastian P. J., Chan D. Y., Nelson W. G., Pavlovich C. P., High concordance of gene methylation in post-digital rectal examination and post-biopsy urine samples for prostate cancer detection, *J. Urol.* 2006 November; 176(5):2280-4).

Genomic DNA will be extracted from the pellet using a column as above. DNA will then be sodium bisulfite treated and quantitative Pyrosequencing performed using our panel of loci CAV1, EVX1, MCF2L, FGF1 and NCR2, as well as additional markers validated from the above described experiments in this Example. Methylation of individual loci will be compared between the TA and NTA groups using two-tailed student's t-tests conducted at a significance level of 0.026 (a rough false discovery rate). Additional analyses will be performed using logistic regression to determine if multiple loci, total PSA, free PSA, PSA density, or age improves the ability to predict which individuals belong to the TA group. Assuming that 150 of the 300 subjects belong to the TA group and the other 150 belong to the NTA group, we will have at least 80% power for detecting as significant a 0.3557 standard deviation shift in the mean methylation value between groups. Further subgroup analyses will be performed based on tumor volume, age, pathologic stage, and cancer grade.

In conjunction with the above approaches, we will seek to develop alternate technologies to quantitate methylation to permit widespread application. The original Nimblegen methylation arrays allows detection of methylation at specific sites, but not at basepair resolution. However, complete analysis of the prognostic potential of these sites will require a thorough analysis of the entire locus to identify specific nucleotides where methylation is predictive of disease course. Although the pyrosequencing approach is an established technique within our laboratory, one of its limitations is that it can only scan a limited number of methylation sites encompassing 100-300 bp within a single run and it is time consuming and expensive.

We will confirm alternate technologies which improve assay sensitivity and commercial applicability by: i) developing a methylation-sensitive qPCR multiplex approach based on amplification of multiple specific methylated loci (Campan M., Weisenberger D. J., Trinh B., Laird P. W. MethyLight. Methods Mol. Biol. 2009; 507:325-37), and ii) implementing direct sequencing of samples by utilizing next generation sequencing technology (available from the UW Biotech Center) to digitally detect methylation sites at basepair resolution. We will rely on methylation-specific priming combined with both methylation and unmethylation-specific fluorescent probes. This assay is faster with an accompanying ability to sensitively detect very low frequencies of hypermethylated alleles (Campan M., Weisenberger D. J., Trinh B, Laird P W. MethyLight. Methods *Mol. Biol.* 2009; 507:325-37). Direct sequencing utilizes established sequence capture techniques (for 25-30 loci) and then methylation analyses as described (Gu H., Smith Z. D., Bock C., Boyle P., Gnirke A., Meissner A., Preparation of reduced representation bisulfite sequencing libraries for genome-scale DNA methylation profiling, *Nat. Protoc.* 2011 April; 6(4):468-81). Briefly, the Agilent Sureselect™ system will be used to capture approximately 50 kb nucleotides surrounding each of these loci (approximately 0.1% of entire genome) for at least 100 of the samples. The enriched samples can be barcoded and sequenced in a high-throughput fashion using the Illumina HiSeq™ instrument (or a similar alternate machine) at the UW Biotechnology Center (80 million reads/lane) to identify specific sites of methylation by comparing sequences with bisulfite-converted material, thus providing a digital readout on the percentage of methylation at a specific site in a given sample.

We anticipate being able to detect methylation differences at one or multiple loci in men that have cancer and specifically high grade cancer. By increasing the pool of markers validated in tissues, we will decrease the likelihood that significant markers will not be detected in urine. Given the markers in TA prostate tissues identified so far are also abnormal in the cancer themselves, we anticipate the sensitivity of this approach will be much higher than approaches with markers specifically altered in cancer (Fujita K., Pavlovich C. P., Netto G. J., Konishi Y., Isaacs W. B., Ali S., De Marco A., Meeker A. K. Specific detection of prostate cancer cells in urine by multiplex immunofluorescence cytology. *Hum. Pathol.* 2009 July; 40(7):924-33). Statistical analyses for the methylated loci will likely be improved by the use of PSA, family history, digital rectal exam in statistical analyses.

We perform roughly 500 prostate biopsies a year at UW providing a larger pool of urine samples if necessary. Obtaining urine samples from the Wisconsin Network for Health Research (WNHR) will validate our finding to patients throughout Wisconsin. Roughly 10 ug of DNA can be extracted from 20 ml of urine using this approach (Rogers C. G., Gonzalgo M. L., Yan G., Bastian P. J., Chan D. Y., Nelson W. G., Pavlovich C. P., High concordance of gene methylation in post-digital rectal examination and post-biopsy urine samples for prostate cancer detection, *J. Urol.* 2006 November; 176(5):2280-4). The presence of competing cells of other etiology (including bladder, kidney and WBC) may have altered methylation changes. If this is encountered we will seek to enrich for the prostate cell population by utilizing antibodies to anti-NKX3.1 as described (Fujita K., Pavlovich C. P., Netto G. J., Konishi Y., Isaacs W. B., Ali S., De Marco A., Meeker A. K. Specific detection of prostate cancer cells in urine by multiplex immunofluorescence cytology, *Hum. Pathol.* 2009 July; 40(7):924-33). Given the cancer association of the markers identified, it would be unlikely other cell types will be altered in normal tissues from other sources.

Example 5

Figure 23:
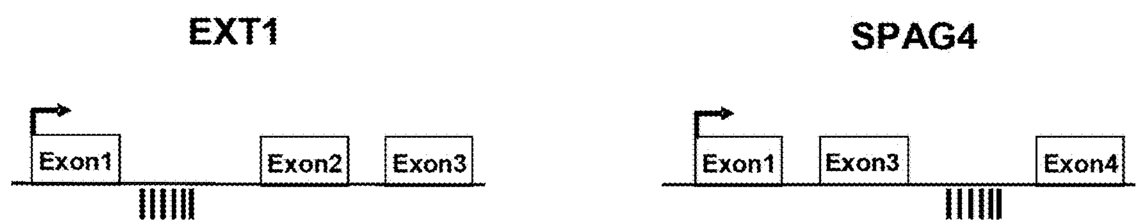
FIG. 23 is a schematic representation of CpGs analyzed by Pyrosequencing. The ratio of ObsCpG/ExpCpG and GC percentage for all regions are: EXT1 0.8, 60%; SPAG4 0.55, 60%.

In an experiment analogous to Example 1, a subset of two genes was chosen for further evaluation, based on genomic location, putative biological function, extent of methylation and primer success in a separate validation using a set of 24 TA and NTA prostate specimens. Quantitative Pyrosequencing was employed to allow a more accurate evaluation of the extent of DNA methylation. Internal controls for the adequacy of bisulfite conversion were performed. Two loci, which were associated with the genes EXT1 and SPAG4 showed significant methylation changes (P<0.05). The locus associated with SPAG4 was hypermethylated and the locus associated with EXT1 was hypomethylated. The location of the probes and CG's assessed by Quantitative Pyrosequencing are shown in FIGS. 23 and 25. The two loci in pyrosequencing are close or overlap the methylation array regions but sequences (FIG. 22) are different. The sequences listed in FIG. 20-21 have covered both array region (FIG. 22) and pyrosequencing regions. These data demonstrate that TA tissues have a methylation profile distinct from men without cancer (NTA) and that these changes alter specific regions of the genome.

Identification of a Widespread Methylation Field Defect in the Peripheral Prostate.

Preferential alteration in tissues adjacent to PCa tumor foci, i.e., field defect, suggests a peritumoral response. To evaluate whether tissues adjacent to PCa tumor foci are preferentially altered, the extent of field defect was assessed in 26 additional histologically normal tissues by looking at the methylation status of these two differentially methylated markers. The inventors micro-dissected normal tissues adjacent (TAA, 2 mm) and distant (TAD, >10 mm) from the main tumor focus for each of the specimens (FIG. 8). Histological 3-dimensional H&E staining and AMACR expression determined by qPCR were applied to rule out any contamination by tumor cells or the presence of high grade prostatic intraepithelial neoplasia (HGPIN), a putative cancer precursor (Ayala, A. G. & Ro, J. Y. Prostatic Intraepithelial Neoplasia: Recent Advances. *Archives of Pathology & Laboratory Medicine* 131, 1257-1266 (2007)). Increased AMACR expression was found in two NTA and three TA tissues that were subsequently excluded from further analysis (FIG. 13).

Figure 24A:
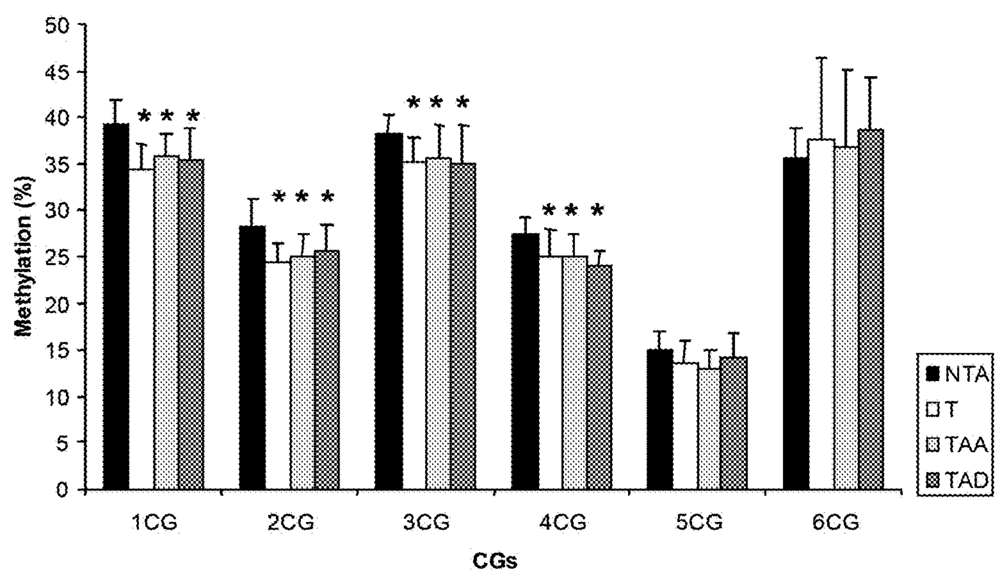
FIGS. 24A and 24B show EXT1 and SPAG4 methylations. To analyze EXT1 methylation, we analyzed methylation of six CpGs and four out of the six CpGs showed significantly increased methylation in T (tumor), TAA (tumor-associated adjacent) and TAD (tumor-associated distant) prostate tissue compared to NTA (non-tumor-associated normal prostate tissue). The figure shows methylation percentages of all six CpGs. *t-test. $P<0.05$ was used for all figures below. To analyze SPAG4 methylation, we tested five CpGs for SPAG4 and five out of the five showed significantly increased methylation in T, TAA and TAD compared to NTA prostate tissues. These figures show methylation percentage of the all five CpGs.
Figure 24B:
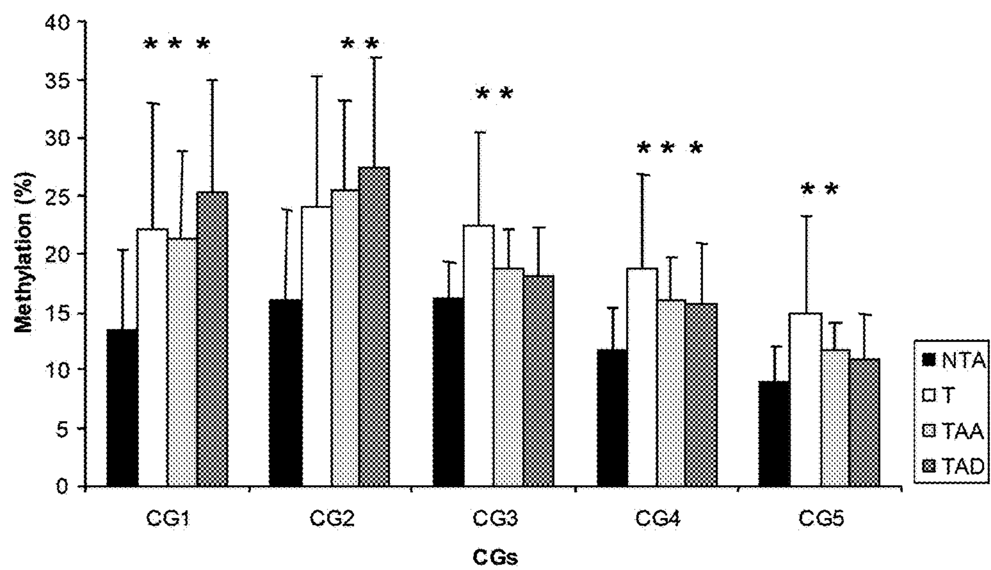
Figure 28A:
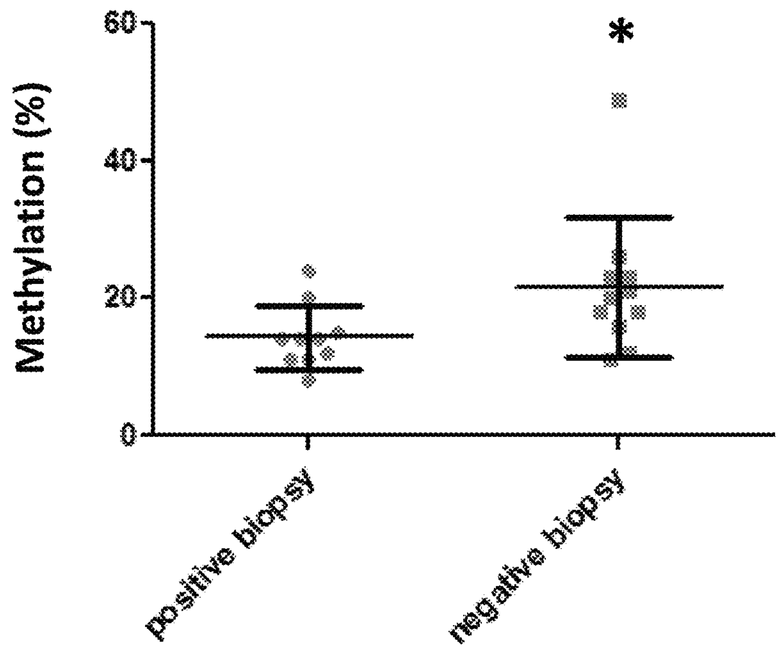
FIGS. 28A, 28B, 28C and 28D show methylation of the EVX1, CAV1, FGF1 and NCR2 in urine from the patients with positive or negative biopsies for prostate cancer.
Figure 28B:
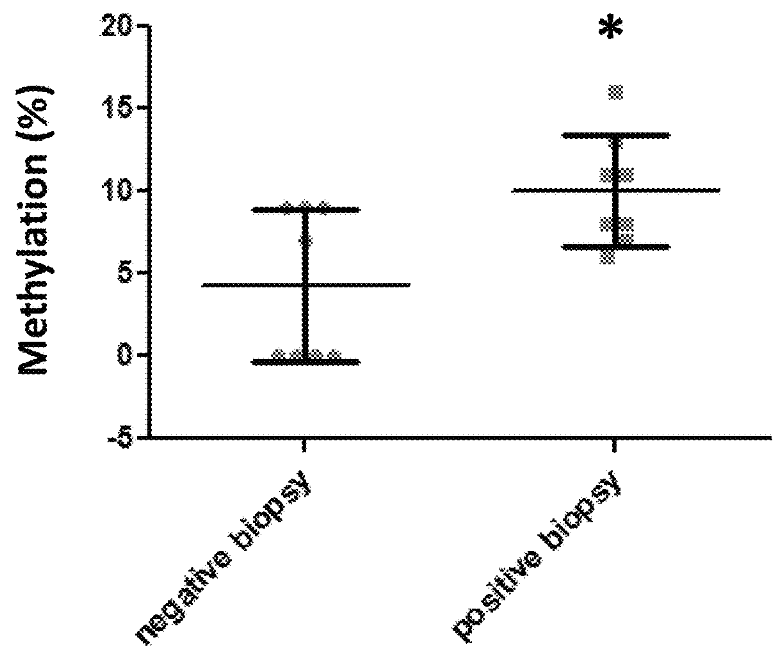
Figure 28C:
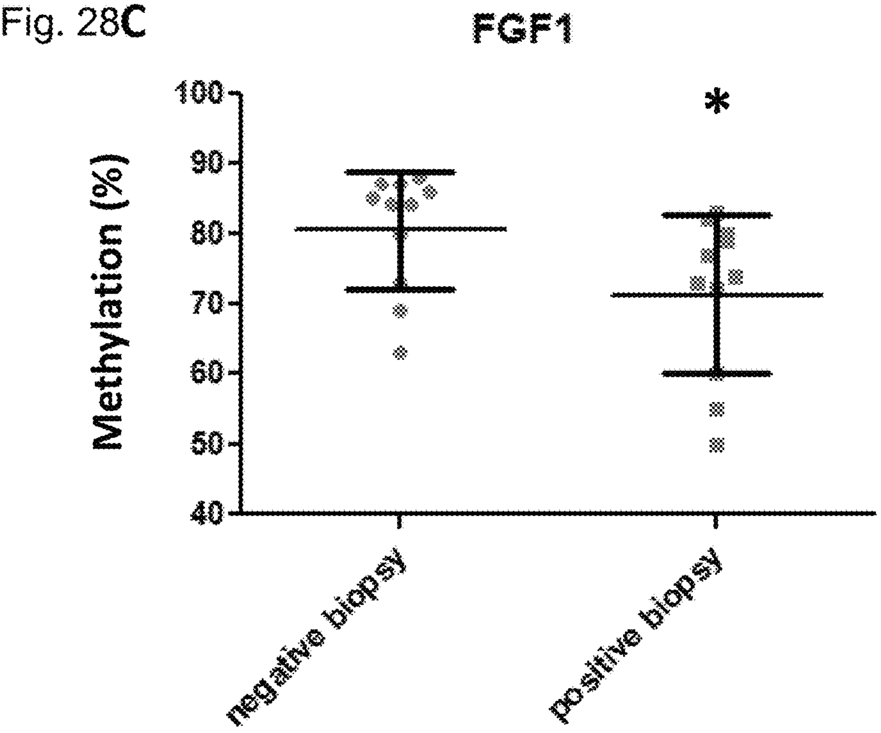
Figure 28D:
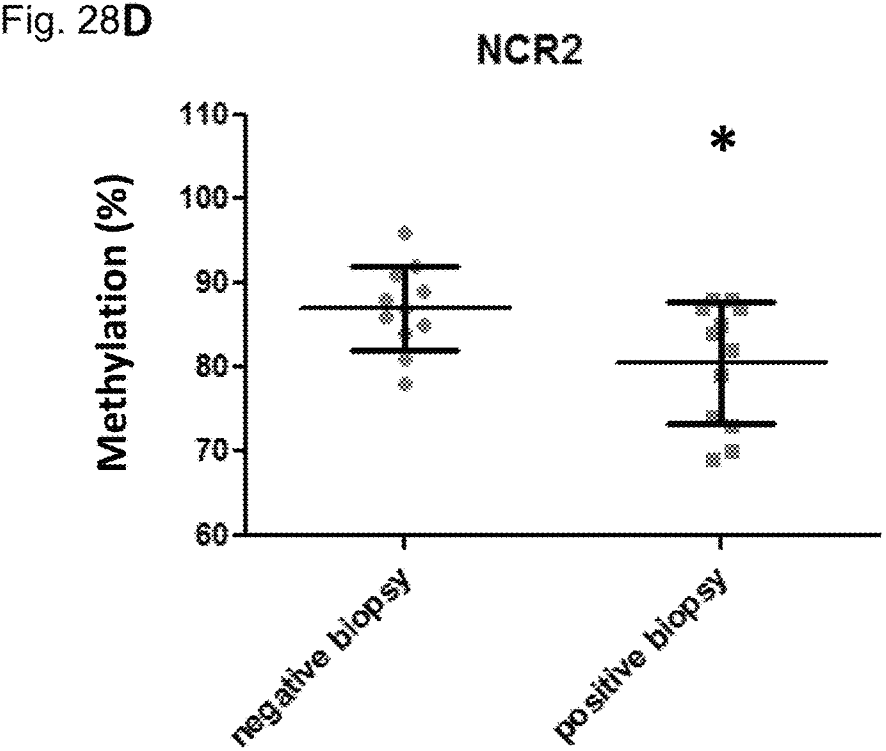

When compared to NTA tissues, hypermethylation of probes associated with SPAG4 and hypomethylation of EXT1 demonstrated significant changes in both TAA, as well as TAD tissues (FIG. 24 and Table 6). Notably, there was no difference in the extent of methylation seen at different distances from the tumor when TAA and TAD tissue sets were compared. Significant methylation changes were also seen in tumor samples when compared to NTA tissues for EXT1 and SPAG4, revealing a persistence of these changes in the associated cancer. These data indicate that the epigenetic field defect in the prostate is widespread and not solely localized to the immediate peritumor environment.

TABLE 6

Methylation Percentage Of All Analyzed CpGs For Each Gene

| | EXT1 | | | SPAG4 | | |
|---|---|---|---|---|---|---|
| | NTA | TAA | TAD | NTA | TAA | TAD |
| CG1 | 39.4 | 34.7* | 34.2* | 13.5 | 21.4* | 25.2* |
| CG2 | 28.3 | 24.1* | 24.5* | 15.9 | 25.4* | 27.3* |
| CG3 | 38.2 | 35.1* | 35.0* | 16.1 | 18.7* | 18.1 |
| CG4 | 27.2 | 24.3* | 24.0* | 11.6 | 15.9* | 15.6* |
| CG5 | 14.8 | 12.8 | 14.0 | 9.0 | 11.5* | 10.8 |
| CG6 | 32.5 | 36.3 | 38.5 | | | |

*P < 0.05

Example 6

CpG Islands

Based on the teachings of Examples 1, 2 and 5, one can also check the CpG islands that are located in the promoter regions of the genes showing significant methylation changes correlating with PCa, preferably the region within about 5 kb upstream of the transcription start site (TSS), because the methylation of these CpG islands will change the gene expressions and affect gene functions. The inventors' primary research (data not shown) showed that one may wish to examine genes EXT1 and SPAG4. The expanded regions of each of these two genes for preferred screening of methylation changes are detailed in FIGS. 26-27.

Both EXT1 and SPAG4 have CpG islands within the promoter regions. For EXT1, the expanded regions for preferred screening of methylation changes would be from 373 bps upstream to 84 downstream of transcription start site (TSS) FIG. 26 (SEQ ID NO:94). For SPAG4 the expanded regions for preferred screening of methylation changes would be from 1100 bps upstream of TSS through the first exon (SEQ ID NO:95), 1180 bps down stream of TSS (intron 1 and exon2, SEQ ID NO:96) and 3640 bps down stream of TSS (intron 9 and exon10, SEQ ID NO:97).

Example 7

DNA Methylation Urine-Based Screen for PCa

A widespread epigenetic field defect can be used to detect prostate cancer in patients with histologically negative biopsies (Truong et al., "Using the Epigenetic Field Defect to Detect Prostate Cancer in Biopsy Negative Patients" (2012) *J Urol*, in press). Prostate biopsies are performed on the patients who have elevated PSA levels. Prostatic massage will be given to each patient to increase the amount of prostate cells voided in the urine, and then voided urine will be collected from them. Those patients classified as having adenocarcinoma will be used in the positive biopsy samples, and the patients with this current biopsy negative and all previous negative biopsy will be used in the negative biopsy samples. The urine is centrifuged for 15 minutes at 1200 rpm at 4° C., the excess supernatant is removed and pellet at −80° C. immediately.

Genomic DNA from urine and biopsy tissue is extracted using Qiagen DNeasy Blood and Tissue Kit, Bench Protocol: Animal Tissues (Qiagen). The DNA is then treated with sodium bisulfite using the Qiagen EpiTect Bisulfite Handbook protocol (Qiagen, Valencia, Calif.) to modify the DNA to turn all the unmethylated cytosine to uracil. The bisulfite modified DNA is amplified by polymerase chain reaction (PCR) using gene specific primers, with either the forward or reverse primer biotinylated. The genes amplified include CAV1, EVX1, WNT2, MCF2L, NCR2, FGF1, EXT1 and SPAG4. Five microliter of the PCR products will be applied for Pyrosequencing to ascertain the actual percent methylation within the gene. The assay is run in a PyroMark™MD Pyrosequencing System (Qiagen). All samples are analyzed with two independent trials and t-test will be used to test for differences in methylation between the positive and negative biopsy urine samples with $p<0.05$ considered statistically significant.

FIG. 28 shows methylation of the genes in urine from the patients who have either positive or negative biopsies for prostate cancer. We have tested the methylation for the six markers EVX1, CAV1, FGF1, MCF2L, WNT2 and NCR2. EVX1, CAV1, FGF1 and NCR2 showed significant methylation difference between the biopsy positive and negative groups, t-test *$P<0.05$.

We claim:

1. A method of amplifying at least one of the eight target DNA sequences comprising the steps of:

(a) providing a reaction mixture comprising: (i) a double-stranded bisulfite modified target DNA; wherein the target DNA is from histologically normal prostate tissue of the a subject and (ii) at least one pair of primers selected from the group designed to amplify at least one gene selected from the group consisting of SEQ ID NO:1, EVX1, MCF2L, FGF1, WNT2, NCR2, EXT1 and SPAG4, wherein the primer pair comprises a first and a second primer that are complementary to the target DNA sequence, (iii) a polymerase and (iv) a plurality of free nucleotides comprising adenine, thymine, cytosine and guanine;

(b) heating the reaction mixture to a first predetermined temperature for a first predetermined time to separate the strands of the target DNA from each other;

(c) cooling the reaction mixture to a second predetermined temperature for a second predetermined time under conditions to allow the first and second primers to hybridize with their complementary sequences on the target DNA and to allow the polymerase to extend the primers; and, (d) repeating steps (b) and (c) at least 10 times wherein an amplified target DNA sample is formed.

2. The method of claim 1 wherein (v) PCR reaction buffer and (vi) $MgCl_2$ are additionally added to step (e).

3. The method of claim 1 wherein the primers are methylated.

4. The method of claim 1 wherein the primers are not methylated.

5. The method of claim 1 wherein the primer pairs are designed to amplify one target.

6. The method of claim 1 wherein the primer pairs are designed to amplify 2, 3, 4, 5, 6, 7, or 8 gene targets.

7. A method of amplifying at least one of the seven target DNA sequences comprising the steps of:

(a) providing a reaction mixture comprising: (i) a double-stranded bisulfite modified target DNA; wherein the target DNA is from histologically normal prostate tissue of the a subject and (ii) at least one pair of primers selected from the group designed to amplify at least one gene selected from the group consisting of EVX1, MCF2L, FGF1, WNT2, NCR2, EXT1 and SPAG4, wherein the primer pair comprises a first and a second primer that are complementary to the target DNA sequence, (iii) a polymerase and (iv) a plurality of free nucleotides comprising adenine, thymine, cytosine and guanine;

(b) heating the reaction mixture to a first predetermined temperature for a first predetermined time to separate the strands of the target DNA from each other;

(c) cooling the reaction mixture to a second predetermined temperature for a second predetermined time under conditions to allow the first and second primers to hybridize with their complementary sequences on the target DNA and to allow the polymerase to extend the primers; and, (d) repeating steps (b) and (c) at least 10 times wherein an amplified target DNA sample is formed.

8. The method of claim 7 wherein (v) PCR reaction buffer and (vi) $MgCl_2$ are additionally added to step (e).

9. The method of claim 7 wherein the primers are methylated.

10. The method of claim 7 wherein the primers are not methylated.

11. The method of claim 7 wherein the primer pairs are designed to amplify one target.

12. The method of claim 7 wherein the primer pairs are designed to amplify 2, 3, 4, 5, 6, or 7 gene targets.

* * * * *

UNITED STATES PATENT AND TRADEMARK OFFICE
CERTIFICATE OF CORRECTION

PATENT NO. : 10,131,953 B2
APPLICATION NO. : 14/226291
DATED : November 20, 2018
INVENTOR(S) : David Frazier Jarrard et al.

Page 1 of 1

It is certified that error appears in the above-identified patent and that said Letters Patent is hereby corrected as shown below:

In the Specification

Column 6, Line 11, "Norm" should be --Nonn--.

In the Claims

Column 203, Claim 1, Line 19, "of the a" should be --of a--.

Column 204, Claim 7, Line 18, "of the a" should be --of a--.

Signed and Sealed this
Twenty-ninth Day of January, 2019

Andrei Iancu
*Director of the United States Patent and Trademark Office*